US010814102B2

(12) United States Patent
Laby et al.

(10) Patent No.: US 10,814,102 B2
(45) Date of Patent: Oct. 27, 2020

(54) BASE STATION, CHARGING STATION, AND/OR SERVER FOR ROBOTIC CATHETER SYSTEMS AND OTHER USES, AND IMPROVED ARTICULATED DEVICES AND SYSTEMS

(71) Applicant: Project Moray, Inc., Belmont, CA (US)

(72) Inventors: Keith Phillip Laby, Oakland, CA (US); Mark D. Barrish, Belmont, CA (US)

(73) Assignee: Project Moray, Inc., Belmont, CA (US)

(*) Notice: Subject to any disclaimer, the term of this patent is extended or adjusted under 35 U.S.C. 154(b) by 251 days.

(21) Appl. No.: 15/719,191

(22) Filed: Sep. 28, 2017

(65) Prior Publication Data

US 2018/0085559 A1   Mar. 29, 2018

Related U.S. Application Data

(60) Provisional application No. 62/400,988, filed on Sep. 28, 2016, provisional application No. 62/401,005, filed on Sep. 28, 2016.

(51) Int. Cl.
*A61M 25/01* (2006.01)
*A61B 34/20* (2016.01)
(Continued)

(52) U.S. Cl.
CPC ....... *A61M 25/0155* (2013.01); *A61B 17/122* (2013.01); *A61B 17/1285* (2013.01);
(Continued)

(58) Field of Classification Search
CPC .......... B25J 9/142; B25J 18/06; A61M 25/01; A61M 25/0105; A61M 25/0152;
(Continued)

(56) References Cited

U.S. PATENT DOCUMENTS 3,284,964 A   11/1966   Saito
3,459,221 A    8/1969   Axelrod
(Continued)

FOREIGN PATENT DOCUMENTS

CN   107835703   3/2018
CN   107835704   3/2018
(Continued)

OTHER PUBLICATIONS

Approppedia.Org, "3-D Printing of Electrically Conductive Materials Literature Review", Appropedia: The sustainability Wiki, by Michigan Tech's Open Sustainability Technology Lab, Jul. 13, 2016, 9 pages.
(Continued)

*Primary Examiner* — Robert A Lynch
(74) *Attorney, Agent, or Firm* — Kilpatrick Townsend & Stockton LLP

(57) ABSTRACT

Articulation devices, systems, methods for articulation, and methods for fabricating articulation structures will often include simple balloon arrays, with inflation of the balloons interacting with elongate skeletal support structures so as to locally alter articulation of the skeleton. The skeleton may comprise a simple helical coil or interlocking helical channels, and the array can be used to locally deflect or elongate an axis of the coil under control of a processor. Liquid inflation fluid may be directed so as to pressurize the balloons from an inflation fluid canister, and may vaporize within a plenum or the channels or balloons of the articulation system, with the inflation system preferably including valves controlled by the processor. The articulation structures can be employed in minimally invasive medical catheter systems, and also for industrial robotics, for supporting imaging systems, for entertainment and consumer products, and the like.

20 Claims, 49 Drawing Sheets

(51) Int. Cl.
*A61F 2/24* (2006.01)
*A61B 17/122* (2006.01)
*A61B 17/128* (2006.01)
*A61M 25/00* (2006.01)
*A61B 90/00* (2016.01)
*A61B 17/00* (2006.01)
*A61B 17/22* (2006.01)

(52) U.S. Cl.
CPC ............ *A61B 34/20* (2016.02); *A61F 2/2427* (2013.01); *A61F 2/2442* (2013.01); *A61F 2/2466* (2013.01); *A61M 25/005* (2013.01); *A61B 2017/00115* (2013.01); *A61B 2017/00243* (2013.01); *A61B 2017/00305* (2013.01); *A61B 2017/00314* (2013.01); *A61B 2017/00318* (2013.01); *A61B 2017/00535* (2013.01); *A61B 2017/00734* (2013.01); *A61B 2017/22098* (2013.01); *A61B 2034/2051* (2016.02); *A61B 2034/2061* (2016.02); *A61B 2034/2063* (2016.02); *A61B 2090/064* (2016.02); *A61M 25/0136* (2013.01); *A61M 2025/0161* (2013.01); *A61M 2205/3331* (2013.01); *A61M 2205/3584* (2013.01); *A61M 2205/50* (2013.01); *A61M 2205/8206* (2013.01); *A61M 2205/8243* (2013.01); *A61M 2209/086* (2013.01)

(58) Field of Classification Search
CPC ........... A61M 25/0155; A61M 25/1011; A61B 1/00016; A61B 1/00059
See application file for complete search history.

(56) References Cited

U.S. PATENT DOCUMENTS

| | | | |
|---|---|---|---|
| 3,523,547 A | 8/1970 | Hatch, Jr. et al. | |
| 3,915,194 A | 10/1975 | Friedrich | |
| 3,934,605 A | 1/1976 | Legris | |
| 4,082,324 A | 4/1978 | Obrecht | |
| 4,230,143 A | 10/1980 | Dettmann et al. | |
| 4,494,417 A | 1/1985 | Larson et al. | |
| 4,762,130 A | 8/1988 | Fogarty et al. | |
| 4,784,042 A | 11/1988 | Paynter | |
| 4,794,912 A | 1/1989 | Lia | |
| 4,838,859 A | 6/1989 | Strassmann | |
| 4,890,611 A | 1/1990 | Monfort et al. | |
| 4,893,613 A | 1/1990 | Hake | |
| 4,900,218 A | 2/1990 | Sutherland | |
| 4,983,165 A * | 1/1991 | Loiterman | A61M 25/01 604/95.03 |
| 5,018,506 A | 5/1991 | Danna et al. | |
| 5,304,132 A | 4/1994 | Jang | |
| 5,308,356 A | 5/1994 | Blackshear, Jr. et al. | |
| 5,337,733 A | 8/1994 | Bauerfeind et al. | |
| 5,413,107 A | 5/1995 | Oakley et al. | |
| 5,469,756 A | 11/1995 | Feiten | |
| 5,489,270 A | 2/1996 | Van Erp | |
| 5,501,667 A | 3/1996 | Verduin, Jr. | |
| 5,529,088 A | 6/1996 | Asou | |
| 5,619,993 A | 4/1997 | Lee | |
| 5,820,595 A | 10/1998 | Parodi | |
| 5,823,955 A | 10/1998 | Kuck et al. | |
| 5,865,801 A | 2/1999 | Houser | |
| 6,066,125 A | 5/2000 | Webster, Jr. | |
| 6,146,339 A | 11/2000 | Biagtan et al. | |
| 6,178,872 B1 | 1/2001 | Schulz | |
| 6,503,194 B2 | 1/2003 | Pauker | |
| 6,527,739 B1 | 3/2003 | Bigus et al. | |
| 6,648,879 B2 | 11/2003 | Joye et al. | |
| 6,811,550 B2 | 11/2004 | Holland et al. | |
| 6,875,170 B2 | 4/2005 | Francois et al. | |
| 6,928,313 B2 | 8/2005 | Peterson | |
| 6,951,226 B2 | 10/2005 | Eriksson et al. | |
| 7,060,062 B2 | 6/2006 | Joye et al. | |
| 7,373,955 B2 | 5/2008 | Steinberg | |
| 7,422,579 B2 | 9/2008 | Wahr et al. | |
| 7,570,981 B2 | 8/2009 | Peterson | |
| 7,578,787 B2 | 8/2009 | Boese et al. | |
| 7,780,723 B2 | 8/2010 | Taylor | |
| 7,824,391 B2 | 11/2010 | Gesswein | |
| 7,850,683 B2 | 12/2010 | Elkins et al. | |
| 7,879,004 B2 | 2/2011 | Seibel et al. | |
| 7,957,790 B2 | 6/2011 | Kleen | |
| 7,963,911 B2 | 6/2011 | Turliuc | |
| 8,125,755 B2 | 2/2012 | Garcia et al. | |
| 8,201,473 B2 | 6/2012 | Knoll | |
| 8,372,055 B2 | 2/2013 | Thornton et al. | |
| 8,388,520 B2 | 3/2013 | Stefanchik et al. | |
| 8,398,540 B2 | 3/2013 | Hassidov et al. | |
| 8,423,115 B2 | 4/2013 | Koblish et al. | |
| 8,469,059 B1 | 6/2013 | Forst | |
| 8,764,725 B2 | 7/2014 | Averbuch | |
| 8,845,523 B2 | 9/2014 | Lawrence et al. | |
| 8,863,608 B2 | 10/2014 | Fischer et al. | |
| 2001/0007070 A1 | 7/2001 | Stewart et al. | |
| 2002/0045929 A1 | 4/2002 | Diaz | |
| 2002/0049408 A1 | 4/2002 | Van Moorlegem et al. | |
| 2002/0058951 A1 | 5/2002 | Fiedler | |
| 2003/0069475 A1* | 4/2003 | Banik | A61B 1/00016 600/152 |
| 2004/0041031 A1* | 3/2004 | Root | A61B 1/00016 235/487 |
| 2006/0058598 A1 | 3/2006 | Esposito | |
| 2006/0084964 A1 | 4/2006 | Knudson et al. | |
| 2006/0235368 A1 | 10/2006 | Oz | |
| 2007/0038293 A1* | 2/2007 | St.Goar | A61B 17/00234 623/2.11 |
| 2007/0060997 A1 | 3/2007 | de Boer | |
| 2007/0100235 A1 | 5/2007 | Kennedy, II | |
| 2007/0123925 A1 | 5/2007 | Benjamin et al. | |
| 2007/0169761 A1 | 7/2007 | Price | |
| 2007/0270686 A1 | 11/2007 | Ritter et al. | |
| 2007/0288095 A1 | 12/2007 | Wirtel et al. | |
| 2008/0091073 A1 | 4/2008 | Park | |
| 2008/0215008 A1 | 9/2008 | Nance et al. | |
| 2009/0076584 A1 | 3/2009 | Mao et al. | |
| 2009/0105816 A1 | 4/2009 | Olsen et al. | |
| 2009/0281523 A1 | 11/2009 | Sacco et al. | |
| 2009/0314119 A1* | 12/2009 | Knoll | A61B 1/00156 74/490.01 |
| 2010/0168665 A1 | 7/2010 | Skerven | |
| 2011/0112632 A1 | 5/2011 | Chau et al. | |
| 2011/0270126 A1 | 11/2011 | Gunday et al. | |
| 2011/0295247 A1 | 12/2011 | Schlesinger et al. | |
| 2011/0295248 A1 | 12/2011 | Wallace et al. | |
| 2012/0116380 A1* | 5/2012 | Madan | A61B 17/00234 606/33 |
| 2012/0271319 A1 | 10/2012 | Bromander et al. | |
| 2012/0310227 A1 | 12/2012 | Katou | |
| 2013/0091974 A1 | 4/2013 | Riwan et al. | |
| 2013/0096377 A1 | 4/2013 | Duindam et al. | |
| 2013/0103019 A1 | 4/2013 | Joye et al. | |
| 2013/0178838 A1 | 7/2013 | Malkowski et al. | |
| 2013/0296983 A1 | 11/2013 | Keller et al. | |
| 2014/0062405 A1* | 3/2014 | Videbaek | A61B 10/0283 320/115 |
| 2014/0142666 A1 | 5/2014 | Phelan et al. | |
| 2014/0243688 A1 | 8/2014 | Caron et al. | |
| 2014/0276933 A1 | 9/2014 | Hart et al. | |
| 2014/0276934 A1 | 9/2014 | Balaji et al. | |
| 2015/0209558 A1 | 7/2015 | Charlebois et al. | |
| 2015/0265807 A1 | 9/2015 | Park et al. | |
| 2016/0128767 A1 | 5/2016 | Azamian et al. | |
| 2016/0279388 A1 | 9/2016 | Barrish et al. | |
| 2017/0021132 A1 | 1/2017 | Laby et al. | |
| 2017/0021143 A1 | 1/2017 | Barrish et al. | |
| 2017/0157361 A1 | 6/2017 | Barrish et al. | |
| 2017/0157363 A1 | 6/2017 | Barrish et al. | |
| 2018/0071492 A1 | 3/2018 | Laby et al. | |
| 2018/0200483 A1 | 7/2018 | Laby et al. | |

(56) References Cited

U.S. PATENT DOCUMENTS

FOREIGN PATENT DOCUMENTS

| CN | 107921236 | 4/2018 |
|---|---|---|
| EP | 3274038 | 1/2018 |
| EP | 3274039 | 1/2018 |
| EP | 3274040 | 1/2018 |
| WO | 2007053625 | 5/2007 |
| WO | 2014128507 | 8/2014 |

OTHER PUBLICATIONS

Arsalan et al., "Comparison of Current Costs and Reimbursement for Transcatheter and Surgical Aortic Valve Replacement", J. Am. Coll. Cardiol., vol. 67, No. 13, ACC.i2 Interventional Cardiology, Available online at http://content.onlinejacc.org/article.aspxarticleid=2508037, Apr. 5, 2016, 2 pages.

Atzori et al., "Indoor Navigation System Using Image and Sensor Data Processing on a Smartphone", Optimization of Electrical and Electronic Equipment (OPTIM), 2012 13th International Conference, Available online at https://www.researchgate.net/publication/261267019_Indoor_navigation_system_using_image_and_sensor_data_processing_on_a_smartphone, May 24-26, 2012, pp. 1158-1163.

Au et al., "Microvalves and Micropumps for BioMEMS", Micromachines, vol. 2, ISSN 2072-666X, Available online at www.mdpi.com/journal/micromachines, 2011, pp. 179-220.

Backer et al., "Percutaneous Transcatheter Mitral Valve Replacement", Circulation: Cardiovascular Interventions, Available online at http://circinterventions.ahajournals.org/content/7/3/400.full, 2014, pp. 400-409.

Bar-Cohen, "Worldwide ElectroActive Polymers", EAP (Artificial Muscles) Newsletter, vol. 16, No. 1, (The 31th issue), Available online at http://eap.jpl.nasa.gov, Jun. 2014, pp. 1-18.

BBC News Science & Environment, "Nanotube Yarns Twist Like Muscles", BBC News, Available online at http://www.bbc.co.uk/news/science-environment-15287185, Oct. 14, 2011, 8 pages.

Beahm et al., "Catheter Bonding Technology Overview", Avaialble online at www.beahmdesigns.com, Apr. 2012, 4 pages.

Biswal et al., "Development of an Active Catheter Mechanism Using IPMC for in Vivo Inspection", Journal of Mechatronics and Automation vol. 1, No. 1, Available online at: http://www.academia.edu/10757534/Development_of_an_Active_Catheter_Mechanism_using_IPMC_for_in_vivo_Inspection, 2014, 10 pages.

Bolling, "Can We Predict Mitral Valve Repair Rates by Individual Surgeons' Mitral Volume", Tex Heart Inst J., vol. 38, No. 6, 8th Current Trends in Aortic and Cardiothoracic Surgery, Available online at http://www.ncbi.nlm.nih.gov/pmc/articles/PMC3233323/, 2011, pp. 703-704.

Buntz, "Forget IoT: The Internet of Moving Things Is Where It Is at", Qmed, Available online at http://www.qmed.com/mpmn/medtechpulse/forget-iot-internet-moving-things-where-it, Dec. 10, 2014, 3 pages.

Buntz, "Graphene Breakthrough Could Be a Boon to Flexible Electronics", Electronic Components, Qmed, Available online at http://www.qmed.com/mpmn/medtechpulse/graphene-breakthrough-could-be-boon-flexible-electronicscid=nl.qmed02, Nov. 14, 2013, 1 page.

Buntz, "How Tiny Artificial Muscles Could Be Huge Energy Savers", Motion Control, Qmed, Available online at http://www.qmed.com/mpmn/medtechpulse/how-tiny-artificial-muscles-could-be-huge-energy-saverscid=nl.qmed02.20150223, Feb. 20, 2015, 3 pages.

Buntz, "Using a T-Shirt Printer to Make Medical Circuits", Qmed, Electronic Components, Available online at http://www.qmed.com/mpmn/medtechpulse/using-t-shirt-printer-make-medical-circuits, Nov. 17, 2014, 3 pages.

Catherine et al., "Comparative Review of Endoscopic Devices Articulations Technologies Developed for Minimally Invasive Medical Procedures", Applied Bionics and Biomechanics, vol. 8, 2011, pp. 151-171.

Chakraborty et al., "Mems Micro-Valve for Space Applications", Sensors and Actuators A: Physical, vol. 83, No. 1-3, 2000, pp. 188-193.

Chandgadkar, "An Indoor Navigation System for Smartphones", Available online at http://www.doc.ic.ac.uk/teaching/distinguished-projects/2013/a.chandgadkar.pdf, Jun. 18, 2013, 80 pages.

Chang et al., "Electrostatically-Actuated Reconfigurable Elastomer Microfluidics", Available online at http://people.eecs.berkeley.edu/~maharbiz/HH_paper_mpchang_0008.pdf, 4 pages.

Chen et al., "High-Pressure On-Chip Mechanical Valves for Thermoplastic Microfluidic Devices", The Royal Society of Chemistry, Lab Chip, vol. 9, 2009, pp. 3511-3516.

Clippard New!, "New 7 mm Electronic Valves", Available online at http://www.clippard.com/products/electronic-valve-7mm, 2 pages.

Conrad et al., "Closed Loop Task Space Control of an Interleaved Continuum-Rigid Manipulator", IEEE International Conference on Robotics and Automation, Available online at http://robotics.engrwisc.edu/cgi-bin/wikiwp/category/continuum-robotics/, 2015, 8 pages.

Corma Inc., "Corrugators and Pulsating Corrugators", Available online at http://corma.com/products/corrugators-pulsating-corrugators/, 2011, 3 pages.

Coyne, "Comprehensive Manufacturing of Microfluidic Diagnostic Devices", IVD, MDDI Medical Device and Diagnostic Industry, Jun. 17, 2014, 4 pages.

Creganna Tactx Medical, "Deflectable and Steerable Catheter Handbook", Terminology Guide & Design Options, Available online at http://www.creganna.com/wp-content/uploads/Steeringand-DeflectionTerminologyrev3.pdf, 7 pages.

Dabove et al., "Inertial Sensors for Smartphones Navigation", SpringerPlus, vol. 4, No. 834, Available online at http://www.ncbi.nlm.nih.gov/pmc/articles/PMC4695469/, 2015, 18 pages.

D'Arcy et al., "Valvular Heart Disease: The Next Cardiac Epidemic", vol. 97, No. 2, Available online at http://heart.bmj.com/content/97/2/91.extract, 2011, pp. 91-93.

De Sars et al., "A Practical Approach to the Design and Control of Active Endoscopes", Mechatronics, vol. 20, Available online at http://www.elsevierscitech.com/pdfs/Mechatronics_DeSars.pdf, 2010, pp. 251-264.

DMQ Inc., "Product Datasheet: silQflo™ Silicon Servo Valve", Available online at http://www.dmq-us.com/wp-content/uploads/2015/02/SSV-Datasheet-Rev-1.001.pdf, 2 pages.

Don et al., "Novel Velocity Model to Improve Indoor Localization Using Inertial Navigation With Sensors on a Smart Phone", Avaialble online at http://arxiv.org/pdf/1601.03004.pdf, Jan. 12, 2016, 5 pages.

Dupont et al., "Snakes, Worms and Catheters: Continuum and Serpentine Robots for Minimally Invasive Surgery", IEEE ICRA Full Day Workshop, May 3, 2010, 60 pages.

Eitel, "The Rise of Soft Robots and the Actuators that Drive Them", Available online at http://machinedesign.com/robotics/rise-soft-robots-and-actuators-drive-them, Sep. 12, 2013, 7 pages.

Elveflow Plug & Play, "Microfluidics and Microfluidic Devices: A Review", Available online at http://www.elveflow.com/microfluidic-tutorials/microfluidic-reviews-and-tutorials/microfluidics-and-microfluidic-device-a-review/, 2015, 10 pages.

EP Vantage Ltd., "Edwards Tightens Transcatheter Valve Stranglehold", Available online at http://www.epvantage.com/Universal/View.aspxtype=Story&id=580885&isEPVantage=yes, Jun. 18, 2015, 2 pages.

Eucog Wiki, "Compliant Robots", Available online at http://www.eucognition.org/eucog-wiki/Compliant_robots, 2012, 5 pages.

Fedak et al., "Evolving Concepts and Technologies in Mitral Valve Repair", American Heart Association, Inc., Contemporary Reviews in Cardiovascular Medicine, vol. 117, No. 7, Available online at http://circ.ahajournals.org/content/117/7/963.full, Feb. 19, 2008, pp. 963-974.

Festo AG & Co. KG, "Systematic Expertise Through Continuous Further Development", Bionic Handling Assistant, Available online at https://www.festo.com/net/supportportal/files/42050/brosch_fc_bha_3_0_en_lo.pdf, Apr. 2012, 6 pages.

Fite et al., "A Gas-Actuated Anthropomorphic Prosthesis for Transhumeral Amputees", IEEE Transactions on Robotics, vol. 24, No. 1, Feb. 2008, pp. 159-169.

(56) References Cited

OTHER PUBLICATIONS

Flexpoint Sensor Systems, Inc., "The Benefits of Using Bend Sensors", Sensor Products Inc., Available online at www.sensorprod.com, 2 pages.
Fornell, "Transcatheter Mitral Valve Replacement Devices in Development", Diagnostic and Interventional Cardiology, Available online at http://www.dicardiology.com/article/transcatheter-mitral-valve-replacement-devices-development, Dec. 30, 2014, 5 pages.
Fu et al., "Research on the Axis Shape of an Active Catheter", Int. J. Med. Robot.; vol. 4, No. 1, Mar. 2008, pp. 69-76.
Fu et al., "Steerable Catheters in Minimally Invasive Vascular Surgery", Int. J. Med. Robot., vol. 5, No. 4, Dec. 2009, pp. 381-391.
Gionata et al., "An Inertial and Qr Code Landmarks-Based Navigation System for Impaired Wheelchair Users", Available online at https://www.researchgate.net/publication/261551014_An_inertial_and_QR_code_landmarks-based_navigation_system_for_impaired_wheelchair_users, May 29, 2014, pp. 205-214.
Grube, "Development of a TMVR Device Challenge to Innovators", ICI meeting, Dec. 13-15, 2015, 30 pages.
Haga et al., "Active Bending Catheter and Endoscope Using Shape Memory Alloy Actuators", Available online at www.intechopen.com, Shape Memory Alloys, 2010, 21 pages.
Haga et al., "Multi-Functional Active Catheter", Available online at http://bdml.stanford.edu/twiki/pub/Haptics/DesignReferencesSummer2009/MultifunctionalActiveCatheter.pdf, pp. 147-186.
Herrmann et al., "Novel Transcatheter Approaches", Heart Valve Summit, American association of Thoracic surgery, Available online at http://aats.org/multimedia/files/valve/2015/Presentations/Thursday/600-Herrmann.pdf, 2015, 26 pages.
Ikeuchi et al., "Development of Pressure-Driven Micro Active Catheter using Membrane Micro Emboss Following Excimer Laser Ablation (MeME-X) Process", IEEE International Conference on Robotics and Automation, Available online at http://ir.nul.nagoya-u.ac.jp/jspui/bitstream/2237/13924/1/ICRA09_MeMEX.pdf, May 12-17, 2009, pp. 4469-4472.
Jagadeesan, "Design and Control of an Active Catheter", Available online at http://scholar.harvard.edu/jayender/activecatheter, Jul. 14, 2016, 2 pages.
Jia et al., "Online Camera-Gyroscope Auto-Calibration for Cellphones", IEEE Transactions on Image Processing, Available online at http://users.ece.utexas.edu/~bevans/papers/2015/autocalibration/autocalibrationIEEETransImageProcPaperDraft.pdf, 2013, 11 pages.
John Muir Health, "U.S. Aortic Stenosis Disease Prevalence and Treatment Statistics", Facts and Figures, Available Online at https://www.johnmuirhealth.com/services/cardiovascular-services/intervention/transcatheter-aortic-valve-replacement/facts-and-figures.html, 2016, 3 pages.
Johnson, "Modeling of Frictional Gas Flow in a Piezoelectrically Actuated High-pressure Microvalve for Flowrate Control", Dec. 16, 2005, 197 pages.
Jung et al., "A Modeling Approach for Continuum Robotic Manipulators: Effects of Nonlinear Internal Device Friction", IEEE/RSJ International Conference on Intelligent Robots and Systems, Sep. 25-30, 2011, pp. 5139-5146.
Kasahara et al., "Surface Modification of Polyethylene Terephthalate (PET) by 172-nm Excimer lamp", Technical paper, 2012, pp. 47-54.
Kato et al., "An Inchworm Type In-Pipe Mobile Microrobot Driven by Three Gas-liquid Phase-change Actuators", Proceedings of the Annual Meeting—American Society for Precision Engineering, 2003, pp. 295-298.
Kim et al., "Materials for Multifunctional Balloon Catheters with Capabilities in Cardiac Electrophysiological Mapping and Ablation Therapy", Nat Mater., vol. 10, No. 4, Available online at http://www.ncbi.nlm.nih.gov/pmc/articles/PMC3132573/, Apr. 2011, pp. 316-323.
Kirby et al., "Microfluidic Routing of Aqueous and Organic Flows at High Pressures: Fabrication and Characterization of Integrated Polymer Microvalve Elements", The Royal Society of Chemistry, Lab Chip, vol. 5, 2005, pp. 184-190.
Korane, "Robot Imitates an Elephant's Trunk", Available online at http://machinedesign.com/robotics/robot-imitates-elephant-s-trunk, Sep. 13, 2010, 5 pages.
Labsmith, Inc., "LabSmith uProcess™ System", LabSmith, Inc., Microfluidic Automation, Available online at http://www.labsmith.com/products/LabSmith_uProcess_Brochure.pdf_ga=1.142274551.472763250.1458083262., 2015, 6 pages.
Langelaar et al., "Modeling of a Shape Memory Alloy Active Catheter", 45th AIAA/ASME/ASCE/AHS/ASC Structures, Structural Dynamics & Materials Conference, American Institute of Aeronautics and Astronautics, Available online at http://citeseerxist.psu.edu/viewdoc/downloaddoi=10.1.1.125.1080&rep=rep1&type=pdf, Apr. 19-22, 2004, 16 pages.
Lee et al., "Fabrication, Characterization, and Computational Modeling of a Piezoelectrically Actuated Microvalve for Liquid Flow Control", Journal of Microelectromechanical Systems, vol. 15, No. 3, IEEE, Jun. 2006, pp. 686-696.
Levy, "Tiny Ultrasound Camera Images Blood Vessel Interior in 3-D", Medical Imaging, Qmed, Available online at http://www.qmed.com/mpmn/medtechpulse/tiny-ultrasound-camera-images-blood-vessel-interior-3-dcid=nl.qmed02, Mar. 3, 2014, 5 pages.
Maglione et al., "Ultra-High-Pressure Balloon Angioplasty for Treatment of Resistant Stenoses Within or Adjacent to Previously Implanted Pulmonary Arterial Stents", Circulation: Cardiovascular Interventions, Available online at http://circinterventions.ahajournals.org/content/2/1/52.full, 2009, pp. 52-58.
Malek et al., "Femtosecond Laser Machining and Lamination for Large-Area Flexible Organic Microfluidic Chips", European Physical Journal: Applied Physics, EDP Sciences, Available online at https://hal.archives-ouvertes.fr/hal-00480155/document, Apr. 2009, 8 pages.
Mazzarese, "Low-Profile Balloon Catheters are Critical to TAVR's Success", Medical Tubing Types by MDDI Staff, Available online at http://www.mddionline.com/article/low-profile-balloon-catheters-are-critical-tavr-success-10-21-2014cid=nl.mddi01.20141023, Oct. 21, 2014, 3 pages.
MDDI, Medical Plastics, "The Effect of Extrusion and Blow Molding Parameters on Angioplasty Balloon Production", Available online at http://www.mddionline.com/article/effect-extrusion-and-blow-molding-parameters-angioplasty-balloon-production, May 1, 1998, 4 pages.
Medtronic, "CoreValve™ System", Transcatheter Aortic Valve Delivery Catheter System Compression Loading System, 2014, 61 pages.
Messenger, "A Comprehensive Guide to the U.S. TAVR Market: Surveying the Field", Available online at http://www.meddeviceonline.com/doc/a-comprehensive-guide-to-the-u-s-tavr-market-surveying-the-field-0001, Apr. 12, 2016, 7 pages.
Mohty et al., "Valvular Heart Disease in Elderly Adults", Available online at http://www.uptodate.com/contents/valvular-heart-disease-in-elderly-adults, 2016, 6 pages.
Mount Sinai Hospital, "Researchers Compare Two-Year Clinical Outcomes of Mitral Valve Replacement and Repair in Treating Severe Valve Regurgitation", Icahn School of Medicine at Mount Sinai, Available online at http://www.mountsinai.org/about-us/newsroom/press-releases/researchers-compare-twoyear-clinical-outcomes-of-mitral-valve-replacement-and-repair-, Nov. 9, 2015, 2 pages.
Mueller et al., "An Overview of Mems-based Micropropulsion Developments at JPL", Acta Astronautica, vol. 52, No. 9-12, Selected Proceedings of the 3rd IAA International Symposium on Small Satellites for Earth Observation, May-Jun. 2003, 15 pages.
Mueller et al., "Design and Fabrication of MEMS-Based Micropropulsion Devices at JPL", Proceedings of SPIE vol. 4558, 2001, pp. 57-71.
Muller et al., "Remote Control Catheter Navigation: Options for Guidance Under MRI", Journal of Cardiovascular Magnetic Resonance, vol. 14, No. 33, Available online at http://www.jcmr-online.com/content/14/1/33, 2012, pp. 1-9.
Newmarker, "How Lasers are Changing MedTech", Lasers, Qmed, Available online at http://www.qmed.com/mpmn/medtechpulse/how-lasers-are-changing-medtechcid=nl.qmed02, Jan. 14, 2014, 3 pages.

(56) References Cited

OTHER PUBLICATIONS

Newmarker, "How Scotch Tape is Driving Diagnostics Breakthroughs", Medical Plastics, Qmed, Available online at http://www.qmed.com/mpmn/medtechpulse/how-scotch-tape-driving-diagnostics-breakthroughscid=nl.qmed02.20141002, Oct. 1, 2014, 3 pages.
Nolker et al., "Differences in Tissue Injury and Ablation Outcomes in Atrial Fibrillation Patients—Manual versus Robotic Catheters", Journal of Atrial Fibrillation, Department of Cardiology, Heart and Diabetes Center, vol. 6, No. 2, Aug.-Sep. 2013, pp. 82-88.
Nucryovascular, LLC, "Peripheral Dilatation Catheter Peripheral Dilatation System", Vascular solutions, PolarCath™ over-the-wire, Available online at www.vasc.com, pp. 1-12.
Oh et al., "A Review of Microvalves", Topical Review, Journal of Micromechanics and Microengineering, vol. 16, 2006, pp. R13-R39.
Omed Qualified Suppliers, "A Tiny Spectrometer that Costs 10 Bucks", Qmed, Available online at http://www.qmed.com/mpmn/medtechpulse/tiny-spectrometer-costs-10-buckscid=nl.qmed02.20141216, Dec. 12, 2014, 3 pages.
Omed Qualified Suppliers, "How 3-D Printing Can Help Accelerate Fluidic Manifold Delivery", Qmed, Available online at http://www.qmed.com/mpmn/medtechpulse/how-3-d-printing-can-help-accelerate-fluidic-manifold-deliverycid=nl.qmed02.20150507, May 6, 2015, 3 pages.
Omed Qualified Suppliers, "Introducing 3-D Injection Molding", Qmed, Available online at http://www.qmed.com/mpmn/gallery/image/4-introducing-3-d-injection-molding, 2014, 2 pages.
Omed Qualified Suppliers, "Overcoming Engineering Challenges: Developing a Tiny Robotically Steerable Guidewire", Qmed, Medtech Pulse Blog, Available online at http://www.qmed.com/mpmn/medtechpulse/overcoming-engineering-challenges-developing-tiny-robotically-steerable-guidewirecid=nl_qmed_daily, Feb. 15, 2013, 2 pages.
Ono et al., "Development of a Cylinder Type Gas-liquid Phase-change Actuator", 2 pages.
Parmar, "FDA Approves St. Jude Medical's Force-Sensing Ablation Catheters for AF", Regulatory and Compliance, MDDI Medical Device and Diagnostic Industry, Available online at http://www.mddionline.com/article/fda-approves-st-jude-medicals-force-sensing-ablation-catheters-af-102714cid=nl.mddi01.20141028, Oct. 27, 2014, 3 pages.
Peelsil™ Tubing, "Scientific Tubing", SGE, Glass Lined Tubing (GLT™), Available online at www.sge.com, Fused Silica Tubing brochure PD-0230-Aw, 2001, 6 pages.
Penning et al., "A Combined Modal-Joint Space Control Approach for Minimally Invasive Surgical Continuum Manipulators", Advanced Robotics, vol. 28, No. 16, Jul. 2014, 41 pages.
Penning et al., "An Evaluation of Closed-Loop Control Options for Continuum Manipulators", IEEE, 2012, 6 pages.
Penning, "ICRA 2012 Recap", Available online at http://robotics.engr.wisc.edu/cgi-bin/wikiwp/2012/11/icra-2012-recap/, Nov. 11, 2012, 2 pages.
Penning et al., "Towards Closed Loop Control of a Continuum Robotic Manipulator for Medical Applications", IEEE, 2011, 6 pages.
Plastics, "Corrugator Technologies: Overview and New Developments", Corrugator technologies overview, Available at http://www.plastics.gl/extrusion-profile/corrugator-technologies-overview/, 2015, 8 pages.
Pollock, "Bionic Ants Could be Tomorrow's Factory Workers", Available online at http://www.reuters.com/article/2015/03/30/us-germany-bionic-ants-idUSKBN0MQ1WD20150330, Mar. 30, 2015, 3 pages.
Preston-Maher et al., "A Technical Review of Minimally Invasive Mitral Valve Replacements", Cardiovascular Engineering and Technology, vol. 6, No. 2, Jun. 2015, pp. 174-184.
Profilepipe Machinery Inc., "Convoluted Tubing to an Outer Diameter of 65 mm", Available online at http://www.profilepipe.com/small_corrugators.html, 2015, 2 pages.

Qmed Qualified Suppliers, "Tiny Artificial Muscles", Available online at http://www.qmed.com/mpmn/gallery/image/1-tiny-artificial-muscles, Jul. 14, 2016, 1 page.
Qmed, Electronic Components, "How Micro-Location Could Boost Healthcare IoT", Available online at http://www.qmed.com/mpmn/medtechpulse/how-micro-location-could-boost-healthcare-iotcid=nl.x.qmed02.edt.aud.qmed.20160606, Jun. 3, 2016, 2 pages.
Quero et al., "A Novel Pressure Balanced Microfluidic Valve", Proc. ISCAS, IEEE, 2002, pp. 1-4.
Rich et al., "Costs for Mitral Valve Surgery According to STS Preoperative Risk: Implications for Transcatheter Mitral Therapies", American Association for Thoracic Surgery, Available Online at http://aats.org/mitral/abstracts/2015/P165.cgi, 2016, 2 pages.
Roriz et al., "Fiber Optic Intensity-Modulated Sensors: A Review in Biomechanics", Photonic Sensors, vol. 2, No. 4, 2012, pp. 315-330.
Rossiter et al., "Printing 3D Dielectric Elastomer Actuators for Soft Robotics", SPIE Proceedings, vol. 7287, Apr. 6, 2009, 2 pages.
Schut, "Corrugator Vacuum Forming", Plastics Technology, Available online at http://www.ptonline.com/articles/'corrugator-vacuum-forming', Jul. 2005, 4 pages.
SGE Analytical Science, "Tubing, Stainless Steel Tubing and Terry-Tool Tubing Cutter", 2011, 10 pages.
Shoa et al., "Conducting Polymer Based Active Catheter for Minimally Invasive Interventions inside Arteries", Conf Proc IEEE Eng Med Biol Soc, Available online at http://mm.ece.ubc.ca/mediawiki/images/b/b7/PID616280.pdf, 2008, pp. 2063-2066.
Sparkfun, "Accelerometer, Gyro and IMU Buying Guide", Available online at https://www.sparkfun.com/pages/accel_gyro_guide, accessed from the internet on Jul. 14, 2016, 10 pages.
Strickland, "Inside an MRI, a Non-Metallic Robot Performs Prostate Surgery", Available online at http://spectrum.ieee.org/automaton/robotics/medical-robots/inside-an-mri-a-nonmetallic-robot-performs-prostate-surgery, Jul. 8, 2015, 3 pages.
Takizawa et al., "Development of a Microfine Active Bending Catheter Equipped with MIF Tactile Sensors", Available online at http://www.ics.forth.gr/bioloch/internal/papers/Olympus.pdf, 1999, 7 pages.
Taramasso et al., "Current Challenges in Interventional Mitral Valve Treatment", J. Thorac. Dis., vol. 7, No. 9, Available online at http://www.ncbi.nlm.nih.gov/pmc/articles/PMC4598533/, 2015, pp. 1536-1542.
Teleflex Incorporated, "Balloons and Balloon Catheters", Available online at http://www.teleflexmedicaloem.com/diagnostic-and-interventional-catheters/balloon-catheters/, 2015, 3 pages.
Temiz et al., "Lab-on-a-Chip Devices: How to Close and Plug the Lab", Microelectronic Engineering, vol. 132, 2015, pp. 156-175.
Tokai Medical Products Inc., "PTA Sphere-Curve", Available online at http://www.tokaimedpro.co.jp/en/products/2009/000056.html, Jul. 14, 2016, 2 pages.
Tung et al., "Laser-Machined Shape Memory Alloy Actuators for Active Catheters", Mechatronics, IEEE/ASME Transactions on, vol. 12, No. 4, Aug. 2007, pp. 439-446.
Van Oosten et al., "Printed Artificial Cilia from Liquid-crystal Network Actuators Modularly Driven by Light", Nature Materials, vol. 8, Available online at http://www.nature.com/nmat/journal/v8/n8/full/nmat2487.html, 2009, pp. 677-682.
Veeramani, "A Transformative Tool for Minimally Invasive Procedures: Design, Modeling and Real-time Control of a Polycrystalline Shape Memory Alloy Actuated Robotic Catheter", 2009, 198 pages.
Walters, "Gas-Flow Calculations: Don't Choke", Applied Flow Technology, Chemical Engineering, Available online at http://www.aft.com/documents/AFT-CE-Gasflow-Reprint.pdf, Jan. 2000, 8 pages.
Wasserman, "Edwards and Medtronic Turn up TAVR Competition with Positive Study Data", Available online at http://www.fiercemedicaldevices.com/story/edwards-and-medtronic-turn-tavr-competition-positive-study-data/2015-03-16, Mar. 16, 2015, 3 pages.
Webb et al., "Transcatheter Aortic Valve Implantation: The Evolution of Prostheses, Delivery Systems and Approaches", Archives of Cardiovascular Disease, vol. 105, 2012, pp. 153-159.
Weber et al., "Side-Selective Atrial Transseptal Laser Puncture", The Journal of Innovations in Cardiac Rhythm Management, vol. 4, Avaiable online at http://www.innovationsincrm.com/cardiac-rhythm-

(56) References Cited

OTHER PUBLICATIONS management/2013/december/524-side-selective-atrial-transseptal-laser-puncture, Dec. 2013, pp. 1481-1485.

Wirtl et al., "White Paper Piezo Technology in Pneumatic Valves", Festo AG & Co. KG, 2014, pp. 1-9.

Wood, "Early Results for Transcatheter Mitral Valve Replacement Reveal Complications and Challenges for the Long Road Ahead", Available online at http://www.tctmd.com/show.aspxid=133937, Feb. 22, 2016, 1 pages.

Wutzler et al., "Robotic Ablation of Atrial Fibrillation", Department of Cardiology, . Vis. Exp. (99), e52560, Available online at http://www.jove.com/video/52560/robotic-ablation-of-atrial-fibrillation, 2015, 14 pages.

Yang et al., "Leak-Tight Piezoelectric Microvalve for High-Pressure Gas Micropropulsion", Journal of Microelectromechanical Systems, vol. 13, No. 5, IEEE, Available Online at http://web.stevens.edu/ses/documents/fileadmin/documents/pdf/JMEMS_hp_valve.pdf, Oct. 2004, pp. 799-807.

Yarbasi et al., "On the Design of a Continuum Robot with Extendable Balloons", Department of Mechanical Engineering, 2015, 1 page.

You et al., "A Doubly Cross-Linked Nano-Adhesive for the Reliable Sealing of Flexible Microfluidic Devices", Lab Chip., vol. 13, No. 7, Available online at http://www.ncbi.nlm.nih.gov/pubmed/23381132, Apr. 2013, pp. 1266-1272.

* cited by examiner

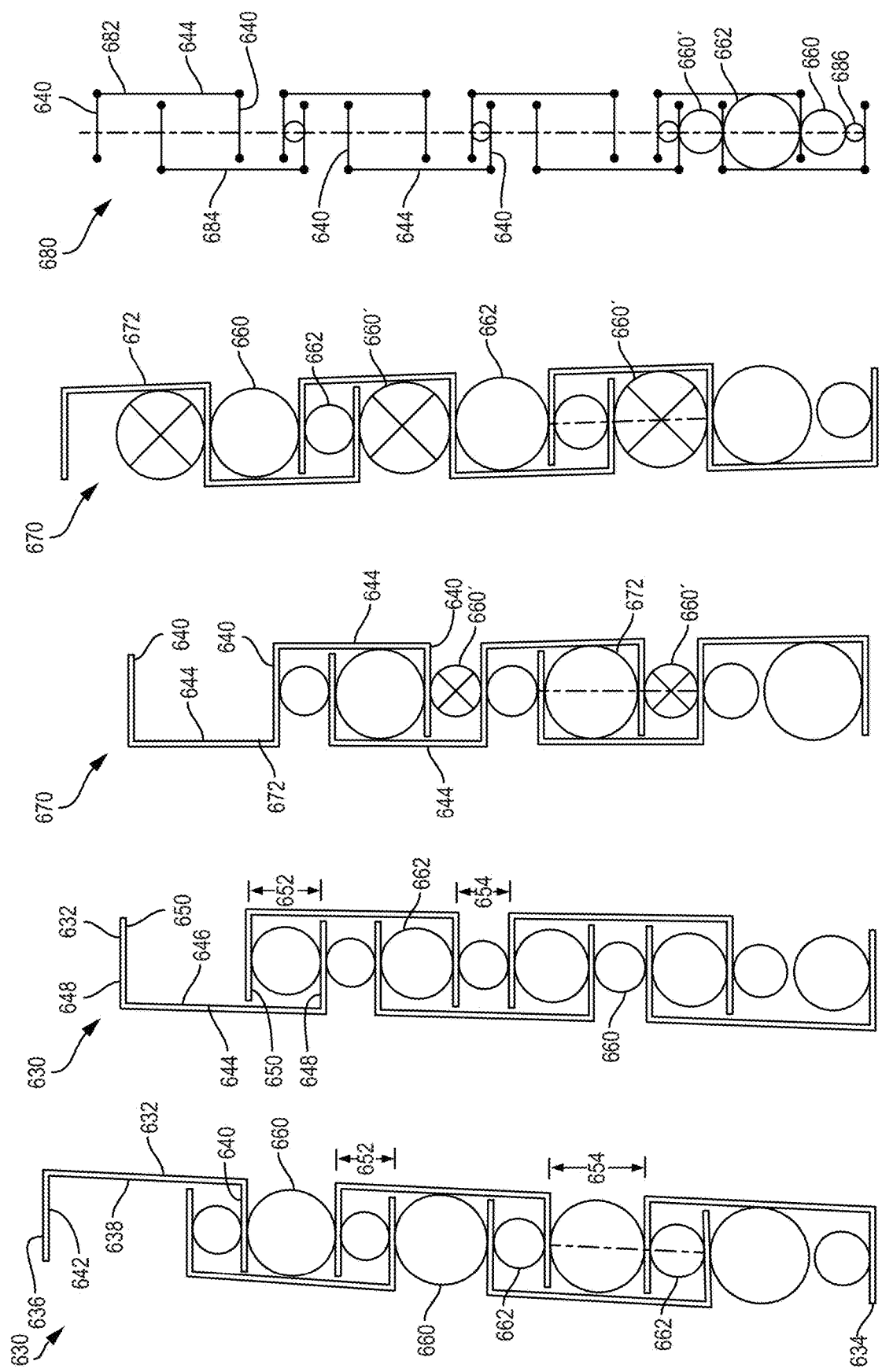

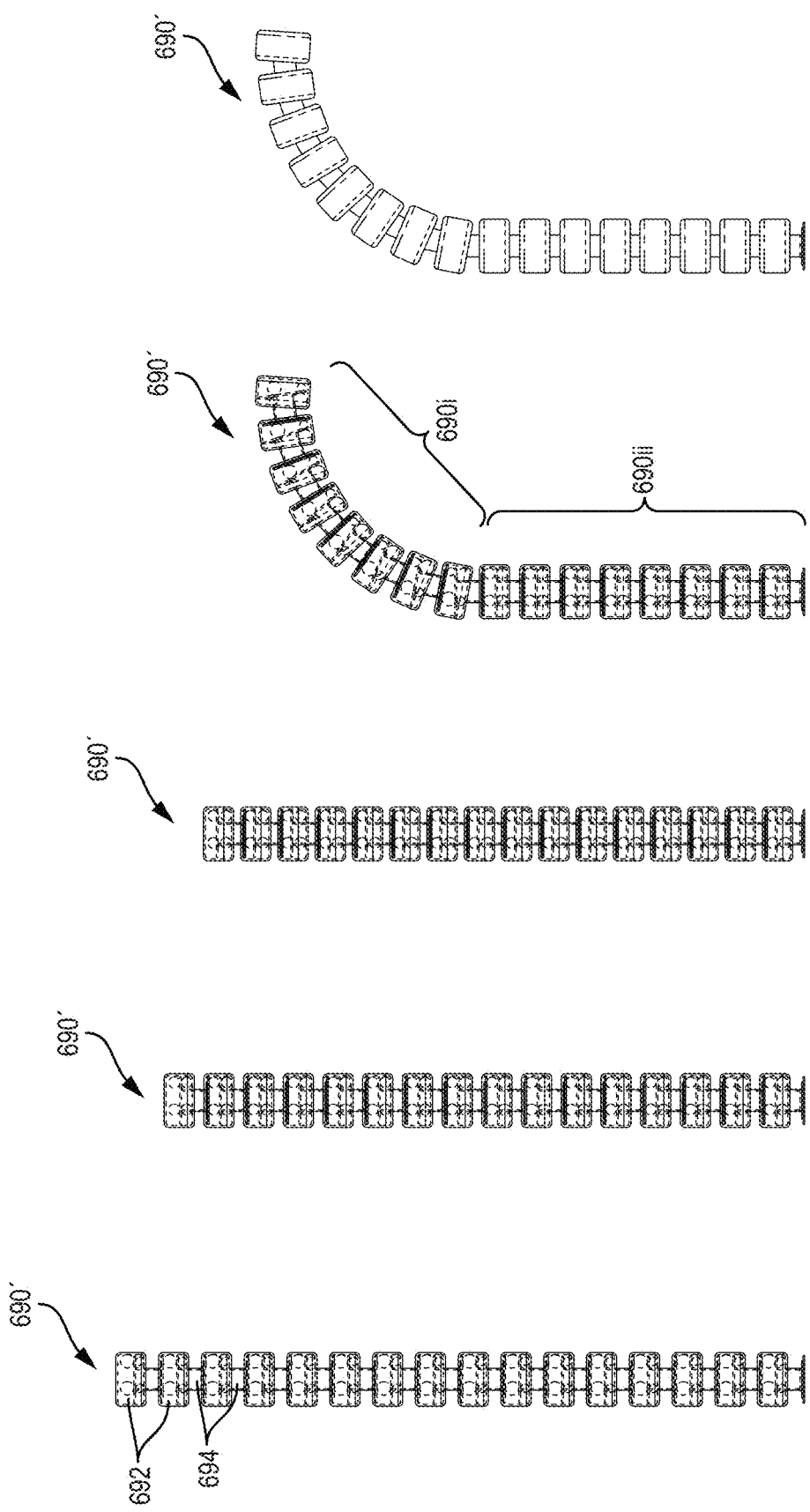

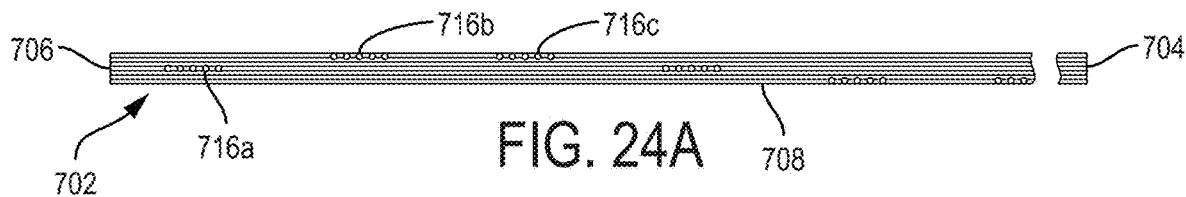
FIG. 24A
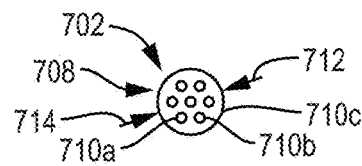
FIG. 24B
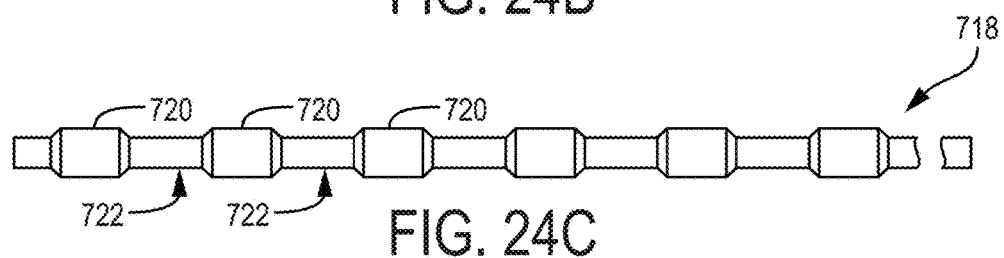
FIG. 24C
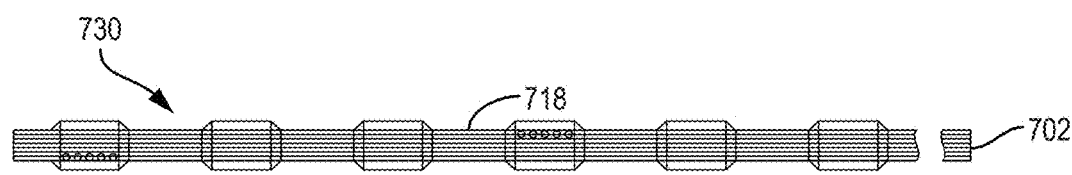
FIG. 24D
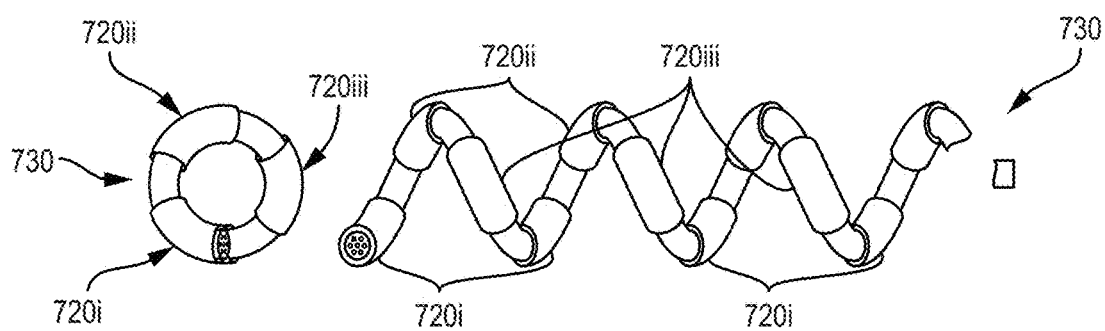
FIG. 24E1　　FIG. 24E
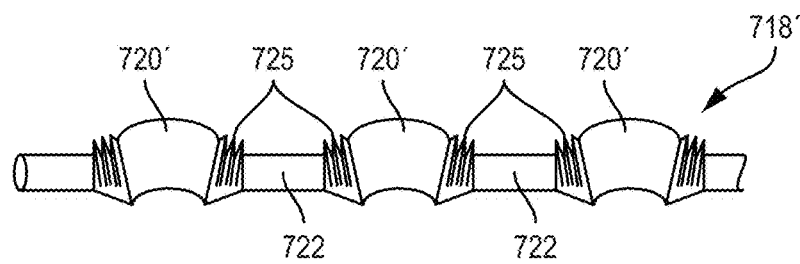
FIG. 24E-2

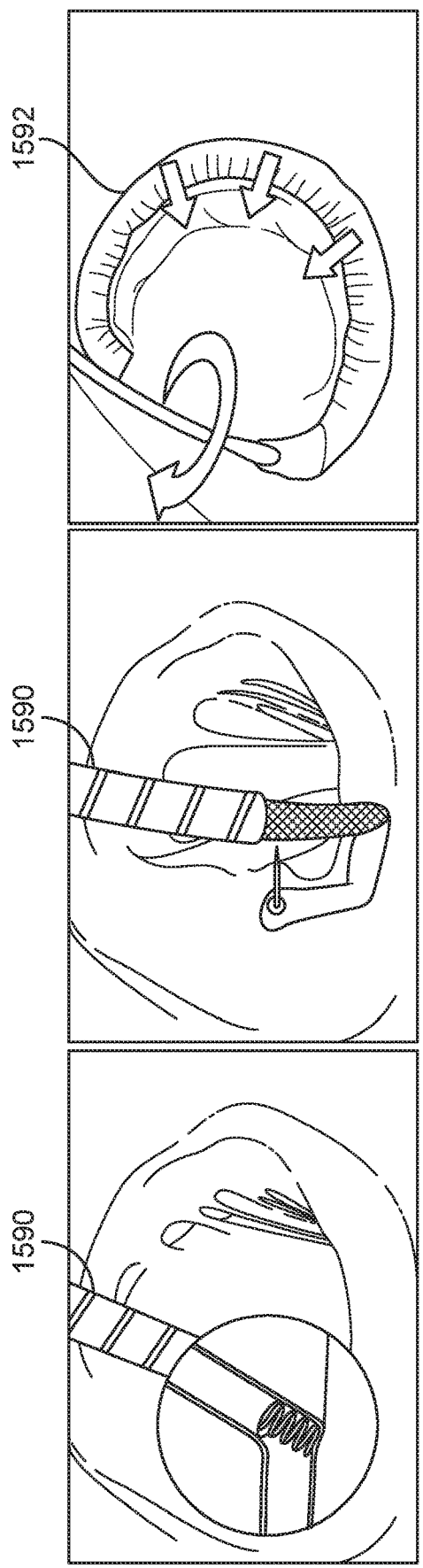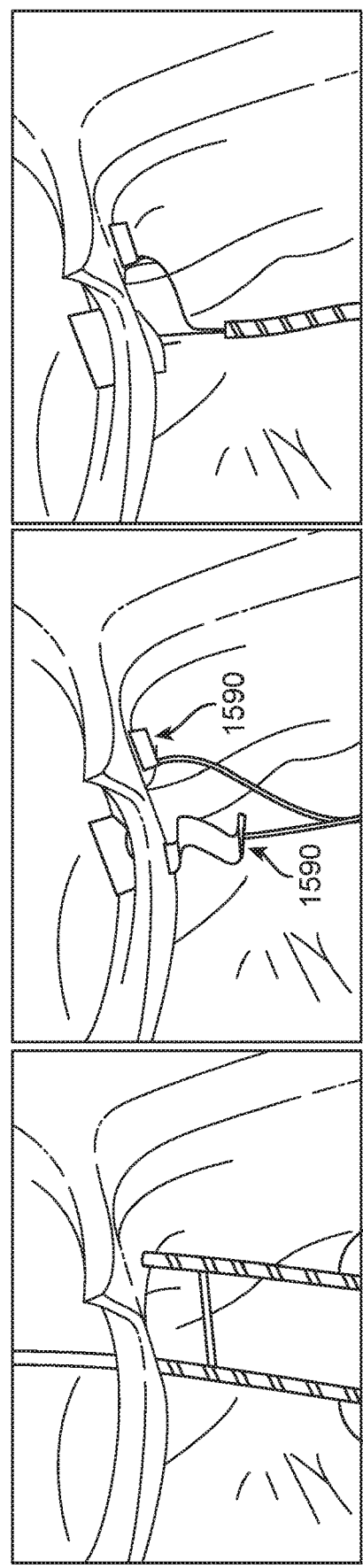

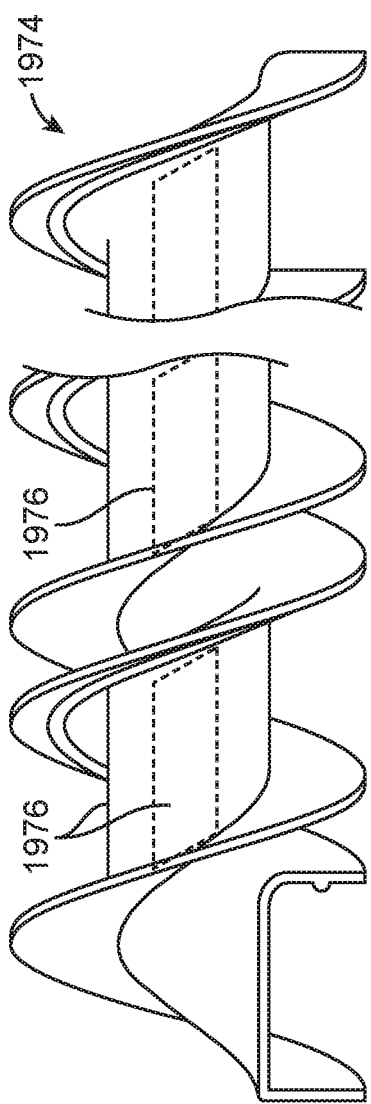
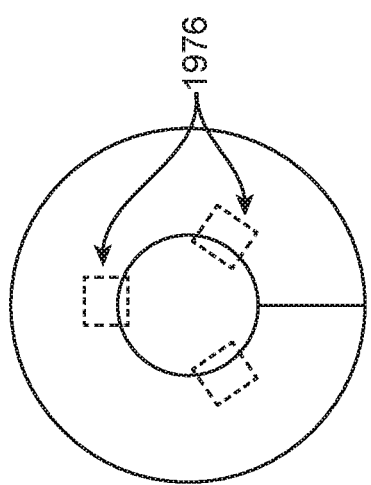
FIG. 37B
FIG. 37A

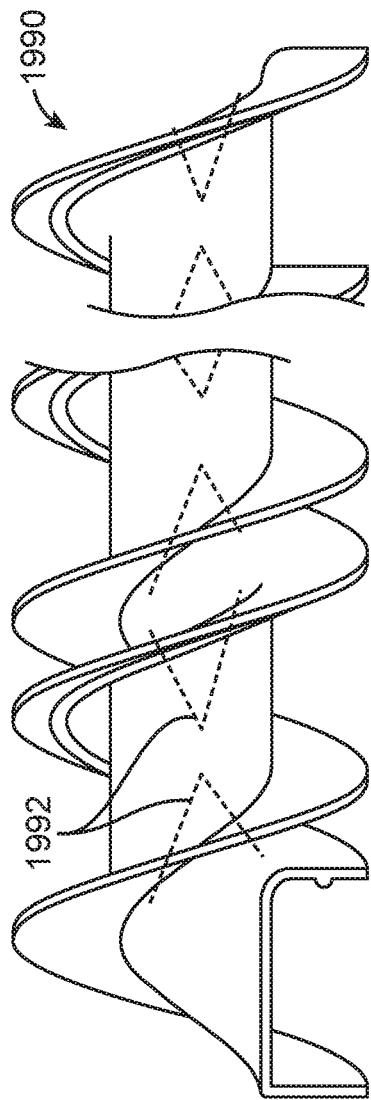
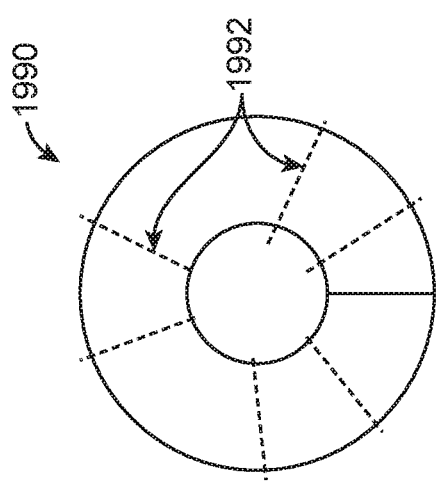
FIG. 38B
FIG. 38A

BASE STATION, CHARGING STATION, AND/OR SERVER FOR ROBOTIC CATHETER SYSTEMS AND OTHER USES, AND IMPROVED ARTICULATED DEVICES AND SYSTEMS

CROSS REFERENCE TO RELATED APPLICATIONS

The subject application claims the benefit of U.S. Provisional Application Ser. Nos. 62/400,988, filed Sep. 28, 2016 entitled "Heart Valve Therapy Delivery Methods, Devices, And Robotic Catheter Systems"; and 62/401,005, filed Sep. 28, 2016 entitled "Base Station Charger And Server For Handheld Robotic Catheter Systems And Other Uses, And Improved Articulated Devices And Systems"; the full disclosures which are incorporated herein by reference in their entirety for all purposes.

The subject matter of the present application is related to that of co-assigned U.S. Provisional Patent App. Nos. 62/139,430 filed Mar. 27, 2015, entitled "Articulation System for Catheters and Other Uses"; 62/175,095 filed Jun. 12, 2015, entitled "Selective Stiffening for Catheters and Other Uses"; 62/248,573 filed Oct. 30, 2015, entitled "Fluid Articulation for Catheters and Other Uses"; 62/263,231 filed Dec. 4, 2015, entitled "Input and Articulation System for Catheters and Other Uses"; and 62/296,409 filed on Feb. 17, 2016, entitled "Local Contraction of Flexible Bodies using Balloon Expansion for Extension-Contraction Catheter Articulation and Other Uses"; the full disclosures which are also incorporated herein by reference in their entirety for all purposes.

The subject matter of the present application is also related to that of co-assigned U.S. patent application Ser. No. 15/080,979, filed Mar. 25, 2016, entitled "Fluid Drive System for Catheter Articulation and Other Uses", and Ser. No. 15/080,949, also filed Mar. 25, 2016, entitled "Fluid-Expandable Body Articulation of Catheters and Other Flexible Structures"; and 62/400,998, filed Sep. 28, 2016 and entitled "Lateral Articulation Anchors For Catheters And Other Uses"; and 62/401,001, filed Sep. 28, 2016 entitled "Arrhythmia Diagnostic And/Or Therapy Delivery Methods, Devices, And Robotic Catheter Systems"; the full disclosures which are also incorporated herein by reference in their entirety for all purposes.

FIELD OF THE INVENTION

In general, the present invention provides structures, systems, and methods for selectively bending or otherwise altering the bend characteristics of catheters and other elongate flexible bodies, the lengths of such bodies, and the like, and also provides improved medical devices, systems, and methods. In exemplary embodiments, the invention provides balloon articulated catheter systems for repairing and/or replacing a valve in a heart of a patient. Embodiments of the invention may be used to reversibly, locally, and/or globally alter the stiffness (such as to stiffen or reduce the stiffness of) elongate flexible bodies used for medical and other applications. The invention may include or be used with articulation structures, systems, and methods for articulation, as well as for controlling and fabricating articulation structures. In exemplary embodiments the invention provides articulated medical systems having a fluid-driven balloon array that can help shape, steer and/or advance a catheter, guidewire, or other elongate flexible structure along a body lumen. Also provided are structures for facilitating access to and/or alignment of medical diagnostic and treatment tools with target tissues, articulation fluid control systems, and medical diagnostic and treatment related methods. Alternative embodiments make use of balloon arrays for articulating (or altering the stiffness of) flexible manipulators and/or end effectors, industrial robots, borescopes, prosthetic fingers, robotic arms, positioning supports or legs, consumer products, or the like.

BACKGROUND OF THE INVENTION

Diagnosing and treating disease often involve accessing internal tissues of the human body. Once the tissues have been accessed, medical technology offers a wide range of diagnostic tools to evaluate tissues and identify lesions or disease states. Similarly, a number of therapeutic tools have been developed that can help surgeons interact with, remodel, deliver drugs to, or remove tissues associated with a disease state so as to improve the health and quality of life of the patient. Unfortunately, gaining access to and aligning tools with the appropriate internal tissues for evaluation or treatment can represent a significant challenge to the physician, can cause serious pain to the patient, and may (at least in the near term) be seriously detrimental to the patient's health.

Open surgery is often the most straightforward approach for gaining access to internal tissues. Open surgery can provide such access by incising and displacing overlying tissues so as to allow the surgeon to manually interact with the target internal tissue structures of the body. This standard approach often makes use of simple, hand-held tools such as scalpels, clamps, sutures, and the like. Open surgery remains, for many conditions, a preferred approach. Although open surgical techniques have been highly successful, they can impose significant trauma to collateral tissues, with much of that trauma being associated with gaining access to the tissues to be treated.

To help avoid the trauma associated with open surgery, a number of minimally invasive surgical access and treatment technologies have been developed. Many minimally invasive techniques involve accessing the vasculature, often through the skin of the thigh, neck, or arm. One or more elongate flexible catheter structures can then be advanced along the network of blood vessel lumens extending throughout the body and its organs. While generally limiting trauma to the patient, catheter-based endoluminal therapies are often reliant on a number of specialized catheter manipulation techniques to safely and accurately gain access to a target region, to position a particular catheter-based tool in alignment with a particular target tissue, and/or to activate or use the tool. In fact, some endoluminal techniques that are relatively simple in concept can be very challenging (or even impossible) in practice (depending on the anatomy of a particular patient and the skill of a particular physician). More specifically, advancing a flexible guidewire and/or catheter through a tortuously branched network of body lumens might be compared to pushing a rope. As the flexible elongate body advances around first one curve and then another, and through a series of branch intersections, the catheter/tissue forces, resilient energy storage (by the tissue and the elongate body), and movement interactions may become more complex and unpredictable, and control over the rotational and axial position of the distal end of a catheter can become more challenging and less precise. Hence, accurately aligning these elongate flexible devices with the desired luminal pathway and target tissues can be a significant challenge.

A variety of mechanisms can be employed to steer or variably alter deflection of a tip of a guidewire or catheter in one or more lateral directions to facilitate endoluminal and other minimally invasive techniques. Pull wires may be the most common catheter tip deflection structures and work well for many catheter systems by, for example, controllably decreasing separation between loops along one side of a helical coil, braid, or cut hypotube near the end of a catheter or wire. It is often desirable to provide positive deflection in opposed directions (generally by including opposed pull wires), and in many cases along two orthogonal lateral axes (so that three or four pull wires are included in some devices). Where additional steering capabilities are desired in a single device, still more pull wires may be included. Complex and specialized catheter systems having dozens of pull wires have been proposed and built, in some cases with each pull wire being articulated by a dedicated motor attached to the proximal end. Alternative articulation systems have also been proposed, including electrically actuated shape memory alloy structures, piezoelectric actuation, phase change actuation, and the like. As the capabilities of steerable systems increase, the range of therapies that can use these technologies should continue to expand.

Unfortunately, as articulation systems for catheters get more complex, it can be more and more challenging to maintain accurate control over these flexible bodies. For example, pull wires that pass through bent flexible catheters often slide around the bends over surfaces within the catheter, with the sliding interaction extending around not only bends intentionally commanded by the user, but also around bends that are imposed by the tissues surrounding the catheter. Hysteresis and friction of a pull-wire system may vary significantly with that sliding interaction and with different overall configurations of the bends, so that the articulation system response may be difficult to predict and control. Furthermore, more complex pull wire systems may add additional challenges. While opposed pull-wires can each be used to bend a catheter in opposite directions from a generally straight configuration, attempts to use both together—while tissues along the segment are applying unknown forces in unknown directions—may lead to widely inconsistent results. Hence, there could be benefits to providing more accurate small and precise motions, to improving the lag time, and/or to providing improved transmission of motion over known catheter pull-wire systems so as to avoid compromising the coordination, as experienced by the surgeon, between the input and output of catheters and other elongate flexible tools.

Along with catheter-based therapies, a number of additional minimally invasive surgical technologies have been developed to help treat internal tissues while avoiding at least some of the trauma associated with open surgery. Among the most impressive of these technologies is robotic surgery. Robotic surgeries often involve inserting one end of an elongate rigid shaft into a patient, and moving the other end with a computer-controlled robotic linkage so that the shaft pivots about a minimally invasive aperture. Surgical tools can be mounted on the distal ends of the shafts so that they move within the body, and the surgeon can remotely position and manipulate these tools by moving input devices with reference to an image captured by a camera from within the same workspace, thereby allowing precisely scaled micro-surgery. Alternative robotic systems have also been proposed for manipulation of the proximal end of flexible catheter bodies from outside the patient so as to position distal treatment tools. These attempts to provide automated catheter control have met with challenges, which may be in-part because of the difficulties in providing accurate control at the distal end of a flexible elongate body using pull-wires extending along bending body lumens. Still further alternative catheter control systems apply large magnetic fields using coils outside the patient's body to direct catheters inside the heart of the patient, and more recent proposals seek to combine magnetic and robotic catheter control techniques. While the potential improvements to control surgical accuracy make all of these efforts alluring, the capital equipment costs and overall burden to the healthcare system of these large, specialized systems is a concern.

In light of the above, it would be beneficial to provide improved articulation systems and devices, methods of articulation, and methods for making articulation structures. Improved techniques for controlling the flexibility of elongate structures (articulated or non-articulated) would also be beneficial. It would be particularly beneficial if these new technologies were suitable to provide therapeutically effective control over movement of a distal end of a flexible guidewire, catheter, or other elongate body extending into a patient body. It would also be beneficial if the movement provided by these new techniques would allow enhanced ease of use; so as to facilitate safe and effective access to target regions within a patient body and help achieve desired alignment of a therapeutic or diagnostic tool with a target tissue. It would also be helpful if these techniques could provide motion capabilities that could be tailored to at least some (and ideally a wide) range of distinct devices.

In light of the above, it would also be beneficial to provide new and improved devices, system, and methods for driving elongate flexible structures. It would also be beneficial to provide improved medical devices, systems, and methods, particularly those that involve the use of elongate flexible bodies such as catheters, guidewires, and other flexible minimally invasive surgical tools. It would be desirable to take advantage of recent advances in microfluidic technologies and fabrication techniques to provide fluid drive systems having a relatively large number of fluid channels that could be used to control catheters and other elongate flexible structures within a patient, or that could otherwise be used to accurately control flow to and/or within a multi-lumenal shaft, ideally without having to resort to large, expensive systems having large numbers of motors or the like.

In light of the above, it would further be beneficial to provide new and improved articulation devices, system, and methods for use with elongate flexible structures. It would also be beneficial to provide improved medical devices, systems, and methods, particularly those that involve the use of elongate flexible bodies such as catheters, guidewires, and other flexible minimally invasive surgical tools. It would be desirable if these improved technologies could offer improved controllability over the resting or nominal shape of a skeleton of a flexible body, and still allow the overall body to bend (safely and predictably) against soft tissues, ideally without requiring the use of very expensive components, large numbers of parts, and/or exotic materials.

BRIEF SUMMARY OF THE INVENTION

The present invention generally provides articulation devices, systems, methods for articulation, along with methods for fabricating articulation structures. The articulations structures described herein will often include simple balloon arrays, with inflation of the balloons interacting with elongate skeletal support structures so as to locally alter articulation of the skeleton. The balloons can be supported by a substrate of the array, with the substrate having channels that can direct inflation fluid to a subset of the balloons. The articulation array structure may be formed using extrusion, planar 3-D printing, and/or laser micromachining techniques. The skeleton may comprise interlocking helical channels, a simple helical coil, or a printed tubular structure, and the array can be used to locally deflect or elongate an axis of the frame under control of a processor. Liquid inflation fluid may be directed from an inflation fluid canister so as to pressurize the balloons, and may vaporize within a plenum or the channels or balloons of the articulation system, with the inflation system preferably including valves controlled by the processor. A flexible vacuum chamber surrounding the balloons may ensure fluid integrity. The articulation structures can be employed in minimally invasive medical catheter systems, and also for industrial robotics, for supporting image capture devices, for entertainment and consumer products, and the like. The invention also provides new medical devices, systems, and methods for diagnosing and/or treating a valve of a heart. The invention may be used to align a diagnostic or treatment tool with a mitral or other valve. As the articulation balloons can generate articulation forces at the site of articulation, the movement of the articulated catheter within the beating heart may be better controlled and/or provide greater dexterity than movements induced by transmitting articulation forces proximally along a catheter body that winds through a tortuous vascular pathway.

In a first aspect, the invention provides a catheter system comprising an elongate catheter body having a proximal end and a distal end and defining an axis therebetween. The catheter body has an articulated portion adjacent the distal end. A proximal housing can be coupleable with the proximal end of the catheter body, and the proximal housing will often be sized for movement by a hand of a user. The proximal housing may support an articulation drive system configured to effect articulation of the articulated portion, and a processor coupled to the drive system so as to transmit drive signals thereto in response to commands input by the user. The housing may also support a battery coupled to the processor and to a charge receiving coupler. The catheter system may also include a base station having a receptacle configured to receive the housing. The base station may have a charge providing coupler positioned so as to couple with the charge receiving coupler when the housing is in the receptacle.

Optionally, the charge receiving coupler may comprise an inductive charge receiving coupler, and the charge providing coupler may similarly comprise an inductive charge providing coupler. The base station may further comprise a server coupleable with a network. The processor of the proximal housing may be coupleable with the server so as to transmit data between the network and the processor. The server of the base station may include or be coupled with a first wireless communication module, and the proximal housing may contain a second wireless communication module configured to communication with the first wireless communication module so as to transmit the data.

In general, the catheter may have an ID tag embodying machine-readable catheter identity data. The processor in the housing may transmit ID data, in response to the catheter identity data of the tag, to the server when the server is coupled with the processor. The server may obtain approval data from the network, and the processor can inhibit use of the catheter absent the approval data.

A preferred option is to further include a sterile barrier, typically between the base station and the proximal housing, with the sterile barrier often configured for maintaining sterile separation between the base station and the proximal housing when the housing is in the receptacle.

As a general feature, the articulated portion may include an array of articulation balloons.

In another aspect, the invention provides an articulated system comprising an elongate helical frame having a proximal end and a distal end with an axis therebetween. The helical frame includes a first axial region having a first plurality of loops and a second axial region having a second plurality of loops. A plurality of actuators is coupled to the helical frame so as to alter associated separations between adjacent loops. The first loops having a first helical wind orientation such that when the actuators increase the separations between the first loops, the frame along the first region twists about the axis in a first twist orientation. The second loops have a second helical wind orientation opposite the first wind orientation such that when the actuators increase the separations between the second loops, the frame along the second region twists about the axis in a second twist orientation opposite the first twist orientation.

In another aspect, the invention provides a manifold for articulating an elongate body. The body has an array of articulation balloons, and the manifold comprises a liquid inflation fluid source and a gas inflation fluid source. A fluid supply system can be configured to couple the fluid sources to the body so as to selectably direct liquid inflation fluid from the liquid fluid source to at least some of the balloons, and so as to direct gas inflation fluid from the gas source to at least some of the balloons.

Optionally, the fluid supply system may comprise a processor, and at least one fluid channel of the system may contain both gas inflation fluid and liquid inflation fluid. The processor may be configured to alter relative amounts of the gas inflation fluid and liquid inflation fluid in the channel in response to a command to change a compliance of a subset of the balloons in communication with the channel. In some embodiments, the system may direct only gas or liquid to some or all of the inflation channels included in a multi-lumen articulatable body.

In another aspect, the invention provides a manifold for articulating an elongate body, the body having an array of articulation balloons. The manifold comprises (or be configured to receive) a canister having a first inflation fluid, and a plenum containing a deformable diaphragm with a first side and a second side. The manifold may be configured so that, in use, a second inflation fluid will be disposed along the second side. A pressure control valve may couple the canister to the plenum along the first side of the diaphragm so as to control a pressure of the first and second inflation fluids in the plenum. A plurality of inflation fluid control valves can be configured to couple the balloons to the plenum along the second side of the diaphragm so as to selective inflate the balloons with the second inflation fluid.

Optionally, the body comprises a catheter body, and the first inflation fluid comprises a gas (such as N2O) and the second inflation fluid comprises a liquid (such as saline). In some embodiments, the manifold may receive a coupler of the catheter along a receptacle surface of a manifold plate. The inflation control valves may be disposed along the edge of the plate, and a surface opposite the receptacle surface may be recessed relative the edge of the plate so as to decrease a length of pressure sensing channels extending between the recessed and fluid inflation channels of the inflation fluid supply system.

In general, a first plurality of the actuators can be coupled with the first plurality of loops so as to alter the associated separations and a length of the fist region. A second plurality of the actuators can be coupled with the second plurality of loops so as to alter the associated separations and a length of the second region.

Optionally, the first actuators may be coupled together to be actuated as a first subset of the actuators, and the second actuators may be coupled together to be actuated as a second subset of the actuators. The first actuators and the first region of the frame may be included in a first axial segment of the articulated system, and the second actuators and the second region of the frame may be included in a second axial segment of the articulated system. The first and second segments may be independently articulatable by actuating the first and second subsets so as to provide a desired combined twist in response to a twist command at a total length of the first and second regions.

Alternatively, the first actuators can be coupled together with the second actuators to be actuated as a first subset of the actuators. The first actuators and the first region of the frame and the second actuators and the second region of the frame may be included together in a first axial segment of the articulated system. The first segment can be articulatable by actuating the first and second subsets together so that the twist of the first region counteracts the twist of the second region during changes in length of the segment.

A variety of arrangements may be used to take advantage of the rotational/axial coupling of these helical frame structures. For example, a first articulated segment can be offset from the first and second regions, the first articulated segment being laterally articulatable, independently of the first and second regions, in a first lateral orientation and in a second lateral orientation. The first segment may also be laterally articulatable in a second lateral orientation transverse to the first lateral orientation. Optionally, a second axial segment can be offset from the first segment and the first and second regions. The second segment may be articulatable in third and fourth transverse lateral orientations, allowing the system to have 6 degrees of freedom including twisting about the axis.

Preferably, the actuators comprise articulation balloons. The helical frame and actuators may be included in a flexible catheter body configured to be introduced into a patient body.

In many embodiments, the elongate body comprises a catheter body. A number of features may, independently or in combination, enhance the safe and accurate use of such catheters. The catheter body can include a skeleton having pairs of interface regions with offsets therebetween, the balloons typically being disposed between the interface regions of the pairs. Preferably, the skeleton comprises a helical member, the balloons being supported by the member and the offsets between the interface pairs extending primarily axially and angling circumferentially, often in correlation with a pitch of the helical member. Advantageously, a sheath can be sealed around the balloons so as to form a pressure chamber (ideally in the form of a vacuum chamber). The chamber can be operatively coupled to a fluid source so as to inhibit transmission of the liquid from the source in response to deterioration of a vacuum within the chamber. Typically, the balloons are included in an array of balloons and are mounted to a substrate. The substrate can have channels providing fluid communication between the fluid source and the balloons. The substrate can optionally comprise a multi-lumen shaft, with some substrate shafts being helical, and others extending coaxially with the frame.

As one of a number of features (that are not tied to any specific embodiment), the fluid source will often include a canister, the exemplary canister being a single-use canister having a frangible seal, preferably containing less than 10 oz. of the liquid (and often less than 5 oz., with many containing less than 1 oz). The liquid often comprises a relatively benign cryogen such as N2O. The liquid can be disposed in the canister at a canister pressure, with the canister pressure generally being higher than a fully inflated balloon pressure so that no pumps or the like are needed to transfer the liquid from the canister to the balloons. The liquid may, when at body temperature, vaporize into the inflation gas, with the vaporization typically occurring at a vaporization pressure that is less than the canister pressure and more than the fully inflated balloon pressure. Note, however, that the balloon pressure may approach or even exceed the canister pressure, for example, when the valves are closed and the articulated structure is subjected to sufficient environmental pressure to compress a fully inflated balloon. While the enthalpy of vaporization may result in localized cooling along the system, in many embodiments no therapeutic cooling of tissues or other structures may be provided, and much or all of the liquid may be vaporized prior to the inflation fluid reaching the balloon(s). Other embodiments may make use of a portion of the liquid from the source for cryogenic cooling (typically near a distal end of the articulated structure), but will often provide a separate cryogenic cooling channel along the articulated body for such cooling so as to improve articulation response, though such cooling may make use of a separate cooling fluid supply canister than that of the articulation system, with that canister typically containing a larger quantity of the same (or a different) cryogen.

Independent of the specific embodiment, one or more of a number of different features can be provided to enhance functionality. The fluid supply often maintains the liquid with a pressure of over 40 atm., with the fluid supply optionally having a heater to keep the canister at a relatively constant temperature and pressure during use of the system. A first valve can be disposed between the fluid source and the first balloon, and a second valve can be disposed between the fluid source and the second balloon. The first and second valves can be configured to independently transmit minimum increments of 50 nl or less of the liquid, with the flowing cooling fluid often remaining liquid till it traverses a throat of the valve. A third valve can be disposed between the first balloon and a surrounding atmosphere, and a fourth valve can be disposed between the second balloon and the surrounding atmosphere. The third and fourth valves can be configured to independently transmit at least 0.1 scc/s of the gas. Including all four such valves in the system may facilitate independent pressure control over two balloons (or two subsets of balloons, with each subset being inflated using a common inflation lumen), with additional inflation and deflation valves for additional balloons (or subsets of balloons). Optionally, the minimum liquid increment for inflation may be 25 nl (or even 15 nl) or less, while the minimum gas flow for deflation may be 0.5 scc/s (or even 1 scc/s) or more. The system may employ multi-way valves that can be used to control both inflation fluid flowing into the balloon and deflation fluid exhausted from the balloon, with accuracy of control (despite the different inflation and deflation flows) being maintained by differing valve throats, by differing orifices or other flow restricting devices adjacent the valve(s), by proportional flow control of sufficient range, and/or by a sufficiently rapid valve response rate. A pressure-controlled plenum can be disposed between the fluid source and the first and second balloon, or the liquid may otherwise vaporize to the gas before the valve so that none of the liquid transits a valves between the plenum and the balloons.

Optionally, the elongate body comprises a catheter body, and the distal end is configured for insertion into a patient. The chamber can flex laterally with the catheter body, and a pressure sensing lumen may extend proximally from the chamber toward the proximal end. The balloons can be supported by and/or mounted on a substrate, and the substrate can contain a plurality of lumens for inflating the balloons along with the pressure sensing lumen. An exemplary substrate comprises a multi-lumen shaft, the balloons having balloon walls extending around the shaft.

Any of a number of features can be included to enhance the functionality of the chamber. Optionally, a vacuum source may be in fluid communication with the chamber so as to reduce a pressure of the chamber, so that the chamber comprises a vacuum chamber. The elongate body will preferably remain flexible while the chamber is under a vacuum, with the vacuum typically being from a few inches of mercury to half an atmosphere or more. A fluid control system having a sensor can be coupled with the chamber, and a shut-off valve can be disposed between an inflation fluid source and the balloons. The shut-off valve can inhibit inflation fluid flow to the balloons in response to signals from the sensor indicating that the vacuum is degrading, as such signals may be associated with a leak of the inflation fluid, a leak of the outer sheath, a leak of an inner sheath to which the outer sheath is sealed, a leak of a proximal and/or distal seal of the chamber, or the like. Hence, the use of the chamber can significantly enhance safety and serve as a fault-detection system that identifies and prevents undesirable or dangerous leakage, thereby facilitating (for example) use of gas as an inflation fluid for catheters or the like.

Advantageously, the controlled stiffness provided by a balloon array can be varied along a length of a catheter or other flexible structure, can be varied circumferentially (so as to provide differing stiffness in differing lateral bending orientations), and/or may be modulated so as to provide any of a plurality of different local or global stiffnesses, and/or to provide a desired stiffness anywhere within a continuous range. For example, the skeleton may have a first axial segment and a second axial segment, and the pairs of offsets may be distributed axially along the first and second axial segments. Selectively increasing or decreasing inflation of a first subset of the balloons disposed along the first segment may be used to inhibit or facilitate changes to the offsets along that first segment so as to selectively increase or decrease a lateral bending stiffness of the first segment (respectively). The second segment stiffness (and/or a stiffness of a third, fourth, or other segments) may be independently altered. As another example, the skeleton may have a first lateral bending orientation and a second lateral bending orientation, and the pairs of offsets may be distributed circumferentially along the first and second lateral bending orientations. Selectively increasing or decreasing inflation pressure of a first subset of the balloons disposed along the first lateral bending orientation can inhibit or facilitate changes to the offsets along the first lateral bending orientation so as to selectively increase or decrease a lateral bending stiffness in the first lateral bending orientation, respectively, while altering inflation of second, third, or optionally fourth subsets of offsets may similarly alter lateral bending stiffness along second, third, or fourth lateral orientations (with opposed orientations often being coupled).

A number of different approaches may be employed to provide control over stiffness. The skeleton and array may be configured so that decreasing an inflation pressure of a first subset of balloons increases a lateral bending stiffness of the skeleton. For example, when the skeleton is in the form of a helical coil that is biased to a straight configuration having direct loop/loop engagement, the first subset of balloons may have balloon walls positioned between apposed interface regions of adjacent loops, so that inflation of the balloons may locally weaken a column strength of the skeleton. More specifically, the loops can be biased to compress and deflate the balloons, so that axial forces are transmitted between loops by solid materials of the loops and balloon walls when the balloons are fully deflated, thereby providing a first lateral stiffness. In contrast, axial forces may be transmitted by fluid pressure within the balloons when the balloons are partially inflated so as to provide a second lateral stiffness that is lower than the first lateral stiffness.

Alternatively, increasing an inflation pressure of a first subset of balloons may increase a lateral bending stiffness of the skeleton. For example, the interface regions of the pairs may be oriented radially, and the first subset of balloons may span the pairs of interface surfaces and may radially engage the interface surfaces when the first subset of balloons are inflated. The fluid pressure of the inflated balloons can thereby urge the inflated balloons against the interface regions so as to inhibit changes in the associated offsets. As another example, the first subset of balloons may comprise a pair of opposed balloons disposed in a channel of the skeleton with a flange of the skeleton between the opposed balloons. The offsets may comprise separations between apposed surfaces of the flange and the channel, and increasing inflation pressure of the apposed balloons may increase a stiffness of the position of the flange within the channel, and hence the overall lateral bending stiffness of the skeleton. Advantageously, the flange and the channel may comprise helical structures engaged by a plurality of opposed pairs of balloons, and the offsets may extend primarily axially, and may angle circumferentially with the pitch of the helical structures.

A number of features may be provided to enhance functionality of the catheters provided herein, many of which are identified in the preceding and following paragraphs. As another example, an unarticulated flexible proximal body portion of the catheter may be disposed between the proximal end and the balloon array. Fluid channels can span the proximal body portion, but may not provide control over a shape (and optionally, may not even allow control over stiffness) of that portion. This can help keep the complexity and size of the system down, with any articulation functionality being concentrated along a distal portion and the proximal portion being configured to flex to follow a body lumen or the like.

In a related aspect, the invention provides a method comprising selectively inflating a first subset of balloons, the balloons included in an array of balloons supported by a helical skeleton. The array is distributed axially and circumferentially about the skeleton. The inflation of the first subset inducing a first change in the shape and/or stiffness of the helical skeleton. A second subset of the balloons is selectively inflated, the inflation of the second subset inducing a second change in the shape and/or stiffness of the helical skeleton. The second change in shape and/or stiffness is offset axially and/or circumferentially from the first change.

Having processor-controlled valves is an optional feature of the systems and devices described herein, and any of a range of refinements may be included to further enhance capabilities of the system. Rather than having to resort to heavy and complex motors and pumps, by using a simple fluid source (such as a pre-pressurized canister or the like) and processor controlled valves (optionally including at least 8, 16, 32, or even 64 valves), the system can control shape and/or stiffness of an elongate flexible system with large number of degrees of freedom. Where a processor is provided, a plurality of pressure sensors may couple some of the channels with the processor, the processor configured to actuate the valves so as to control pressure within the subsets of balloons. With or without processor controlled valves, another optional feature is that the articulation devices may have balloon arrays with at least 9, 18, 36, 72, or even 108 balloons. Where the articulated catheter has an outer cross-sectional diameter, the balloon array may have an axial density of at least 3, 4, 6, 8, or even 9 balloons per diameter of axial length to provide, for example, a desirable bend capability.

The structures described herein will often include simple balloon arrays, with inflation of the balloons interacting with elongate skeletal support structures so as to locally alter articulation of the skeleton. The balloons can be mounted to a substrate of the array, with the substrate having channels that can direct inflation fluid to a subset of the balloons. The skeleton may comprise a simple helical coil, and the array can be used to locally deflect or elongate an axis of the coil under control of a processor. Inflation fluid may be directed to the balloons from an inflation fluid reservoir of an inflation system, with the inflation system preferably including valves controlled by the processor. Such elongate flexible articulation structures can be employed in minimally invasive medical catheter systems, and also for industrial robotics, for supporting imaging systems, for entertainment and consumer products, and the like. As the articulation array structure may be formed using simple planar 3-D printing, extrusion, and/or micromachining techniques, the costs for producing structures having large numbers of kinematic degrees of freedom may be much, much lower than those associated with known powered articulation techniques.

The devices, systems, and methods described herein can selectively, locally, and/or reversibly alter the bend characteristics of an elongate body. Bending of an elongate body is addressed in detail herein, and some of the technologies described herein are also suitable for altering the stiffness along an elongate catheter body, with the stiffness often being altered by inflation of one or more balloons. A number of different stiffening approaches may be employed. Optionally, inflation of a balloon can induce engagement between the balloon and the loops of a helical, cut-tube, braided, or other elongate flexible skeleton, so that the balloon may act as a brake or latch to inhibit flexing. The balloon will often be eccentrically mounted relative to the skeleton, and may be included in a balloon array. Selective inflation of a subset of the balloon array can selectively and locally increase axial stiffness of the overall body. In other embodiments, modulating a balloon inflation pressure can allow the balloon to variably counteract a compressive force of a helical coil or other biasing structure, effectively modulating the stiffness of an assembly locally adjacent the balloon. In still other embodiments, independently modulating pressure of two opposed balloons can be used to both impose a bend or elongation and to modulate a stiffness in at least one orientation. Hence, stiffening and bending or elongation balloons can be combined, using either separate balloon arrays or a multifunctional array having differing types of balloons.

The balloons can be configured so that inflation of the balloons will, in use, alter a bending state of the articulatable body. The articulatable body may include six or more, nine or more, or even 12 or more balloons, optionally having multiple segments with 12 or more balloons each, and typically comprises a catheter but may alternatively comprise an industrial continuum robotic structure, a consumer or entertainment device, or the like. Optionally, a first subset of the balloons is distributed along a first loop and a second subset of the balloons is distributed along a second loop; a plurality of additional subsets may be distributed along other loops. In those or other embodiments, a third subset of the balloons can be offset from the axis and aligned along a first lateral bending orientation, and a fourth subset of the balloons can be offset from the axis and aligned along a second lateral bending orientation offset from the axis and from the first lateral orientation. The ports associated with the third subset of balloons may be in fluid communication with a first lumen of the shaft, and the ports associated with the fourth subset of balloons may be in fluid communication with a second lumen of the shaft. The third and fourth subsets will often include balloons of the first, second, and other subsets, and yet another subset of the balloons can be offset from the axis and aligned along a third lateral orientation offset from the first and second lateral orientations.

In most embodiments, the balloons define an M×N array, with M lateral subsets of the balloons being distributed circumferentially about the axis, each of the M lateral subsets including N balloons aligned along an associated lateral bending orientation. For example, M may be three or four, so that there are three or four lateral subsets of balloons distributed about the axis of the articulatable body (the centers of the subsets optionally being separated by 120 or 90 degrees). Note that there may be some coupling between an axial elongation state of an articulated segment and the lateral bending orientations, for example, with the helical coil unwinding slightly when the segment increases in length, so that a line connecting the centerlines of the N balloons may curve or spiral slightly along the axis in at least some configurations of the segment (rather than the N balloons always being exactly in alignment parallel to the axis). The ports associated with the balloons of each of the M lateral subsets may provide fluid communication between N balloons and an associated lumen, so that each of the lateral orientations is associated with (often being inflated and/or deflated via) a particular lumen of the shaft. The array will often comprise a first array extending along a first segment of the articulatable body. The first segment can be configured to be driven in two, three, or more degrees of freedom by fluid transmitted along the lumens associated with the M lateral subsets of the first array. A second segment of the articulatable body can also be provided, typically axially offset from the first segment. The second segment can have a second array and can be configured to be driven in a plurality of degrees of freedom by fluid transmitted along lumens of the shaft associated with the second array, which will often be separate from those of the first array. Articulatable bodies may have from 1 to 5 independently articulatable segments or more, with each segment preferably providing from one to three degrees of freedom, each segment often being configured to have consistent bend characteristics and/or elongation between its proximal end and distal end, but the different segments being driven to different bend and/or elongation states.

In many embodiments, the balloon walls comprise a non-compliant balloon wall material, although semi-compliant wall materials may be used, with the balloons often being small enough and having sufficient thickness to allow pressures beyond those used in larger balloons, often including pressures above 20 atm., 30 atm, or even 40 atm. Preferably, at least some of the balloons comprise a continuous balloon wall tube sealingly affixed around the shaft at a plurality of seals. The seals can be separated along the shaft axis so that the tube defines the balloon walls of the plurality of balloons. The balloon wall tube can have a plurality of balloon cross-section regions interleaved with a plurality of seal cross-section regions, the balloon cross-section regions being larger than the seal cross-section regions to facilitate fluid expansion of the balloons away from the shaft. Optionally, a reinforcement band can be disposed over the balloon adjacent the seal so as to inhibit separation of the balloon from the shaft associated with inflation of the balloon. Suitable reinforcement bands may comprise a metal structure similar to a marker band that is swaged over the balloon tube and shaft along the seal, a fiber that is wound on, or the like. Typically, an elongate structural skeleton will support the multi-lumen shaft, the skeleton having pairs of interface regions separated by axial offsets, the offsets changing with flexing of the skeleton, wherein the balloons are disposed between the regions of the pairs.

Optionally, the substrates of the system provided herein may have first and second opposed major surfaces and a plurality of layers extending along the major surfaces. The channel system can be sealed by bonding layers of the substrate together. The substrate can be curved in a cylindrical shape, for example, by rolling a substrate/balloon assembly after it has been fabricated in a planar configuration. A plurality of valves can be disposed along the channels so as to provide selective fluid communication between the proximal end and the balloons. Optionally, the balloons can have balloon walls that are integral with a first layer of the substrate, such as by blowing at least a portion of a shape of the balloon from the layer material.

Alternatively, the substrate may comprise a helical multi-lumen shaft. The balloon array optionally comprises an M×N array of balloons supported by the substrate, with M being three or four such that 3 or four subsets of balloons are distributed circumferentially about the axis. Each of the M subsets can aligned along an associated lateral orientation offset from the axis. N may comprise 2, such that each of the M subsets includes two or more axially separated balloons.

As a general approach, the shaft axis can be straight during the sealing of the shaft within the lumen of the balloon tube. Hence, the shaft may be bent with the balloon tube to form a helical shaft. Alternatively, the shaft may be slid into the lumen of the balloon tube after bending the shaft in some embodiments.

The loops of the skeletons or structural frames described herein can have proximal interface regions and distal interface regions. The balloons may comprise expandable bodies, and the balloons that are between loops may be disposed between a distal interface of the first associated loop and a proximal interface of the second associated loop, the proximal and distal interfaces defining pairs of interfaces and having offsets therebetween. The balloons may optionally be mounted over a third loop of the coil between the first and second loops, or on an additional helical structure having loops between the loops of the helical coil. The helical coil may be included in a skeleton of the articulation system.

The substrate may comprise a flexible multi-lumen shaft or tubular body, optionally including an extruded polymer multi-lumen tube with the channels being defined by the extruded lumens together with micromachined radial ports; the multi-lumen tubular body ideally bending to follow a helical curve. The skeleton may be integrated into such a multi-lumen helical body, disposed within such a multi-lumen helical body, or interleaved with such a multi-lumen helical body. The actuation array may also include a plurality of fluid-expandable bodies distributed across and/or along the substrate. The expandable bodies can be coupled with associated pairs of the interfaces, and the channels can provide fluid communication between the expandable bodies and the fluid supply system so as to facilitate selective inflation of a subset of the expandable bodies. Advantageously, the expandable bodies can be operatively coupled to the offsets so that the selective inflation alters articulation of the skeleton adjacent the subset.

The skeleton may comprise a tubular series of loops, such as when the skeleton is formed from a helical coil, a braid, a hypotube or other medical-grade tubular material having an axial series of lateral incisions or openings so as to provide more lateral flexibility than a continuous tube would have, or the like. Each pair of interfaces may comprise, for example, a first associated surface region of a first associated loop and a second associated surface region of a second associated loop adjacent the first loop, so that inflation of the expandable bodies can alter flexing of the skeleton between the loops. Note that expandable bodies that are coupled to a pair of interfaces may optionally be coupled to only the pair of interfaces (so that inflation of that structure does not largely alter flexing of the skeleton between other loops), but that in other embodiments the expandable body may be coupled with not only the pair of loops but with one or more additional loops so that flexing of the skeleton may be altered over an axial portion extending beyond the pair. As an example, an elongate balloon may extend axially along an inner or outer surface of several loops, so that when the balloon is inflated bending of the coil axis along those loops is inhibited.

Where at least some of the expandable bodies or balloons are coupled with pairs of interfaces, the first interfaces of the pairs may optionally be distally oriented and the second interfaces of the pairs may be proximally oriented, with the precise orientation of the interfaces optionally angling somewhat per a pitch of a helical frame structure. The relevant expandable bodies can be disposed axially between the first and second interfaces. Expansion of each of these expandable bodies may urge the associated loops of such pairs apart, often so that the skeleton adjacent the associated first and second loops bends laterally away from the expanded balloon. A lateral orientation of the bend(s) relative to the skeletal axis may be associated with the location of the expandable bodies relative to that axis. A quantity or angle, an axial location, and/or a radius of the articulation or bend imposed by any such inflation may be associated with characteristics of the expandable body or bodies (and the associated changes in offset they impose on the skeleton due to inflation), with characteristics of the skeleton, with location(s) of the expandable body or bodies that are expanded, and/or with a number and density of the bodies expanded. More generally, bend characteristics may be selected by appropriate selection of the subset of expandable bodies, as well as by the characteristics of the structural components of the system.

At least some expandable bodies or balloons of the array (or of another separate articulation array) may be mounted to the skeleton or otherwise configured such that they do not force apart adjacent loops to impose bends on the axis of the skeleton. In fact, some embodiments may have no fluid-expandable structure that, upon expansion or deflation but without an external environmental force, induces bending of the skeleton axis at all. As an optional feature, one or more of the expandable bodies or balloons of the actuation arrays described herein may optionally be used to locally and reversibly alter strength or stiffness of the skeleton, optionally weakening the skeleton against bending in a lateral orientation and/or at a desired axial location. In one particular example, where the skeleton comprises a resilient helical coil in which a pair of adjacent coils are resiliently urged against each other by the material of the coil, a balloon (or set of balloons) disposed axially between one pair of loops of the coil (or a set of loops) may be inflated to a pressure which is insufficient to overcome the compressive force of the coil, but which will facilitate bending of the coil under environmental forces at the inflated pair (or pairs). More generally, inflation of a subset of balloons may locally weaken the coil so as to promote bending under environmental forces at a first location, and changing the subset may shift the weak location (axially and/or circumferentially) so that the same environmental stress causes bending at a different location. In other embodiments, the interfaces may, for example, include a first pair, and a first interface of the first pair may be radially oriented. Similarly, a second interface of the first pair may be radially oriented, and a first expandable body may be radially adjacent to and extend axially between the first and second interfaces of the first pair so that expansion of the first expandable body axially couples the first expandable body with the first and second interfaces of the first pair. This axial coupling may result in the first expandable body supporting the relative positions of the interfaces of the pair, inhibiting changes to the offset between the interfaces of the first pair and helping to limit or prevent changes in bend characteristics of the axis of the skeleton adjacent the first pair when the expandable body is expanded. Advantageously, if such an expandable body is expanded when the axis is locally in a straight configuration, the expandable body may prevent it from bending; if such an expandable body is expanded when the axis is locally in a bent configuration, it may prevent the axis from straightening.

In any of the articulation systems described above, the pairs may include a first pair of the interfaces offset laterally from the axis along a first lateral axis. An associated first expandable body may be disposed between the interfaces of the first pair. In such embodiments, a second expandable body may be disposed between a second pair of the interfaces that is offset laterally from the axis along a second lateral axis transverse to the first lateral axis. Hence, inflation of the second expandable body may bend the axis of the skeleton away from the second lateral axis and inflation of the first lateral body may bend the axis of the skeleton away from the first lateral axis. In other embodiments, a second pair of the interfaces may be offset laterally from the axis and may be opposed to the first lateral axis and to the first pair so that the axis extends between the first pair and the second pair, such that inflation of a second expandable body disposed between the second pair together with the first expandable body urges the skeleton to elongate axially. In still other embodiments, a second expandable body may be disposed between a second pair of the interfaces, with the second pair axially offset from the first pair and sufficiently aligned along the first lateral axis with the first pair so that inflation of the first expandable body urges the skeleton to bend laterally away from the first lateral axis, and inflation of the second expandable body together with the first expandable body urges the skeleton to bend laterally further away from the first lateral axis. Of course, many embodiments will include multiple such combinations of these structures and capabilities, with a plurality of pairs being along laterally offset, a plurality being opposed relative to the axis, and/or a plurality being axially aligned so that by inflating appropriate subsets of the expandable bodies (as disposed between associated pluralities of pairs of interface surfaces or structures), the axis can be bent laterally in a single orientation by different incremental amounts, the skeleton can be axially lengthened by different incremental amounts, and/or the axis can be bent laterally in a plurality of different lateral orientations by differing incremental amounts, all sequentially or simultaneously. Combinations of any two or more of these desired structures and capabilities can be provided with the relatively simple structures described herein.

Optionally, the expandable bodies may comprise non-compliant balloon walls, and each expandable body can have an expanded configuration defined by expansion with a pressure within a full expansion pressure range, and an unexpanded configuration. The offsets of the skeleton can have associated open and closed states, respectively. The skeleton (and/or structures mounted thereto) will optionally be sufficiently biased to urge the axial offsets toward a closed state when the balloons are in the unexpanded configuration and no environmental loads are imposed.

The skeletons and arrays will often be included in a catheter configured for insertion into a body of a patient. The articulation systems for medical or non-medical uses may also include an input configured for receiving a catheter articulation command from a user, and a processor coupling the input to the fluid supply source. The processor may be configured to selectively direct the fluid to a subset of the expandable bodies in response to the command. For example, when the input is configured so that the command comprises a desired direction of articulation, and when the fluid supply comprises a plurality of valves coupled to the plurality of channels, the processor may identify and actuate a subset of the valves in response to the direction. A number of additional and/or alternative relationships between the input commands and valves may also be incorporated into the processor. As alternative examples (that may or may not be combined with the preceding example and/or with each other) when the input is configured so that the command comprises a desired location of articulation, the processor may identify and actuate a subset of valves in response to the location; when the input is configured so that the command comprises a radius of articulation, the processor may identify and actuate a subset of valves in response to the radius; when the input is configured so that the command comprises a desired axial elongation quantity, the processor may identify and actuate a subset of valves in response to the elongation quantity; etc.

The systems may operate in an open-loop manner, so that the actual articulation actuation is not sensed by data processing components of the system and feed back to any processor. Other systems may include circuitry to generate feedback signals indicative of the state of some or all of the balloons or offsets optionally by printing or otherwise including appropriate electrical components on or in the balloon walls. Some embodiments may sense an orientation (and/or relative position) of a proximal or "base" portion of the skeleton adjacent the array-driven distal portion so as to align desired and commanded orientations, regardless of any movement control feedback, with suitable position and/or orientation sensors optionally being selected from among known components that rely on imaging technologies (such as optical, fluoroscopic, magnetic resonance, ultrasound, computed tomography, positron emission tomography, or the like) and use known image processing techniques, and/or being selected from known minimally invasive tool tracking technologies (such as electrical, ultrasound, or other inserted device and active fiducial locating systems), and/or being selected from known catheter bend monitoring techniques (such as optical fiber systems or the like). Processors of some embodiments may employ any of these or other sensors for feedback on the actual location, orientation, movement and/or pose and for determining further valve actuation signals.

Optionally, a plurality of the valves may be coupled to the proximal end of the skeleton. Instead (or in addition), a plurality of the valves may be disposed along the array. For example, the substrate of the array may comprise first and second substrate layers with a substrate layer interface therebetween, and the channels may comprise channel walls extending into the first layer from the substrate interface.

The expandable bodies of any of the arrays described herein may be distributed axially and circumferentially along the substrate, so that the array may define (for example) an at least two dimensional array. Actuation fluid containment sheathing may encase the skeleton and balloons, with the sheathing optionally being integrated with the substrate. This may allow used inflation fluid to flow proximally from the balloons outside the channels of the substrate and thereby facilitate balloon deflation without releasing the used inflation fluid inside a body or the like.

Prior to use, the array will often be coupled with a skeleton structure so that expansion of the expandable bodies alters an axis of the skeleton. Typically, the flexible substrate will be flexed from an initial shape during mounting of the array to the skeleton, and may also be further flexed during articulation of the skeleton by the array.

Optionally, the skeleton may include a helical coil, which may have spaces between the loops when in a relaxed state or the coil may instead be biased so that adjacent loops of the coil axially engage each other when the coil is in a relaxed state, which can help to transmit axially compressive loads between the loops. Alternative skeletons may include hypotube or other tubing having a plurality of lateral slots so as to define the loops there between, and/or a braided tubular structure having a plurality of braid elements defining the loops.

Typically, the first balloon is eccentric of the skeleton and is disposed radially between the skeleton and a radial support structure. The radial support can have opposed inner and outer surfaces and can be configured to limit radial displacement of the first balloon relative to the skeleton during expansion, so that expansion of the first balloon from the deflated configuration to the inflated configuration induces the desired bend-inhibiting radial engagement between the first balloon and the first and second loops of the skeleton. Suitable radial supports may comprise a helical coil or even a circumferential band of material, often being a polymer material disposed radially outward of the skeleton so that expansion of the first balloon imposes a circumferential tensile load in the band. The radial support may optionally be integrated into a substrate of a balloon array, with the first balloon being included in the array structure.

Optionally, the first balloon is included in an array of balloons distributed along the skeleton, circumferentially, axially, or both. Each of the balloons is expandable from a deflated configuration to an inflated configuration, and some or all of the balloons have a plurality of associated loops of the skeleton including a first associated loop and a second associated loop, the first associated loop movable axially relative to the second associated loop during bending of the axis adjacent the balloon when the balloon is in the deflated configuration. These balloons each radially engage the first and second associated loops in the inflated configuration so as to inhibit relative axial movement and bending of the axis adjacent those balloon when the balloons are in the inflated configuration. A fluid supply system will often be in fluid communication with the balloons during use so as to selectively inflate a desired subset of the balloons such that bending of the axis adjacent the subset is inhibited. In some exemplary embodiments, these balloons are circumferentially distributed about the skeleton, and inflation of a first subset of the balloons distributed about a first axial segment of the skeleton inhibits bending of the skeleton in orthogonal bend orientations across the axis along the first segment. A second subset of the balloons extend along a second axial segment of the skeleton can also be provided, the second segment axially adjacent to or overlapping with the first segment and at least partially extending axially beyond the first segment so that inflation of the first and second subsets inhibits axial bending of the skeleton in the orthogonal bend orientations contiguously along the first and second axial segments of the skeleton. The balloon arrays for inhibiting bending can be combined with balloon arrays for selective articulation (either by providing both types of balloon arrays or by including both types of balloons in an integrated array), and the arrays may share substrate, channel, and/or fluid control components and techniques.

As an optional feature, the skeleton comprises a plurality of circumferential loops of a helical coil, the coil including a helical axis winding around the axis of the skeleton, and the balloons include at least one balloon wall disposed around the helical axis along at least a portion of an associated loop of the coil. The associated pair of regions may be disposed on adjacent loops of the coil, so that inflation of the balloon may push both adjacent loops away from the loop on which the balloon is mounted. Advantageously, a plurality of balloons may be formed from a continuous tube of material over a helical core by intermittently varying the size of the material outward (such as by blowing the material using balloon forming techniques) or inward (such as by intermittently heat shrinking the material) or both. The core may include one or more balloon inflation lumens, and by appropriate positioning of the balloons along the helical axis, appropriate sizing, shaping, and spacing of the balloons, and by proving ports through a wall of the core into a lumen associated with each balloon, the balloon array may be fabricated with limited cost and tooling.

The fluid channel system will often comprise one or more helical lumen extending along one or more helical axis of one or more helical structures. For example, a first plurality of the balloons can be offset from the axis along a first lateral orientation and in fluid communication with the helical lumen, the helical coil comprises a first helical coil. A second helical coil may be offset axially from and coaxial with the first helical coil, the second helical coil having second loops interspersed with the loops of the helical coil along the axis of the catheter or other elongate body. The second helical coil may have a second helical lumen in fluid communication with a second plurality of the balloons offset from the axis along a second lateral orientation so that transmission of fluid along the first and second helical lumens deflects the skeleton along the first and second lateral orientations, respectively.

In some embodiments, the fluid channel system comprises a second helical lumen extending along the helical axis. A first plurality of the balloons may be offset from the axis along a first lateral orientation and in fluid communication with the first helical lumen, and a second plurality of the balloons may be offset from the axis along a second lateral orientation and in fluid communication with the second helical lumen. This can allow transmission of fluid along the first and second helical lumens of the same helical coil to deflect the axis along the first and second lateral orientations, respectively.

The invention also provides an optional manifold architecture that facilitates separate computer-controlled fluid-actuated articulation of a plurality of actuators disposed along the flexible body. The manifold often includes fluid supply channels that are distributed across several regions of a manifold body, the manifold body optionally comprising modular plates with plate-mounted valves to facilitate fluid communication through a plurality of fluid transmission channels included in one or more multi-lumen shafts of the articulated flexible body. The actuators preferably comprise balloons within a balloon array, and will often be mounted on one, two, or more extruded multi-lumen shafts. Valve/plate modules can be assembled in an array or stack, and a proximal interface of the shaft(s) may have ports for accessing the transmission channels, with the ports being distributed along an axis of the proximal interface. By aligning and engaging the proximal interface with a receptacle that traverses the plates or regions of the manifold assembly, the ports can be quickly and easily sealed to associated channels of the various valve/plate modules using a quick-disconnect fitting.

In many of the devices and systems described herein, the articulated structure comprises a catheter. Other articulated structures that can be used include guidewires, endoscopes and endoscope support devices, boroscopes, industrial manipulators or manipulator portions (such as grippers or the like), prostheses, and the like. The actuators of the articulated structures will often include a plurality of balloons, with the balloons often being included in a balloon array that is distributed axially and circumferentially about an elongate body of the articulated structure. In exemplary embodiments, the number of independent fluid channels that are coupled through the interface/receptacle pairing will be between 5 and 60, there typically being from 6 to 50 channels, preferably from 12 to 42 articulation fluid channels, and ideally from 12 to 24 articulation fluid channels included within 1-4 extruded multi-lumen shafts or other multi-lumen substrate structures.

The manifold body often comprises a plurality of plates. Each plate will typically have opposed major surfaces, with the regions of the manifold body being bordered by the plate surfaces. The receptacle typically traverses the plates. Note that the plates of the manifold may optionally be included in modular valve/plate units, so that an assembly of the plates and valves controls and directs fluid flow. In other embodiments, the manifold may comprise a simple interface structure that can, for example, direct fluid between a more complex module assembly (having valves, pressure sensors, and the like) and one or more flexible multi-lumen shafts of the articulated body. In other embodiments, the port-supporting proximal interface of the articulable structure comprises a single rigid contiguous structure. Though the receptacle may span across several regions or plates of the manifold assembly, the receptacle of the assembled manifold often comprises a contiguous feature such that alignment of the proximal interface with the receptacle registers all the channels with all the ports. Note that there may be additional couplers or connectors that are flexibly attached to the proximal interface (such as one or more separately positionable electrical connector, optical fiber connector, and/or separate fluid connectors(s) for therapeutic fluids (such as for irrigation, aspiration, drug delivery, or the like) or even actuation (such as for a prosthesis deployment balloon or the like). In other embodiments, one, some, or all of these connectors may be integrated into the proximal interface and receptacle. Regardless, one or more quick-disconnect fitting (such as the type that are manually movable between a first or latched configuration and a second or detached configuration) may be used to facilitate and maintain sealed fluid communication between the ports and associated channels, and to allow quick and easy removal and replacement of the proximal portion so as to replace the articulated structure with a different alternative articulated structure.

The proximal interface of the articulatable structure will optionally facilitate one or more additional form of communication beyond the sealed port/channel fluid coupling. For example, the proximal interface may include a radio frequency identification (RFID) label, an electrical connector, and/or an optical fiber connector. In such embodiments, the receptacle will often include an RFID reader, an electrical connector, and/or an optical fiber connector, respectively. RFID data, or electronic identification data, optical identification data, or other forms of data can be used by a processor coupled to the manifold to identify a type of the articulable structure (and optionally the specific articulable structure itself). Transmitting this identification data across such a communication link between the proximal interface and the receptacle facilitates a plug-and-play operability of the system, allowing a processor of the system to tailor fluid transmissions between the manifold and the articulable structure to the particular type of articulable structure that is in use, allowing the system to induce desired articulations without having to manually reconfigure the processor or manifold. Identification data can also help prevent unsafe and inappropriate re-use of high-pressure balloon articulation devices. Articulation state feedback may be provided using electrical interface/receptacle connectors (such as using known electromagnetic internal navigation systems) or optical interface/receptacle connectors (such as using known optical fiber Bragg grating flex sensors). Such connectors may also be used by diagnostic or therapeutic tools carried by the articulatable structure.

The proximal interface and the receptacle may take any of a variety of (typically corresponding) forms. The receptacle or the proximal interface may, for example, comprise an array of posts, with the other comprising an array of indentations. The posts will typically extend along parallel axes (often from an underlying surface of the proximal interface) and be matable with the indentations (typically being on the receptacle), often so that the posts can all be inserted into the indentations with a single movement of a proximal interface body toward the receptacle. Seals around the posts can provide sealed, isolated fluid communication between the ports and the channels. The total cross-sectional area of the posts and indentations that is exposed to the fluid(s) therein may be limited to less than two square inches, and typically being less than one square inch, most often being less than 0.1 square inches, and ideally being about 0.025 square inches or less so as to avoid excessive ejection forces. In many such post-indentation embodiments, the articulable structure can transmit the fluid flows from the manifold toward the actuators using a multi-lumen shaft. To transmit a relatively large number of independent flows, the articulable structure may have a plurality of multi-lumen shafts, such as an integer number A of multi-lumen shafts extending distally from the proximal interface, A being greater than 1 (and typically being 2 or 3). Each multi-lumen shaft can have an integer number B of lumens with associated ports and associated actuators, B also being greater than 1 (and typically being from 3 to 15, more typically being 6 to 15). The array of posts may comprise an A×B array of posts, and the post/indentation engagements may be distributed among B valve module plates of the manifold. In exemplary embodiments, each plate comprises a plurality of plate layers, and each plate has a lateral plate receptacle member that is affixed to the plate layers. The receptacle can be defined by lateral surfaces of the receptacle members.

In alternative forms of the proximal interface and receptacle, the receptacle may be defined by receptacle passages that extend entirely through some, most, or even all of the plates of the manifold. The plates may be stacked into an array (typically with the opposed major surfaces in apposition), and the receptacle passages can be axially aligned in the assembled manifold so as to facilitate inserting the proximal interface therein. In such embodiments, the proximal interface of the articulatable body may comprise a shaft having axially distributed ports. Exemplary proximal interface structures may take the form of a simple extruded polymer multi-lumen shaft, with the ports comprising lateral holes drilled into the various lumens. The multi-lumen shaft itself may be inserted into and seal against the receptacle, or there may be an intermediate interface body having a tube or shaft that facilitates the use of the manifold with different articulable structures. Regardless, the shaft can be configured and sized to be inserted into the receptacle so as to provide sealing engagement between the ports, and which can result in sealed communication between the ports and their associated fluid channels. Optionally, a compression member couples the plates of the manifold together so as to impose axial compression. Deformable seals may be disposed between the plates, and those seals may protrude radially inwardly into the receptacle so as to seal between the ports when the compression member squeezes the plates together. Alternative seal structures may protrude radially outwardly to provide sealing against a surrounding surface.

Many of the manifold bodies can make use of a modular manifold assembly structure having an array of interchangeable plate modules. The plate modules include valves and one or more plate layers. The plate layers of each module define a proximal major surface of the module and a distal major surface of the plate module. The major surfaces of adjacent plate modules may be in direct apposition with direct plate material-plate material contact (optionally with the engaging plate surfaces fused together), but may more typically have deformable sealing material (such as O-rings, formed in place gasket material, laser cut gaskets, 3D printed sealing material, or the like) or with a flexible film (such as a flex circuit substrate and/or a deformable sealing member adhesively bonded to one of the adjoining plates) between the plate structures. In some embodiments (particularly those in which the plates are laterally supported by a receptacle member) there may be gaps between some or all of the plates in the array. Regardless, an axial spacing between the ports of the proximal interface can correspond to a module-to-module separation between the fluid channels of the adjacent modules. Hence, alignment of the proximal interface with the receptacle can, when the axes of the interface and the receptacle are aligned, register each of the ports with an associated fluid channel (despite the channels being included on different plate modules). Alternative module body structures may comprise 3D printed structures, with valves, sensors and the like optionally being integrally printed or affixed to the manifold body.

The plate modules will optionally be disposed between a proximal end cap of the manifold and a distal end cap of the manifold. The plate modules may each include a plurality of plate module layers, with the fluid channels typically being disposed between the layers (such as by molding or laser micromachining an open channel into the surface of one layer and sealing the channel by bonding another layer over the open channel). In some embodiments, inflation passages extend through some, most, or even all of the modular plate layers, and these inflation passages can be aligned in the stacked plates of the modular manifold assembly to form a continuous inflation fluid header (with the ends of the inflation header typically being sealed by the end caps). Inflation valves can be disposed along inflation channels between the inflation header and the receptacle so as to control a flow of pressurized inflation fluid transmitted from the header toward a particular port of the articulated structure. Optionally, deflation passages may similarly extend through some, most, or all of the plate layers and align in the modular manifold assembly to form a continuous deflation header, deflation valves being disposed along deflation channels between the deflation header and the receptacle. Alternative embodiments may simply port the deflation fluid from each plate directly to the atmosphere, foregoing the deflation header. However, use of the deflation header may be provide advantages; a deflation plenum can be in fluid communication with the deflation header, and a deflation valve can be disposed between the deflation plenum and a deflation exhaust port (for releasing deflation fluid to the atmosphere of the like). By coupling a pressure sensor to the deflation plenum, the deflation back-pressure can be monitored and/or controlled.

In most of the manifold assemblies provided herein, a plurality of pressure sensors are coupled to the channels of the plate modules. The pressure sensors are also coupled to a processor, and the processor transmits valve commands to valves of the plate modules in response to pressure signals from the pressure sensors. Preferably, most or all of the channels having an associated port in the articulated assembly will also have a pressure sensor coupled thereto so as to all the pressures of fluids passing through the ports of the interface to the monitored and controlled.

A pressurized canister containing inflation fluid can optionally be used as the inflation fluid source. The inflation fluid preferably comprises an inflation liquid in the canister, though the inflation liquid will often vaporize to an inflation gas for use within the actuators. The pressurized canister can be mated with a canister receptacle or socket of the manifold so as to transmit the inflation fluid toward the fluid channels, with the socket often having a pin that pierces a frangible seal of the canister. The vaporization of liquid in the canister can help maintain a constant fluid inflation pressure without having to resort to pumps or the like. An exemplary inflation fluid comprises a cryogenic fluid such as nitrous oxide, with the canister preferably containing less than 10 oz. of the inflation fluid, often from 0.125 oz. to 7½ oz., typically from 0.25 oz to 3 oz. Fluid pressures in the manifold may range up to about 55 atm. or more, with controlled pressures often being in a range from about 3 atm. to about 40, optionally being less than about 35, and in many cases being about 27 atm. or less.

The valve of the fluid control manifolds may include an inflation valve disposed between the fluid source and a first balloon, and a deflation valve disposed between a second balloon and a surrounding atmosphere. The first valve can be configured to independently transmit minimum increments of 50 nl or less of the liquid, with the flowing cooling fluid often remaining liquid till it traverses a throat of the valve. The second valve can be configured to independently transmit at least 0.1 scc/s of the gas. Including such valves in the system for inflation lumen of the articulated device may facilitate independent pressure control over the balloons (or the subsets of balloons, with each subset being inflated using a common inflation lumen). The minimum liquid increment may be 25 nl (or even 15 nl) or less, while the minimum gas flow may be 0.5 scc/s (or even 1 scc/s) or more. Some embodiments may employ multi-way valves that can be used to control both inflation fluid flowing into the balloon and deflation fluid exhausted from the balloon, with accuracy of control (despite the different inflation and deflation flows) being maintained by differing valve throats, by differing orifices or other flow restricting devices adjacent the valve, by proportional flow control of sufficient range, and/or by a sufficiently rapid valve response rate. In some embodiments, a pressure-controlled plenum can be disposed between the fluid source and the first and second balloon, or the liquid may otherwise vaporize to the gas before the valve so that none of the liquid transits a valves between the plenum and the balloons.

To facilitate the safe use of inflation fluids for articulation of catheters and other articulatable structures, a fluid shutoff valve may be disposed upstream of the fluid channels. Moreover, a vacuum source and a vacuum sensing system may also be included, with the actuators being disposed within a sealed chamber of the articulation structure and the vacuum source being coupleable to that chamber. The vacuum sensing system can couple the chamber to the shutoff valve so as to inhibit transmission of inflation fluid to the actuators of the articulable structure in response to deterioration of vacuum within the chamber. Advantageously, the vacuum source may comprise a simple positive displacement pump (such as a syringe pump with a latchable handle), and electronic sensing of the vacuum can provide continuous safety monitoring. The chamber of the articulatable structure can be provided using an outer sheath around the balloon array, and optionally an inner sheath within a helical or other annular balloon array arrangement. By sealing the array proximally and distally of the balloons, the space surrounding the array can form a vacuum chamber in which the vacuum will deteriorate if any leakage of the inflation fluid out of the array, and or any leakage of blood, air, or other surrounding fluids into the chamber.

The articulation devices, systems, and methods for articulating elongate flexible structures often have a fluid-driven balloon array that can be used to locally contract a flexible elongate frame or skeleton (for example, along one or more selected side(s) of one or more selected axial segment(s)) of an elongate flexible body so as to help define a resting shape or pose of the elongate body. In preferred embodiments, the skeleton structures described herein will often have pairs of corresponding axially oriented surface regions that can move relative to each other, for example, with the regions being on either side of a sliding joint, or coupled to each other by a loop of a deformable helical coil structure of the skeleton. A balloon of the array (or some other actuator) may be between the regions of each pair. One or more of these pairs of surfaces may be separated by an offset that increases when the axis of the skeleton is compressed near the pair. While it is counterintuitive, axial expansion of the balloon (or another actuator) between such regions can axially contract or shorten the skeleton near the balloon, for example, bending the skeleton toward a balloon that is offset laterally from the axis of the elongate body. Advantageously, the skeleton and balloon array can be configured so that different balloons apply opposing local axial elongation and contraction forces. Hence, selective inflation of subsets of the balloons and corresponding deflation of other subsets of the balloons can be used to controllably urge an elongate flexible body to bend laterally in a desired direction, to change in overall axial length, and/or to do a controlled combination of both throughout a workspace. Furthermore, varying the inflation pressures of the opposed balloons can controllably and locally modulate the stiffness of the elongate body, optionally without changing the pose of the articulated elongate body.

In one aspect, the invention provides an articulable catheter comprising at least one elongate skeleton having a proximal end and a distal end and defining an axis therebetween. The skeleton includes an inner wall and an outer wall with a first flange affixed to the inner wall and a second flange affixed to the outer wall. Opposed major surfaces of the walls may be oriented primarily radially, and opposed major surfaces of the flanges may be oriented primarily axially. A plurality of axial contraction balloons can be disposed radially between the inner wall and the outer wall, and axially between the first flange and the second flange so that, in use, inflation of the contraction balloons pushes the first and second flanges axially apart so as to urge an axial overlap of the inner and outer walls to increase. This can result in the skeleton adjacent the inflated contraction balloons being locally urged to axially contract in response to the inflating of the balloon.

In some embodiments, the skeleton comprises a plurality of annular or ring structures, often including a plurality of inner rings having the inner walls and a plurality of outer rings having the outer walls. The flanges of such embodiments may comprise annular flanges affixed to the walls, and the annular structures or rings may be axially movable relative to each other. Typically, each ring will include an associated wall and will have a proximal ring end and a distal ring end, with the wall of the ring affixed to an associated proximal flange at the proximal ring end and to an associated distal flange at the distal ring end, the first and second flanges being included among the proximal and distal flanges.

In other embodiments, the skeleton comprises at least one helical member. For example, the walls may comprise helical walls, and the flanges may comprise helical flanges affixed to the helical walls, the helical member(s) including the walls and the flanges. The helical member may define a plurality of helical loops and the loops may be axially movable relative to each other sufficiently to accommodate articulation of the skeleton. Preferably, each loop has an associated wall with a proximal loop edge and a distal loop edge, the wall being affixed to an associated proximal flange at the proximal loop edge and to an associated distal flange at the distal loop edge (the first and second flanges typically being included among these proximal and distal flanges).

In the ring embodiments, the helical embodiments, and other embodiments, a plurality of axial extension balloons may be disposed axially between adjacent flanges of the skeleton. Typically, only one of the walls of the skeleton (for example, an inner wall or an outer wall but not both) may be disposed radially of the extension balloons themselves. In other words, unlike many of the contraction balloons, the extension balloons are preferably not contained radially in a space between an inner wall and an outer wall. As a result, and unlike the contraction balloons, inflation of the extension balloons during use will push the adjacent flanges axially apart so as to urge the skeleton adjacent the inflated extension balloons to locally elongate axially.

Advantageously, the extension balloons and the contraction balloons can be mounted to the skeleton in opposition so that inflation of the extension balloons and deflation of the contraction balloons locally axially elongates the skeleton, and so that deflation of the extension balloons and inflation of the contraction balloons locally axially contracts the skeleton. Note that the balloons can be distributed circumferentially about the axis so that selective inflation of a first eccentric subset of the balloons and selective deflation of a second eccentric subset of the balloons can laterally deflect the axis toward a first lateral orientation, and so that selective deflation of the first eccentric subset of the balloons and selective inflation of the second eccentric subset of the balloons can laterally deflect the axis away from the first lateral orientation. The balloons can also (or instead) be distributed axially along the axis so that selective inflation of a third eccentric subset of the balloons and selective deflation of a fourth eccentric subset of the balloons may laterally deflect the axis along a first axial segment of the skeleton, and selective deflation of a fifth eccentric subset of the balloons and selective inflation of a sixth eccentric subset of the balloons laterally deflects the axis along a second axial segment of the skeleton, the second axial segment being axially offset from the first axial segment.

Most of the systems and devices provided herein, and particularly those having skeletons formed using helical structural members, may benefit from groups of the balloons having outer surfaces defined by a shared flexible tube. The tube may have a cross-section that varies periodically along the axis, and a multi-lumen shaft can be disposed within the flexible tube. The tube may be sealed to the shaft intermittently along the axis, with radial ports extending between interiors of the balloons and a plurality of lumens of the multi-lumen shaft so as to facilitate inflation of selectable subsets of the balloons by directing inflation fluid along a subset of the lumens. In exemplary embodiments, the inflation fluid may comprise gas within the balloons and liquid within the inflation lumens.

Optionally, the system allows the stiffness to be controllably and selectably increased from a nominal non-energized actuator stiffness to an intermediate stiffness configuration (with the actuators partially energized, and/or to a relatively high stiffness configuration (with the actuators more fully or fully energized). Different axial segments may be controllably varied (so that a first segment has any of a plurality of different stiffnesses, and a second segment independently has any of a plurality of different stiffnesses). In exemplary embodiments, the energy supply system may comprise a pressurized fluid source and the energizing of the actuators may comprise pressurizing the actuators (the actuators often comprising fluid-expandable bodies such as balloons or the like).

Optionally, a first subset of the fluid-expandable bodies can be disposed substantially axisymmetrical along the segment of the skeleton such that inflation of the first subset axially elongates the segment. A second subset of the fluid-expandable bodies may be distributed eccentrically along the segment such that inflation of the second subset laterally bends the segment along the first lateral bending axis. A third subset of the fluid-expandable bodies may be distributed eccentrically along the segment such that inflation of the third subset laterally bends the segment along the second lateral bending axis and transverse to the first bending axis. The second and third subsets will often axially overlap the first subset. Optionally, a fourth subset of the fluid-expandable bodies may be supported by the skeleton substantially in opposition to the first subset and a fifth subset of the fluid-expandable bodies can similarly be substantially in opposition to the second subset, with a sixth subset of the fluid expandable bodies substantially in opposition to the third subset. This can facilitate using selective inflation of the subsets to controllably and reversibly articulate the segment throughout a three-dimensional workspace.

In another aspect, the invention provides an articulatable structure comprising an elongate flexible body having a proximal end and a distal end with an axis therebetween. An array of actuators can be mounted along the body so as to articulate the body.

Optionally, a manifold can be provided for articulating the elongate body. The array of actuators can include an array of articulation balloons, and the manifold can include a liquid inflation fluid source and a gas inflation fluid source. A processor can also be included, and, in use, at least one fluid channel of the structure may contain both a gas inflation fluid and a liquid inflation fluid. The processor can be configured to alter relative amounts of the gas inflation fluid and liquid inflation fluid in the channel in response to a command to change a compliance of a subset of the balloons in communication with the channel.

Still further advantageous features can being included in any of the manifolds that will be used for articulating the elongate body. For example, when the body has an array of articulation balloons or other fluid expandable bodies, the manifold may include a receptacle configured to receive a canister having a first inflation fluid. A deformable diaphragm of the manifold may have a first side and a second side, and in use, the first side may be in fluid communication with the first inflation fluid and the second side may be in fluid communication with a second inflation fluid. A valve can couple the canister to the first side of the diaphragm so as to control a pressure of the first and second inflation fluids. The second side of the diaphragm can be in fluid communication with the balloons to selectively inflate the balloons with the second inflation fluid. This may be beneficial, for example, if the body comprises a catheter body, the first inflation fluid comprises a gas and the second inflation fluid comprises a liquid.

A number of refinements may be included the other components of the systems and structures. For example, the body may include a helical frame having a proximal flange and a distal flange with an axial wall extending therebetween. The actuators may urge the flanges axially so as to locally deflect the axis. The frame may have opening, slots, or cuts in the axial wall, with these slots or cuts being located circumferentially between the actuators so as to enhance lateral flexibility of the frame.

A number of different data processing features may also be included. For example, the body may have an ID tag embodying machine-readable data, and the structure or system may further include a processor coupled with the actuators so as to transmit drive signals thereto. The processor can be configured for coupling with a server that is, in turn, in communication with a network, so as to transmit ID data. If the actuators comprise fluid expandable bodies, the structures or systems may further include a plurality of pressure sensors in communication with the fluid expandable bodies. A source of pressurized fluid may also be included, and a plurality of valves can be between the fluid source and the expandable bodies. The processor may be configured to induce movement of the body toward a new position in response to a command input by a system user, and the processor may include a closed loop valve controller configured to actuate the valves and provide specific pressures in the expandable bodies, as sensed by the sensors. Optionally, the processor comprises a module configured to determine a desired state of the body, an inverse kinematics module configured to determine a desired joint state, a module configured to determine a difference between an actual joint state and the desired joint state so as to define a joint error, and a joint trajectory planner. The trajectory planner can define a joint error trajectory in response to the desired joint state and the joint error, and the joint trajectory can be transmitted to an inverse fluidic calculator to determine command signals for the valves. In still further optional features, the system or structure also includes a feedback system configured to sense an actual position or state of the body or other articulated structure using a sensor. The sensor may comprise, for example, an electromagnetic navigation system, an ultrasound navigation system, an image processor coupled to a 3D image acquisition system, an optical fiber shape sensor, and/or an electrical shape sensors.

In another aspect, the invention provides a heart valve therapy system for structurally altering a valve of a heart in a patient body. The therapy system comprises an elongate flexible cardiac catheter body having a proximal end and a distal end with an axis therebetween. A therapeutic valve tool can be mounted near the distal end of the catheter body, the tool having an axis. The catheter body can have an articulated portion adjacent the distal end, and the articulated portion may include an array of articulation balloons.

Optionally, the balloons may include a first subset and a second subset, and inflation of the first subset may articulate the articulated portion along a first articulation orientation (such as bending the articulated catheter in an X direction). Inflation of the second subset may articulating the articulated portion along a second orientation transverse to the first orientation (such as by bending the catheter in a Y direction). In many of the embodiments provided herein, the tool comprises a replacement valve (such as a transcatheter prosthetic mitral valve). Alternative embodiments can be make use of a tool comprising a valve leaflet plication clip, a prosthetic structure that can be provide a less-invasive therapy similar to the Alfieri stitch. Still further alternative embodiments may make use of a tool comprising a transcatheter annuloplasty ring, or annular plication tool to decrease the size of the valve annulus. Whatever specific form the tool takes, the catheter body may optionally form a component of a transceptal access/treatment system, with known transceptal components (a transeptal needle, a septum dilation tip, a blood pressure sensing system for verifying access to the left atrium, a steerable sheath or guide catheter, and/or the like) often also being provided. Transceptal access may not be needed for other procedures, and the therapy may be directed at any of the valves of the heart, including the aortic, mitral, tricuspid, and/or pulmonary.

In some embodiments, the catheter system may be configured to access heart tissues via the aortic arch of the patient. For example, articulation of the articulated portion of the catheter body may have an articulated configuration with the tool at an angle relative to a proximal end of the articulated portion sufficient to inhibit traumatic engagement between the tool and a surface of the aortic arch throughout advancement of the tool across the aortic arch. Such systems may optionally include a prosthetic aortic valve, but may alternatively include a prosthetic mitral valve. Where the heart has a left ventricle, an aortic valve, and a mitral valve, articulation of the articulated portion of the catheter body may drive the catheter body to a bent configuration with the tool at an angle relative to a proximal base of the articulated portion sufficient to allow retrograde engagement between the tool and the tissue of the mitral valve when the body of the catheter extends through the mitral valve or the aortic valve.

When the tool comprises a mitral valve, the articulated portion may have a first axial segment and a second axial segment distal of the first segment, the first segment have a range of motion encompassing about a 90 degree lateral bend along the first orientation so that a distal end of the first segment can be oriented transceptally when a proximal base of the first segment extends along a vena cava. The second segment may have a range of motion encompassing about a 90 degree lateral bend along the first orientation so that a distal end of the second segment can extend apically when the distal end of the first segment is oriented transceptally. Preferably, articulation of the segments within their ranges of motions will be independent. Optionally, the first and second segments may each also have an independent range of motion along a second orientation transverse to the first orientation. In some embodiments, the articulated portion further comprises a third independently articulatable segment disposed proximally of the second segment, the third segment articulatable between an anchor configuration and a small profile configuration within a third range of motion. The third segment may be elongatable along the axis within a second range of motion, whether or not it has a specialized anchor configuration.

In another aspect, the invention provides a heart valve therapy method for repairing or replacing a valve of a heart in a patient body. The method comprises articulating an elongate flexible cardiac catheter body within a patient body. The catheter body has a proximal end and a distal end with an axis therebetween. A therapeutic valve tool is mounted near the distal end of the catheter body, and the articulating of the catheter body within the patient is performed by inflating a subset of an array of articulation balloons disposed along the catheter body.

BRIEF DESCRIPTION OF THE DRAWINGS

FIG. 1-1 schematically illustrates a catheter articulation system having a hand-held proximal housing and a catheter with a distal articulatable portion in a relaxed state.

FIGS. 14A-16 illustrate components of an alternative embodiment having a plurality of interleaved multi-lumen polymer helical cores interleaved with a plurality of resilient coil structures having axially oriented surfaces configured to radially restrain the balloons.

FIGS. 18A-18C are perspective views showing an alternative modular manifold assembly having modules that each include valves, supply fluid channels, exhaust fluid channels, and passages through the plates of the modules that align in the stacked-plate assembly for use as multi-lumen shaft receptacles, fluid headers, and the like.

FIGS. 20A-22A schematically illustrate skeletons structures having frames or members with balloons mounted in opposition so as to axially extend with inflation of one subset of the balloons, and to axially contract with inflation of another subset of balloons.

FIGS. 23A-23J are illustrations of alternative elongate articulated flexible structures having annular skeletons and two sets of opposed balloons, and show how a plurality of independently controllable axial segments can be combined to allow control of the overall elongate structure with 6 or more degrees of freedom.

FIGS. 24A-24G illustrate components of another alternative elongate articulated flexible structure having axial expansion balloons and opposed axial contraction balloons, the structures here having helical skeleton members and helical balloon assemblies.

FIGS. 35A-35C illustrate a catheter deployment system for an annuloplasty ring.

FIGS. 35D-35F illustrate a catheter deployment system for an annuloplasty plication suture.

FIGS. 38A and 38B schematically illustrate an alternative helical inner frame having enhanced flexibility.

DETAILED DESCRIPTION OF THE INVENTION

Figure 1:
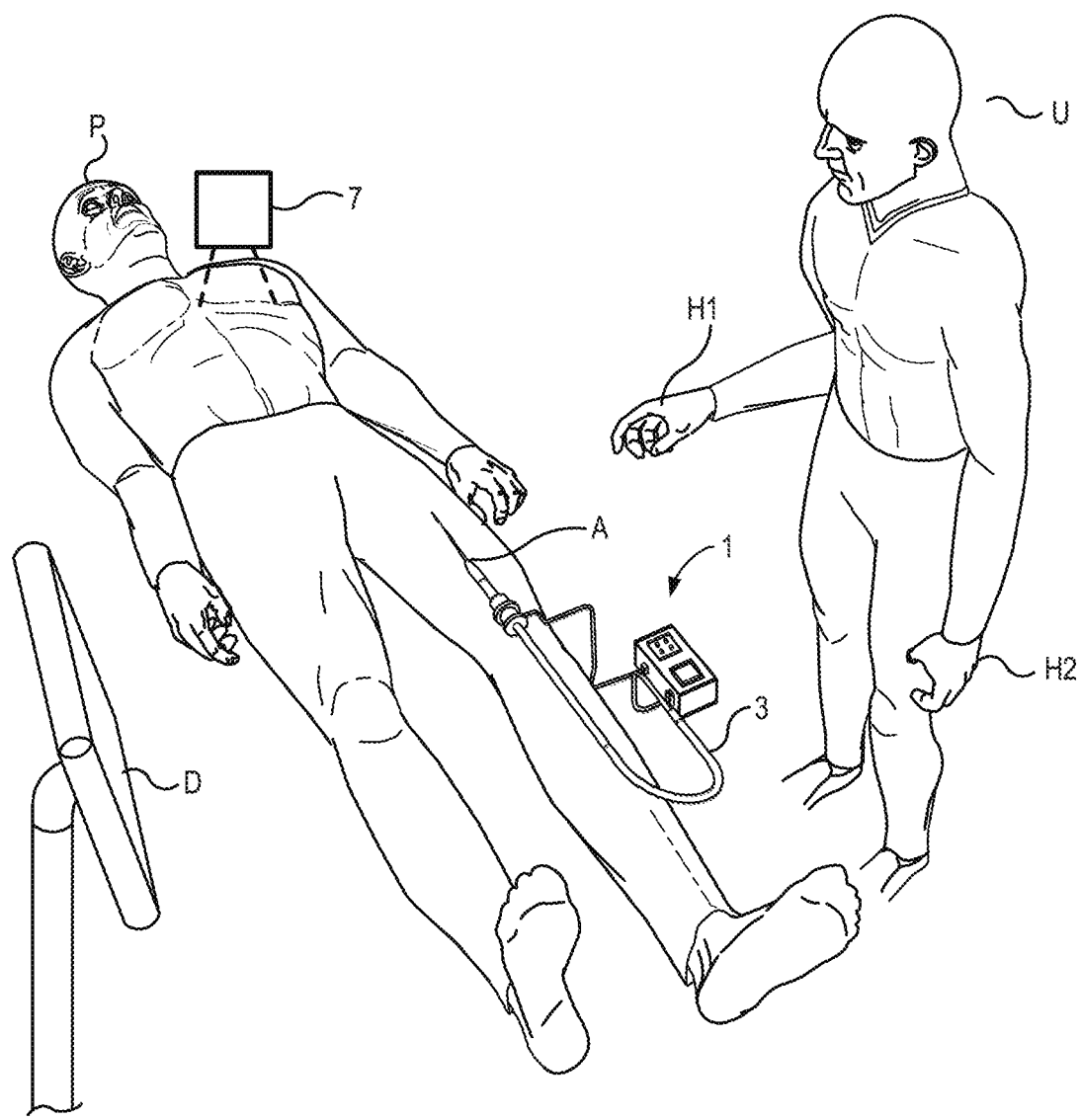
FIG. 1 is a simplified perspective view of a medical procedure in which a physician can input commands into a catheter system so that a catheter is articulated using systems and devices described herein.
Figure 1:
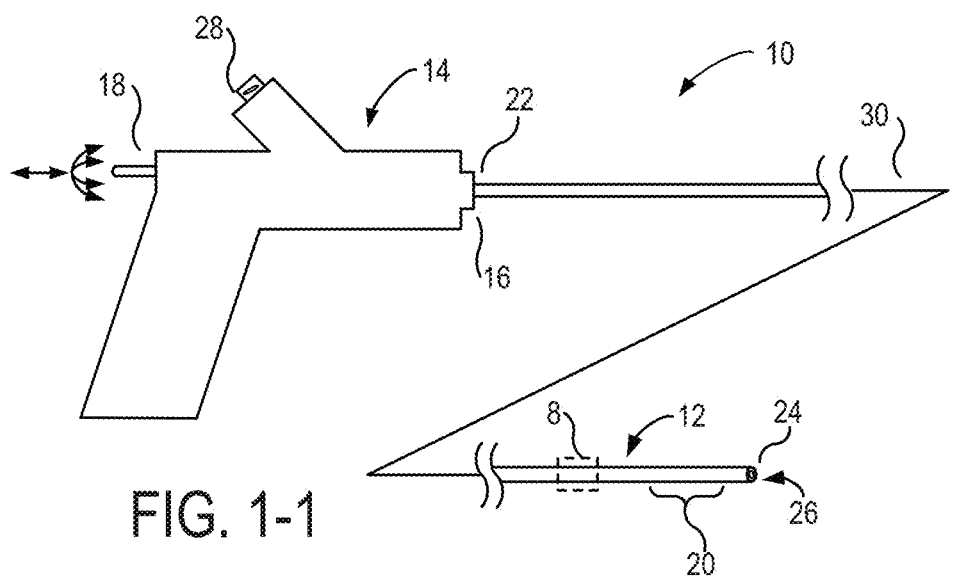

The present invention generally provides fluid control devices, systems, and methods that are particularly useful for articulating catheters and other elongate flexible structures. In exemplary embodiments the invention provides a modular manifold architecture that includes plate-mounted valves to facilitate fluid communication along a plurality of fluid channels included in one or more multi-lumen shafts, often for articulating actuators of a catheter. Preferred actuators include balloons or other fluid-expandable bodies, and the modular manifold assemblies are particularly well suited for independently controlling a relatively large number of fluid pressures and/or flows. The individual plate modules may include valves that control fluid supplied to a catheter or other device, and/or fluid exhausted from the catheter or other device. A receptacle extending across a stack of such modules can receive a fluid flow interface having a large number of individual fluid coupling ports, with the total volume of the modular valve assembly, including the paired receptacle and fluid flow interface of the device often being quite small. In fact, the modular manifold will preferably be small enough to hold in a single hand, even when a controller (such as a digital processor), a pressurized fluid source (such as a canister of cryogenic fluid), and an electrical power source (such as a battery) are included. When used to transmit liquids that will vaporize to a gas that inflates a selected subset of microballoons within a microballoon array, control over the small quantities of inflation liquids may direct microfluidic quantities of inflation fluids. Microelectromechanical system (MEMS) valves and sensors may find advantageous use in these systems; fortunately, suitable microfluidic and MEMS structures are now commercially available and/or known valve structures may be tailored for the applications described herein by a number of commercial service providers and suppliers.

The present invention also provides improved medical devices, systems, and methods, with exemplary embodiments providing improved systems for diagnosing and/or treating a valve of a heart. The invention optionally makes use of an array of articulation balloons to control movement of a distal portion of a catheter inside the heart, and may be used to align a diagnostic or treatment tool with a mitral or other valve. As the articulation balloons can generate articulation forces at the site of articulation, the movement of the articulated catheter within the beating heart may be better controlled and/or provide greater dexterity than movements induced by transmitting articulation forces proximally along a catheter body that winds through a tortuous vascular pathway.

Embodiments provided herein may use balloon-like structures to effect articulation of the elongate catheter or other body. The term "articulation balloon" may be used to refer to a component which expands on inflation with a fluid and is arranged so that on expansion the primary effect is to cause articulation of the elongate body. Note that this use of such a structure is contrasted with a conventional interventional balloon whose primary effect on expansion is to cause substantial radially outward expansion from the outer profile of the overall device, for example to dilate or occlude or anchor in a vessel in which the device is located. Independently, articulated medial structures described herein will often have an articulated distal portion, and an unarticulated proximal portion, which may significantly simplify initial advancement of the structure into a patient using standard catheterization techniques.

The catheter bodies (and many of the other elongate flexible bodies that benefit from the inventions described herein) will often be described herein as having or defining an axis, such that the axis extends along the elongate length of the body. As the bodies are flexible, the local orientation of this axis may vary along the length of the body, and while the axis will often be a central axis defined at or near a center of a cross-section of the body, eccentric axes near an outer surface of the body might also be used. It should be understood, for example, that an elongate structure that extends "along an axis" may have its longest dimension extending in an orientation that has a significant axial component, but the length of that structure need not be precisely parallel to the axis. Similarly, an elongate structure that extends "primarily along the axis" and the like will generally have a length that extends along an orientation that has a greater axial component than components in other orientations orthogonal to the axis. Other orientations may be defined relative to the axis of the body, including orientations that are transvers to the axis (which will encompass orientation that generally extend across the axis, but need not be orthogonal to the axis), orientations that are lateral to the axis (which will encompass orientations that have a significant radial component relative to the axis), orientations that are circumferential relative to the axis (which will encompass orientations that extend around the axis), and the like. The orientations of surfaces may be described herein by reference to the normal of the surface extending away from the structure underlying the surface. As an example, in a simple, solid cylindrical body that has an axis that extends from a proximal end of the body to the distal end of the body, the distal-most end of the body may be described as being distally oriented, the proximal end may be described as being proximally oriented, and the surface between the proximal and distal ends may be described as being radially oriented. As another example, an elongate helical structure extending axially around the above cylindrical body, with the helical structure comprising a wire with a square cross section wrapped around the cylinder at a 20 degree angle, might be described herein as having two opposed axial surfaces (with one being primarily proximally oriented, one being primarily distally oriented). The outermost surface of that wire might be described as being oriented exactly radially outwardly, while the opposed inner surface of the wire might be described as being oriented radially inwardly, and so forth.

Referring first to FIG. 1, a first exemplary catheter system 1 and method for its use are shown. A physician or other system user U interacts with catheter system 1 so as to perform a therapeutic and/or diagnostic procedure on a patient P, with at least a portion of the procedure being performed by advancing a catheter 3 into a body lumen and aligning an end portion of the catheter with a target tissue of the patient. More specifically, a distal end of catheter 3 is inserted into the patient through an access site A, and is advanced through one of the lumen systems of the body (typically the vasculature network) while user U guides the catheter with reference to images of the catheter and the tissues of the body obtained by a remote imaging system.

Exemplary catheter system 1 will often be introduced into patient P through one of the major blood vessels of the leg, arm, neck, or the like. A variety of known vascular access techniques may also be used, or the system may alternatively be inserted through a body orifice or otherwise enter into any of a number of alternative body lumens. The imaging system will generally include an image capture system 7 for acquiring the remote image data and a display D for presenting images of the internal tissues and adjacent catheter system components. Suitable imaging modalities may include fluoroscopy, computed tomography, magnetic resonance imaging, ultrasonography, combinations of two or more of these, or others.

Catheter 3 may be used by user U in different modes during a single procedure, including two or more of a manual manipulation mode, an automated and powered shape-changing mode, and a combination mode in which the user manually moves the proximal end while a computer articulates the distal portion. More specifically, at least a portion of the distal advancement of catheter 3 within the patient may be performed in a manual mode, with system user U manually manipulating the exposed proximal portion of the catheter relative to the patient using hands H1, H2. Catheter 3 may, for example, be manually advanced over a guidewire, using either over-the-wire or rapid exchange techniques. Catheter 3 may also be self-guiding during manual advancement (so that for at least a portion of the advancement of catheter 3, a distal tip of the catheter may guide manual distal advancement). Automated lateral deflection of a distal portion of the catheter may impose a desired distal steering bend prior to a manual movement, such as near a vessel bifurcation, followed by manual movement through the bifurcation. In addition to such manual movement modes, catheter system 1 may also have a 3-D automated movement mode using computer controlled articulation of at least a portion of the length of catheter 3 disposed within the body of the patient to change the shape of the catheter portion, often to advance or position the distal end of the catheter. Movement of the distal end of the catheter within the body will often be provided per real-time or near real-time movement commands input by user U, with the portion of the catheter that changes shape optionally being entirely within the patient so that the movement of the distal portion of the catheter is provided without movement of a shaft or cable extending through the access site. Still further modes of operation of system 1 may also be implemented, including concurrent manual manipulation with automated articulation, for example, with user U manually advancing the proximal shaft through access site A while computer-controlled lateral deflections and/or changes in stiffness over a distal portion of the catheter help the distal end follow a desired path or reduce resistance to the axial movement.

Referring next to FIG. 1-1 components which may be included in or used with catheter system 1 or catheter 3 (described above) can be more fully understood with reference to an alternative catheter system 10 and its catheter 12. Cather 12 generally includes an elongate flexible catheter body and is detachably coupled to a handle 14, preferably by a quick-disconnect coupler 16. Catheter body 12 has an axis 30, and an input 18 of handle 14 can be moved by a user so as to locally alter the axial bending characteristics along catheter body 12, often for variably articulating an actuated portion 20 of the catheter body. Catheter body 12 will often have a working lumen 26 into or through which a therapeutic and/or diagnostic tool may be advanced from a proximal port 28 of handle 14. Alternative embodiments may lack a working lumen, may have one or more therapeutic or diagnostic tools incorporated into the catheter body near or along actuated portion 20, may have a sufficiently small outer profile to facilitate use of the body as a guidewire, may carry a tool or implant near actuated portion 20 or near distal end 26, or the like. In particular embodiments, catheter body 12 may support a therapeutic or diagnostic tool 8 proximal of, along the length of, and/or distal of actuated portion 20. Alternatively, a separate elongate flexible catheter body may be guided distally to a target site once catheter body 20 has been advanced (with the elongate body for such uses often taking the form and use of a guidewire or guide catheter).

The particular tool or tools included in, advanceable over, and/or introducible through the working lumen of catheter body 20 may include any of a wide range of therapeutic and/or treatment structures. Examples include cardiovascular therapy and diagnosis tools (such as angioplasty balloons, stent deployment balloons or other devices, atherectomy devices, tools for detecting, measuring, and/or characterizing plaque or other occlusions, tools for imaging or other evaluation of, and/or treatment of, the coronary or peripheral arteries, structural heart tools (including prostheses or other tools for valve procedures, for altering the morphology of the heart tissues, chambers, and appendages, and the like), tools for electrophysiology mapping or ablation tools, and the like); stimulation electrodes or electrode implantation tools (such as leads, lead implant devices, and lead deployment systems, leadless pacemakers and associated deployments systems, and the like); neurovascular therapy tools (including for accessing, diagnosis and/or treatment of hemorrhagic or ischemic strokes and other conditions, and the like); gastrointestinal and/or reproductive procedure tools (such as colonoscopic diagnoses and intervention tools, transurethral procedure tools, transesophageal procedure tools, endoscopic bariatric procedure tools, etc.); hysteroscopic and/or falloposcopic procedure tools, and the like; pulmonary procedure tools for therapies involving the airways and/or vasculature of the lungs; tools for diagnosis and/or treatment of the sinus, throat, mouth, or other cavities, and a wide variety of other endoluminal therapies and diagnoses structures. Such tools may make use of known surface or tissue volume imaging technologies (including imaging technologies such as 2-D or 3-D cameras or other imaging technologies; optical coherence tomography technologies; ultrasound technologies such as intravascular ultrasound, transesophogeal ultrasound, intracardiac ultrasound, Doppler ultrasound, or the like; magnetic resonance imaging technologies; and the like), tissue or other material removal, incising, and/or penetrating technologies (such a rotational or axial atherectomy technologies; morcellation technologies; biopsy technologies; deployable needle or microneedle technologies; thrombus capture technologies; snares; and the like), tissue dilation technologies (such as compliant or non-compliant balloons, plastically or resiliently expandable stents, reversibly expandable coils, braids or other scaffolds, and the like), tissue remodeling and/or energy delivery technologies (such as electrosurgical ablation technologies, RF electrodes, microwave antennae, cautery surfaces, cryosurgical technologies, laser energy transmitting surfaces, and the like), local agent delivery technologies (such as drug eluting stents, balloons, implants, or other bodies; contrast agent or drug injection ports; endoluminal repaving structures; and the like), implant and prosthesis deploying technologies, anastomosis technologies and technologies for applying clips or sutures, tissue grasping and manipulation technologies; and/or the like. In some embodiments, the outer surface of the articulation structure may be used to manipulate tissues directly. Other examples of surgical interventions which can impose significant collateral damage, and for which less-invasive endoluminal approaches may be beneficial, include treatments of the brain (including nerve stimulation electrode implantation, neurovascular therapies including for diagnosis and/or treatment of hemorrhagic or ischemic strokes and other conditions, and the like); cardiovascular therapies and diagnoses (including evaluation and/or treatments of the coronary or peripheral arteries, structural heart therapies such as valve procedures or closure of atrial appendages, electrophysiology procedures such as mapping and arrhythmia treatments, and the like); gastrointestinal and/or reproductive procedures (such as colonoscopic diagnoses and interventions, transurethral procedures, transesophageal procedures, endoscopic bariatric procedures, etc.); hysteroscopic and/or falloposcopic procedures, and the like; pulmonary procedures involving the airways and/or vasculature of the lungs; diagnosis and/or treatment of the sinus, throat, mouth, or other cavities, and a wide variety of other endoluminal therapies and diagnoses. Unfortunately, known structures used for different therapies and/or insertion into different body lumens are quite specialized, so that it will often be inappropriate (and possibly ineffective or even dangerous) to try to use a device developed for a particular treatment for another organ system. Non-medical embodiments may similarly have a wide range of tools or surfaces for industrial, assembly, imaging, manipulation, and other uses.

Addressing catheter body 12 of system 10 (and particularly articulation capabilities of actuated portion 20) in more detail, the catheter body generally has a proximal end 22 and a distal end 24 with axis 30 extending between the two. As can be understood with reference to FIG. 2, catheter body 12 may have a short actuated portion 20 of about 3 diameters or less, but will often have an elongate actuated portion 20 extending intermittently or continuously over several diameters of the catheter body (generally over more than 3 diameters, often over more than 10 diameters, in many cases over more than 20 diameters, and in some embodiments over more than 40 diameters). A total length of catheter body 12 (or other flexible articulated bodies employing the actuation components described herein) may be from 5 to 500 cm, more typically being from 15 to 260 cm, with the actuated portion optionally having a length of from 1 to 150 cm (more typically being 2 to 20 cm) and an outer diameter of from 0.65 mm to 5 cm (more typically being from 1 mm to 2 cm). Outer diameters of guidewire embodiments of the flexible bodies may be as small as 0.012" though many embodiments may be more than 2 Fr, with catheter and other medical embodiments optionally having outer diameters as large as 34 French or more, and with industrial robotic embodiments optionally having diameters of up to 1" or more. Exemplary catheter embodiments for structural heart therapies (such as trans-catheter aortic or mitral valve repair or implantation, left atrial appendage closure, and the like) may have actuated portions with lengths of from 3 to 30 cm, more typically being from 5 to 25 cm, and may have outer profiles of from 10 to 30 Fr, typically being from 12 to 18 Fr, and ideally being from 13 to 16 Fr. Electrophysilogy therapy catheters (including those having electrodes for sensing heart cycles and/or electrodes for ablating selected tissues of the heart) may have sizes of from about 5 to about 12 Fr, and articulated lengths of from about 3 to about 30 cm. A range of other sizes might also be implemented for these or other applications.

Figure 1A:
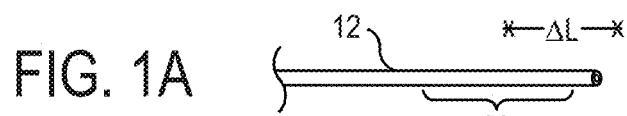
FIGS. 1A-1C schematically illustrate a plurality of alternative articulation states of the distal portion of the catheter in the system of FIG. 1.
Figure 1B:
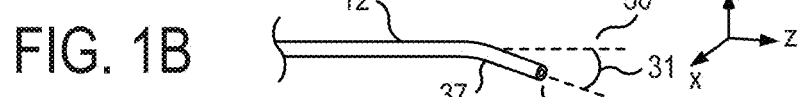
Figure 1C:
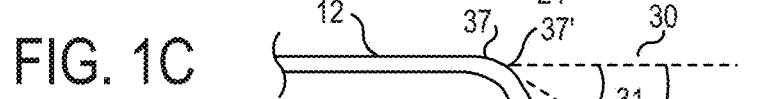

Referring now to FIGS. 1A, 1B, and 1C, system 10 may be configured to articulate actuated portion 20. Articulation will often allow movement continuously throughout a range of motion, though some embodiments may provide articulation in-part or in-full by selecting from among a plurality of discrete articulation states. Catheters having opposed axial extension and contraction actuators are described herein that may be particularly beneficial for providing continuous controlled and reversible movement, and can also be used to modulate the stiffness of a flexible structure. These continuous and discrete systems share many components (and some systems might employ a combination of both approaches).

First addressing the use of a discrete state system, FIG. 1A, system 10 can, for example, increase an axial length of actuated portion 20 by one or more incremental changes in length $\Delta L$. An exemplary structure for implementation of a total selectable increase in length $\Delta L$ can combine a plurality of incremental increases in length $\Delta L = \Delta L_1 + \Delta L_2 + \ldots$ ), as can be understood with reference to FIG. 5. As shown in FIGS. 1B and 1C, system 10 may also deflect distal end 24 to a first bent state having a first bend angle 31 between unarticulated axis 30 and an articulated axis 30' (as shown schematically in FIG. 1B), or to a second bent state having a total bend angle 33 (between articulated axis 30 and articulated axis 30"), with this second bend angle being greater than the first bend angle (as shown schematically in FIG. 1C). An exemplary structure that could optionally be used by combining multiple discrete bend angle increments to form a total bend angle 33 (and/or which could also provide continuous movement) can be understood with reference to FIG. 4C. Regardless, the additional total cumulative bend angle 33 may optionally be implemented by imposing the first bend 31 (of FIG. 1B) as a first increment along with one or more additional bend angle increments 35. The incremental changes to actuated portion 20 may be provided by fully inflating and/or deflating actuation balloons of the catheter system. In fact, some embodiments could even be capable of only a single bend and/or elongation increment, but would more often have significantly more incremental articulation state options beyond those shown in FIGS. 1A-1C (and still more often would provide bending throughout a continuous range), so that a number of bend angles, bend orientations, axial lengths, and the like can and will often be available. For example, system 10 may be configured to provide any of a plurality of discrete alternative total bend angles (often being 3 or more, 5 or more, 10 or more, 20 or more, or even 40-100 angles, with embodiments providing between 3 and 20 alternative bend angles in a given lateral orientation), with one of the alternative bend angles typically comprising a resting or unarticulated angle (optionally being straight or having a zero degree bend angle; alternatively having some preset or physician-imposed bend). Incremental or continuous bend capabilities may be limited to a single lateral orientation, but will more typically be available in different lateral orientations, most typically in any of 3 or 4 orientations (for example, using balloons positioned along two pairs of opposed lateral axes, sometimes referred to as the +X, −X, +Y and −Y orientations), and by combining different bend orientations, in intermediate orientations as well. Continuous positioning may be implemented using similar articulation structures by partially inflating or deflating balloons or groups of balloons.

System 10 may also be configured to provide catheter 12 with any of a plurality of discrete alternative total axial lengths. As with the bend capabilities, such length actuation may also be implemented by inflating balloons of a balloon array structure. To provide articulation with the simple balloon array structures described herein, each actuation may be implemented as a combination of discrete, predetermined actuation increments (optionally together with one or more partial or modulated actuation) but may more often be provided using modulated or partial inflation of some, most, or all of the balloons. Hence, regardless of whether or not a particular catheter includes such bend-articulation capabilities, system 10 may be configured to provide catheter 12 with at least any of a plurality of discrete alternative total axial lengths (often being 3 or more, 5 or more, 10 or more, 20 or more, or even 40-100 lengths, with most embodiments providing between 3 and 20 alternative total lengths), more typically providing lengths throughout an elongation range. Nonetheless, embodiments of system 10 can be configured to implement each total actuation, in-part or in-full, as a combination of discrete, predetermined actuation increments. Some or all of the discrete actuation increments (and the associated balloon(s)) may have an associated location 37 or length segment along axis 30 within actuated portion 20, optionally an associated lateral X-Y orientation, and/or an associated predetermined incremental actuation amount. The lateral X-Y orientation of at least some of the actuation increments may be transverse to the local axis of catheter body 12 (shown as the Z axis in FIG. 1B) and the relationship between the positions of the various actuation balloons 36 and the lateral deflection axes X-Y can be understood with reference to FIG. 4. Regarding the incremental actuation amount, inflation and/or deflation of a particular balloon may be characterized using an incremental bend angle, an axial offset change, axial elongation displacement, and/or the like. Each actuation increment (including inflation or deflation of one or more balloon) may also have an associated increment actuation time (for full inflation or deflation of the balloon, with these often being different). While these times may be variably controlled in some embodiments, optionally with controlled variations in fluid flow (such as ramp-up or ramp downs) during a single actuation increment, many embodiments may instead use relatively uniform incremental actuation pressures and flow characteristics (optionally via fixed throttled or damped fluid flows into and/or out of the balloons). Nonetheless, controllable (and relatively high) overall distal velocities may be provided from coordinated timing of the discrete actuation increments along the length of the catheter body, for example, by controlled initiating of inflation of multiple balloons so that at least a portion of their associated inflation times overlap. An actuation increment implementation structure (generally one or more associated actuation balloons) can be associated with each actuation increment, with the actuation structure optionally being commanded to be in either an actuated configuration or an unactuated configuration (such as with the actuation balloon being fully inflated or fully deflated, respectively). Varying of the bend angles may, for example, be implemented by changing the number of balloons along one side of the catheter body 12 that are commanded to be fully inflated at a given time, with each additional balloon inflation incrementally increasing the overall bend angle. The balloons will often have differing associated axial locations 37, 37' along actuated portion 20. This can allow the axial location of a commanded bend increment to be selected from among a plurality of discrete axial locations 37, 37' by selection of the associated balloon axial locations to be included in the inflated group, which will typically be less than all of the balloons in an array. Desired total actuations can be implemented by identifying and combining a sub-set of bend increments (and/or other actuation increments) from among the available incremental actuations and inflating the associated sub-set of actuation balloons from among the overall balloon array or arrays). Hence, along with allowing control over the total bend angle, appropriate selection of the sub-set from among the pre-determined bend increments along actuated portion 20 may allow control over an average radius of the bend, for example, by axially distributing or separating the subset of discrete bend increments over an overall length of the bend. Control over an axial location of the overall bend can be provided by selecting the axial locations of the inflated balloon subset; and control over the lateral X-Y orientation of the total bend can be provided by selecting the subset from among the differing available incremental lateral orientations so as to combine together to approximate a desired orientation; and the like.

As suggested above, actuated portion 20 can often be articulated into any of a plurality of different overall bend profiles with a plurality of differing bend angles. Additionally, and often substantially independently of the bend angle, actuated portion 20 can be reconfigured so as to bend in any of a plurality of differing lateral bend directions (in the cross-sectional or X-Y plane, often through a combination of discrete incremental bend orientations), can bend at any of a plurality of axial locations, and/or can be actuated to bend with any of a plurality of differing overall bend radii. Furthermore, the bend orientation and/or bend radius may controllably differ along the axial length of actuated portion 20. Interestingly, and contrary to most catheter steering systems, some embodiments of the present invention may not be capable of driving axis 30 of catheter body 20 to intermediate bend angles between sums of the discrete bend increments 31, 35, as total articulation may be somewhat digital in nature. Note, however, that while some or all of the actuation increments may be uniform, the individual bend angles and the like may alternatively be non-uniform (such as by including balloons of different sizes within the array), so that a subset of the pre-determined bend increments can be configured to allow fine-tuning of bend angle and the like. Alternatively, as total actuation will often be a sum of a series of incremental actuations, one or more balloons can be configured to provide analog (rather than digital) articulation, with the analog movement often being sufficient to bridge between discrete digital articulations and thereby providing a continuous position range. This can be implemented, for example, by configuring the system to variably partially inflate one or more of the balloons of the array (rather than relying on full inflation or deflation) such as by using an associated positive displacement pump. Still more commonly, balloons or groups of balloons may be inflated to variable pressures throughout a range, providing effectively analog movement throughout the range of motion of the system.

Conveniently, the overall actuation configuration or state of catheter body 12 may be described using a plurality of scalar quantities that are each indicative of the states of associated actuation increments and balloons, with those incremental states optionally being combined to define an actuation state vector or matrix. Where the actuation increments are digital in nature (such as being associated with full inflation or full deflation of a balloon), some or all of the actuation state of catheter 12 may be described by a digital actuation state vector or matrix. Such digital embodiments (particularly those without analog components) may take advantage of these simple digital state vectors or digital state matrices to significantly facilitate data manipulations and enhance control signal processing speeds, helping to lessen minimum desired processing capabilities and overall system costs. Note also that many of the resolution, flexibility, and accuracy advantages of the balloon array systems described above are also available when all of the balloons of the array are inflatable to variable inflation states. Hence, some embodiments of the systems described herein may include fluid control systems that direct modulated quantities and/or pressures of fluids to multiple balloons along one or more fluid transmission channels. Control systems for such embodiments may employ similar processing approaches, but with the balloon inflation scalar values having variable values in a range from minimal or no effective inflation to fully inflated.

Figure 2:
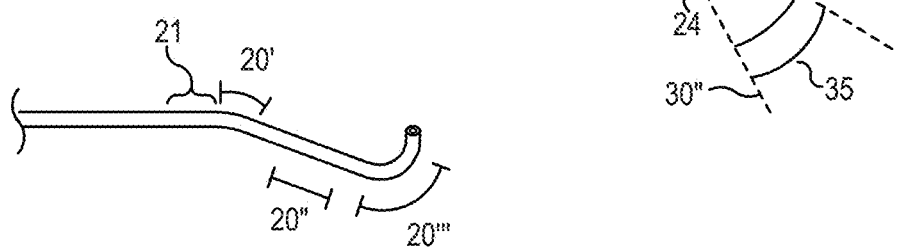
FIG. 2 schematically illustrates an alternative distal structure having a plurality of articulatable sub-regions or segments so as to provide a desired total number of degrees of freedom and range of movement.

Referring now to FIGS. 1-1 and 2, embodiments of articulation system 10 will move the distal end 24 of catheter 12 toward a desired position and/or orientation in a workspace relative to a base portion 21, with the base portion often being adjacent to and proximal of actuated portion 20. Note that such articulation may be relatively (or even completely) independent of any bending of catheter body 12 proximal of base portion 21. The location and orientation of proximal base 21 (relative to handle 14 or to another convenient fixed or movable reference frame) may be identified, for example, by including known catheter position and/or orientation identification systems in system 10, by including radiopaque or other high-contrast markers and associated imaging and position and/or orientation identifying image processing software in system 10, by including a flexible body state sensor system along the proximal portion of catheter body 12, by foregoing any flexible length of catheter body 12 between proximal handle 14 and actuated portion 20, or the like. A variety of different degrees of freedom may be provided by actuated portion 20. Exemplary embodiments of articulation system 10 may allow, for example, distal end 24 to be moved with 2 degrees of freedom, 3 degrees of freedom, 4 degrees of freedom, 5 degrees of freedom, or 6 degrees of freedom relative to base portion 21. The number of kinematic degrees of freedom of articulated portion 20 may be much higher in some embodiments, particularly when a number of different alternative subsets of the balloon array could potentially be in different inflation states to give the same resulting catheter tip and/or tool position and orientation.

Note that the elongate catheter body 12 along and beyond actuated portion 20 may (and often should) remain flexible before, during, and after articulation, so as to avoid inadvertently applying lateral and/or axial forces to surrounding tissues that are beyond a safe threshold. Nonetheless, embodiments of the systems described herein may locally and controllably increase a stiffness of one or more axial portions of catheter body 12, along actuated portion 20, proximal of actuated portion 20, and/or distal of actuated portion 20. Such selective stiffening of the catheter body may be implemented with or without active articulation capabilities, may extend along one or more axial portion of catheter body 12, and may alter which portions are stiffened and which are more flexible in response to commands from the user, sensor input (optionally indicating axial movement of the catheter), or the like.

As shown in FIG. 2, actuated portion 20 may comprise an axial series of 2 or more (and preferably at least 3) actuatable sub-portions or segments 20', 20", 20''', with the segments optionally being adjacent to each other, or alternatively separated by relatively short (less than 10 diameters) and/or relatively stiff intermediate portions of catheter 12. Each sub-portion or segment may have an associated actuation array, with the arrays working together to provide the desired overall catheter shape and degrees of freedom to the tip or tool. At least 2 of the sub-portions may employ similar articulation components (such as similar balloon arrays, similar structural backbone portions, similar valve systems, and/or similar software). Commonality may include the use of corresponding actuation balloon arrays, but optionally with the characteristics of the individual actuation balloons of the different arrays and the spacing between the locations of the arrays varying for any distal tapering of the catheter body. There may be advantages to the use of differentiated articulation components, for example, with proximal and distal sub portions, 20', 20''' having similar structures that are configured to allow selective lateral bending with at least two degrees of freedom, and intermediate portion 20" being configured to allow variable axial elongation. In many embodiments, however, at least two (and preferably all) segments are substantially continuous and share common components and geometries, with the different segments having separate fluid channels and being separately articulatable but each optionally providing similar movement capabilities.

For those elongate flexible articulated structures described herein that include a plurality of axial segments, the systems will often determine and implement each commanded articulation of a particular segment as a single consistent articulation toward a desired segment shape state that is distributed along that segment. In some exemplary embodiments, the nominal or resting segment shape state may be constrained to a 3 DOF space (such as by continuous combinations of two transverse lateral bending orientations and an axial (elongation) orientation in an X-Y-Z work space). In some of the exemplary embodiments described herein (including at least some of the helical extension/contraction embodiments), lateral bends along a segment may be at least approximately planar when the segment is in or near a design axial length configuration (such as at or near the middle of the axial or Z range of motion), but may exhibit a slight but increasing off-plane twisting curvature as the segment moves away from that design configuration (such as near the proximal and/or distal ends of the axial range of motion). The off-plane bending may be repeatably accounted for kinematically by determining the changes in lateral orientation of eccentric balloons resulting from winding and unwinding of helical structures supporting those balloons when the helical structures increase and decrease in axial length. For example, a segment may be commanded (as part of an overall desired pose or movement) to bend in a −Y orientation with a 20 degree bend angle. If the bend is to occur at a design axial length (such as at the middle of the axial range of motion), and assuming balloons (or opposed balloon pairs) at 4 axial bend locations can be used to provide the commanded bend, the balloons (or balloon pairs) may each be inflated or deflated to bend the segment by about 5 degrees (thereby providing a total bend of 5*4 or 20 degrees) in the −Y orientation. If the same bend is to be combined with axial lengthening of the segment to the end of its axial range of motion, the processor may determine that the segment may would exhibit some twist (say 2 degrees) so that there would be a slight +X component to the commanded bend, so that the processor may compensate for the twist by commanding a corresponding −X bend component, or by otherwise compensating in the command for another segment of the flexible body.

Figure 3:
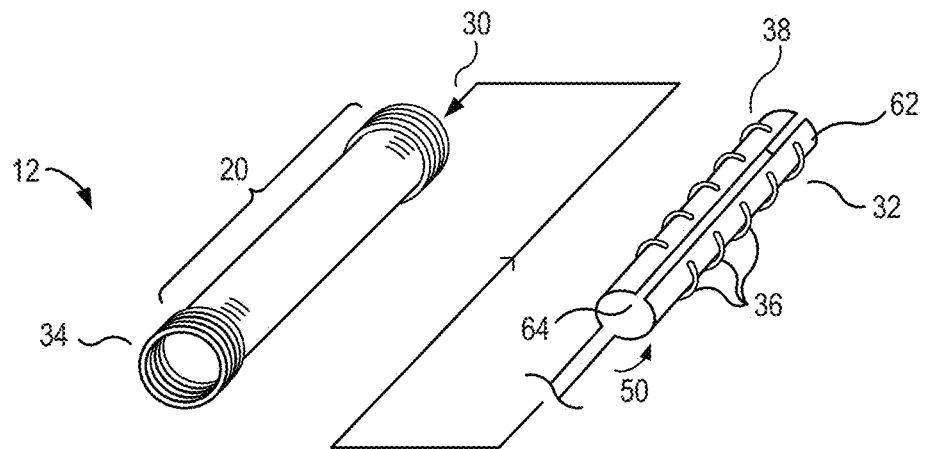
FIG. 3 is a simplified exploded perspective view showing a balloon array that can be formed in a substantially planar configuration and rolled into a cylindrical configuration, and which can be mounted coaxially to a helical coil or other skeleton framework for use in the catheter of the system of FIGS. 1 and 2.
Figure 5:
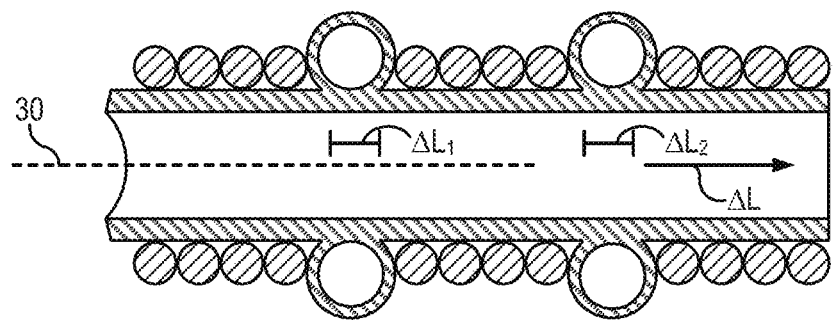
FIG. 5 is a simplified transverse cross-section of the articulatable catheter of FIG. 4, with a plurality of laterally opposed balloons inflated so that the catheter is in an axially elongated state.

Referring to FIGS. 3 and 5, catheter body 12 of system 10 includes an actuation array structure 32 mounted to a structural skeleton (here in the form of a helical coil 34). Exemplary balloon array 32 includes fluid expandable structures or balloons 36 distributed at balloon locations along a flexible substrate 38 so as to define an M×N array, in which M is an integer number of balloons distributed about a circumference 50 of catheter 12 at a given location along axis 30, and N represents an integer number of axial locations along catheter 12 having actuation balloons. Circumferential and axial spacing of the array element locations will generally be known, and will preferably be regular. This first exemplary actuation array includes a 4×4 array for a total of 16 balloons; alternative arrays may be from 1×2 arrays for a total of 2 balloons to 8×200 arrays for a total of 1600 balloons (or beyond), more typically having from 3×3 to 6×20 arrays. While balloon arrays of 1×N may be provided (particularly on systems that rely on rotation of the catheter body to orient a bend), M will more typically be 2 or more, more often being from 3 to 8, and preferably being 3 or 4. Similarly, while balloon arrays of M×1 may be provided to allow imposition of a single bend increment at a particular location in any of a number of different desired lateral orientations, array 32 will more typically have an N of from 2 to 200, often being from 3 to 20 or 3 to 100. In contraction/expansion embodiments described below, multiple arrays may be provided with similar M×N arrays mounted in opposition. Not all array locations need have inflatable balloons, and the balloons may be arranged in more complex arrangements, such as with alternating circumferential numbers of balloons along the axis, or with varying or alternating separation between balloons along the axial length of the array.

The balloons of a particular segment or that are mounted to a common substrate may be described as forming an array, with the actuation balloon array structure optionally being used as a sub-array in a multi-segment or opposed articulation system. The combined sub-arrays together may form an array of the overall device, which may also be described simply as an array or optionally an overall or combined array. Exemplary balloon arrays along a segment or sub-portion of articulated portion 20 include 1×8, 1×12, and 1×16 arrays for bending in a single direction (optionally with 2, 3, 4, or even all of the balloons of the segment in fluid communication with a single common inflation lumen so as to be inflated together) and 4×4, 4×8, and 4×12 arrays for X-Y bending (with axially aligned groups of 2-12 balloons coupled with 4 or more common lumens for articulation in the +X, −X, +Y, and −Y orientations). Exemplary arrays for each segment having the opposed extension/retraction continuous articulation structures described herein may be in the form of a 3×2N, 3×3N, 4×2N, or 4×3N balloons arrays, for example, 3×2, 3×4, 3×6, 3×8, 3×10, 3×12, 3×14, and 3×16 arrays with 6 to 48 balloons, with the 3 lateral balloon orientations separated by 120 degrees about the catheter axis. Extension balloons will often be axially interspersed with contraction balloons along each lateral orientation, with separate 3×N arrays being combined together in a 3×2N extension/contraction array for the segment, while two extension balloons may be positioned axially between each contraction balloon for 3×3N arrangements. The contraction balloons may align axially and/or be in plane with the extension balloons they oppose, though it may be advantageous in some embodiments to arrange opposed balloons offset from a planer arrangement, so that (for example) two balloons of one type balance one balloon of the other, or vice versa. The extension balloons along each orientation of the segment may share a common inflation fluid supply lumen while the contraction balloons of the segment for each orientation similarly share a common lumen (using 6 fluid supply lumens per segment for both 3×2N and 3×3N arrays). An extension/contraction catheter may have from 1 to 8 such segments along the articulated portion, more typically from 1 to 5 segments, and preferably being 2 to 4 segments. Other medical and non-medical elongate flexible articulated structures may have similar or more complex balloon articulation arrays.

As can be seen in FIGS. 3, 4A, 4B, and 4C, the skeleton will often (though not always) include an axial series of loops 42. When the loops are included in a helical coil 34, the coil may optionally be biased so as to urge adjacent loops 42 of the coil 34 toward each other. Such axially compressive biasing may help urge fluid out and deflate the balloons, and may by applied by other structures (inner and/or outer sheath(s), pull wires, etc.) with or without helical compression. Axial engagement between adjacent loops (directly, or with balloon walls or other material of the array between loops) can also allow compressive axial forces to be transmitted relatively rigidly when the balloons are not inflated. When a particular balloon is fully inflated, axial compression may be transmitted between adjacent loops by the fully inflated balloon wall material and by the fluid within the balloons. Where the balloon walls are non-compliant, the inflated balloons may transfer these forces relatively rigidly, though with some flexing of the balloon wall material adjacent the balloon/skeleton interface. Rigid or semi-rigid interface structures which distribute axial loads across a broader balloon interface region may limit such flexing. Axial tension forces (including those associated with axial bending) may be resisted by the biasing of the skeleton (and/or by other axial compressive structures). Alternative looped skeleton structures may be formed, for example, by cutting hypotube with an axial series of lateral incisions across a portion of the cross-section from one or more lateral orientations, braided metal or polymer elements, or the like. Non-looped skeletons may be formed using a number of alternative known rigid or flexible robotic linkage architectures, including with structures based on known soft robot structures. Suitable materials for coil 34 or other skeleton structures may comprise metals such as stainless steel, spring steel, superelastic or shape-memory alloys such as Nitinol™ alloys, polymers, fiber-reinforced polymers, high-density or ultrahigh-density polymers, or the like.

When loops are included in the skeleton, actuation array 32 can be mounted to the skeleton with at least some of the balloons 36 positioned between two adjacent associated loops 42, such as between the loops of coil 34. Referring now to FIG. 4C, an exemplary deflated balloon 36i is located between a proximally adjacent loop 42i and a distally adjacent loop 42ii, with a first surface region of the balloon engaging a distally oriented surface of proximal loop 34i, and a second surface region of the balloon engaging a proximally oriented surface of distal loop 42ii. The walls of deflated balloon 36i have some thickness, and the proximal and distal surfaces of adjacent loops 42i and 42ii maintain a non-zero axial deflated offset 41 between the loops. Axial compression forces can be transferred from the loops through the solid balloon walls. Alternative skeletal structures may allow the loops to engage directly against each other so as to have a deflated offset of zero and directly transmit axial compressive force, for example by including balloon receptacles or one or more axial protrusions extending from one or both loops circumferentially or radially beyond the balloon and any adjacent substrate structure. Regardless, full inflation of the balloon will typically increase the separation between the adjacent loops to a larger full inflation offset 41'. The simplified lateral cross-sections of FIGS. 4B, 4C, and 5 schematically show a direct interface engagement between a uniform thickness thin-walled balloon and a round helical coil loop. Such an interface may result in relatively limited area of the balloon wall engaging the coil and associated deformation under axial loading. Alternative balloon-engaging surface shapes along the coils (often including locally increased convex radii, locally flattened surfaces, and/or local concave balloon receptacles) and/or along the coil-engaging surfaces of the balloon (such as by locally thickening the balloon wall to spread the engagement area), and/or providing load-spreading bodies between the balloons and the coils may add axial stiffness. A variety of other modifications to the balloons and balloon/coil interfaces may also be beneficial, including adhesive bonding of the balloons to the adjacent coils, including folds or material so as to inhibit balloon migration, and the like.

Inflation of a balloon can alter the geometry along catheter body 12, for example, by increasing separation between loops of a helical coil so as to bend axis 30 of catheter 12. As can be understood with reference to FIGS. 1B, 1C and 4-4C, selectively inflating an eccentric subset of the balloons can variably alter lateral deflection of the catheter axis. As can be understood with reference to FIGS. 1A, 4, and 5, inflation of all (or an axisymmetric subset) of the balloons may increase an axial length of the catheter structure. Inflating subsets of the balloons that have a combination of differing lateral orientations and axial positions can provide a broad range of potential locations and orientations of the catheter distal tip 26, and/or of one or more other locations along the catheter body (such as where a tool is mounted).

Some or all of the material of substrate 38 included in actuation array 32 will often be relatively inelastic. It may, however, be desirable to allow the skeleton and overall catheter to flex and/or elongate axially with inflation of the balloons or under environmental forces. Hence, array 32 may have cutouts 56 so as to allow the balloon array to move axially with the skeleton during bending and elongation. The array structure could alternatively (or in addition) be configured for such articulation by having a serpentine configuration or a helical coiled configuration. Balloons 36 of array 32 may include non-compliant balloon wall materials, with the balloon wall materials optionally being formed integrally from material of the substrate or separately. Note that elastic layers or other structures may be included in the substrate for use in valves and the like, and that some alternative balloons may include elastic and/or semi-compliant materials.

Figure 4A:
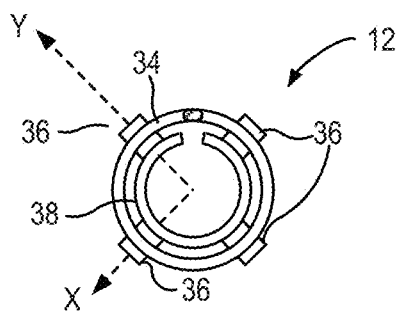
FIGS. 4A and 4B are a simplified cross-section and a simplified transverse cross-section, respectively, of an articulatable catheter for use in the system of FIG. 1, shown here with the balloons of the array in an uninflated, small axial profile configuration and between loops of the coil.
Figure 4B:
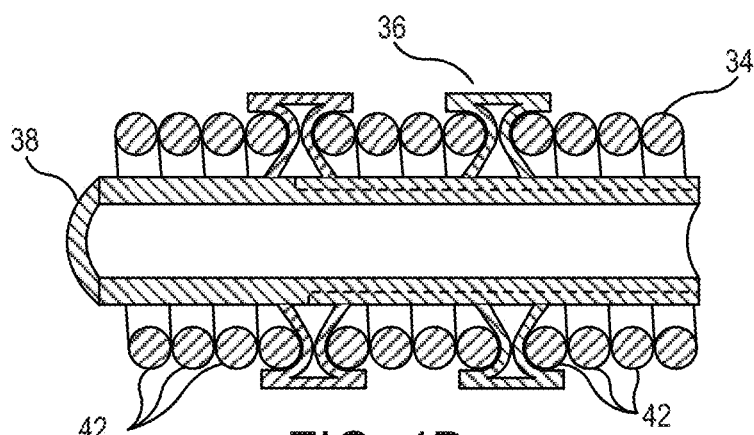
Figure 4C:
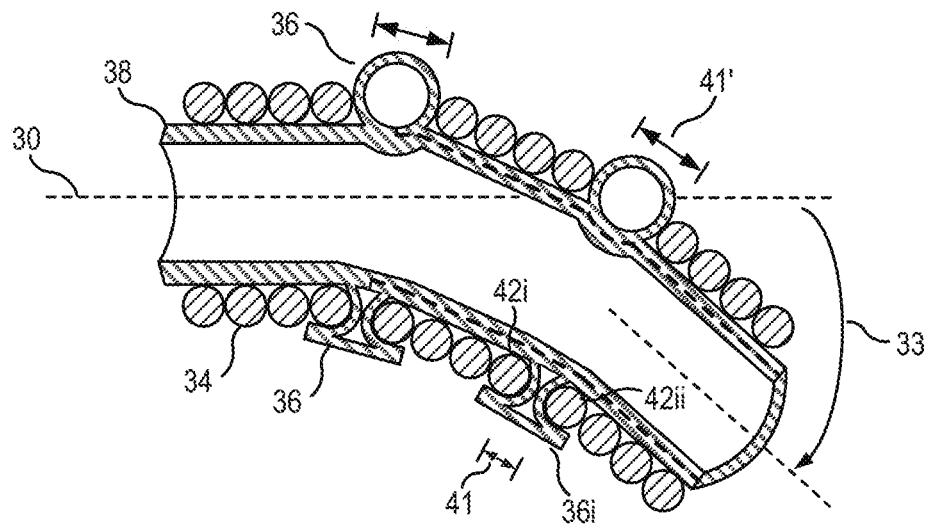
FIG. 4C is a simplified transverse cross-section of the articulatable catheter of FIGS. 4A and 4B, with a plurality of axially aligned balloons along one side of the articulatable region of the catheter inflated so that the catheter is in a laterally deflected state.

Referring to FIGS. 3, 4A, and 5, substrate 38 of array 32 is laterally flexible so that the array can be rolled or otherwise assume a cylindrical configuration when in use. The cylindrical array may be coaxially mounted to (such as being inserted into or radially outwardly surrounding) the helical coil 34 or other structural backbone of the catheter. The cylindrical configuration of the array will generally have a diameter that is equal to or less than an outer diameter of the catheter. The opposed lateral edges of substrate 38 may be separated by a gap as shown, may contact each other, or may overlap. Contacting or overlapping edges may be affixed together (optionally so as to help seal the catheter against radial fluid flow) or may accommodate relative motion (so as to facilitate axial flexing). In some embodiments, lateral rolling or flexing of the substrate to form the cylindrical configuration may be uniform (so as to provide a continuous lateral curve along the major surfaces), while in other embodiments intermittent axial bend regions of the substrate may be separated by axially elongate relatively flat regions of the substrate so that a cylindrical shape is approximated by a prism-like arrangement (optionally so as to limit bending of the substrate along balloons, valves, or other array components).

It will often (though not always) be advantageous to form and/or assemble one or more components of the array structure in a flat, substantially planar configuration (and optionally in a linear configuration as described below). This may facilitate, for example, partial or final formation of balloons 36 on substrate 38, or alternatively, attachment of pre-formed balloons to the substrate. The flat configuration of the substrate may also facilitate the use of known extrusion or microfluidic channel fabrication techniques to provide fluid communication channels 52 so as to selectively couple the balloons with a fluid inflation fluid source or reservoir 54, and the like. Still further advantages of the flat configuration of the substrate may include the use of electrical circuit printing techniques to fabricate electrical traces and other circuit components, automated 3-D printing techniques (including additive and/or removal techniques) for forming valves, balloons, channels, or other fluid components that will be supported by substrate 38, and the like. When the substrate is in a rolled, tubular, or flat planar configuration, the substrate will typically have a first major surface 62 adjacent balloons 36, and a second major surface 64 opposite the first major surface (with first major surface 62 optionally being a radially inner or outer surface and second major surface 64 being a radially outer or inner surface, respectively, in the cylindrical configuration). To facilitate flexing substrate 38 and array 32 into the rolled configuration, relief cuts or channels may be formed extending into the substrate from the first and/or second major surfaces, or living hinge regions may otherwise be provided between relatively more rigid portions of the substrate. To further avoid deformation of the substrate adjacent any valves or other sensitive structures, local stiffening reinforcement material may be added, and/or relief cuts or apertures may be formed partially surrounding the valves. In some embodiments, at least a portion of the array components may be formed or assembled with the substrate at least partially in a cylindrical configuration, such as by bonding layers of the substrate together while the substrate is at least locally curved, forming at least one layer of the substrate as a tube, selectively forming cuts in the substrate (optionally with a femtosecond, picosecond, or other laser) to form fluid, circuit, or other components or allow for axial flexing and elongation (analogous to cutting a stent to allow for axial flexing and radial expansion) and/or to form at least some of the channels, and bonding the layers together after cutting.

As can be understood with reference to FIGS. 5-5C, substrate 38 of array 32 may include one or more layers 70, 72, 74 . . . of flexible substrate material. The substrate layers may comprise known flexible and/or rigid microfluidic substrate materials, such as polydimethylsiloxane (PDMS), polyimide (PI), polyethylene (PE) and other polyolefins, polystyrene (PS), polyethylene terephthalate (PET), polypropylene (PP), polycarbonate (PC), nanocomposite polymer materials, glass, silicon, cyclic olefin copolymer (COC), polymethyl methacrylate (PMMA), polyetheretherketone (PEEK), polyester, polyurethane (PU), and/or the like. These and still further known materials may be included in other components of actuation array 32, including known polymers for use in balloons (which will often include PET, PI, PE, polyether block amide (PEBA) polymers such as PEBAX™ polymers, nylons, urethanes, polyvinyl chloride (PVC), thermoplastics, and/or the like for non-compliant balloons; or silicone, polyurethane, semi-elastic nylons or other polymers, latex, and/or the like for compliant or semi-compliant balloons). Additional polymers than may be included in the substrate assembly may include valve actuation elements (optionally including shape memory alloy structures or foils; phase-change actuator materials such as paraffin or other wax, electrical field sensitive hydrogels, bimetallic actuators, piezoelectric structures, dielectric elastomer actuator (DEA) materials, or the like). Hence, while some embodiments may employ homogenous materials for actuation array 32, many arrays and substrate may instead be heterogeneous.

Fortunately, techniques for forming and assembling the components for actuation array 32 may be derived from a number of recent (and relatively widely-reported) technologies. Suitable techniques for fabricating channels in substrate layer materials may include laser micromachining (optionally using femtosecond or picosecond lasers), photolithography techniques such as dry resist technologies, embossing (including hot roller embossing), casting or molding, xerographic technologies, microthermoforming, stereolithography, 3-D printing, and/or the like. Suitable 3-D printing technologies that may be used to form circuitry, valves, sensors, and the like may include stereolithography, digital light processing, laser sintering or melting, fused deposition modeling, inkjet printing, selective deposition lamination, electron beam melting, or the like. Assembly of the components of actuation array 32 may make use of laser, thermal, and/or adhesive bonding between layers and other components, though laser, ultrasound, or other welding techniques; microfasteners, or the like may also be used. Electrical element fabrication of conductive traces, actuation, signal processor, and/or sensor components carried by substrate 38 may, for example, use ink-jet or photolithography techniques, 3-D printing, chemical vapor deposition (CVD) and/or more specific variants such as initiated chemical vapor deposition (iCVD), robotic microassembly techniques, or the like, with the electrical traces and other components often comprising inks and other materials containing metals (such as silver, copper, or gold) carbon, or other conductors. Many suitable fabrication and assembly techniques have been developed during development of microfluidic lab-on-a-chip or lab-on-a-foil applications. Techniques for fabricating medical balloons are well developed, and may optionally be modified to take advantage of known high-volume production techniques (optionally including those developed for fabricating bubble wrap, for corrugating extruded tubing, and the like). Note that while some embodiments of the actuation array structures described herein may employ fluid channels sufficiently small for accurately handling of picoliter or nanoliter fluid quantities, other embodiments will include channels and balloons or other fluid-expandable bodies that utilize much larger flows so as to provide desirable actuation response times. Balloons having at least partially flexible balloon walls may provide particular advantages for the systems described herein, but alternative rigid fluid expandable bodies such as those employing pistons or other positive displacement expansion structures may also find use in some embodiments.

The structures of balloons 36 as included in actuation array 32 may be formed of material integral with other components of the array, or may be formed separately and attached to the array. For example, as shown in FIGS. 5B and 5C, balloons 36 may be formed from or attached to a first sheet 74 of substrate material that can be bonded or otherwise affixed to another substrate layer 72 or layers. The material of the balloon layer 74 may optionally cover portions of the channels directly, or may be aligned with apertures 78 that open through an intermediate substrate layer surface between the channels and the balloons. Apertures 78 may allow fluid communication between each balloon and at least one associated channel 52. Alternative methods for fabricating individual balloons are well known, and the formed balloons may be affixed to the substrate 38 by adhesive bonding. Balloon shapes may comprise relatively simple cylinders or may be somewhat tailored to taper to follow an expanded offset between loops of a coil, to curve with the cylindrical substrate and/or to engage interface surfaces of the skeleton over a broader surface area and thereby distribute actuation and environmental loads. Effective diameters of the balloons in the array may range from about 0.003 mm to as much as about 2 cm (or more), more typically being in a range from about 0.3 mm to about 2 mm or 5 mm, with the balloon lengths often being from about 2 to about 15 times the diameter. Typical balloon wall thicknesses may range from about 0.0002 mm to about 0.004 mm (with some balloon wall thicknesses being between 0.0002 mm and 0.020 mm), and full inflation pressures in the balloons may be from about 0.2 to about 40 atm, more typically being in a range from about 0.4 to about 30 atm, and in some embodiments being in a range from about 10 to about 30 atm, with high-pressure embodiments operating at pressures in a range as high as 20-45 atm and optionally having burst pressures of over 50 atm.

Referring now to FIG. 5, balloons 36 will generally be inflated using a fluid supply system that includes a fluid source 54 (shown here as a pressurized single-use cartridge) and one or more valves 90. At least some of the valves 90 may be incorporated into the balloon array substrate, with the valves optionally being actuated using circuitry printed on one or more layers of substrate 38. With or without substrate-mounted valves that can be used within a patient body, at least some of the valves may be mounted to housing 14, or otherwise coupled to the proximal end of catheter 12. Valves 90 will preferably be coupled to channels 52 so as to allow the fluid system to selectively inflate any of a plurality of alternative individual balloons or subsets of balloons 36 included in actuation array 32, under the direction of a processor 60. Hence, processor 60 will often be coupled to valves 90 via conductors, the conductors here optionally including flex circuit traces on substrate 38.

Figure 6:
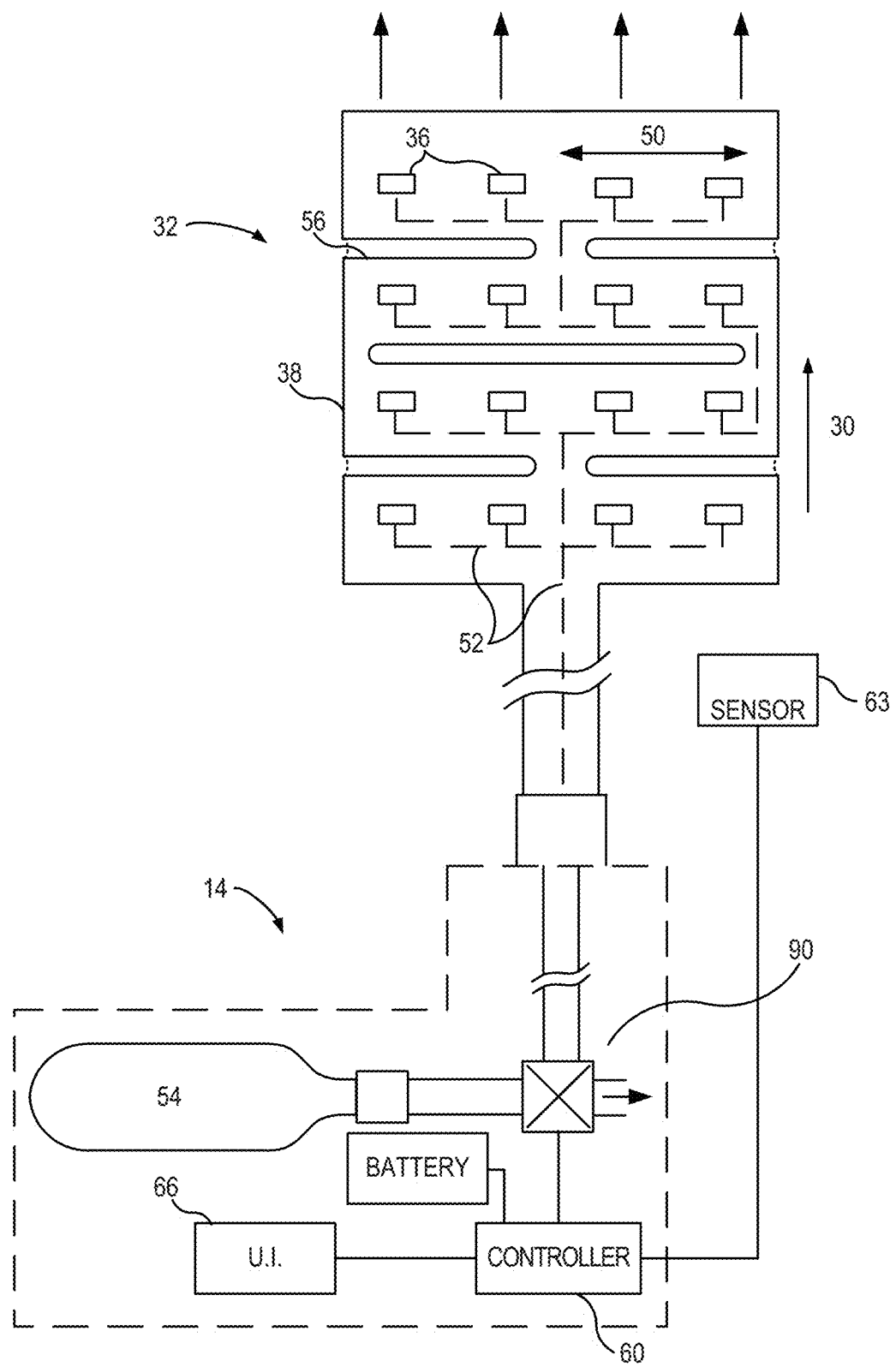
FIG. 6 schematically illustrates components for use in the catheter system of FIG. 1, including the balloon array, inflation fluid source, fluid control system, and processor.

Referring still to FIG. 6, fluid source 54 may optionally comprise a separate fluid reservoir and a pump for pressurizing fluid from the reservoir, but will often include a simple tank or cartridge containing a pressurized fluid, the fluid optionally being a gas or a gas-liquid mixture. The cartridge will often maintain the fluid at a supply pressure at or above a full inflation pressure range of balloons 36, with the cartridge optionally being gently heated by a resistive heater or the like (not shown) in housing 14 so as to maintain the supply pressure within a desired range in the cartridge during use. Supply pressures will typically exceed balloon inflation pressures sufficiently to provide balloon inflation times within a target threshold given the pressure loss through channels 52 and valves 90, with typical supply pressures being between 10 and 210 atm, and more typically being between 20 and 60 atm. Suitable fluids may include known medical pressurized gases such as carbon dioxide, nitrogen, oxygen, nitrous oxide, air, known industrial and cryogenic gasses such as helium and/or other inert or noble gasses, refrigerant gases including fluorocarbons, and the like. Note that the pressurized fluid in the canister can be directed via channels 52 into balloons 36 for inflation, or the fluid from the canister (often at least partially a gas) may alternatively be used to pressurize a fluid reservoir (often containing or comprising a benign biocompatible liquid such as water or saline) so that the balloon inflation fluid is different than that contained in the cartridge. Where a pressurized liquid or gas/liquid mixture flows distally along the catheter body, enthalpy of vaporization of the liquid in or adjacent to channels 52, balloons 36, or other tissue treatment tools carried on the catheter body (such as a tissue dilation balloon, cryogenic treatment surface, or tissue electrode) may be used to therapeutically cool tissue. In other embodiments, despite the use of fluids which are used as refrigerants within the body, no therapeutic cooling may be provided. The cartridge may optionally be refillable, but will often instead have a frangible seal so as to inhibit or limit re-use.

As the individual balloons may have inflated volumes that are quite small, cartridges that are suitable for including in a hand-held housing can allow more than a hundred, optionally being more than a thousand, and in many cases more than ten thousand or even a hundred thousand individual balloon inflations, despite the cartridge containing less than 10 ounces of fluid, often less than 5 ounces, in most cases less than 3 ounces, and ideally less than 1 ounce. Note also that a number of alternative fluid sources may be used instead of or with a cartridge, including one or more positive displacement pumps (optionally such as simple syringe pumps), a peristaltic or rotary pump, any of a variety of microfluidic pressure sources (such as wax or other phase-change devices actuated by electrical or light energy and/or integrated into substrate 38), or the like. Some embodiments may employ a series of dedicated syringe or other positive displacement pumps coupled with at least some of the balloons by channels of the substrate, and/or by flexible tubing.

Referring still to FIG. 6, processor 60 can facilitate inflation of an appropriate subset of balloons 36 of actuation array 32 so as to produce a desired articulation. Such processor-derived articulation can significantly enhance effective operative coupling of the input 18 to the actuated portion 20 of catheter body 12, making it much easier for the user to generate a desired movement in a desired direction or to assume a desired shape. Suitable correlations between input commands and output movements have been well developed for teleoperated systems with rigid driven linkages. For the elongate flexible catheters and other bodies used in the systems described herein, it will often be advantageous for the processor to select a subset of balloons for inflation based on a movement command entered into a user interface 66 (and particularly input 18 of user interface 66), and on a spatial relationship between actuated portion 20 of catheter 12 and one or more component of the user interface. A number of differing correlations may be helpful, including orientational correlation, displacement correlation, and the like. Along with an input, user interface 66 may include a display showing actuated portion 20 of catheter body 12, and sensor 63 may provide signals to processor 60 regarding the orientation and/or location of proximal base 21. Where the relationship between the input, display, and sensor are known (such as when they are all mounted to proximal housing 14 or some other common base), these signals may allow derivation of a transformation between a user interface coordinate system and a base coordinate system of actuated portion 20. Alternative systems may sense or otherwise identify the relationships between the sensor coordinate system, the display coordinate system, and/or the input coordinate system so that movements of the input result in catheter movement, as shown in the display. Where the sensor comprises an image processor coupled to a remote imaging system (such as a fluoroscopy, MRI, or ultrasound system), high-contrast marker systems can be included in proximal base 21 to facilitate unambiguous determination of the base position and orientation. A battery or other power source (such as a fuel cell or the like) may be included in housing 14 and coupled to processor 60, with the housing and catheter optionally being used as a handheld unit free of any mechanical tether during at least a portion of the procedure. Nonetheless, it should be noted that processor 60 and/or sensor 63 may be wirelessly coupled or even tethered together (and/or to other components such as a separate display of user interface 66, an external power supply or fluid source, or the like).

Regarding processor 60, sensor 63, user interface 66, and the other data processing components of system 10, it should be understood that the specific data processing architectures described herein are merely examples, and that a variety of alternatives, adaptations, and embodiments may be employed. The processor, sensor, and user interface will, taken together, typically include both data processing hardware and software, with the hardware including an input (such as a joystick or the like that is movable relative to housing 14 or some other input base in at least 2 dimensions), an output (such as a medical image display screen), an image-acquisition device or other sensor, and one or more processor. These components are included in a processor system capable of performing the image processing, rigid-body transformations, kinematic analysis, and matrix processing functionality described herein, along with the appropriate connectors, conductors, wireless telemetry, and the like. The processing capabilities may be centralized in a single processor board, or may be distributed among the various components so that smaller volumes of higher-level data can be transmitted. The processor(s) will often include one or more memory or storage media, and the functionality used to perform the methods described herein will often include software or firmware embodied therein. The software will typically comprise machine-readable programming code or instructions embodied in non-volatile media, and may be arranged in a wide variety of alternative code architectures, varying from a single monolithic code running on a single processor to a large number of specialized subroutines being run in parallel on a number of separate processor sub-units.

Figure 7:
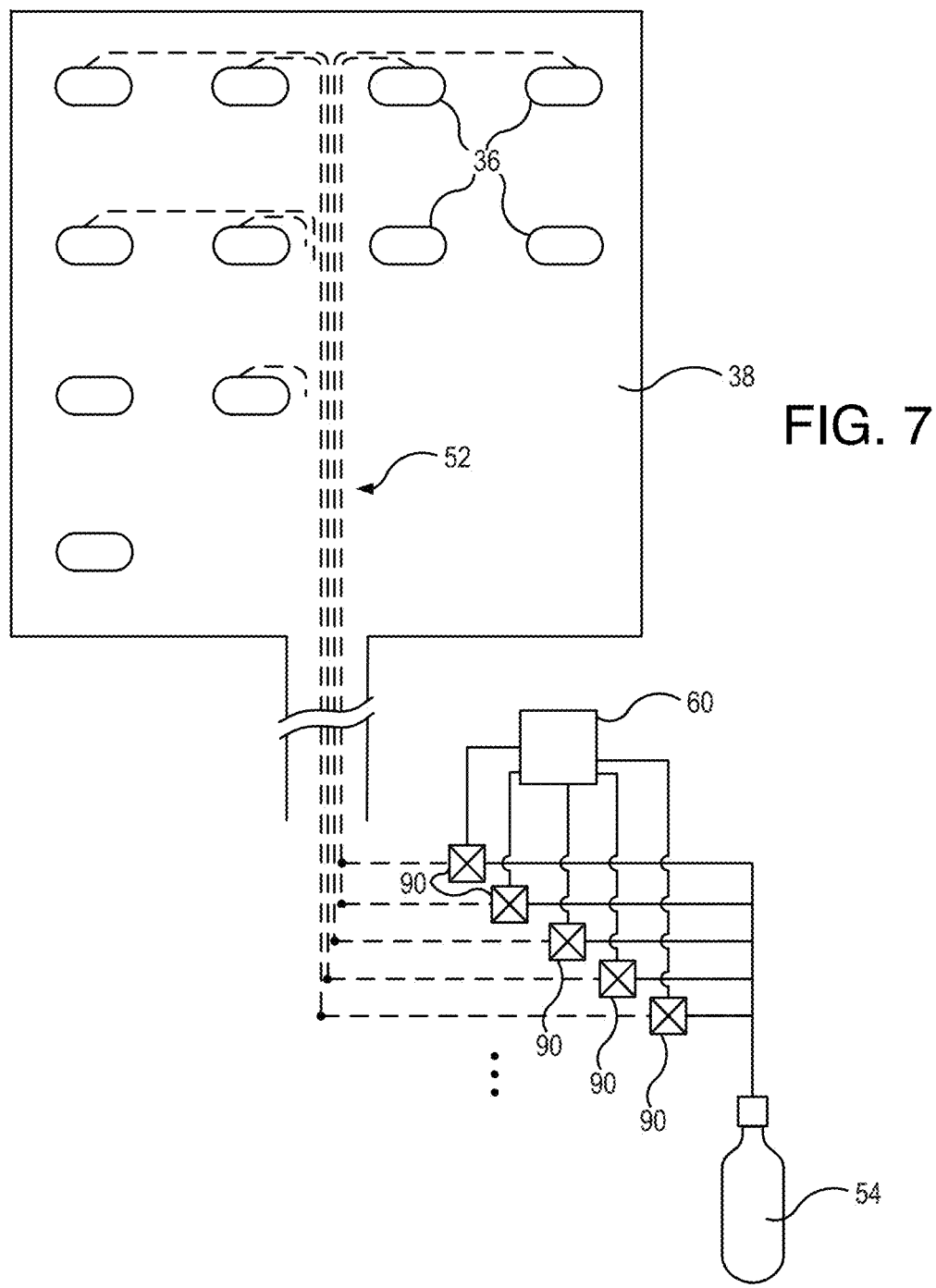
FIG. 7 is a simplified schematic of an alternative balloon array and fluid control system, in which a plurality of valves coupled with the proximal end of the catheter can be used to direct fluid to any of a plurality of channels of the array and thereby selectably determine a subset of balloons to be expanded.
Figure 8:
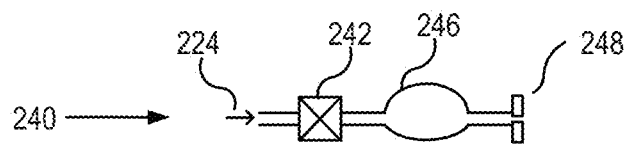
FIGS. 8-13 schematically illustrate valve and balloon arrangements which may be used and/or combined in the inflation fluid supply systems of the systems and devices described herein.
Figure 9:
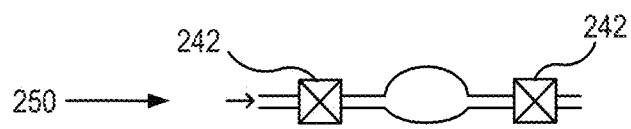

Referring now to FIG. 7, an alternative actuation array and fluid supply system are shown schematically. As in the above embodiment, balloons 36 are affixed along a major surface of substrate 38, optionally prior to rolling the substrate and mounting of the actuation array to the skeleton of the catheter body. In this embodiment, each balloon has an associated dedicated channel 52 of substrate 38, and also an associated valve 90. Processor 60 is coupled with valves 90, and by actuating a desired subset of the valves the associated subset of balloons can be inflated or deflated. In some embodiments, each valve can be associated with more than one balloon 36, so that (for example), opening of a single valve might inflate a plurality (optionally 2, 3, 4, 8, 12, or some other desired number) of balloons, such as laterally opposed balloons so as to elongate the distal portion of the catheter. In these or other embodiments, a plurality of balloons (2, 3, 4, 5, 8, 12, or another desired number) on one lateral side of the catheter could be in fluid communication with a single associated valve 90 via a common channel or multiple channels so that opening of the valve inflates the balloons and causes a multi-balloon and multi-increment bend in the axis of the catheter. Still further variations are possible. For example, in some embodiments, channels 52 may be formed at least in-part by flexible tubes affixed within an open or closed channel of substrate 38, or glued along a surface of the substrate. The tubes may comprise polymers (such as polyimide, PET, nylon, or the like), fused silica, metal, or other materials, and suitable tubing materials may be commercially available from Polymicro Technologies of Arizona, or from a variety of alternative suppliers. The channels coupled to the proximal end of the actuatable body may be assembled using stacked fluidic plates, with valves coupled to some or all of the plates. Suitable electrically actuated microvalues are commercially available from a number of suppliers. Optional embodiments of fluid supply systems for all balloon arrays described herein may have all values mounted to housing 14 or some other structure coupled to and/or proximal of) the proximal end of the elongate flexible body. Advantageously, accurately formed channels 52 (having sufficiently tight tolerance channel widths, depths, lengths, and/or bends or other features) may be fabricated using microfluidic techniques, and may be assembled with the substrate structure, so as to meter flow of the inflation fluid into and out of the balloons of all of the actuation arrays described herein.

A number of inflation fluid supply system component arrangements for use in any or all of the articulation, stiffening, and/or bend control systems described herein can be understood with reference to FIGS. 8-13. As noted above, the valves, ports, and the like may be included in a proximal housing, may be incorporated into a substrate of the balloon array, or a combination of both. First addressing a simple inflation control arrangement 240 of FIG. 8, a single on/off gate valve 242 may be along a fluid flow path between a fluid source 244 and a balloon 246. A limited flow exhaust port 248 remains open, and opening of valve 242 allows sufficient fluid from the source to inflate balloon despite a limited flow of fluid out of limited port 248, which can have an orifice or other fixed flow restriction. When gate valve 242 is closed, flow out of the limited port 248 allows the balloon to deflate. The two-valve arrangement 250 of FIG. 9 uses two separate gate valves 242 to independently control flow into and out of the balloon, thereby limiting the loss of fluid while the balloon remains inflated and also preventing deflation speed from being limited more than might otherwise be desired. While the inflow channel into the balloon and out of the balloon are shown as being separate here, both valves may instead be coupled to the inflow channel, with the deflation valve typically being between the inflation valve and the balloon.

Figure 10:
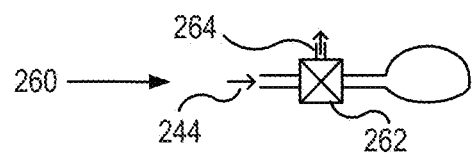

A two-way valve arrangement 260 is shown in FIG. 10, with a two way valve 262 having a first mode that provides fluid communication between supply 244 and balloon 246, and a second mode that provides fluid communication between the balloon and an exhaust port 264 (while the supply is sealed to the port and balloon).

Figure 11:
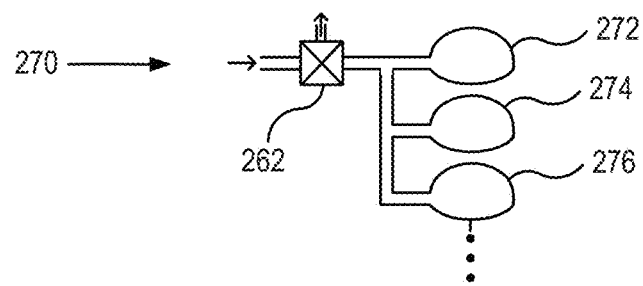

A ganged-balloon arrangement 270 is shown in FIG. 11, with a two way valve 262 between supply 244 and a plurality of balloons 272, 274, 276, . . . . Such an arrangement allows a number (typically between 2 and 10 balloons) to be inflated and deflated using a single valve, which may be used when a subset of balloons are often to be inflated, such as for elongation of an axial segment, for imposing a desired base curvature (to which other incremental axial bend components may be added), for imposing multi-balloon incremental axial bend components or the like.

Figure 12:
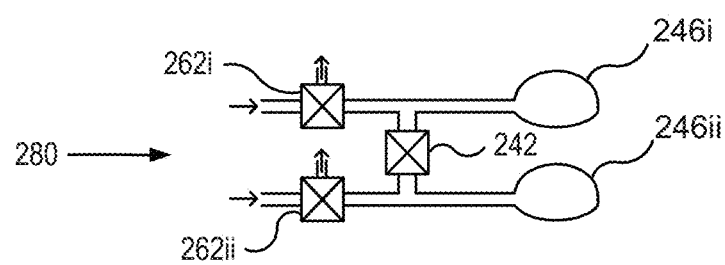

A transfer-bend valve arrangement 280 is shown in FIG. 12, with two way valves 262$i$, 262$ii$ each allowing inflation of an associated balloon 246$i$, 246$ii$, respectively. Additionally, a transfer gate valve 242 between balloons 246$i$ and 246$ii$ allows inflation fluid to flow from one (or more) balloon to another (one or more) balloon. This may allow, for example, a bend associated with one balloon to be transferred partially or fully to a bend associated with a different balloon in response to environmental forces against the flexible body, such as when a catheter is pushed axially within a bent body lumen (so that the bend transfers axially), when a catheter is rotated within a bent body lumen (so that the bend transfers laterally), a combination of the two, or the like. A transfer valve may also be used, for example, help determine a catheter shape that limits forces imposed between a surrounding lumenal wall and the catheter structure. For this (and potentially other advantageous uses) a valve may be opened between a full-inflation pressure source and one or more balloon to initially inflate such balloon(s) so that the catheter is urged toward an initial state. At least one transfer valve may be opened between the inflated balloon(s) and one or more uninflated balloons so as to drive the catheter configuration having a bend. If the tissue surrounding the bend (and internal balloon compression structures of the catheter) urge deflation of the inflated balloons with sufficient force, and if the surrounding tissue urge the catheter to assume another bend associated with those uninflated balloon(s) so as to mitigate the internal balloon compression structures of the catheter, inflation fluid can be forced from the inflated balloon(s) to the uninflated balloon(s), and the catheter can then allow the tissue to assume a more relaxed shape. Interestingly, changes in the catheter bend configuration associated with inflation fluid flowing between balloons may at least in part be pseudo-plastic, with fluid flow resistance limiting elastic return to the prior state. Use of a flow modulating transfer valve (as opposed to a simple on/off gate valve) may allow corresponding modulation of this pseudo-plastic bend state change. Alternatively, a transfer valve and associated channel may have a tailored flow resistance (such as an orifice or controlled effective diameter section) to tailor the pseudo-plastic properties.

Figure 13:
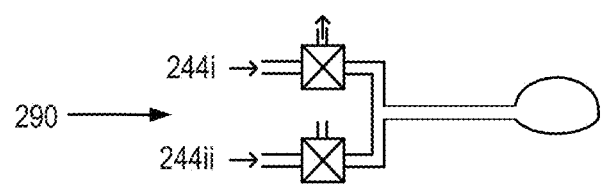

A multi-pressure valve arrangement 290 is shown in FIG. 13, in which a two-way valve allows inflation or deflation of an associated balloon from a full inflation supply 244$i$ as described above. Alternatively, a partial inflation fluid supply 244ii can direct fluid at a lower (optionally fixed) partial inflation pressure to the same balloon. The partial inflation pressure may be insufficient to overcome the bias of the helical coil and the like toward balloon deflation and a straight-coil configuration, and thus may not alone bend the flexible body (absent tissue or other environmental forces against the catheter), but can selectively reduce the strength of the catheter against a bend associated with the partially inflated balloon. Alternatively, the pressure may be sufficient to partially inflate the balloon and induce a portion of a full-inflation bend. Regardless, one or more partial inflation fluid supply pressures may be provided using one or more associated valves, with the inflation fluid being a one or more incremental pressures between a full balloon inflation pressure and atmospheric pressure. Note that partial inflation may alternatively be provided by modulating a variable valve for a limited inflation time so as to control total fluid flow quantity to one or more balloons, by controlling one or more on/off pulse cycles times of a gate valve, or the like. Still other combinations of inflation fluid directing components may be included in many embodiments, with at least some of the components (and particularly channels between the valves and the balloons) being integrated into the balloon array, at least some of the components (particularly the pressurized fluid canister or other source) being in a proximal housing coupled to a proximal end of the catheter or other flexible body, and others (portions of the channels, valves, ports, valve actuation circuitry, etc.) being in either or distributed in both. In some embodiments, a non-actuating positive inflation fluid pressure (greater than the atmosphere surrounding the balloon array but insufficient to separate loops of a coil) may be maintained in some or all of the balloons that are in a nominally non-inflated state. This may pre-inflate the balloons so that the fluid partially fills the balloon and the balloon wall expands where it does not engage the coil, decreasing the quantity of fluid that flows to the balloon to achieve full inflation.

A wide variety of desirable inflation fluid supply system capabilities can be provided using one or more valve component arrangements described above. For example, rather than including a separate partial inflation pressure fluid supply, a transfer valve can be used to first fully inflate a first balloon, after which a transfer valve can be used to transfer a portion of the fluid from the inflated balloon to one or more other balloons, resulting in gang partial inflation of multiple balloons. A fluid supply system may have a network of channels with a combination of inflation gate valves and deflation gate valves so as to allow selective inclusion of any of a plurality of individual balloons in an inflated subset, selected ganged balloons that pre-define some or all of the members of subsets that will be used simultaneously, and the like.

Referring now to FIGS. 14A-16, a still further embodiment of an articulated catheter includes first and second interleaved helical multi-lumen balloon fluid supply/support structures 440a, 440b, along with first and second resilient helical coils 442a, 442b. In this embodiment, a series of balloons (not shown) are mounted around each of the multi-lumen structures, with the balloons spaced so as to be aligned along three lateral bending orientations that are offset from each other around the axis of the catheter by 120 degrees. Six lumens are provided in each multi-lumen structure, 440a, 440b, with one dedicated inflation lumen and one dedicated deflation lumen for each of the three lateral bending orientations. Radial fluid communication ports between the lumens and associated balloons may be provided by through cuts through pairs of the lumens.

By spacing the cuts 444a, 444b, 444c, as shown, and by mounting balloons over the cuts, the inflation and deflation lumens can be used to inflate and deflate a subset of balloons aligned along each of the three bending orientations. Advantageously, a first articulated segment having such a structure can allow bending of the catheter axis in any combination of the three bend orientations by inflating a desired subset of the balloons along that segment. Optionally, the bend angle for that subset may be controlled by the quantity and/or pressure of fluid transmitted to the balloons using the 6 lumens of just one multi-lumen structure (for example, 440a), allowing the segment to function in a manner analogous to a robotic wrist. Another segment of the catheter axially offset from the first segment can have a similar arrangement of balloons that are supplied by the 6 lumens of the other multi-lumen structure (in our example, 440b), allowing the catheter to position and orient the end of the catheter with flexibility analogous to that of a serial wrist robotic manipulators. In other embodiments, at least some of the balloons supplied by the two multi-lumen structures may axially overlap, for example, to allow increasing bend angles and/or decreasing bend radii by combining inflation of overlapping subsets of the balloons. Note also that a single lumen may be used for both inflation and deflation of the balloons, and that multi-lumen structures of more than 6 lumens may be provided, so that still further combinations these degrees of freedom may be employed.

Figure 14A:
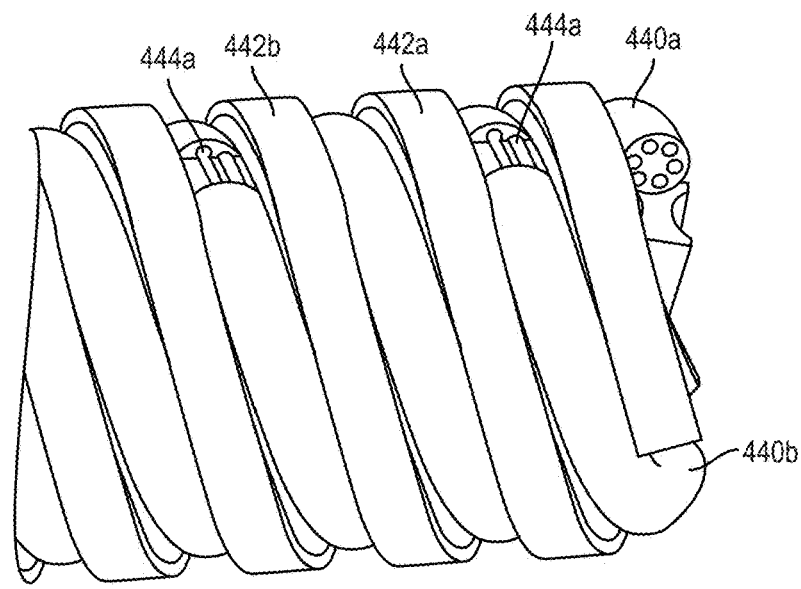
Figure 15:
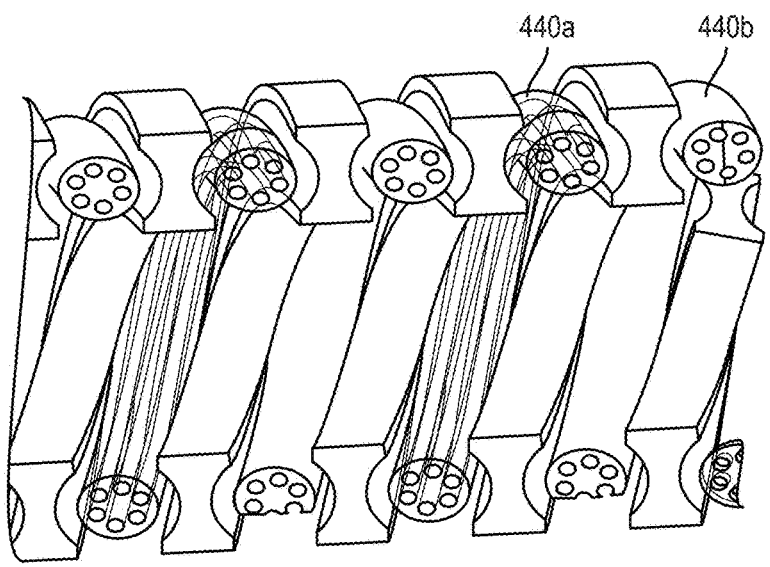
Figure 16:
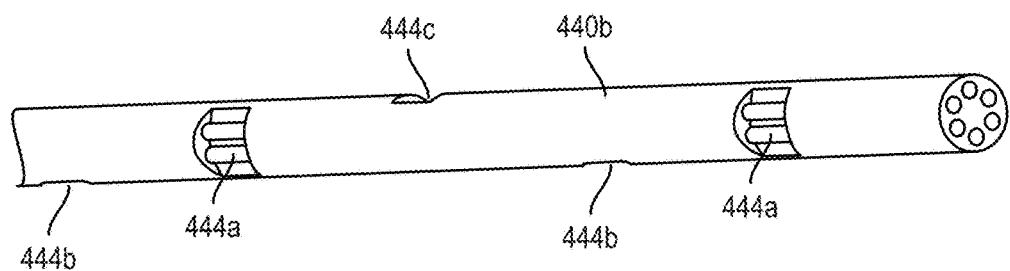

In the embodiment illustrated in the side view of FIG. 14A and in the cross-section of FIG. 15, the outer diameter of the helical coils is about 0.130 inches. Multi-lumen structures 440a, 440b have outer diameters in a range from about 0.020 inches to about 0.030 inches (optionally being about 0.027 inches), with the lumens having inner diameters of about 0.004 inches and the walls around each lumen having a minimum thickness of 0.004 inches. Despite the use of inflation pressures of 20 atm or more, the small diameters of the lumens help limit the strain on the helical core structures, which typically comprise polymer, ideally being extruded. Rather than including a resilient wire or the like in the multi-lumen structure, axial compression of the balloons (and straightening of the catheter axis after deflation) is provided primarily by use of a metal in coils 442a, 442b. Opposed concave axial surfaces of coils 442 help maintain radial positioning of the balloons and multi-lumen structures between the coils. Affixing the ends of resilient coils 442 and balloon supply/support structures 440 together to the inner and outer sheaths at the ends of the coils, and optionally between segments may help maintain the helical shapes as well. Increasing the axial thickness of coils 442 and the depth of the concave surfaces may also be beneficial to help maintain alignment, with the coils then optionally comprising polymer structures. Still other helical-maintaining structures may be included in most or all of the helical embodiments described herein, including periodic structures that are affixed to coils 442 or other helical skeleton members, the periodic structures having protrusions that extend between balloons and can engage the ends of the inflated balloon walls to maintain or index lateral balloon orientations.

Many of the embodiments described herein provide fluid-driven articulation of catheters, guidewires, and other elongate flexible bodies. Advantageously, such fluid driven articulation can rely on very simple (and small cross-section) fluid transmission along the elongate body, with most of the forces being applied to the working end of the elongate body reacting locally against the surrounding environment rather than being transmitted back to a proximal handle or the like. This may provide a significant increase in accuracy of articulation, decrease in hysteresis, as well as a simpler and lower cost articulation system, particularly when a large number of degrees of freedom are to be included. Note that the presence of relatively high pressure fluid, and/or low temperature fluid, and/or electrical circuitry adjacent the distal end of an elongate flexible body may also be used to enhance the functionality of tools carried by the body, particularly by improving or adding diagnostic tools, therapeutic tools, imaging or navigations tools, or the like.

Figure 17A:
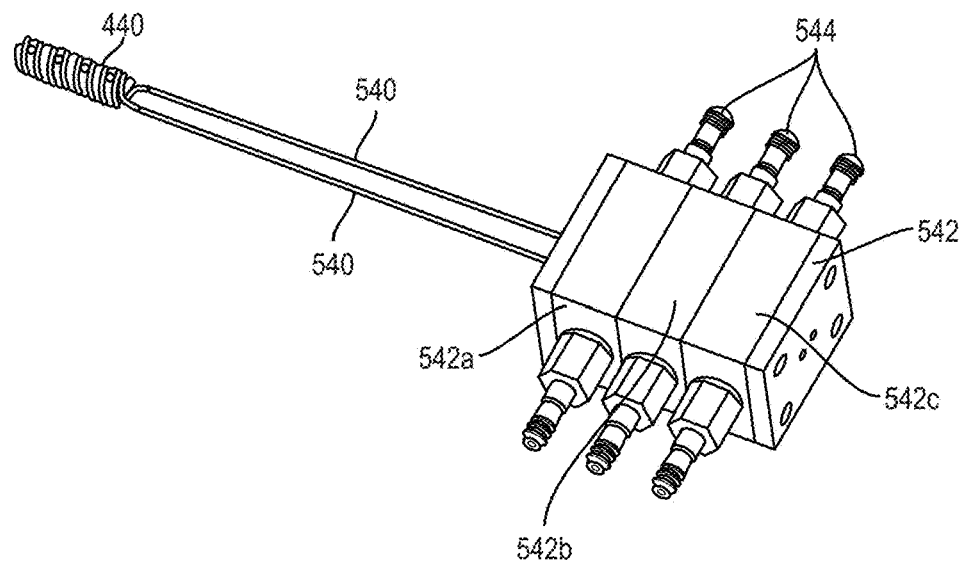
FIGS. 17A and 17B are a perspective view and a cross-section of components of a catheter and fluid supply manifold system.
Figure 17B:
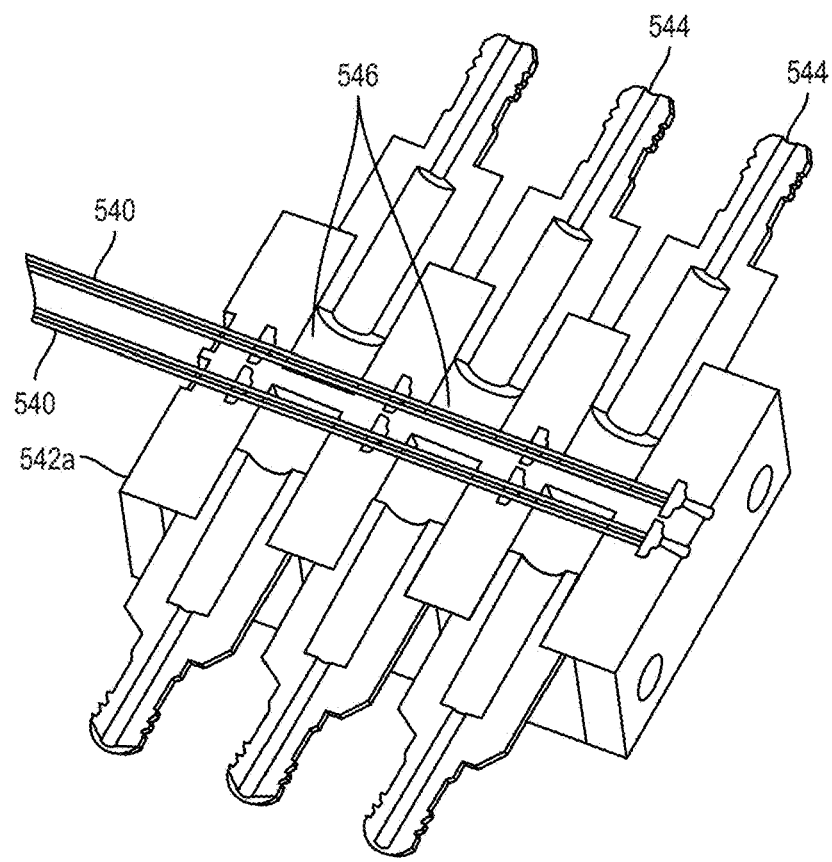

Referring now to FIGS. 17A and 17B, articulation system components related to those of FIGS. 14A-16 can be seen. Two multi-lumen polymer helical cores 440 can be interleaved with axially concave helical springs along the articulated portion of a catheter. Curved transition zones extend proximal of the helical cores to axially straight multi-lumen extensions 540, which may extend along a passive (unarticulated) or differently articulated section of the catheter, or which may extend through articulated segments that are driven by fluid transmitted by other structures (not shown). Advantageously, a portion of each proximal extension 540 near the proximal end can be used as a proximal interface 550 (See FIG. 17C), often by employing an axial series of lateral ports formed through the outer walls of the multi-lumen shaft into the various lumens of the core. This proximal interface 550 can be mated with a receptacle 552 of a modular valve assembly 542, or with a receptacle of non-modular valve assembly, or with a connector or interface body that couples to a manifold so as to provide sealed, independently controlled fluid communication and a controlled flow of inflation fluid to desired subsets of the balloons from a pressurized inflation fluid source, along with a controlled flow of exhaust fluid from the balloons to the atmosphere or an exhaust fluid reservoir.

Extensions 540 extend proximally into a valve assembly 542 so as to provide fluid communication between fluid pathways of the valve assembly and the balloons of the articulated segment. Valve assembly 542 includes an axial series of modular valve units 542a, 542b, 542c, etc. End-plates and bolts seal fluid paths within the valve assembly and hold the units in place. Each valve unit of assembly 542 includes at least one fluid control valve 544, and preferably two or more valves. The valves may comprise pressure modulating valves that sense and control pressure, gate valves, three-way valves (to allow inflation fluid along a channel to one or more associated balloons, to seal inflation fluid in the inflation channel and associated balloons while flow from the fluid source is blocked, and to allow inflation fluid from the channels and balloons to be released), fluid dispersing valves, or the like. O-rings provide sealing between the valves and around the extensions 540, and unthreading the bolts may release pressure on the O-rings and allow the extensions to be pulled distally from the valve assembly, thereby providing a simple quick-disconnect capability. Radial ports 546 are axially spaced along extensions 540 to provide fluid communication between the valves and associated lumens of the multi-lumen polymer extensions, transitions, and helical coils. Advantageously, where a greater or lesser number of inflation channels will be employed, more or fewer valve units may be axially stacked together. While valves 544 are here illustrated with external fluid tubing connectors (to be coupled to the fluid source or the like), the fluid paths to the valves may alternatively also be included within the modular valve units, for example, with the fluid supply being transmitted to each of the valves along a header lumen that extends axially along the assembly and that is sealed between the valve units using additional O-rings or the like. Note that while modular units 542a, 542b, . . . may comprise valves, in alternative embodiments these units may simply comprise ferrules, posts, or other interface structures that allow the assembly to be used as a connector or interface body that helps provide fluid communication between the multi-lumen shaft or core and some of the components of the fluid supply system.

Figure 17C:
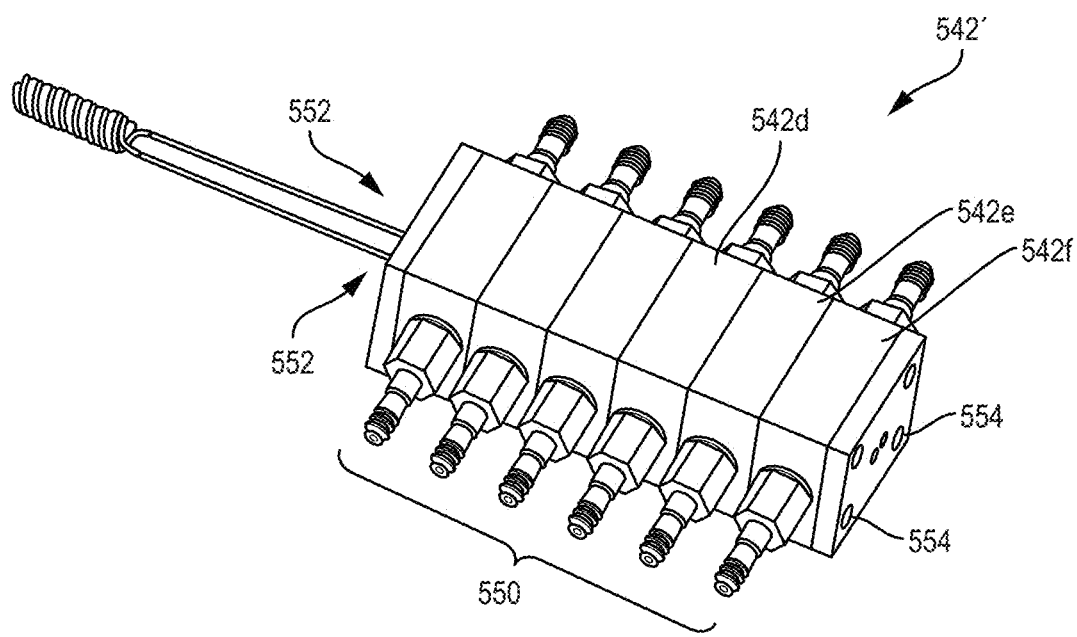
FIG. 17C is a perspective view of a fluid supply manifold having components similar to those of FIGS. 17A and 17B, showing how additional interchangeable modules can be included in the manifold assembly for controlling fluid systems having greater numbers of fluid channels.

Referring now to FIG. 17C, additional modular valve units 542d, 542e, and 542f are included in the valve and manifold assembly 542' so as facilitate independent control of inflation fluid flows to and from lumens of the multi-lumen cores. The modular valve units are preferably interchangeable, and will often include electrical circuitry and a pressure sensor for each inflation lumen, along with the valves, plate structures, and channels. The electrical circuitry for each plate will often be supported by a flex circuit substrate and may optionally be adhesively bonded to one of the major surfaces of the plates, or it may be between layers of the plate or held compressively between plates. Along with conductive traces for communication between the valves, sensors, and system processor, the flex circuit may also support electronics to facilitate multiplexing among the plate modules, plug-and-play plate module capabilities, daisy chaining or networking of the plate modules, and/or the like. In exemplary embodiments described below, the flex circuits substrate may also support (and help provide electrical coupling with MEMS valves and/or MEMS pressure sensors. The flex circuit substrate or another film substrate material may optionally help support O-rings, gaskets, or other seal materials surrounding passages through the plates (or layers thereof), including passages that form receptacles 552, inflation headers, deflation headers, and the like; though some or all of the seals for these structures may instead be independently positioned. As noted above, one or more quick-disconnect fitting 554 may be configured to help seal the ports of the multi-lumen shaft (or of an intermediate body) to the fluid channels of the plates. Where the ports are included on a shaft that extends through the plates, the quick-disconnect fitting may take the form of a compression member that is manually movable between a detachable configuration (in which little or no compression is applied between plates) and a sealed configuration (in which sufficient compression is applied between plates to squeeze seal material from between the plates of the stack and against the shafts). The quick-disconnect fitting may comprise one or more over-center latch, one or more threaded connector, one or more cam unit, or the like.

Figure 18A:
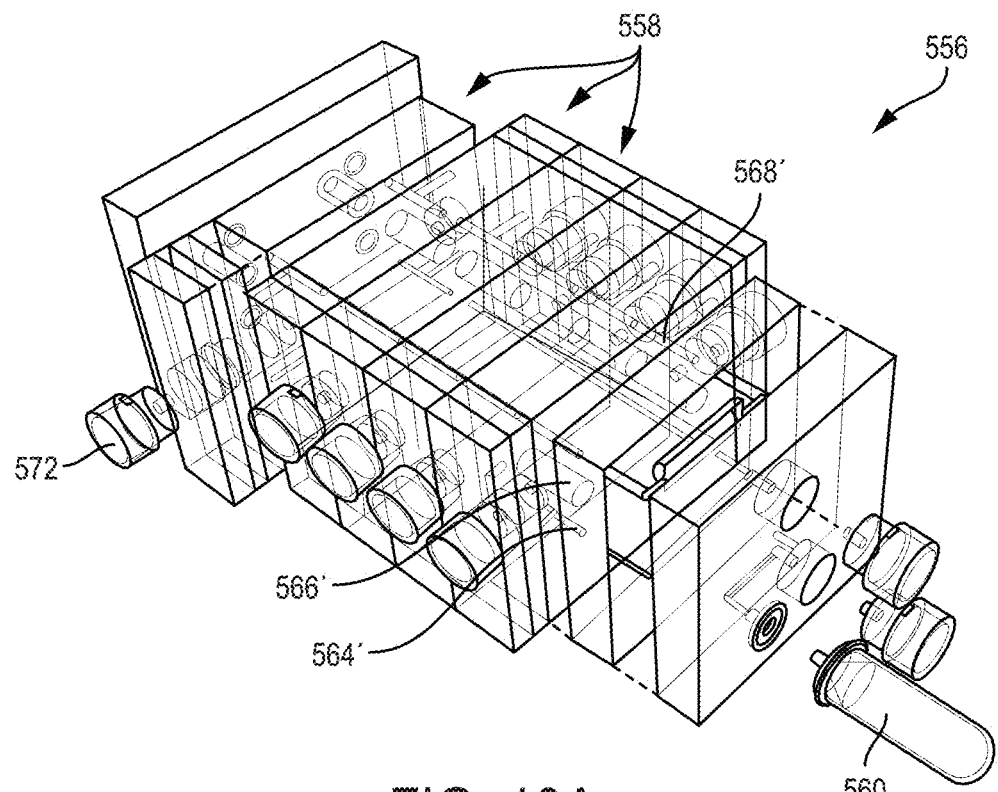
Figure 18:
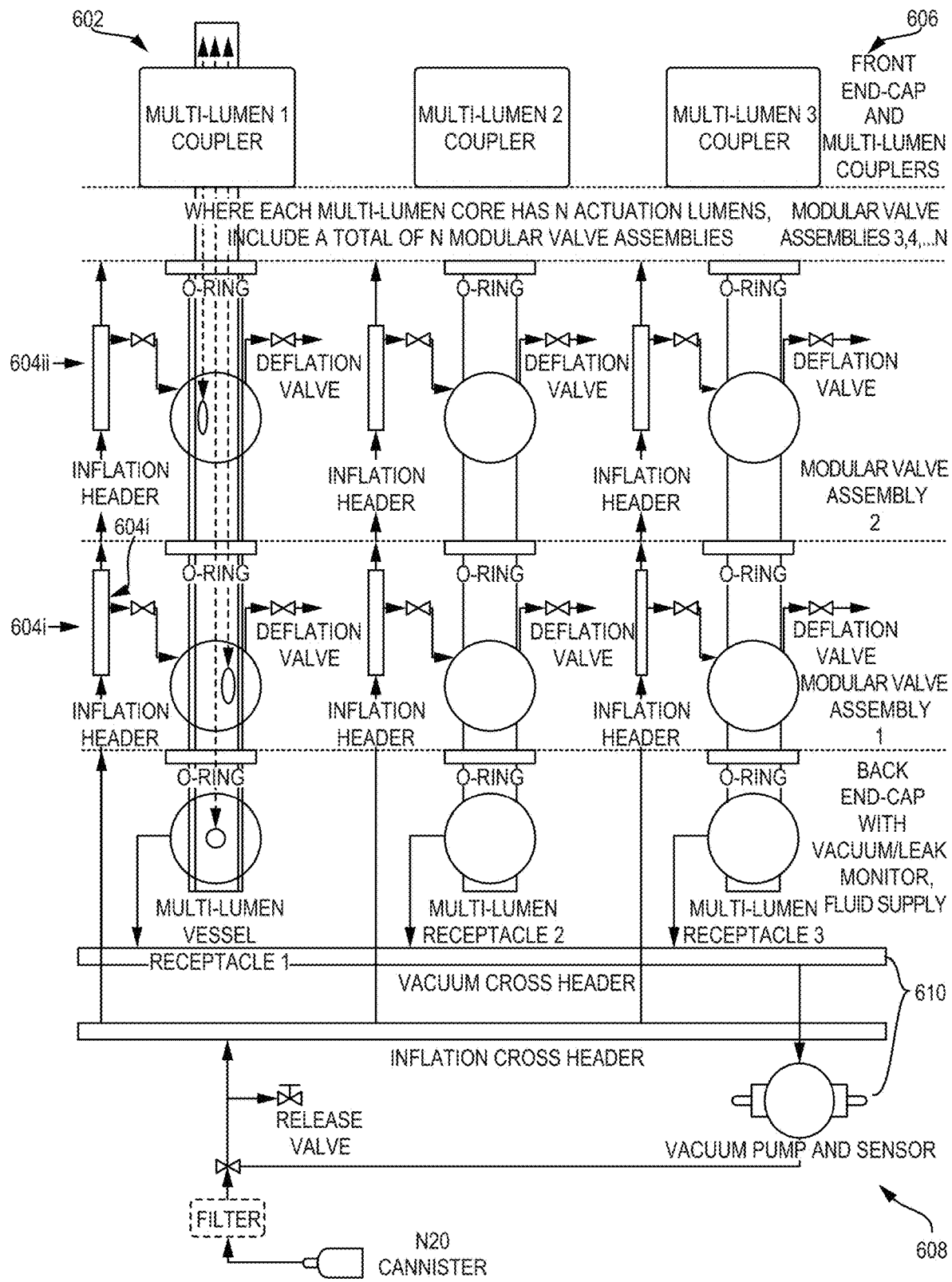
FIG. 18 is a simplified schematic of a modular manifold having a stack of valve plate assemblies through which a multi-lumen connector extends so as to provide controlled fluid flow to and from balloons of an array.

Referring now to FIG. 18, a simplified manifold schematic shows fluid supply and control components of an alternative manifold 602. As generally described above, manifold 602 has a plurality of modular manifold units or valve assembly plates 604i, 604ii, . . . stacked in an array. The stack of valve plates are sandwiched between a front end cap 606 and a back end-cap 608, and during use the proximal portion of the multi-lumen conduit core(s) extend through apertures in the front cap and valve plates so that the proximal end of the core is adjacent to or in the back cap, with the apertures defining a multi-lumen core receptacle. The number of manifold units or modules in the stack is sufficient to include a plate module for each lumen of each of the multi-lumen core(s). For example, where an articulatable structure has 3 multi-lumen core shafts and each shaft has 6 lumens, the manifold assembly may include a stack of 6 plates. Each plate optionally includes an inflation valve and a deflation valve to control pressure in one of the lumens (and the balloons that are in communication with that lumen) for each multi-lumen shaft. In our 3-multi-lumen shaft/6 lumen each example, each plate may include 3 inflation valves (one for a particular lumen of each shaft) and 3 deflation valves (one for that same lumen of each shaft). As can be understood with reference to the multi-lumen shaft shown in receptacle 1 of FIG. 18, the spacing between the ports along the shaft corresponds to the spacing between the fluid channels along the receptacle. By inserting the core shaft fully into the multi-lumen shaft receptacle, the plate channel locations can be registered axially with the core, and with the ports that were drilled radially from the outer surface of the multi-lumen core. The processor can map the axial locations of the valves along the receptacle with the axial locations of the ports along the core shafts, so that a port into a particular lumen of the core can be registered and associated with a fluid channel of specific inflation and deflation valves. One or more inflation headers can be defined by passages axially through the valve-unit plates; a similar deflation header (not shown) can also be provided to monitor pressure and quantity of fluid released from the lumen system of the articulated device. O-rings can be provided adjacent the interface between the plates surrounding the headers and receptacles. Pressure sensors (not shown) can monitor pressure at the interface between each plate and the multi-lumen receptacle.

Along with monitoring and controlling inflation and deflation of all the balloons, manifold 602 can also include a vacuum monitor system 610 to verify that no inflation fluid is leaking from the articulated system within the patient body. A simple vacuum pump (such as a syringe pump with a latch or the like) can apply a vacuum to an internal volume or chamber of the articulated body surrounding the balloon array. Alternative vacuum sources might include a standard operating room vacuum supply or more sophisticated powered vacuum pumps. Regardless, if the seal of the vacuum chamber degrades the pressure in the chamber of the articulated structure will increase. In response to a signal from a pressure sensor coupled to the chamber, a shut-off valve can automatically halt the flow of gas from the canister, close all balloon inflation valves, and/or open all balloon deflation valves. Such a vacuum system may provide worthwhile safety advantages when the articulated structure is to be used within a patient body and the balloons are to be inflated with a fluid that may initially take the form of a liquid but may vaporize to a gas. A lumen of a multi-lumen core shaft may be used to couple a pressure sensor of the manifold to a vacuum chamber of the articulated structure via a port of the proximal interface and an associated channel of the manifold assembly, with the vacuum lumen optionally comprising a central lumen of the multi-lumen shaft and the vacuum port being on or near the proximal end of the multi-lumen shaft.

Figure 18B:
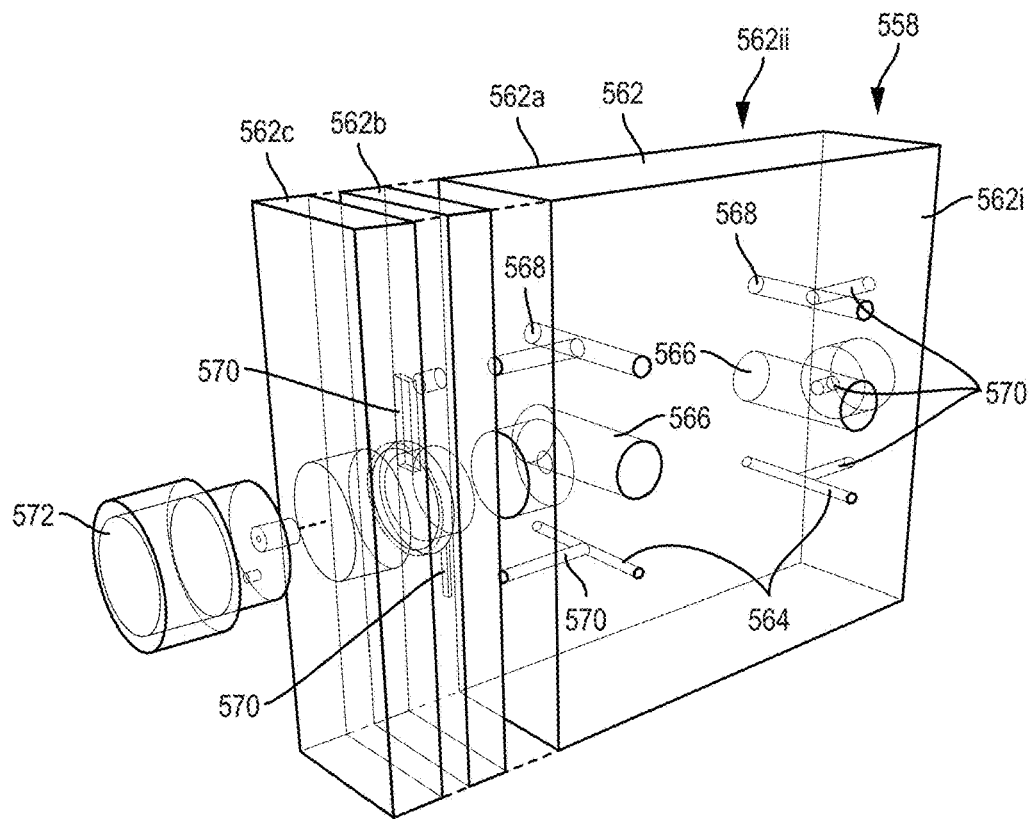
Figure 18C:
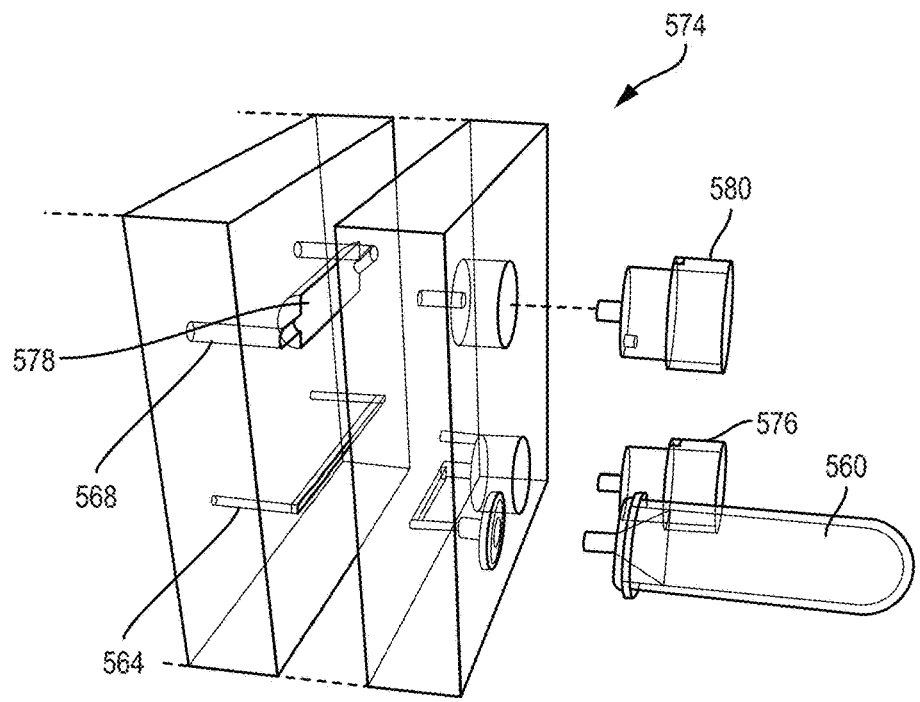

Referring now to FIGS. 18A-18C, an exemplary alternative modular manifold assembly 556 has fluid supply and deflation exhaust channels that are internal to a stack of plate modules 558. Plate modules 558 are stacked between a front end cap and a back end cap, with the front end cap being at the distal end and having passages or apertures for receiving each of the multi-lumen shafts, and the back end being at the proximal end and having a socket for receiving a canister 560 of N2O. As seen most clearly in FIG. 18B, each plate module 558 includes a plate 562 formed using multiple plate layers 562a, 562b, 562c . . . . While the plate layers shown here extend across the stack, other layers may be stacked axially along the stack. Regardless, each plate 562 has opposed proximal and distal major surfaces 562i, 562ii. A series of passages extend through the plate between the major surfaces, including one or more inflation fluid passage 564, one or more receptacle passages 566, and one or more deflation fluid passages 568. When the plates and end caps are assembled within manifold assembly 556, these passages combine to form one or more inflation header 564', one or more receptacle 566', and one or more deflation header 568', with each of the passages providing surfaces that serve as a portion of the assembled structure. Channels 570 extend within plates 562 between the headers 564, 568 and the receptacle, with inflation valves disposed along the channels between the inflation header 564 and receptacle 566 and deflation valves disposed along the channels between the receptacles and the deflation headers 568. Note that the manifold assembly of FIGS. 18A-18C includes multi-coil three way valves 572 that function as both inflation valves and deflation valves, with two three way valves for two multi-lumen core shafts.

Figure 18D:
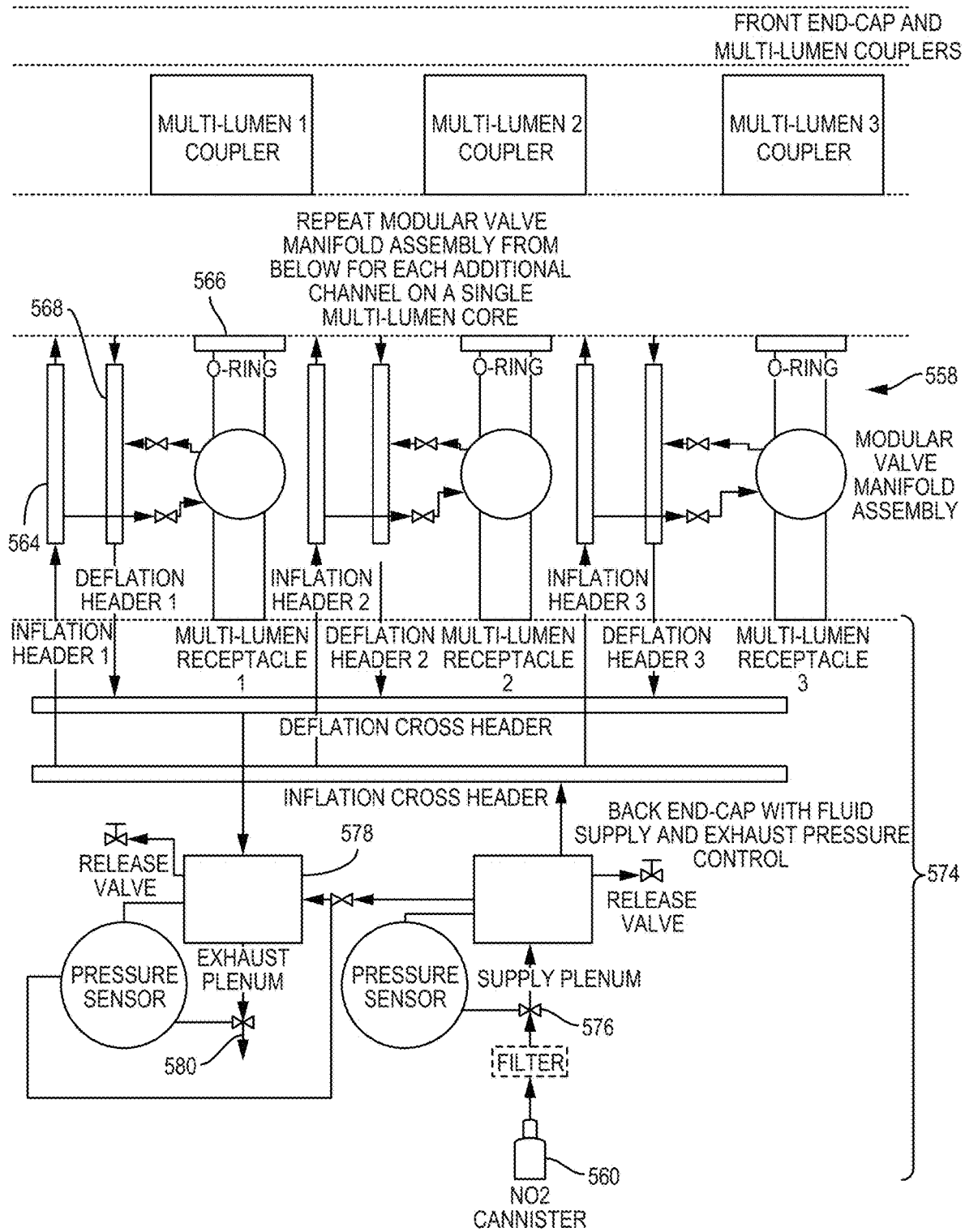
FIGS. 18D and 18E are alternative simplified schematics of modular fluid manifold systems showing additional components and systems that can be combined with those of FIG. 18.

Referring now to FIGS. 18C and 18D, additional optional components of the manifold assembly can be understood. The functionality of one, some, or all of these components may be included in any of the manifold assembly embodiments described herein. Back end cap 574 here includes a system fluid supply valve 576 disposed along channels coupling the inflation fluid canister 560 with the inflation header 564. Note that the end cap may include one or more cross headers to allow separate inflation or exhaust headers for the different multi-lumen core shafts. The system supply valve may halt or allow all of the fluid flow to the remaining components of the manifold and articulation structure. In some embodiments, fluid from canister 560 is used to pressurize a supply plenum, with a pressure sensor and the system supply valve being used to control the supply plenum pressure. This may be beneficial if it is desired to use a non-volatile balloon inflation liquid such as saline or the like, and/or if it is desired to preclude inflation of the balloons above a pressure that is below that of canister 560. However, transmitting inflation fluid directly from canister 560 to the inflation valves of the modular plates may present advantages, including enhanced inflation fluid flows through the small channels of the manifold and articulated structure when transmitting liquid or a liquid/gas mixture using the full canister pressure, as well as the relatively constant pressure that can be provided by vaporization of liquid within the canister. To keep the gas/liquid inflation fluid pressure within the canister even more constant, a resistive heater may be thermally coupled with the outer surface of the canister so as to compensate for the enthalpy of vaporization that occurs therein.

Referring still to FIGS. 18C and 18D, there may be more significant advantages to having an exhaust plenum 578 between one, some or all of the exhaust channels (often between the one or more exhaust header 568) and an exhaust port 580 to atmosphere. A pressure sensor or flow sensor coupled with exhaust plenum 578 can be used to monitor exhaust fluid flow. In some embodiments, a pressure sensor coupled to exhaust plenum 578 and an exhaust valve along a channel coupling the exhaust plenum to the exhaust port 580 can be used as a back-pressure control system to help control exhaust flows, to provide a uniform pressure to a number of balloons (via the deflation valves), or and/or to calibrate the individual pressure sensors of the plate modules. Manual release valves may optionally be included between the inflation and deflation headers and the surrounding environment to allow the system to be fully depressurized in case of failure of a valve or the like.

Figure 18E:
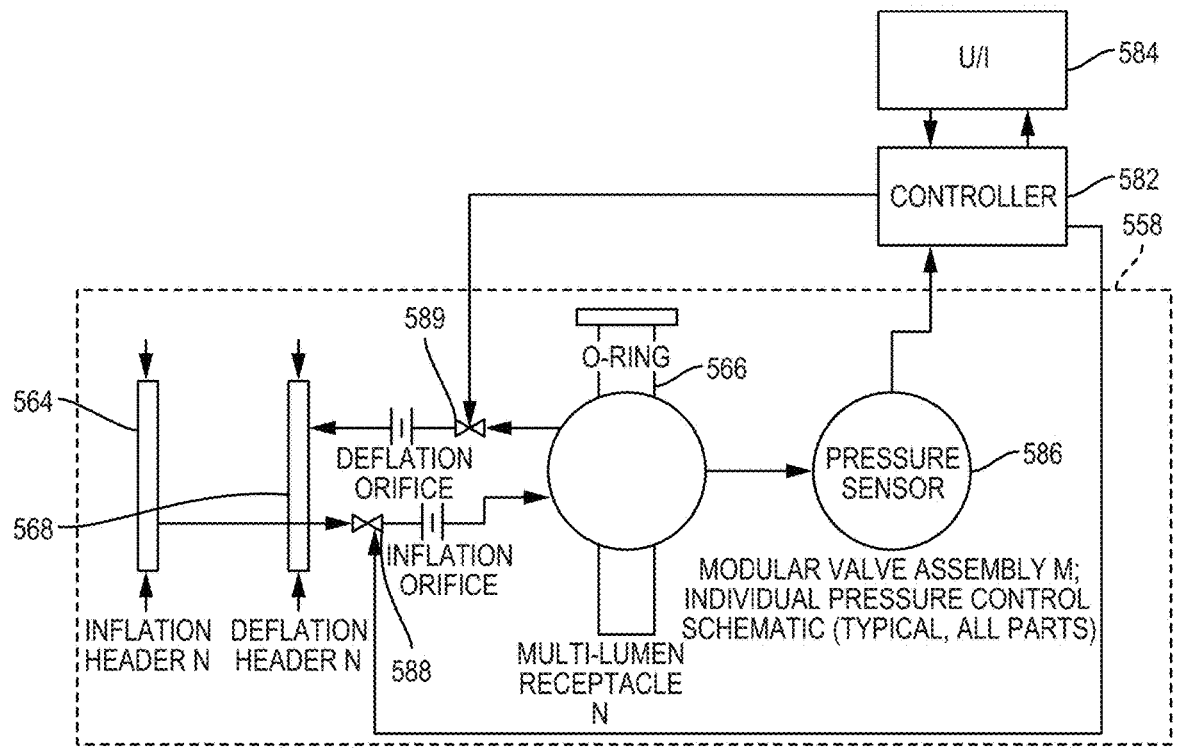

Referring now to FIG. 18E, a simplified pressure control schematic illustrates some of the components of a pressure control system as used to control the pressure in a single channel of a single plate module (as well as in an associated balloon or balloons coupled with the channel via a port of a multi-lumen shaft sealed in fluid communication with the channel. Pressure control of all the channels may be maintained by the system controller 582, with the desired pressures typically being determined by the controller in response to a movement or stiffness command input by the user via a user interface 584. A pressure difference or error signal for a particular channel is determined from a difference between a sensed pressure (as determined using a pressure sensor 586) and the desired pressure for that channel. In response to the error signal, controller 582 transmits commands to an inflation valve 588 and/or a deflation valve 589 so as to raise or lower the pressure in the channel. Though the same fluid is flowing to and from the balloons, there may be significant differences between the flows from the canister through inflation valve 588 (which may comprise liquid, often being primarily liquid or even substantially entirely liquid) and the flows from the balloons through deflation valve 589 (which may comprise gas, often being primarily gas or even substantially entirely gas). To provide accurate inflation and deflation flow control, there may be advantages to including an inflation orifice between the inflation valve and the receptacle (ideally so as to inhibit vaporization prior to the inflation valve), and/or to including a deflation orifice between the receptacle and the deflation header 568. Such orifices may facilitate accurate flow control despite the use of similar valve structures for use as inflation valve 588 and deflation valve 589. There may, however, be beneficial differences between the inflation and deflation valves, including the use of normally closed valves for inflation and normally open valves for deflation (so the balloons will deflate if there is a power failure). Additionally, inflation valve 588 may have a smaller throat and/or a fast response to controllably transmit small volumes of liquid (optionally 50 nl or less, often 25 nl or less, and preferably 15 nl or less, and ideally 10 nl or less to provide desirably small movement increments); while deflation valve 589 will allow gas flows of at least 0.1 scc/s, preferably being at least 0.5 scc/s or even 1 scc/s or more (to provide desirably fast articulation response). Hence, the throat sizes of these two valves may be different in some embodiments. Note that in some embodiments (particularly those with a pressure-controlled plenum between a canister and the inflation valves, or those having non-cryogenic pressurized fluid sources), the fluids flowing to and from may be more similar, for example, with liquid flowing to and from the balloons, gas flowing to and from the balloons, or the like.

Figure 18F:
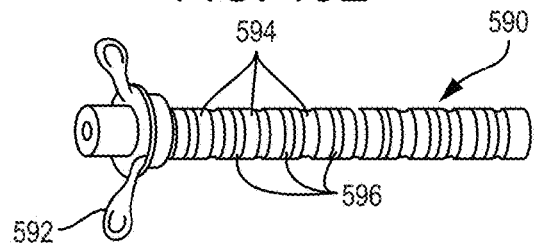
FIGS. 18F and 18G illustrate an interface for coupling any of a plurality of alternative multi-lumen shafts having differing sizes and/or shapes to a stacked-plate fluid manifold assembly.
Figure 18G:
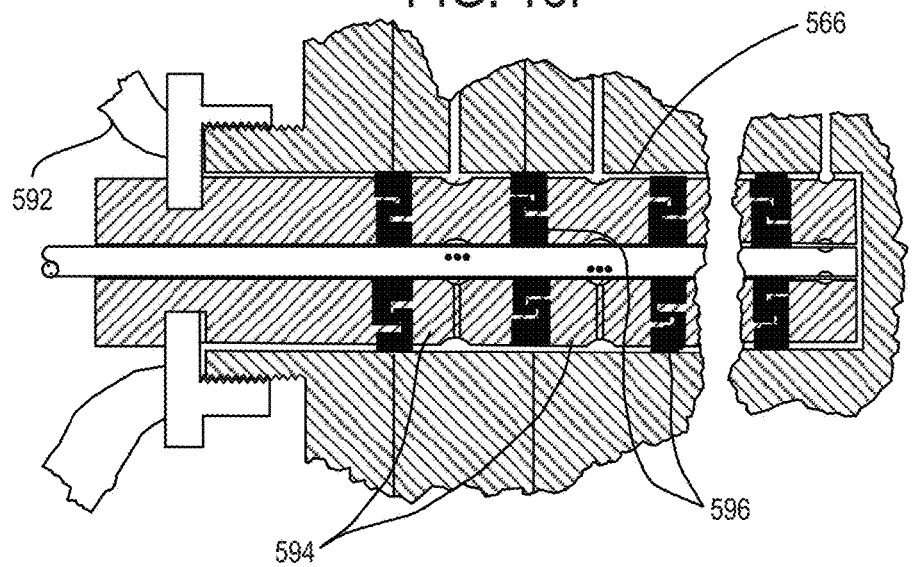

Referring to FIGS. 18F and 18G, it may be desirable to use a manifold assembly (or components thereof) with a number of different types of articulatable structures, for example with catheters having different sizes and/or shapes of multi-lumen shafts. Toward that end, it may be beneficial to include an interface body 590 for coupling a multi-lumen core shaft 592 (or other lumen-contain substrate) of the articulatable structure with a receptacle 566 of a manifold assembly 556. Interface body 590 has a proximal end and a distal end with an axial lumen extending therebetween. The axial lumen receives a multi-lumen shaft proximally, and the shaft may extend entirely through the interface body (so that registration between the ports of the shaft and the channels of the plate modules relies on engagement of the shaft with a surface of the back cap as shown in FIG. 18G, the receptacle comprising a blind hole) or the proximal end of the shaft may engage a bottom of the lumen in the interface body (so that the interface body is registered with the receptacle and the lumen is registered with the interface body). A quick disconnect fitting 592 is near the distal end of the interface body. Interface body 590 comprises a set of relatively rigid annular structures or rings 594 (optionally comprising metal or a relatively high-durometer polyme) interleaved with elastomeric seal material 596 (optionally overmolded on the rings or the like). Indentations optionally run circumferentially around the inner and outer surfaces in the middle of each ring, and one or more gas passages run radially between an inner surface of the ring and an outer surface of the ring, optionally between the indentations. Features may be included on the axial ends of the rings to inhibit separation of the body into axial segments.

Referring still to FIGS. 18F and 18G, the receptacle of the manifold may optionally comprise a smooth blind hole that extends through all valve plates of the stack. The valve plates may have fluid channels running into and out of the receptacle between the plate/plate borders. A feature of the manifold will often facilitate coupling, here being a short threaded tube that extends distally from the manifold around the opening of the receptacle. This feature mates with quick-disconnect fitting 592, shown as a wing-nut to affix the interface body and the mullti-lumen shaft to the manifold. To connect the catheter to the manifold, the user inserts the multi-lumen shaft into the interface body, slides them both together into the receptacle of the manifold till the proximal end of the shaft hits the bottom of the receptacle (or till the interface body engages a registration feature). The user can engage and tightens the threads which axially compresses the connector shaft, causing the elastomeric seal material 596 to bulge inward (to seal around the multi-lumen shaft) and outward (to seal around the interface body), separating the receptacle into an axial series of sealed zones, one for each plate. Different interface bodies having different inner diameters and/or different inner cross-sections can be made for different shaft sizes and shapes. A single thread, fastener, or latch may optionally apply axial pressure to seal around a plurality of multi-lumen shafts, or separate quick-disconnect fittings may be included for each shaft.

Figure 19:
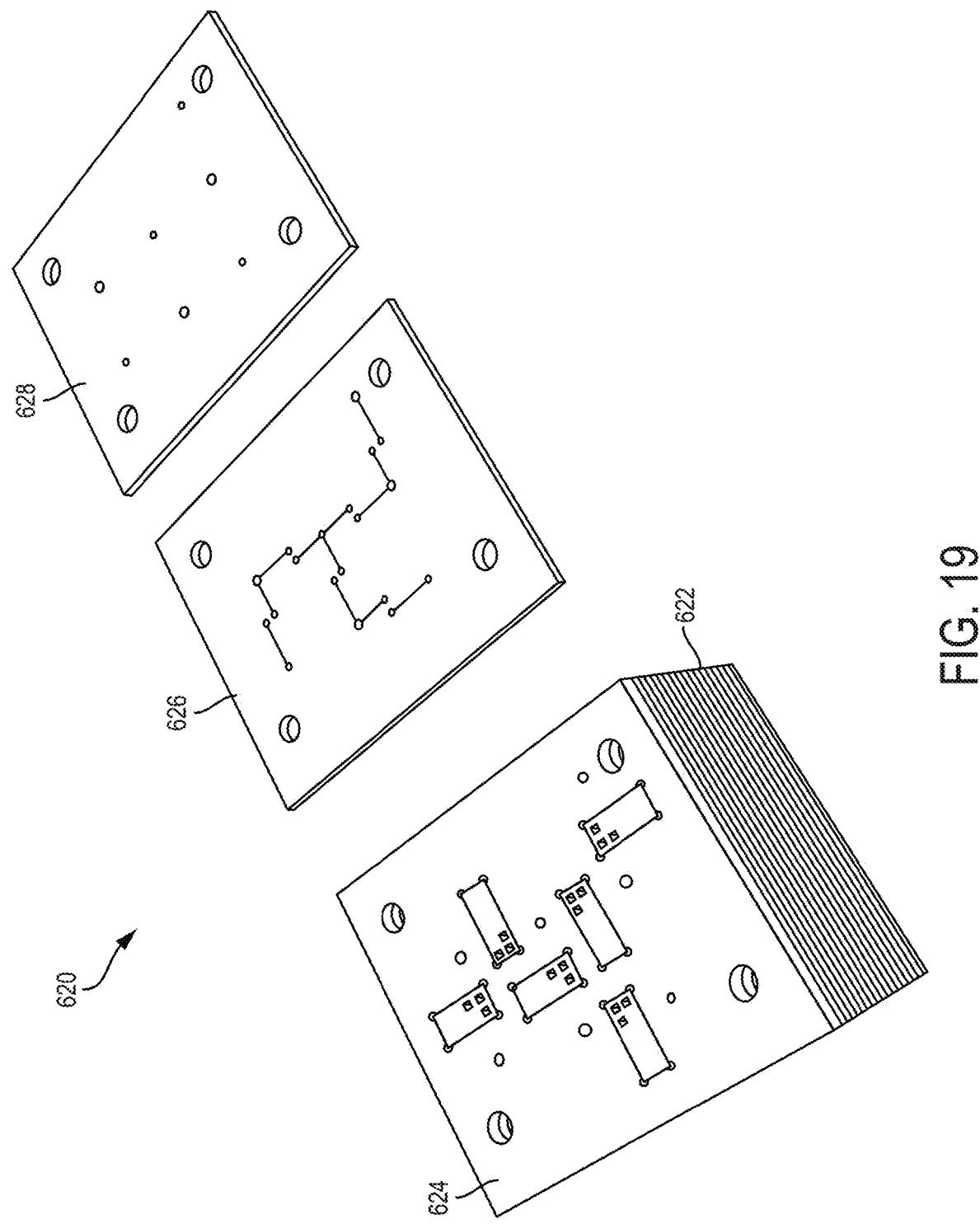
FIG. 19 is a perspective view of a modular manifold with the layers of one of the valve assemblies exploded so as to show the associated valves, axial passages, and lateral channels.

Referring now to FIG. 19, a further alternative manifold structure 620 includes a stack of valve unit plates 622 in which each valve unit is formed with three layers 624, 626, 628. All the layers include axial passages, and these passages are aligned along the axis of the inserted multi-lumen core shafts to define multi-lumen receptacles, inflation headers, deflation headers, and the like. First layer 624 includes valve receptacles containing discrete microelectromechanical system (MEMS) valves, which may be electrically coupled to the processor and/or mounted to the plate layer using a flex circuit adhesively bonded to the back side of the layer (not shown), with the flex circuit optionally having O-rings mounted or formed thereon to seal between adjacent valve unit plates. Second valve layer 626 may have through-holes coupled by channels to provide flow between the valve ports, headers, and multi-lumen receptacles, and may be sealingly bonded between third plate layer 628 and first plate layer 624 (optionally with O-rings engaging the valves around the valve ports. Suitable MEMS valves may be available from DunAn Microstaq, Inc., of Texas, NanoSpace of Sweeden, Moog of California, or others. The assembled modular valve-unit stack may have dimensions of less than 2½"×2½"×2" for a two or three multi-lumen core system having 12 lumens per core (and thus including 36 separately controllable lumen channels, and having an inflation valve and a deflation valve for each lumen for a total of at least 64 valves). Plate layers 624, 626, 628 may comprise polymers (particularly polymers which are suitable for use at low temperatures (such as PTFE, FEP, PCTFE, or the like), metal (such as aluminum, stainless steel, brass, alloys, an amorphous metal alloy such as a Liquidmetal™ alloy, or the like), glass, semiconductor materials, or the like, and may be mechanically machined or laser-micromachined, 3D printed, or patterned using stereolithography, but will preferable be molded. Alternative MEMS valve systems may have the valve structure integrated into the channel plate structure, further reducing size and weight.

Figure 19A:
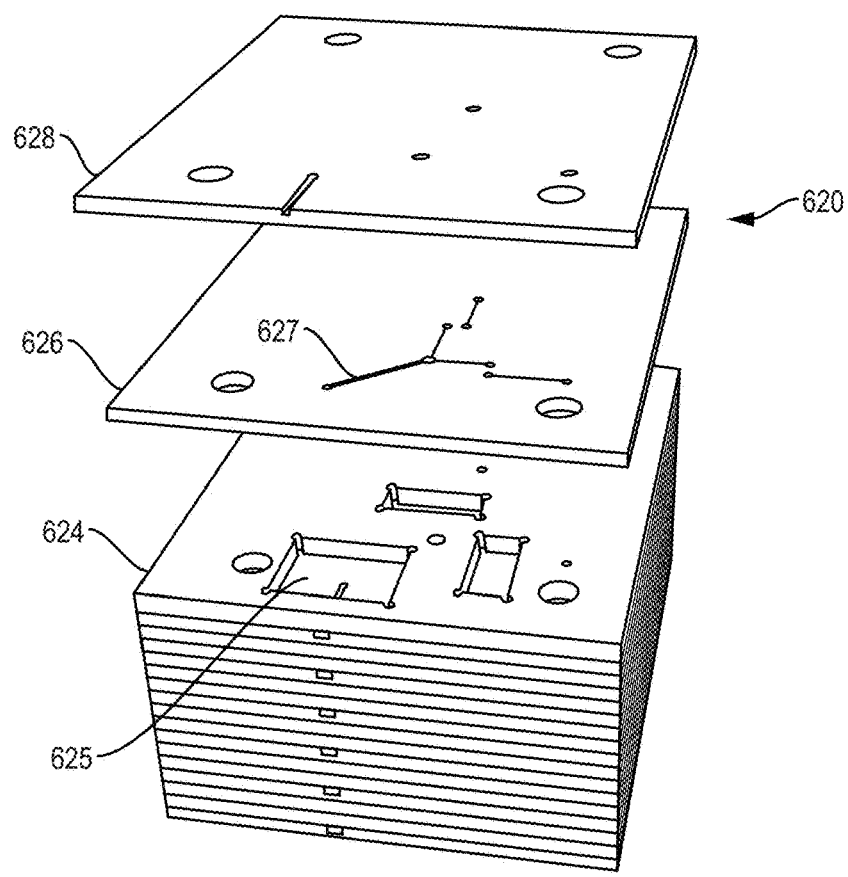
FIGS. 19A and 19B are a simplified perspective view and a schematic cross-section of plate layers used in a modular manifold similar to that of FIG. 19, showing channels and passages for one of multi-lumens shafts.
Figure 19B:
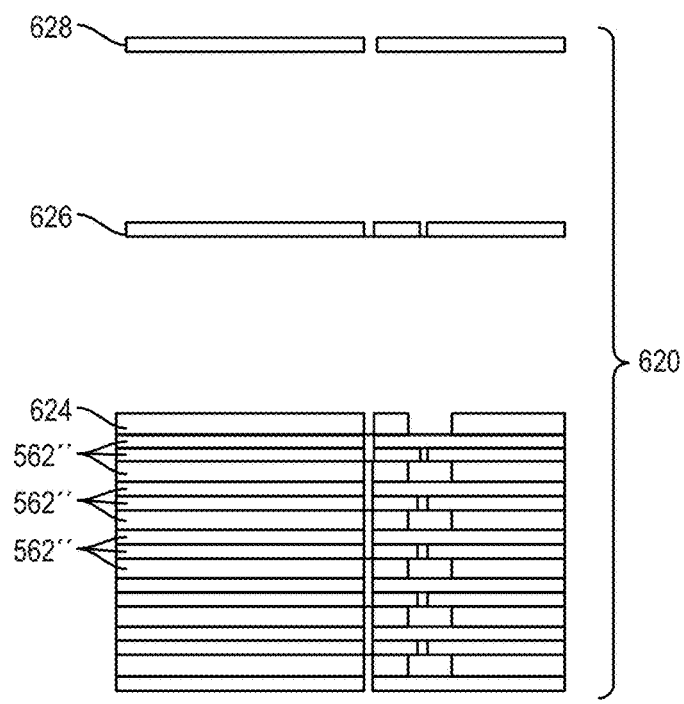

Referring to FIGS. 19A and 19B, additional features that can be included in the plate layer structure of MEMS manifold 620 can be understood. Many of the channels, passages, and features shown here are for interfacing with a single multi-lumen shaft for simplicity; additional features may be included for additional shafts. As control over the fluid channels may benefit from pressure sensors coupled with the channels of each plate module, an aperture for a MEMS pressure sensor 625 is included in first plate 624, with an associated channel 627 (extending between the receptacle and a pressure sensing region of the pressure sensor) being included in second plate 626. Suitable pressure sensors may be commercially available from Merit Sensor Systems and a number of alternative suppliers. As the pressure sensor and the valve may have different thicknesses, it may be beneficial to separate first layer 624 into two layers (with the aperture for the thicker components provided in both, and the aperture for the thinner component only being provided through one). As the pressure sensor may benefit from an external reference pressure, a relief channel may be formed in third plate 628 extending from a reference pressure location on the sensor to an external port. As can be understood with reference to FIG. 19B, the layers combine to form a plate structure 562", with each plate having opposed proximal and distal major surfaces. The plates (and the components supported thereon to make up the plate modules) can be stacked to form the modular manifold array.

Many of the flexible articulated devices described above rely on inflation of one or more balloons to articulate a structure from a first resting state to a second state in which a skeleton of the flexible structure is resiliently stressed. By deflating the balloons, the skeleton can urge the flexible structure back toward the original resting state. This simple system may have advantages for many applications. Nonetheless, there may be advantages to alternative systems in which a first actuator or set of actuators urges a flexible structure from a first state (for example, a straight configuration) to a second state (for example, a bent or elongate configuration), and in which a second actuator or set of actuators are mounted in opposition to the first set such that the second can actively and controllably urge the flexible structure from the second state back to the first state. Toward that end, exemplary systems described below often use a first set of balloons to locally axially elongate a structural skeleton, and a second set of balloons mounted to the skeleton to locally axially contract the structural skeleton. Note that the skeletons of such opposed balloon systems may have very little lateral or axial stiffness (within their range of motion) when no balloons are inflated.

Referring now to FIGS. 20A and 20B, a simplified exemplary C-channel structural skeleton 630 (or portion or cross section of a skeleton) is shown in an axially extended configuration (in FIG. 19), and in an axially contracted configuration (in FIG. 20). C-frame skeleton 630 includes an axial series of C-channel members or frames 632 extending between a proximal end 634 and a distal end 636, with each rigid C-channel including an axial wall 638, a proximal flange 640, and a distal flange 642 (generically referenced as flanges 640). The opposed major surfaces of the walls 644, 646 are oriented laterally, and the opposed major surfaces of the flanges 648, 650 are oriented axially (and more specifically distally and proximally, respectively. The C-channels alternate in orientation so that the frames are interlocked by the flanges. Hence, axially adjacent frames overlap, with the proximal and distal surfaces 650, 648 of two adjacent frames defining an overlap offset 652. The flanges also define additional offsets 654, with these offsets being measured between flanges of adjacent similarly oriented frames.

In the schematics of FIGS. 19 and 20, three balloons are disposed in the channels of each C-frame 632. Although the balloons themselves may (or may not) be structurally similar, the balloons are of two different functional types: extension balloons 660 and contraction balloons 662. Both types of balloons are disposed axially between a proximally oriented surface of a flange that is just distal of the balloon, and a distally oriented surface of a flange that is just proximal of the balloon. However, contraction balloons 662 are also sandwiched laterally between a first wall 638 of a first adjacent C-channel 632 and a second wall of a second adjacent channel. In contrast, extension balloons 660 have only a single wall on one lateral side; the opposite sides of extension balloons 660 are not covered by the frame (though they will typically be disposed within a flexible sheath or other components of the overall catheter system).

A comparison of C-frame skeleton 630 in the elongate configuration of FIG. 19 to the skeleton in the short configuration of FIG. 20 illustrates how selective inflation and deflation of the balloons can be used to induce axial extension and contraction. Note that the C-frames 632 are shown laterally reversed from each other in these schematics. In FIG. 19, extension balloons 660 are being fully inflated, pushing the adjacent flange surfaces apart so as to increase the axial separation between the associated frames. As two contraction balloons 662 are disposed in each C-channel with a single extension balloon, and as the size of the channel will not significantly increase, the contraction balloons will often be allowed to deflate at least somewhat with expansion of the extension balloons. Hence, offsets 654 will be urged to expand, and contraction offsets 652 will be allowed to decrease. In contrast, when skeleton 630 is to be driven toward the axially contracted configuration of FIG. 20, the contraction balloons 662 are inflated, thereby pushing the flanges of the overlapping frames axially apart to force contraction overlap 652 to increase and axially pull the local skeleton structure into a shorter configuration. To allow the two contraction balloons 662 to expand within a particular C-channel, the expansion balloons 660 can be allowed to deflate.

While the overall difference between C-frame skeleton 630 in the contracted configuration and in the extended configuration is significant (and such skeletons may find advantageous uses), it is worthwhile noting that the presence of one extension balloon and two contraction balloons in a single C-channel may present disadvantages as compared to other extension/contraction frame arrangements described herein. In particular, the use of three balloons in one channel can limit the total stroke or axial change in the associated offset that some of the balloons may be able to impose. Even if similar balloon/core assemblies are used as extension and contraction balloons in a three-balloon wide C-channel, the two contraction balloons may only be used for about half of the stroke of the single extension balloon, as the single extension stroke in the channel may not accommodate two full contractions strokes. Moreover, there are advantages to limiting the number of balloon/core assemblies used in a single articulated segment.

Note that whichever extension/contraction skeleton configuration is selected, the axial change in length of the skeleton that is induced when a particular subset of balloons are inflated and deflated will often be local, optionally both axially local (for example, so as to change a length along a desired articulated segment without changing lengths of other axial segments) and—where the frames extend laterally and/or circumferentially—laterally local (for example, so as to impose a lateral bend by extending one lateral side of the skeleton without changing an axial length of the other lateral side of the skeleton). Note also that use of the balloons in opposition will often involve coordinated inflating and deflating of opposed balloons to provide a maximum change in length of the skeleton. There are significant advantages to this arrangement, however, in that the ability to independently control the pressure on the balloons positioned on either side of a flange (so as to constrain an axial position of that flange) allows the shape and the position or pose of the skeleton to be modulated. If both balloons are inflated evenly at with relatively low pressures (for example, at less than 10% of full inflation pressures), the flange may be urged to a middle position between the balloons, but can move resiliently with light environmental forces by compressing the gas in the balloons, mimicking a low-spring force system. If both balloons are evenly inflated but with higher pressures, the skeleton may have the same nominal or resting pose, but may then resist deformation from that nominal pose with a greater stiffness.

An alternative S-channel skeleton 670 is shown schematically in contracted and extended configurations in FIGS. 21A and 21B, respectively, which may have both an improved stroke efficiency (giving a greater percent change in axial skeleton length for an available balloon stroke) and have fewer components than skeleton 632. S-skeleton 670 has many of the components and interactions described above regarding C-frame skeleton 630, but is here formed of structural S-channel members or frames 672. Each S-channel frame 672 has two walls 644 and three flanges 640, the proximal wall of the frame having a distal flange that is integral with the proximal flange of the distal wall of that frame. Axially adjacent S-channels are again interlocked, and in this embodiment, each side of the S-channel frame has a channel that receives one extension balloon 660 and one contraction balloon 662. This allows all extension balloons and all contraction balloons to take full advantage of a common stroke. Moreover, while there are two extension balloons for each contraction balloon, every other extension balloon may optionally be omitted without altering the basic extension/contraction functionality (though the forces available for extension may be reduced). In other words, if the extension balloons 660' as marked with an X were omitted, the skeleton could remain fully constrained throughout the same nominal range of motion. Hence, S-channel frame 672 may optionally use three or just two sets of opposed balloons for a particular articulation segment.

Figure 22F:
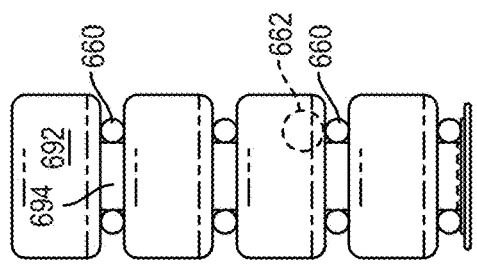
FIGS. 22D-22H are illustrations of elongate flexible articulated structures having annular skeletons with three opposed sets of balloons, and show how varying inflation of the balloons can be used to axially contract some portions of the frame and axially extend other portions to bend or elongate the frame and to control a pose or shape of the frame in three dimensions.
Figure 22E:
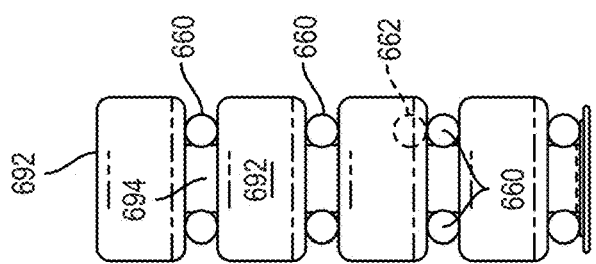
Figure 22D:
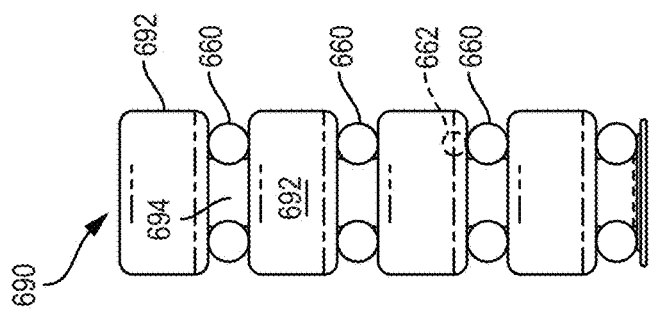

Referring now to FIG. 22A, a modified C-frame skeleton 680 has components that share aspects of both C-frame skeleton 630 and S-frame skeleton 670, and may offer advantages over both in at least some embodiments. Modified C skeleton 680 has two different generally C-frames or members: a C-frame 682, and a bumper C-frame 684. C-frame 682 and bumper frame 64 both have channels defined by walls 644 and flanges 648 with an axial width to accommodate two balloon assemblies, similar to the channels of the S-frames 672. Bumper frame 684 also has a protrusion or nub 686 that extends from one flange axially into the channel. The adjacent axial surfaces of these different frame shapes engage each other at the nub 686, allowing the frames to pivot relative to each other and facilitating axial bending of the overall skeleton, particularly when using helical frame members.

Figure 22C:
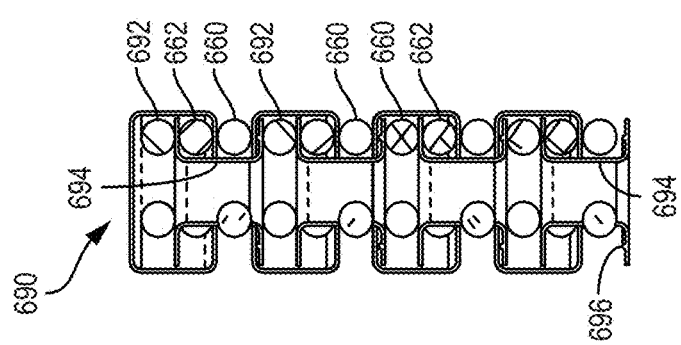
FIGS. 22B and 22C are a schematic illustration of an exemplary axial expansion/contraction skeleton with axial expansion and axial contraction balloons; and a corresponding cross-section of a skeleton having an axial series of annular members or rings articulated by the axial expansion and axial contraction balloons, respectively.
Figure 22B:
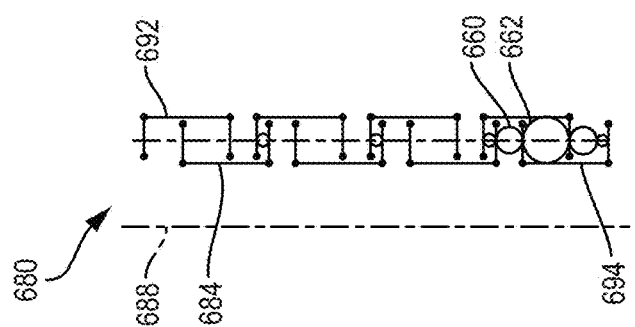

Referring now to FIGS. 22B and 22C, a relationship between the schematic extension/retraction frame illustration of FIGS. 20A-22A and a first exemplary three dimensional skeleton geometry can be understood. To form an axisymmetric ring-frame skeleton structure 690 from the schematic modified C-frame skeleton 680 of FIG. 22B, the geometry of frame members 682, 684 can be rotated about an axis 688, resulting in annular or ring frames 692, 694. These ring frames retain the wall and flange geometry described above, but now with annular wall and flanges being interlocked. The annular C-frames 682, 684 were facing different directions in schematic skeleton 680, so that outer C-frame ring 692 has an outer wall (sometimes being referred to as outer ring frame 692) and a channel that opens radially inwardly, while bumper C-frame ring 694 has a channel that is open radially outwardly and an inner wall (so that this frame is sometimes referred to as the inner ring frame 694). Ring nub 696 remains on inner ring frame 694, but could alternatively be formed on the adjacent surface of the outer ring frame (or using corresponding features on both). Note that nub 696 may add more value where the frame deforms with bending (for example, the frame deformation with articulation of the helical frame structures described below) as the deformation may involve twisting that causes differential angles of the adjacent flange faces. Hence, a non-deforming ring frame structure might optionally omit the nub in some implementations.

Referring now to FIGS. 22C-22F, uniform axial extension and contraction of a segment of ring-frame skeleton 690 is performed largely as described above. To push uniformly about the axis of the ring frames, three balloons are distributed evenly about the axis between the flanges (with centers separated by 120 degrees). The balloons are shown here as spheres for simplicity, and are again separated into extension balloons 660 and contraction balloons 662. In the straight extended configuration of FIG. 22D, the extension balloons 660 of the segment are all fully inflated, while the contraction balloons 662 are all fully deflated. In an intermediate length configuration shown in FIG. 22E, both sets of balloons 660, 662 are in an intermediate inflation configuration. In the short configuration of FIG. 22F, contraction balloons 662 are all fully inflated, while extension balloons 660 are deflated. Note that the state of the balloons remains axisymmetrical, so that the lengths on all lateral sides of the ring frame skeleton 690 remain consistent and the axis of the skeleton remains straight.

Figure 22G:
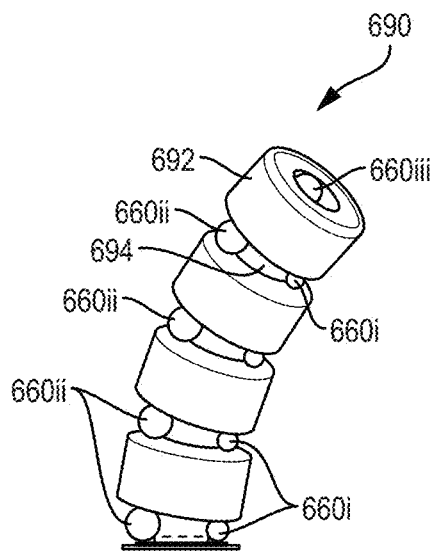
Figure 22H:
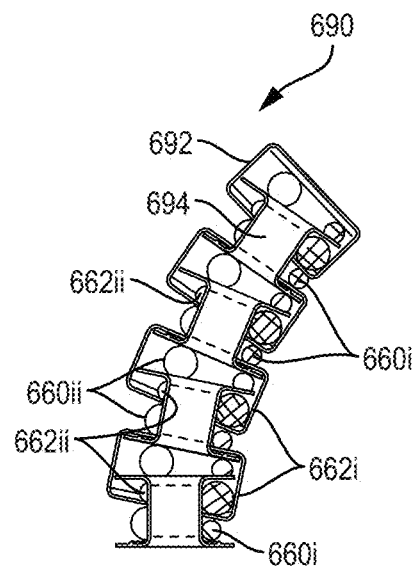

As can be understood with reference to FIGS. 22G and 22H, lateral bending or deflection of the axis of ring-frame skeleton 690 can be accomplished by differential lateral inflation of subsets of the extension and contraction balloons. There are three balloons distributed about the axis between each pair of articulated flanges, so that the extension balloons 660 are divided into three sets 660*i*, 660*ii*, and 660*iii*. Similarly, there are three sets of contraction balloons 662*i*, 662*ii*, and 662*iii*. The balloons of each set are aligned along the same lateral orientation from the axis. In some exemplary embodiments, each set of extension balloons (extension balloons 660*i*, extension balloons 660*ii*, and extension balloons 660*iii*) along a particular segment is coupled to an associated inflation fluid channel (for example, a channel i for extension balloons 660*i*, a channel ii for extension balloons 660*ii*, and a channel iii for extension balloons 660*iii*, the channels not shown here). Similarly, each set of contraction balloons 662*i*, 662*ii*, and 662*iii* is coupled to an associated inflation channel (for example, channels iv, v, and vi, respectively) so that there are a total of 6 lumens or channels per segment (providing three degrees of freedom and three orientation-related stiffnesses). Other segments may have separate fluid channels to provide separate degrees of freedom, and alternative segments may have fewer than 6 fluid channels. Regardless, by selectively deflating the extension balloons of a first lateral orientation 660*i* and inflating the opposed contraction balloons 662*i*, a first side of ring frame skeleton 690 can be shortened. By selectively inflating the extension balloons of the other orientations 660*ii*, 660*iii*, and by selectively deflating the contraction balloons of those other orientations 662*ii*, 662*iii*, the laterally opposed portion of ring frame skeleton 690 can be locally extended, causing the axis of the skeleton to bend. By modulating the amount of elongation and contraction distributed about the three opposed extension/contraction balloon orientations, the skeleton pose can be smoothly and continuously moved and controlled in three degrees of freedom.

Figure 23A:
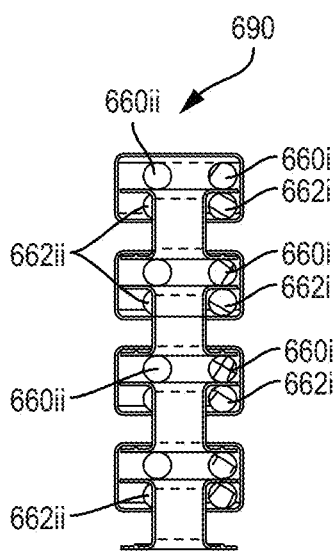
Figure 23B:
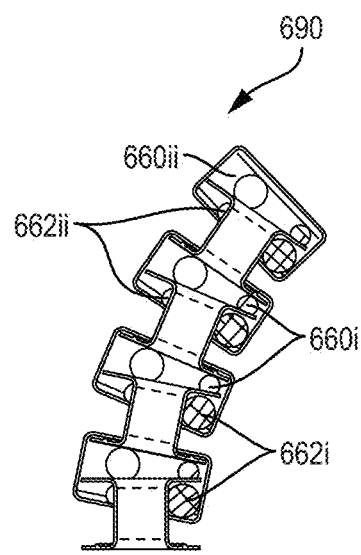

Referring now to FIGS. 23A and 23B, as described above with reference to FIGS. 21A and 21B, while it is possible to include balloons between all the separated flanges so as to maximize available extension forces and the like, there may be advantages to foregoing kinematically redundant balloons in the system for compactness, simplicity, and cost. Toward that end, ring frame skeletons having 1-for-1 opposed extension and contraction balloons (660*i*, 660*ii*, and 660*iii*; and 662*i*, 662*ii*, and 662*iii*) can provide the same degrees of freedom and range of motion as provided by the segments of FIGS. 22G and 22H (including two transverse X-Y lateral bending degrees of freedom and an axial Z degree of freedom), and can also control stiffness, optionally differentially modulating stiffness of the skeleton in different orientations in 3D space. The total degrees of freedom of such a segment may appropriately be referenced as being 4-D (X, Y, Z, & S for Stiffness), with the stiffness degree of freedom optionally having 3 orientational components (so as to provide as many as 5-D or 6-D. Regardless, the 6 fluid channels may be used to control 4 degrees of freedom of the segment.

As can be understood with reference to FIGS. 23C-23E and 23H, elongate flexible bodies having ring-frame skeletons 690' with larger numbers of inner and outer ring frames 692, 694 (along with associated larger numbers of extension and retraction balloons) will often provide a greater range of motion than those having fewer ring frames. The elongation or Z axis range of motion that can be provided by balloon articulation array may be expressed as a percentage of the overall length of the structure, with larger percentage elongations providing greater ranges of motion. The local changes in axial length that a balloon array may be able to produce along a segment having ring frames 690, 690' (or more generally having the extension contraction skeleton systems described herein) may be in a range of from about 1 percent to about 45 percent, typically being from about 2½ percent to about 25 percent, more typically being from about 5 percent to about 20 percent, and in many cases being from about 7½ percent to about 17½ percent of the overall length of the skeleton. Hence, the longer axial segment length of ring frame skeleton 690' will provide a greater axial range of motion between a contracted configuration (as shown in FIG. 23E) and an extended configuration (as shown in FIG. 23C), while still allowing control throughout a range of intermediate axial length states (as shown in FIG. 23D).

As can be understood with reference to FIGS. 23A, 23B, 23D and 23H, setting the balloon pressures so as to axially contract one side of a ring frame skeleton 690' (having a relatively larger number of ring frames) and axially extend the other side laterally bends or deflects the axis of the skeleton through a considerable angle (as compared to a ring frame skeleton having fewer ring frames), with each frame/frame interface typically between 1 and 15 degrees of axial bend angle, more typically being from about 2 to about 12 degrees, and often being from about 3 to about 8 degrees. A catheter or other articulated elongate flexible body having a ring frame skeleton may be bent with a radius of curvature (as measured at the axis of the body) of between 2 and 20 times an outer diameter of the skeleton, more typically being from about 2.25 to about 15 times, and most often being from about 2.4 to about 8 times. While more extension and contraction balloons 660, 662 are used to provide this range of motion, the extension and contraction balloon subsets (660*i*, 660*ii*, and 660*iii*; and 662*i*, 662*ii*, and 662*iii*) may still each be supplied by a single common fluid supply lumen. For example, 6 fluid supply channels may each be used to inflate and deflate 16 balloons in the embodiment shown, with the balloons on a single lumen being extension balloons 660*i* aligned along one lateral orientation.

Figure 23I:
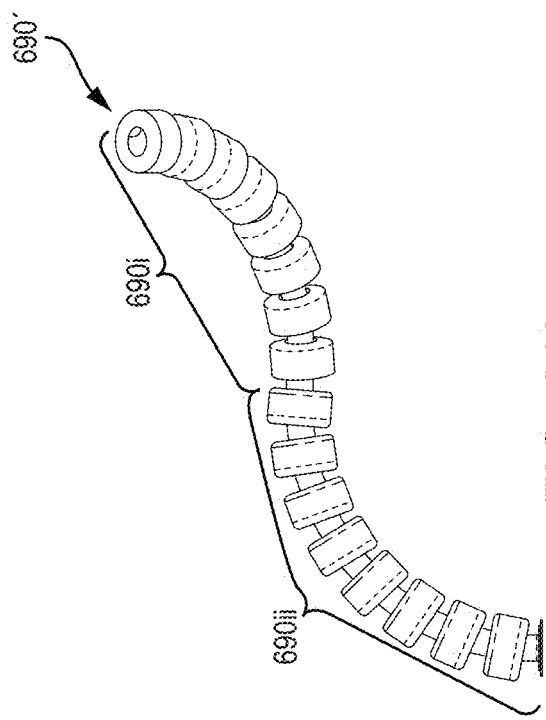
Figure 23H:
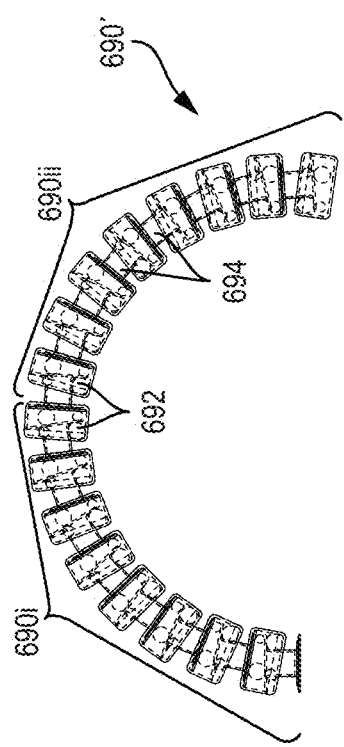

As can be understood with reference to ring frame skeleton 690' in the straight configuration of FIG. 23D, in the continuously bent configuration of FIG. 23H, and in the combined straight and bent configuration of FIG. 23F, exemplary embodiments of the elongate skeleton 690' and actuation array balloon structures described herein may be functionally separated into a plurality of axial segments 690*i*, 690*ii*. Note that many or most of the skeleton components (including frame members or axial series of frame members, and the like) and actuation array components (including the substrate and/or core, some or all of the fluid channels, the balloon outer tube or sheath material, and the like), along with many of the other structures of the elongate flexible body (such as the inner and outer sheaths, electrical conductors and/or optical conduits for diagnostic, therapeutic, sensing, navigation, valve control, and other functions) may extend continuously along two or more axial segments with few or no differences between adjacent segments, and optionally without any separation in the functional capabilities between adjacent segments. For example, an articulated body having a two-segment ring frame skeleton 690' system as shown in FIG. 23H may have a continuous axial series of inner and outer ring frames 692, 694 that extends across the interface between the joints such that the two segments can be bent in coordination with a constant bend radius by directing similar inflation fluid quantities and pressures along the fluid supply channels associated with the two separate segments. As can be understood with reference to FIG. 23G, other than differing articulation states of the segments, there may optionally be few or no visible indications of where one segment ends and another begins.

Figure 23J:
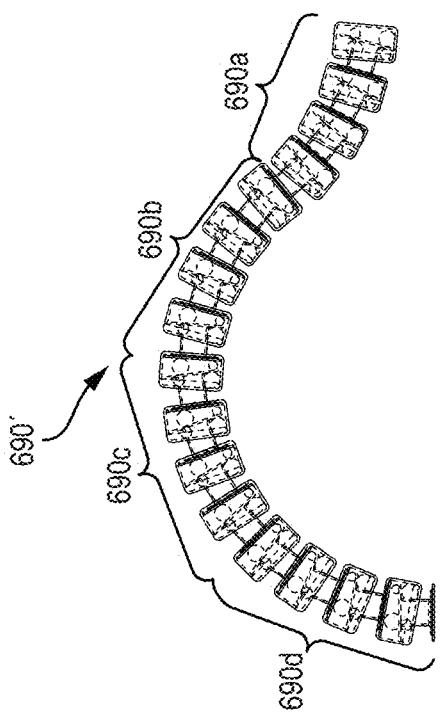

Despite having many shared components (and a very simple and relatively continuous overall structure), functionally separating an elongate skeleton into segments provides tremendous flexibility and adaptability to the overall articulation system. Similar bend radii may optionally be provided with differing stiffnesses by applying appropriately differing pressures to the opposed balloons 660, 662 of two (or more) segments 690*i*, 690*ii*. Moreover, as can be understood with reference to FIG. 23F, two (or more) different desired bend radii, and/or two different lateral bend orientations and/or two different axial segments lengths can be provided by applying differing inflation fluid supply pressures to the opposed contraction/extension balloon sets 660*i*, 660*ii*, 660*iii*, 662*i*, 662*ii*, 662*iii* of the segments. Note that the work spaces of single-segment and two-segment systems may overlap so that both types of systems may be able to place an end effector or tool at a desired position in 3D space (or even throughout a desired range of locations), but multiple-segment systems will often be able to achieve additional degrees of freedom, such as allowing the end effector or tool to be oriented in one or more rotational degrees of freedom in 6D space. As shown in FIG. 23J, articulated systems having more than two segments offer still more flexibility, with this embodiment of ring frame skeleton 690' having 4 functional segments 690*a*, 690*b*, 690*c*, and 690*d*. Note that still further design alternatives may be used to increase functionality and cost/complexity of the system for a desired workspace, such as having segments of differing length (such as providing a relatively short distal segment 690*a* supported by a longer segment having the combined lengths of 690*b*, 690*c*, and 690*d*. While many of the multi-segment embodiments have been shown and described with reference to planar configurations of the segments where all the segments lie in a single plane and are either straight or in a fully bent configuration, it should also be fully understood that the plurality of segments 690*i*, 690*ii*, etc., may bend along differing planes and with differing bend radii, differing axial elongation states, and/or differing stiffness states, as can be understood with reference to FIG. 23I.

Catheters and other elongate flexible articulated structures having ring frame skeletons as described above with reference to FIGS. 22C-23I provide tremendous advantages in flexibility and simplicity over known articulation systems, particularly for providing large numbers of degrees of freedom and when coupled with any of the fluid supply systems described herein. Suitable ring frames may be formed of polymers (such as nylons, urethanes, PEBAX, PEEK, HDPE, UHDPE, or the like) or metals (such as aluminum, stainless steel, brass, silver, alloys, or the like), optionally using 3D printing, injection molding, laser welding, adhesive bonding, or the like. Articulation balloon substrate structures may initially be fabricated and the balloon arrays assembled with the substrates in a planar configuration as described above, with the arrays then being assembled with and/or mounted on the skeletons, optionally with the substrates being adhesively bonded to the radially inner surfaces of the inner rings and/or to the radially outer surfaces of the outer rings, and with helical or serpentine axial sections of the substrate bridging between ring frames. While extension and retraction balloons 660, 662 associated with the ring frame embodiments are shown as spherical herein, using circumferentially elongate (and optionally bent) balloons may increase an area of the balloon/skeleton interface, and thereby enhance axial contraction and extension forces. A huge variety of modifications might also be made to the general ring-frame skeletal arrangement and the associated balloon arrays. For example, rather than circumferentially separating the balloons into three lateral orientations, alternative embodiments may have four lateral orientations (+X, −X, +Y, and −Y) so that four sets of contraction balloons are mounted to the frame in opposition to four sets of extension balloons. Regardless, while ring-frame skeletons have lots of capability and flexibility and are relatively geometrically simple so that their functionality is relatively easy to understand, alternative extension/contraction articulation systems having helical skeleton members (as described below) may be more easily fabricated and/or more easily assembled with articulation balloon array components, particularly when using the advantageous helical multi-lumen core substrates and continuous balloon tube structures described above.

First reviewing components of an exemplary helical frame contraction/expansion articulation system, FIGS. 24A-24E illustrate actuation balloon array components and their use in a helical balloon assembly. FIGS. 24F and 24G illustrate exemplary outer and inner helical frame members. After reviewing these components, the structure and use of exemplary helical contraction/expansion articulation systems (sometimes referred to herein as helical push/pull systems) can be understood with reference to FIGS. 25 and 26.

Referring now to FIGS. 24A and 24B, an exemplary multi-lumen conduit or balloon assembly core shaft has a structure similar to that of the core described above with reference to FIGS. 14 and 15. Core 702 has a proximal end 704 and a distal end 706 with a multi-lumen body 708 extending therebetween. A plurality of lumens 710*a*, 710*b*, 710*c*, . . . extend between the proximal and distal ends. The number of lumens included in a single core 702 may vary between 3 and 30, with exemplary embodiments have 3, 7 (of which one is a central lumen), 10 (including 1 central), 13 (including 1 central), 17 (one being central), or the like. The multi-lumen core will often be round but may alternatively have an elliptical or other elongate cross-section as described above. When round, core 702 may have a diameter 712 in a range from about 0.010" to about 1", more typically being in a range from about 0.020" to about 0.250", and ideally being in a range from about 0.025" to about 0.100" for use in catheters. Each lumen will typically have a diameter 714 in a range from about 0.0005" to about 0.05", more preferably having a diameter in a range from about 0.001" to about 0.020", and ideally having a diameter in a range from about 0.0015" to about 0.010". The core shafts will typically comprise extruded polymer such as a nylon, urethane, PEBAX, PEEK, PET, other polymers identified above, or the like, and the extrusion will often provide a wall thickness surrounding each lumen of more than about 0.0015", often being about 0.003" or more. The exemplary extruded core shown has an OD of about 0.0276"", and 7 lumens of about 0.004" each, with each lumen surrounded by at least 0.004" of the extruded nylon core material.

Referring still to FIGS. 24A and 24B, the lumens of core 702 may have radial balloon/lumen ports 716*a*, 716*b*, 716*c*, . . . , with each port comprising one or more holes formed through the wall of core 702 and into an associated lumen 710*a*, 710*b*, 710*c*, . . . respectively. The ports are here shown as a group of 5 holes, but may be formed using 1 or more holes, with the holes typically being round but optionally being axially elongate and/or shaped so as to reduce pressure drop of fluid flow therethrough. In other embodiments (and particularly those having a plurality of balloons supplied with inflation fluid by a single lumen), having a significant pressure drop between the lumen and the balloon may help even the inflation state of balloons, so that a total cross section of each port may optionally be smaller than a cross-section of the lumen (and/or by limiting the ports to one or two round lumens). Typical ports may be formed using 1 to 10 holes having diameters that are between 10% of a diameter of the associated lumen and 150% of the diameter of the lumen, often being from 25% to 100%, and in many cases having diameters of between 0.001" and 0.050". Where more than one hole is included in a port they will generally be grouped together within a span that is shorter than a length of the balloons, as each port will be contained within an associated balloon. Spacing between the ports will correspond to a spacing between balloons to facilitate sealing of each balloon from the axially adjacent balloons.

Regarding which lumens open to which ports, the ports along a distal portion of the core shaft will often be formed in sets, with each set being configured to provide fluid flow to and from an associated set of balloons that will be distributed along the loops of the core (once the core is bent to a helical configuration) for a particular articulated segment of the articulated flexible body. When the number of lumens in the core is sufficient, there will often be separate sets of ports for different segments of the articulated device. The ports of each set will often form a periodic pattern along the axis of the multi-lumen core 702, so that the ports provide fluid communication into M different lumens (M being the number of different balloon orientations that are to be distributed about the articulated device axis, often being 3 or 4, i.e., lumen 710*a*, lumen 710*b*, and lumen 710*c*) and the pattern repeating N times (N often being the number of contraction balloons along each orientation of a segment). Hence, the multi-lumen core conduit can function as a substrate that supports the balloons, and that defines the balloon array locations and associated fluid supply networks described above. Separate multi-lumen cores 702 and associated balloon arrays may be provided for contraction and expansion balloons.

As one example, a port pattern might be desired that includes a 3×5 contraction balloon array for a particular segment of a catheter. This set of ports might be suitable when the segment is to have three lateral balloon orientations (M=3) and 5 contraction balloons aligned along each lateral orientation (N=5). In this example, the distal-most port 716*a* of the set may be formed through the outer surface of the core into a first lumen 710*a*, the next proximal port 716*b* to lumen 710*b*, the next port 716*c* to lumen 710*c*, so that the first 3 (M) balloons define an "a, b, c" pattern that will open into the three balloons that will eventually be on the distal-most helical loop of the set. The same pattern may be repeated 5 times (for example: a, b, c, a, b, c, a, b, c, a, b, c, a, b, c) for the 5 loops of the helical coil that will support all 15 contraction balloons of a segment to the fluid supply system such that the 5 contraction balloons along each orientation of the segment are in fluid communication with a common supply lumen. Where the segment will include expansion balloons mounted 1-to-1 in opposition to the contraction balloons, a separate multi-lumen core and associated balloon may have a similar port set; where the segment will include 2 expansion balloons mounted in opposition for each contraction balloon, two separate multi-lumen cores and may be provided, each having a similar port set.

If the same multi-lumen core supplies fluid to (and supports balloons of) another independent segment, another set of ports may be provided axially adjacent to the first pattern, with the ports of the second set being formed into an M'×N' pattern that open into different lumens of the helical coil (for example, where M'=3 and N'=5: d, e, f, d, e, f, d, e, f, d, e, f, d, e, f), and so on for any additional segments. Note that the number of circumferential balloon orientations (M) will often be the same for different segments using a single core, but may be different in some cases. When M differs between different segments of the same core, the spacing between ports (and associated balloons mounted to the core) may also change. The number of axially aligned contraction balloons may also be different for different segments of the same helical core, but will often be the same. Note also that all the balloons (and associated fluid lumens) for a particular segment that are on a particular multi-lumen core will typically be either only extension or only contraction balloons (as the extension and contraction balloon arrays are disposed in helical spaces that may be at least partially separated by the preferred helical frame structures described below). A single, simple pattern of ports may be disposed near the proximal end of core shaft 702 to interface each lumen with an associated valve plate of the manifold, the ports here being sized to minimized pressure drop and the port-port spacing corresponding to the valve plate thickness. Regardless, the exemplary core shown has distal ports formed using groups of 5 holes (each having a diameter of 0.006", centerline spacing within the group being 0.012"), with the groups being separated axially by about 0.103".

Referring still to FIGS. 24A and 24B, an exemplary laser drilling pattern for forming ports appropriate for an articulated two distal segments, each having a 3×4 balloon array, may be summarized in table form as shown in Table 1:

TABLE 1

| Drill to Lumen #s \ | Theta 1 | Theta 2 | Theta 3 |
|---|---|---|---|
| Segment 1, | | | |
| N1 | 1 | 2 | 3 |
| N2 | 1 | 2 | 3 |
| N3 | 1 | 2 | 3 |
| N4 | 1 | 2 | 3 |
| Segment 2, | | | |
| N1 | 4 | 5 | 6 |
| N2 | 4 | 5 | 6 |
| N3 | 4 | 5 | 6 |
| N4 | 4 | 5 | 6 |

Theta 1, Theta 2, and Theta 3 here indicate the three lateral bending orientations, and as M=3, the balloons will typically have centerlines separated by about 120 degrees once the balloon/shaft assembly is coiled. Hence, the centerline spacing between the ports along the straight shaft (prior to coiling) will typically correspond to a helical segment length having about a 120 degree arc angle of the final articulated structure, both within a particular N subset and between adjacent N subsets of a segment. However, the alignment of each circumferential subset along a lateral bending axis does not necessarily mean that adjacent balloons are separated by precisely 120 degrees, or that the N balloons of a subset are aligned exactly parallel to the axis when the segment is in all configurations. For example, there may be some unwinding of the helical core associated with axial elongation, and there may be benefits to having the balloons along a particular bending orientation trending slightly circumferentially around the axis (when going from balloon to balloon of a lateral bending subset) so that lateral bends are closer to being planer in more segment states. The separation between balloons may remain consistent between segments, or may be somewhat longer to accommodate affixation of the balloon/shaft assembly to frames and inner and outer sheaths. Drill patterns for the proximal end may be somewhat simpler, as a single port may be drilled to provide fluid communication between each lumen and an associated valve plate module of the manifold assembly, as shown in Table 2:

TABLE 2

|  | Drill to Lumen #s |
|---|---|
| Plate 1 | 1 |
| Plate 2 | 2 |
| Plate 3 | 3 |
| Plate 4 | 4 |
| Plate 5 | 5 |
| Plate 6 | 6 |
| Plate 7 |  |
| Plate 8 |  |

Note that this tabular data provides a correlation between valves of a plate and subsets of articulation balloons, and thus of the kinematics of the system. Hence, the system processor will often have access to this or related data when an articulated structure is coupled with the manifold, preferably on a plug-and-play basis. Similar (though possibly different) drill patterns may correlate the drill patterns of other multi-lumen cores with the valves and kinematics.

Referring now to FIGS. 24C and 24D, a continuous tube of flexible balloon wall material 718 may be formed by periodically varying a diameter of tube wall material to form a series of balloon shapes 720 separated by smaller profile sealing zones 722. Balloon tube 718 may include between about 9 and about 290 regularly spaced balloon shapes 720, with the sealing zones typically having an inner diameter that is about equal to the outer diameters of the multi-lumen helical core shafts 702 described above. In some embodiments, the inner diameters of the sealing zones may be significantly larger than the outer diameters of the associated cores when the balloon tube is formed, and the diameters of the sealing zones may be decreased (such as by heat shrinking or axially pull-forming) before or during assembly of the balloon tube and core shaft. The sealing zone may have a length of between about 0.025" and about 0.500", often being between about 0.050" and about 0.250". Decreasing the length of the sealing zone allows the length of the balloon to be increased for a given catheter size so as to provide larger balloon/frame engagement interfaces (and thus greater articulation forces), while longer sealing zones may facilitate assembly and sealing between balloons so as to avoid cross-talk between articulation channels.

Referring still to FIGS. 24C and 24D, the balloon shapes 720 of the balloon tube 718 may have diameters that are larger than the diameters of the sealing zones by between about 10% and about 200%, more typically being larger by an amount in a range from about 20% to about 120%, and often being from about 40% to about 75%. The thickness of balloon tube 718 will often vary axially with the varying local diameter of the tube, the locally large diameter portions forming the balloon shapes optionally being in a range from about 0.00008' (or about 2 microns) to about 0.005", typically being from about 0.001" and about 0.003". Balloon tube 718 may initially be formed with a constant diameter and thickness, and the diameter may be locally expanded (by blow forming, by vacuum forming, by a combination of both blow forming and vacuum forming, or by otherwise processing the tube material along the balloon shapes 720), and/or the diameter of the balloon tube may be locally decreased (by heat shrinking, by axial pull-forming, by a combination of both heat shrinking and pull forming, or by otherwise processing the tube material along the sealing zones), with the tube material often being processed so as to both locally expand the diameter along the desired balloon shapes and to locally contract the diameter along the sealing zones. Particularly advantageous techniques for forming balloon tubes may include the use of extruded polymer tubing corrugators, including the vertical small bore corrugators commercially available from Unicore, Corma, Fraenkische, and others. Suitable custom molds for such pipe corrugators may be commercially available from GlobalMed, Custom Pipe, Fraenkische, and others. Still more advanced fabrication techniques may allow blow or vacuum corrugation using a robotic shuttle corrugator and custom molds, particularly when it is desirable to change a size or spacing of balloons along a continuous tube. It should be noted that while a single continuous balloon tube is shown, a plurality of balloon tubes (each having a plurality (or in some cases, at least one) balloon shape) can be sealingly mounted onto a single core. Regardless, the sealing zones will often have a material thickness that is greater than that of the balloon shapes.

The balloon shapes 720 of the balloon tube 718 may each have a relatively simple cylindrical center section prior to assembly as shown. The tapers between the balloon center sections and the sealing zones can take any of a variety of shapes. The tapers may, for example, be roughly conical, rounded, or squared, and will preferably be relatively short so as to allow greater balloon/frame engagement for a given landing zone length. More complex embodiments may also be provided, including forming the balloon shapes with curved cylindrical center sections, optionally while corrugating or undulating the surfaces of the tapers so that the balloon tube overall remains relatively straight. The lengths of each center section is typically sufficient to define an arc-angle of from 5 to 180 degrees about the axis of the desired balloon assembly helix, more typically being from about 10 to about 50 degrees, the lengths of the center sections often being in a range from about 0.010" to about 0.400" for medical applications, more typically being from about 0.020" to about 0.150", and many times being in a range from about 0.025" to about 0.100". The exemplary balloon shapes may have an outer diameter of about 0.051" over a total balloon length (including the tapers) of about 0.059"

As can be understood with reference to FIGS. 24C, 24D, 24E, and 24E-1, balloon tube 718 may be sealingly affixed to core 702, and the core/balloon tube assembly may then be formed into a desired helical shape. The balloon tube may be sealed over the helical core using adhesive (such as any of those described above, often including UV-cured adhesives) thermal bonding, laser bonding, die bonding, and/or the like. Sealing of the balloons may also benefit from a compression structure disposed over the balloon material to help maintain tube/core engagement when the balloons are inflated. Suitable compression structures or techniques may include short sections of heat-shrink materials (such as PET) shrunk onto the sealing zones, high-strength filament windings wrapped circumferentially around the sealing zones and adhesively bonded, swaging of metallic ring structures similar to marker bands over the sealing zones, small bore crimp clamps over the sealing zones, heat-shrinking and/or pull forming the balloon tube onto the core, or the like. Any two or more of these may also be combined, for example, with the balloon tube being adhesively bonded to the core tube by injecting adhesive into the balloon tube around the sealing zone, heat shrinking the balloon tube and a surrounding PET sleeve over the sealing zone, and then swaging a metallic marker band over the sealing PET sleeve (so that the sleeve provides strain relief). Regardless, ports 716 will preferably be disposed within corresponding balloon shapes 720 and will remain open after the balloon/core assembly 730 is sealed together in the straight configuration shown in FIG. 24D. Shape setting of the balloon/core assembly from the straight configuration to the helically curved configuration of FIG. 24E can be performed by wrapping the assembly around and/or within a mandrel and heating the wrapped assembly. Helical channels may be included in the mandrel, which may also have discrete balloon receptacles or features to help ensure alignment of sets of balloons along the desired lateral balloon axes. Regardless, shape setting of the core/balloon assembly can help set the M different lateral orientations of the balloons, so that the balloons of each set 720i, 720ii, 720iii are aligned, as seen in 24E-1. As noted elsewhere, due to some slight changes in the geometry of the coiled assembly during axial elongation and the like, there may be some slight circumferential offset between balloons of the same lateral bending orientation when the articulated structure and/or its components are in some configurations, including when at rest.

Figures 3, 24E:
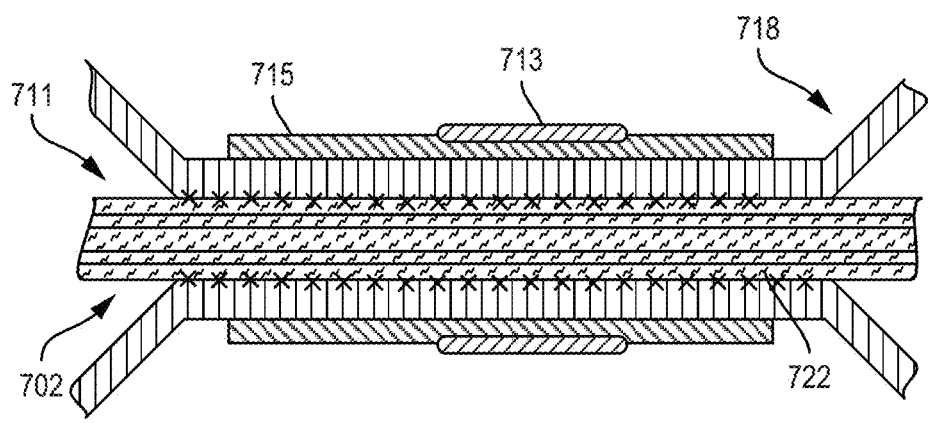
Figure 24F:
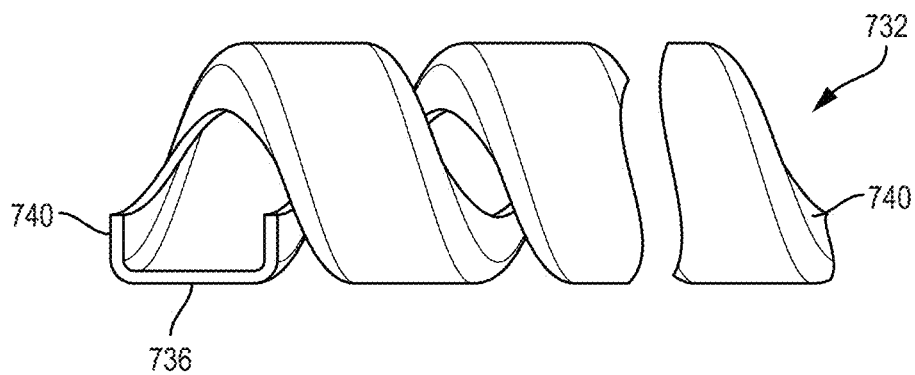
Figure 24G:
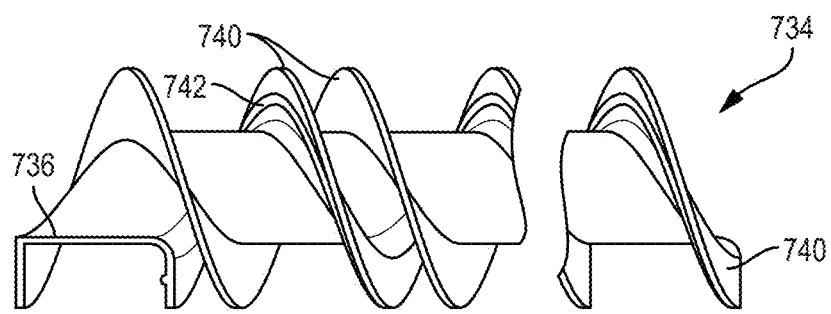

Referring to FIG. 24E-2, an alternative balloon tube 718' has a plurality of pre-curved balloon shapes 720' coupled together by sealing zones 722 to facilitate forming and/or keeping the balloon/core assembly in a helical configuration. The overall configuration of alternative balloon tube 718' is straight, and it may be beneficial to provide asymmetric corrugated transitions 725 between pre-curved balloon shapes 720' and sealing zones 722. Corrugated transitions 725 may have a form analogous to that of a corrugated straw along at least an outer radial portion of the helix, and the balloon shapes may optionally have corrugations along this outer portion instead of or in addition to the pre-curvature shown schematically here. The balloon shapes, transitions, and sealing zones may be formed by blow molding within machined or printed tooling using medical balloon blowing techniques, by blow molding with the moving tooling of a corrugation system, or the like.

Referring to FIG. 24E-3, a detail for an exemplary seal between sealing zone 722 of balloon tube 718 and an outer surface of multi-lumen core 702 is illustrated. In some embodiments, bonding 711 of balloon tube 718 to core 702 employs adhesives, thermal bonding, laser bonding, or the like, and is sufficient to inhibit fluid flow between adjacent balloons. Optionally, a band of radially compressive material 713 can be disposed over the balloon tube and core to help maintain sealing engagement when one or both of the adjacent balloons are inflated. Suitable bands may comprise metal and may be crimped or swaged onto the assembly, with the bands optionally comprise thin tubular marker bands-like structures (optionally comprising stainless steel, silver, gold, platinum, or the like) that are swaged on using standard marker band swaging tools and techniques. Alternative compressive bands may comprise a flexible filament of a polymer such as nylon, polyester, spectra, or the like, and may be wound over the balloon tube and core and adhesively bonded. Still further alternative compressive bands may comprise a micro-crimp clamp, or the like. A strain-relief tube 715 (optionally comprising PET or the like) may optionally be provided between band 713 and balloon tube 718 to inhibit damage along the edge of the band, and/or the band may be flared radially outwardly at the ends. Preferably, the band and any strain relief tube will be compressed onto the balloon so that some or all of the outer surface of the band and strain relief tube are recessed to near or even below the adjacent balloon tube, analogous to when a standard marker band is crimped onto a standard catheter tubing.

Referring now to FIGS. 24F and 24G, exemplary inner and outer helical C-channel frames, 732 and 734 respectively, can be seen. Inner helical frame 732 and outer helical frame 734 incorporate the modified C-channel frame 680 of FIG. 22a, but with the C-channels defined by axially continuous helical walls 736 with flanges 740 along their proximal and distal helical edges. The helical flanges are axially engaged by opposed balloons and allow inflation of the balloons to locally axially contract and/or extend the skeleton and catheter (or other articulatable body) in a manner that is analogous to the annular flanges of the ring frames described above. An optional helical nub 742 protrudes axially into the channel of inner ring frame 734 to allow the frames to pivot against each other along a flange/flange engagement, so that the nub could instead be included on the flange of the outer frame or on both (or may comprise a separate structure that is axially sandwiched between the flanges of the two frames). Alternative embodiments may forego such a pivotal structure altogether.

Referring now to FIGS. 25A-25D, a segment of an exemplary flexible extension/contraction helical frame articulation structure 750 (sometimes referred to herein as a push/pull helical structure) incorporates the components of FIGS. 24A-24G, and provides the functionality of the annular extension/contraction frame embodiments of FIGS. 22B-22I. Push/pull structure includes a skeleton defined by inner and outer helical frames 732, 734, and also includes three balloon/core assemblies 730a, 730b, and 730c, respectively. Each balloon/core assembly includes a set of balloons at three lateral orientations, 720i, 720ii, and 720iii. Balloon/core assembly 730b extends along a helical space that is axially between a flange of the inner frame and a flange of the outer frame, and that is radially between a wall of the inner frame and a wall of the outer frame, so that the frames overlap along this balloon/core assembly. Hence, when balloons 720 of balloon/core assembly 730 inflate, they push the adjacent flanges apart and increase the overlap of the frames, inducing axial contraction of the skeleton, such that the balloons of this assembly function as contraction balloons. In contrast, balloon/core assemblies 730a and 730c are radially adjacent to only inner frame 732 (in the case of assembly 730a) or outer frame 734 (in the case of assembly 730b). Expansion of the balloons 720 of assemblies 730a, 730c pushes axially against frames so as to decrease the overlap of the frames, and acts in opposition to the inflation of balloons 720 of assembly 730b. Hence, balloons 720 of assemblies 730a, 730c function as extension balloons.

Figures 25A, 25B, 25C, 25D, 25E:
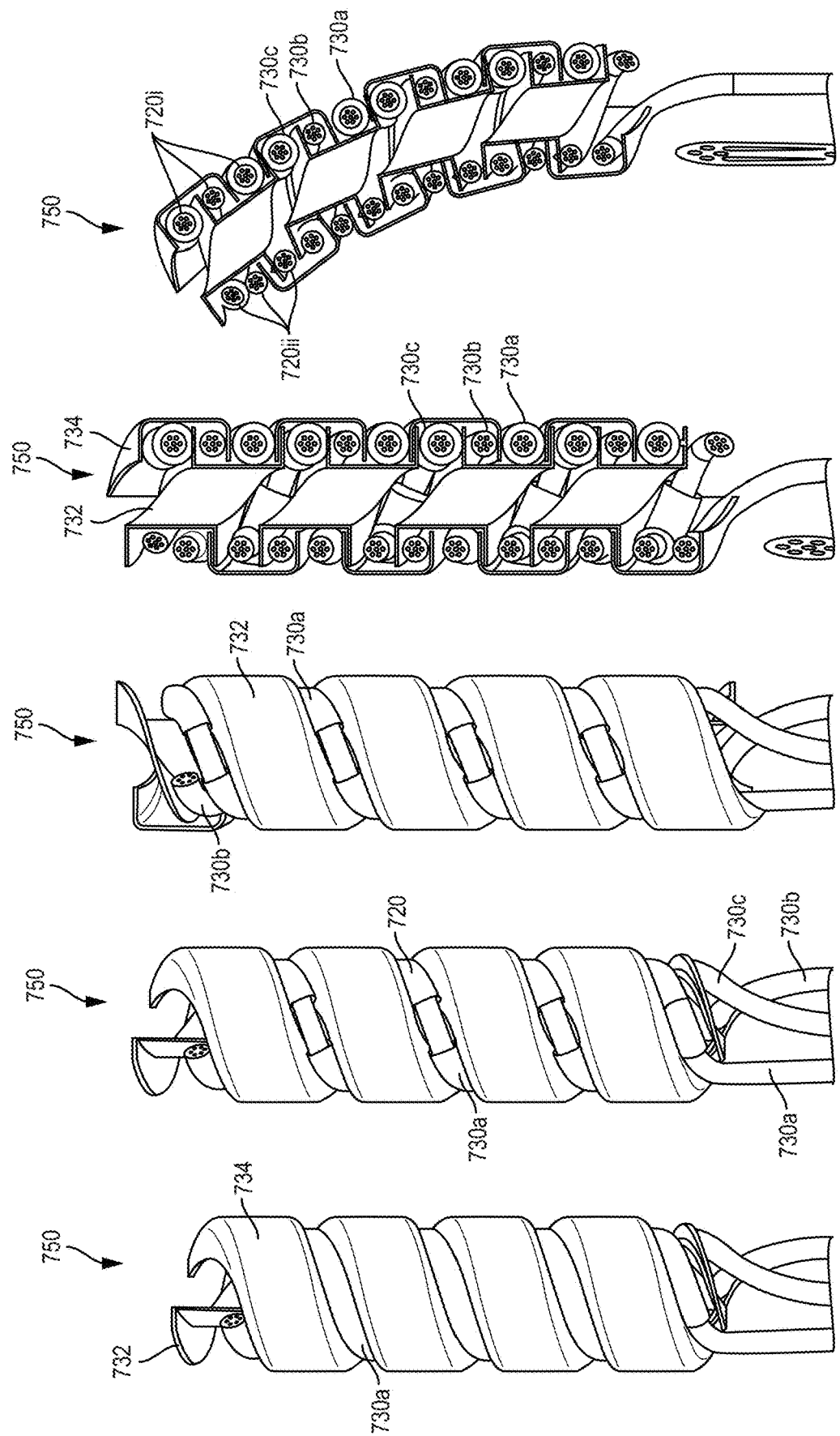
FIGS. 25A-25F illustrate exemplary elongate articulated flexible structures having helical skeleton members and three helical balloon assemblies supported in opposition along the skeleton, and also show how selective inflation of subsets of the balloons can locally axially elongate and/or contract the skeleton to bend the structure laterally and/or alter the overall length of the structure.

Referring now to FIGS. 25A-25C, when all the contraction balloons 720 of assembly 730b are inflated and all the extension balloons of assemblies 730a, 730c are deflated, the push/pull structure 750 is in a straight short configuration as shown in FIG. 25A. Even partial inflation of the extension balloons and even partial deflation of the contraction balloons articulates push/pull structure 750 to a straight intermediate length configuration, and full inflation of all extension balloons of assemblies 730a, 730c (along with deflation of the contraction balloons) fully axially elongates the structure. As with the ring push/pull frames, inflating contraction balloons 720ii along one lateral orientation of assembly 730b (with corresponding deflation of the extension balloons 720ii of assemblies 730a, 730b) locally decreases the axial length of the skeleton along that side, while selective deflation of contraction balloons 720i of assembly 730b (with corresponding inflation of extension balloons 720i of assemblies 730a and 730c) locally increases the length of the skeleton, resulting in the fully laterally bent configuration of FIG. 25E. Note that extension and contraction balloons along the 720iii orientation may be inflated and deflated with the extension and contraction orientation balloons of orientation 720*ii* so as to keep the curvature in the plane of the drawing as shown. Stiffness of the structure may be modulated uniformly or locally (with axial and/or orientation variations) as described above regarding the ring frame embodiments. Similarly, the number of extension and contraction balloons along each orientation (which will often be associated with the number of loops of assemblies 730*a*, 730*b*, etc.) may be determined to provide the desired range of motion, resolution, and response. As described with reference to the push/pull ring frame embodiments, the overall articulated portion of the structure will often be separated into a plurality of independently controllable segments.

Figure 25F:
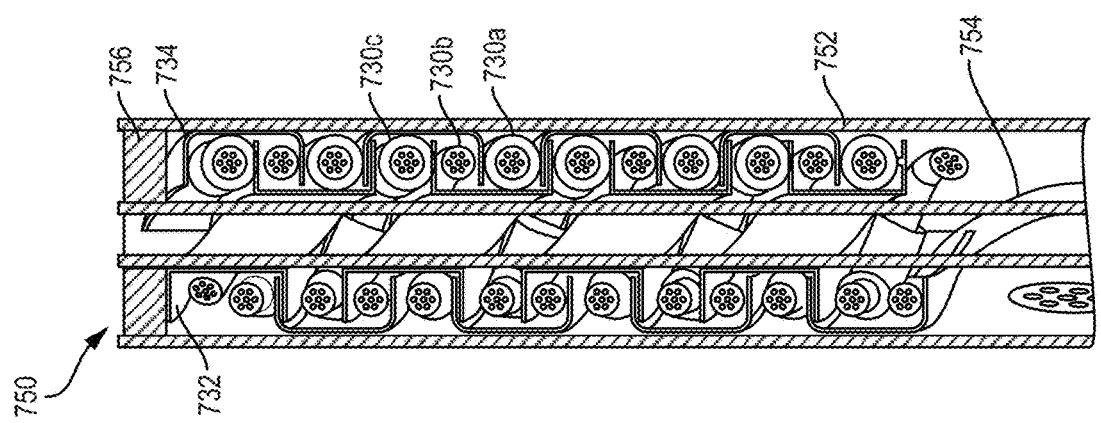

Referring now to FIG. 25F, push/pull structure 750 will often include an outer flexible sheath 752 and an inner flexible sheath 754. Sheaths 752, 754 may be sealed together at a distal seal 756 distal of the inflation lumens and balloons of assemblies 730, and one or more proximal seal (not shown) may be provided proximal of the balloons and/or near a proximal end of the catheter structure, so as to provide a sealed volume surrounding the articulation balloons. A vacuum can be applied to this sealed volume, and can be monitored to verify that no leaks are present in the balloons or inflation lumen system within a patient body.

Figure 26B:
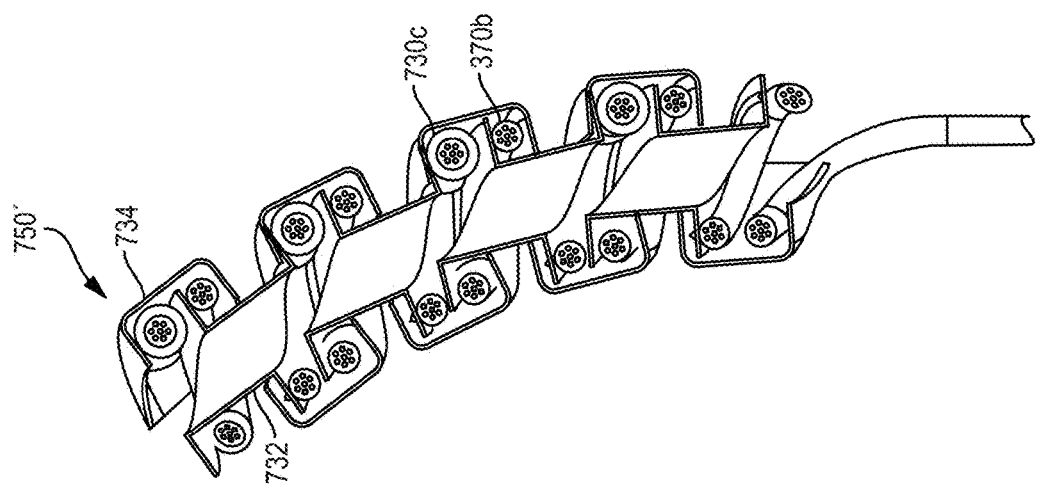
FIGS. 26A and 26B illustrate alternative articulated structures similar to those of FIGS. 25A-25F, here with two balloon assemblies supported in opposition along the frames.
Figure 26A:
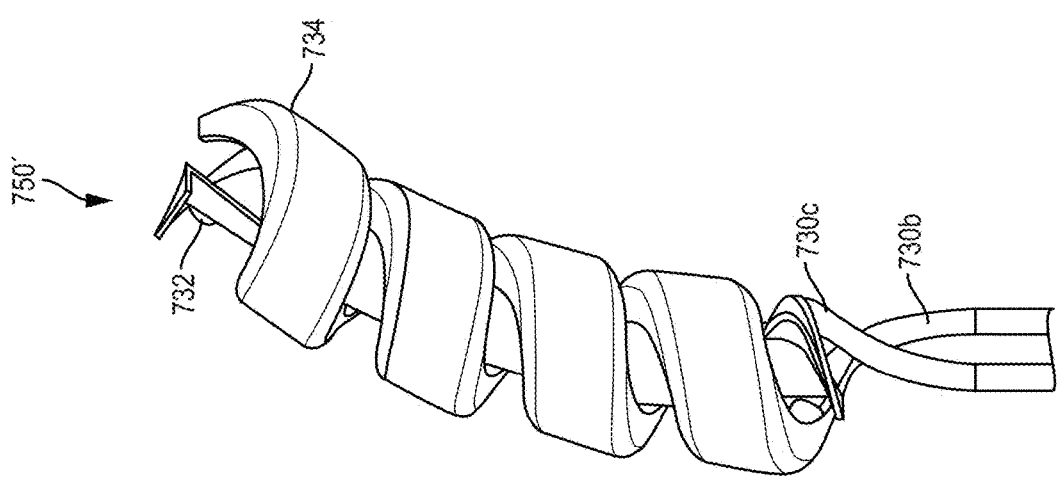

Referring now to FIGS. 26A and 26B, an alternative push/pull structure omits one of the two extension balloon assemblies 730*a*, 730*c*, and uses a 1-to-1 extension/contraction balloon opposition arrangement as described above with reference to FIGS. 23A and 23B. Note that this embodiment retains balloon assembly 730*c* that is radially adjacent to outer frame 734 (so that no balloons are visible even with the sheath removed). Alternative embodiments may retain assembly 730*a* and forego assembly 730*c* (so that balloons could be seen through a clear sheath, for example).

Figure 27:
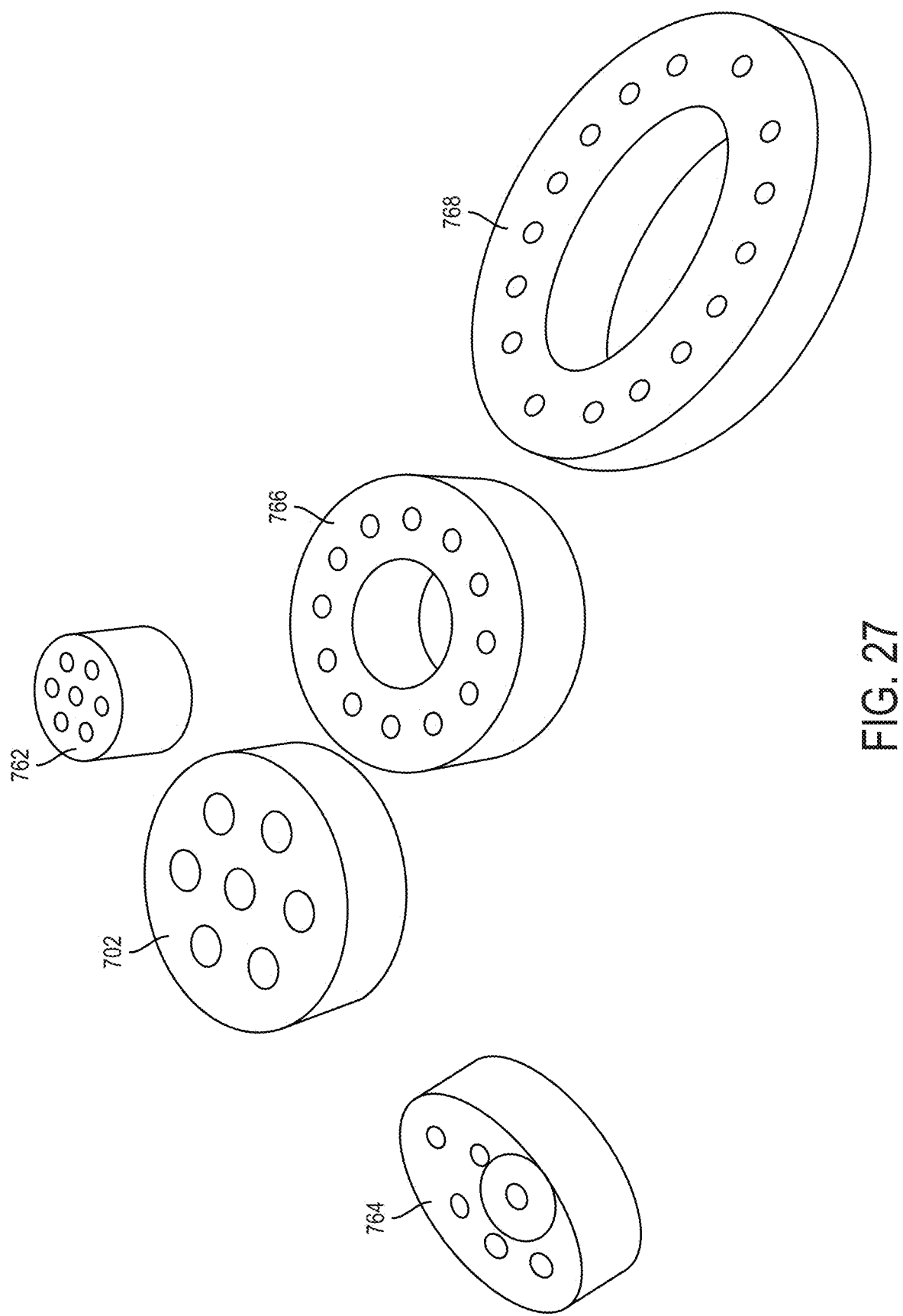
FIG. 27 illustrates alternative multi-lumen conduit or core structures for use in the balloon assemblies of FIGS. 24 and 25, showing a variety of different numbers of channels that can be used with different numbers of articulated segments.

Referring now to FIG. 27, short segments of alternative core structures are shown for comparison. Core shaft 702 has an outer diameter of about 0.028" and 7 lumens, with 6 peripheral lumens having an inner diameter of about 0.004" readily available for formation associated ports and use in transmitting inflation fluid to and from balloons. A central lumen might be used, for example, in monitoring of the vacuum system to verify integrity of the system. Core shaft 702 can be used, for example, in a 14-15 Fr catheter system having two segments that are each capable of providing up to 120 degrees of bending (or alternatively more or less depending on the number of balloons ganged together on each channel), with such a system optionally capable of providing a bend radius sufficient for to fit a 180 degree bend of the catheter within a space of 3 inches or less, ideally within 2½ inches or less, and in some cases within 2 inches or less. Such a system may be beneficial for structural heart therapies, for example, and particularly for mitral valve delivery, positioning, and/or implantation.

Referring still to FIG. 27, other therapies may benefit from smaller catheter profiles, and do not need the bending forces available from a 15 Fr catheter. Electrophysilogy therapies such as AFib ablation from within an atrium of the heart may be good examples of therapies which would benefit from the degrees of freedom that can be provided in small structures using the systems described herein. Scaling the 15 Fr system down for a 7-8 Fr ablation catheter might make use of a directly scaled core 762 having half the overall outer diameter and half the lumen inner diameter of core 702, as the pressure-containing stresses in the material would scale with the lumen diameters. However, there may be cost benefits to maintaining minimum lumen wall thicknesses that are above 0.002", preferably at or above 0.0025", and ideally at or above about 0.003". Toward that end, and to provide 6 contraction or extension lumens for two 3D push/pull segments along a common helical core along with a desirably small bend radius, it may be beneficial to use radially elongate core 764 having a 6 lumens that are all surrounded by at least 0.003" of material. Core 764 has an axial height of half of core 702 and a radial width of that is less than half the balloon diameter of the 14-15 Fr system. There may be benefits to having the radial (elongate) dimension of the cross-section being less than the inflated inner diameter of the balloons mounted thereon, to inhibit trapping of inflation fluid on one axial side of the balloon (away from the inflation port).

Still further advantages may be provided by applying the smaller lumen and wall thickness dimensions of 7 Fr core 762 to a 15 Fr catheter core size, as it results in the 12 inflation lumen core 766. The large $13^{th}$ lumen of this embodiment may help enhance flexibility of the segments, and can again be used to monitor system integrity using a vacuum system. The 12 lumens may allow, for example, a continuous push/pull structure to have 4 independently controllable 3D shape (4D shape+stiffness) segments. A 16 inflation lumen core 768 combines the smaller lumen and wall thickness with a radially elongate cross-section, allowing 5 independently controllable 3D segments. It should be understood that still further numbers of lumens at smaller profiles are possible using known and relatively low cost multilumen extrusion techniques.

It should be understood that still further alternative embodiments may take advantage of the beneficial components and assemblies described herein. For example, as can be understood from the disclosure above regarding many of the flexible structures of FIGS. 3-12, inflation of a balloon may be resiliently opposed by a helical spring or other biasing structure so that the spring deflates the balloon and urges a flexible body back toward a pre-balloon-inflation state when the inflation fluid is released from the balloon. Rather than relying on 6 dedicated opposed expansion and contraction balloon channels for each segment (providing independent contraction and expansion along each lateral orientation) in the push/pull ring frame and push/pull helical frame embodiments described above, two or more of the channels (from the same segments or from different segments) may be grouped together to act as a common baising structure or fluid spring. As an example, all the contraction balloons along two adjacent segments might open to a single lumen that is inflated to less than full pressure. Modulating pressure to the different sets of extension balloons may still allow the extension balloons to articulate each segment with three independent degrees of freedom, as the grouped contraction balloons could selectively be overpowered by the extension balloons (like the coil springs) or may be allowed to deflate the extension balloons. In some embodiments, rather than relying on partial pressure of extension or contraction balloons, an elastomeric material may be mounted over the core of some or all of the extension or contraction balloons of a segment so as to passively oppose a set of the balloons.

Figure 28:
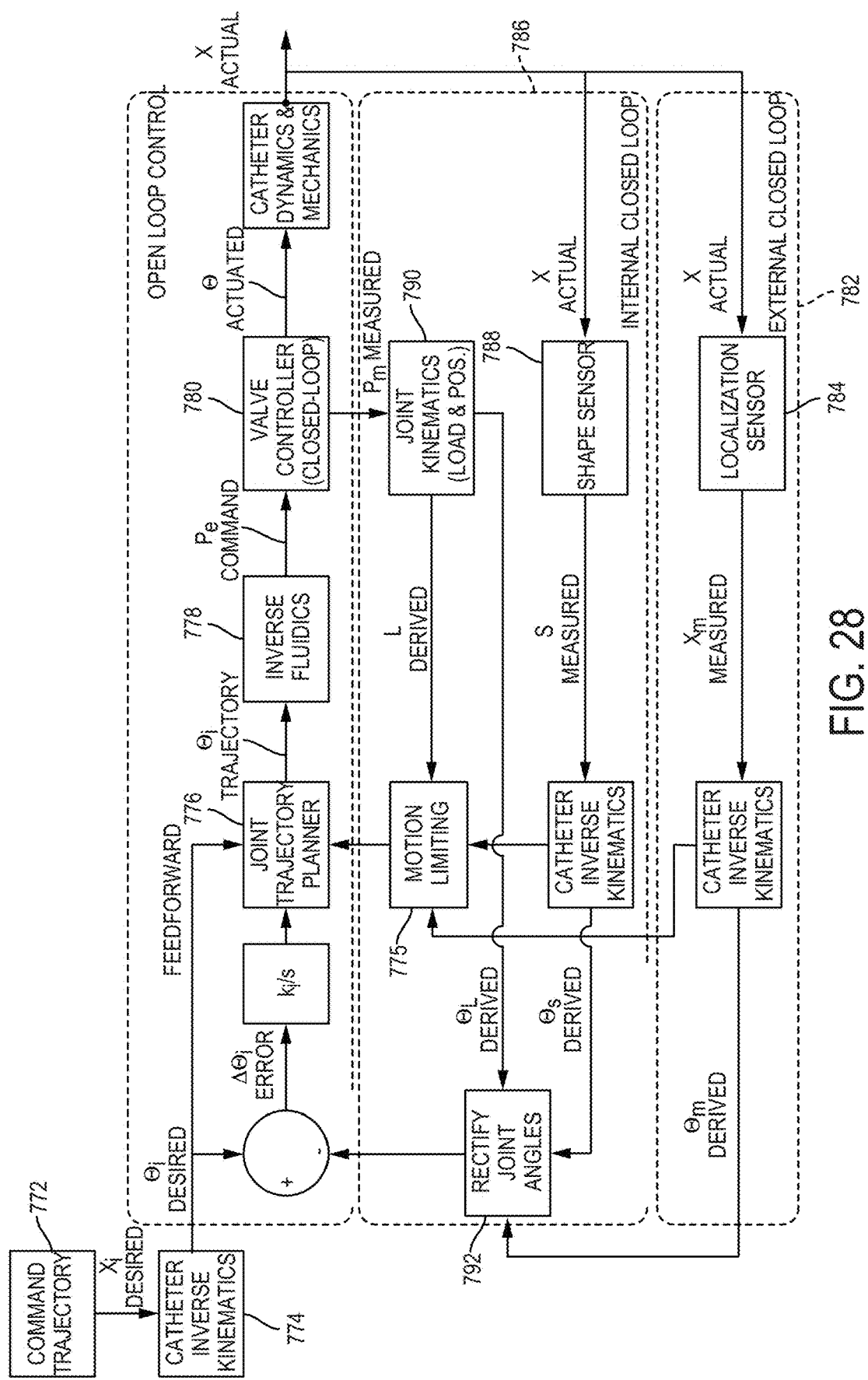
FIG. 28 schematically illustrates control system logic for using the fluid drive systems described herein to articulate catheters and other elongate flexible structures per input provided by a system user.

Referring now to FIG. 28, an articulation controller 770 for directing inflation fluid to and from the actuation balloons of the systems will typically have hardware and/or software configured and programmed to generally seek to cause the articulable structure to assume a new actual position or state $X_{actual}$ in response to a commanded trajectory 772 input by a system user. Many of the articulated flexible structures described herein may be included in robotic systems that can be analyzed and controlled using techniques associated with continuum robots, and the articulated structures will often be under-constrained with more joints then can be directly controlled using a standard controller. These excess or redundant degrees of freedom are often managed and made to cooperate by controller 770 using an internal compliance that directs the joints to be at a similar angle relative to the next joint within the segment. Controller 770 assumes equal joint angles within the segment for solving control equations. The segment bias (towards straight, for example) and strain associated with inducing a bend away from the preferred orientation causes a preference for internal joints to be at similar relative angles. The processor of the system will typically have software modules to determine the next desired position or state of the articulatable structure $X_{iDesired}$, and will apply inverse catheter kinematics 774 to determine the next desired joint state $\Theta_{iDesired}$. A difference between an actual joint state and the next desired joint state is determined to define a joint error, and the desired joint state can be fed forward to a joint trajectory planner 776 along with the joint error to define a joint error trajectory. This joint trajectory can be used in an inverse fluidic calculation 778 to determine command signals that can be fed into a closed-loop valve controller 780 so as to provide an actuated joint state. In some embodiments, closed loop control of the valves may depend on pressure sensing, and may be used to control to specific pressures as determined by valve inverse kinematics. The catheter dynamics and mechanics reaction to the actuated joint state (with the associated environment interactions with the catheter such as tissue forces and the like) result in a new actual position or state $X_{actual}$ of the articulated catheter system.

Feedback on the actual position or state of the articulated system to the controller may be omitted in some embodiments, but other embodiments may benefit from such feedback to provide more precise movements and better correlation (from the system user's perspective) between the command inputs and the actual changes in state. Toward that end, the controller may optionally use one or more closed loop feedback pathways. In some embodiments, a feedback system that is partially or fully external to the articulated structure 782 may sense the actual position or state of the catheter or other articulated structure using a localization sensor 784, such as an electromagnetic navigation system, an ultrasound navigation system, image processing coupled to 3D imaging (such as biplanor fluoroscopy, magnetic resonance imaging, computed tomography, ultrasonography, stereoscopic cameras, or the like; where the imaging modality may optionally also be used to produce images presented to the system user for image guided articulation). In many embodiments, the feedback will be provided using signals obtained from the articulated system itself under an internal closed loop feedback system 786. To obtain a measured shape or state of the articulated structure, a variety of known sensor technologies may be employed as an articulated structure shape sensor 788, including optical fiber shape sensors (such as those using fiber Bragg gratings), electrical shape sensors (such as those which use elastically deformable circuit components), or the like. The measured and/or sensed signals may be processed using inverse kinematics to derive associated measure and/or sensed joint states. Furthermore, balloon array pressure signals will often be available from the pressure sensors of the system, along with information correlating the pressures with the joint or shape state of the articulated system. The history of inflation fluid directed to and exhausted from the articulation balloons may also be used to help determine an estimated inflation fluid quantity present in each balloon (or set of balloons on a common inflation lumen). Where balloons are mounted in opposition or in parallel, the pressure and inflation fluid quantity of these related balloons on separate channels may also be available. Some or all of this pressure information may be processed using a joint kinematics processor 790 to determine a pressure-derived joint position or state (including a derived position of the pressure-articulated joints making up the flexible structure kinematic chain $\Theta_{LDevived}$). The pressure information, preferably along with internal localization information and/or external localization information, may also be used by the joint kinematic processor 790 to derive the loads on the joints, for determining of motion limits 775 as used by the joint trajectory planner 776, and the like. Where more than one is available, the external localization-based feedback joint state, the internal shape-sensor based joint state, and the pressure-derived joint state may be rectified 792 and the rectified (or otherwise any available) joint state compared to the desired joint state to determine the joint error signal.

Figure 29:
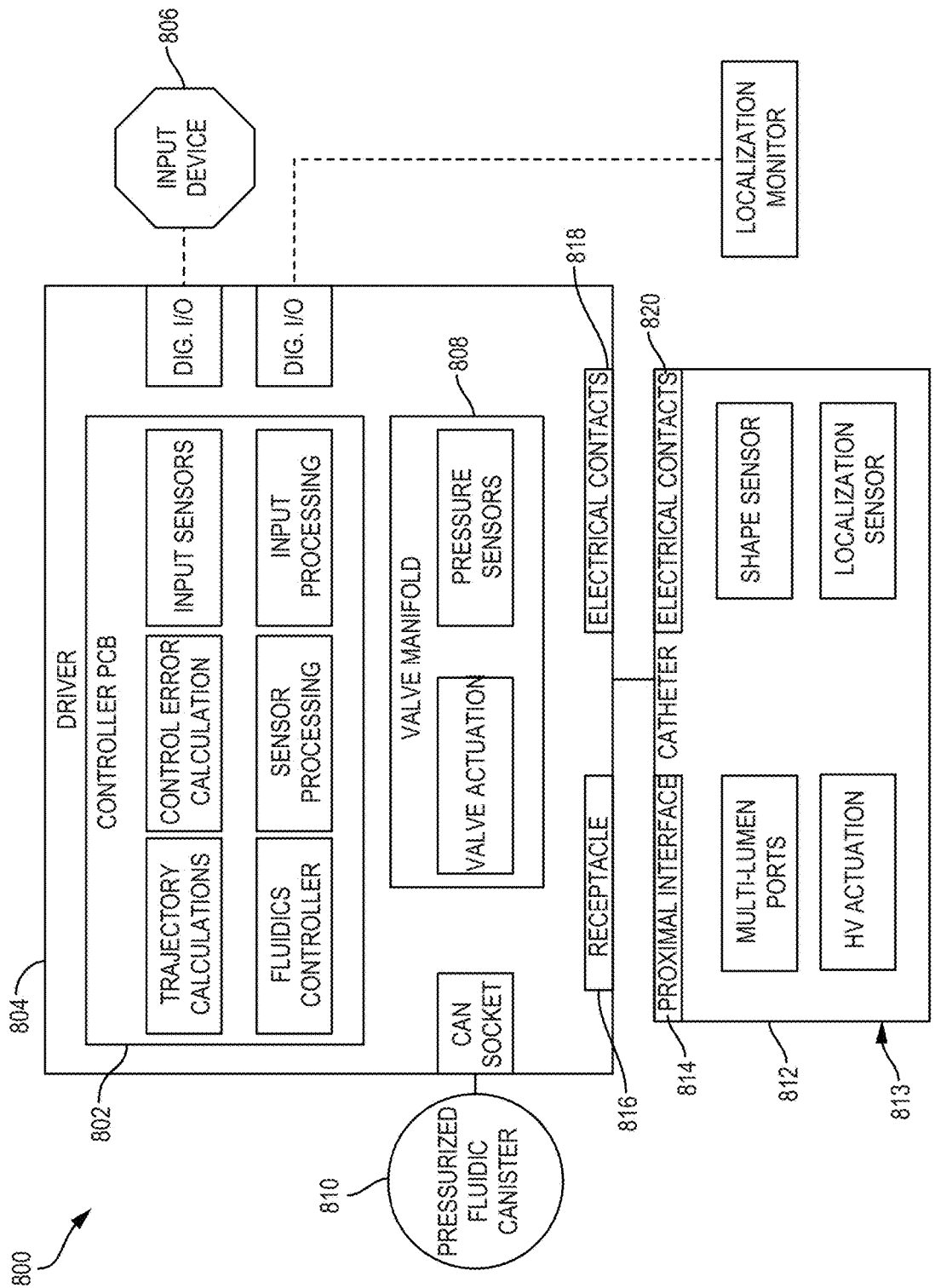
FIG. 29 schematically illustrates a data acquisition and processing system for use within the systems and methods described herein.

Referring now to FIG. 29, an exemplary data processing structure 800 for controlling the shape of a catheter or other articulated elongate flexible bodies described herein can be understood. Much of the data processing occurs on a controller board 802 of reusable driver 804, with the driver optionally comprising a hand-held capital equipment unit. The input device 806 may optionally include a separate workstation with wired or wireless data telemetry (so as to allow, for example, an interventional cardiologist or the like to perform a portion of the procedure while separated from the radiation field of a fluoroscopy system), or input device 806 may be a user interface integrated into the hand-held driver, or both. Preferably, the valve manifold 808 will comprise one of the modular plate manifold structures described herein, and will be contained within the hand-held driver unit 804. Canister 810 may be affixed to the driver (directly or by coupling of the catheter to the driver), and will often be included within a hand-held proximal assembly of deployment system that includes the driver, the proximal interface of the catheter, and other proximal components of the catheter (such as the heart valve actuation or deployment device 813, or the like) during use. Similarly, a battery of the system (not shown) may be integrated into the driver 804, may be mounted to the proximal interface of the catheter, or both.

A catheter 812 or other elongate flexible body for use with driver 804 will generally have a proximal interface 814 that mates with a receptacle 816 of the driver. As can be understood with reference to the descriptions above, the mating of the proximal interface with the receptacle will often provide sealed fluid communication between a balloon array of the catheter and the valves of the manifold assembly. Coupling of the proximal interface with the receptacle may also result in coupling of electrical contacts of the driver 818 with electrical contacts of the catheter 820, thereby facilitate access to internal shape sensor data, external localization data (which may employ a powered fiducial on the catheter and an external electromagnetic sensor system, or the like). Still further communications between the catheter and the driver may also be facilitated, including transmission of catheter identification data (which may include a catheter type for configuration of the controller, a unique catheter identifier so as to help inhibit undesirable and potentially deleterious re-use of the catheter, and the like). As an alternative to (or in addition to) electrical communication of this data, catheter 812 may have an RFID, bar code, or other machine-readable tag on or near proximal interface 814, and driver 804 may include a corresponding reader one or near receptacle 816.

Figure 29A:
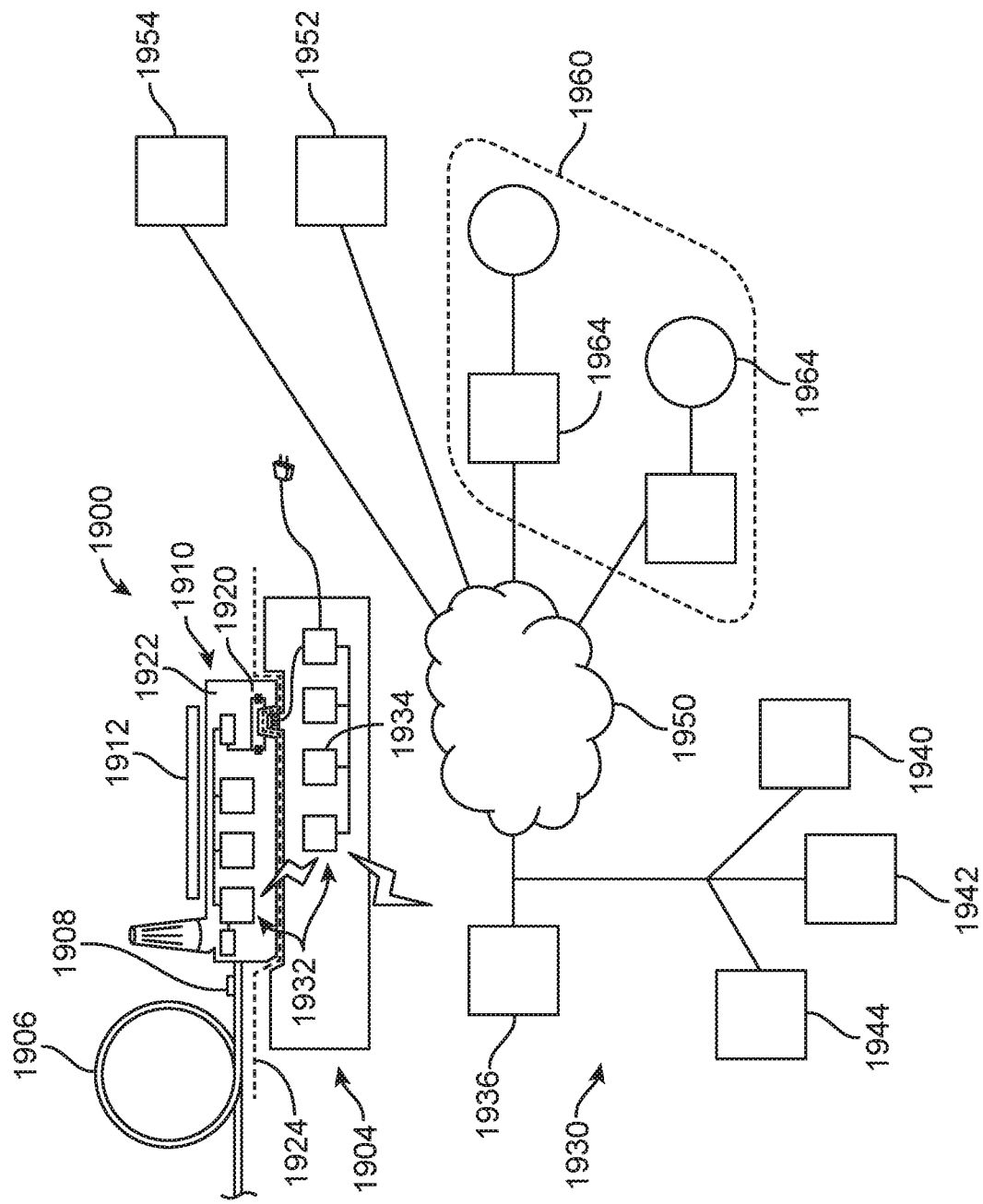
FIG. 29A schematically illustrates a base station and network system for use within the systems and methods described herein.

Referring now to FIG. 29A, a network system 1900, in which an articulated catheter system 1902 is coupled to other networked devices using a base station 1904, is schematically illustrated. Articulated catheter system 1902 may include any of the catheter systems described herein, and generally includes a balloon articulated catheter 1906 having an ID 1908 such as an RFID tag or the like. Catheter 1906 is replaceably connected to a proximal housing 1910, which includes the manifold and fluid handling components of the catheter system, along with many of the electrical and data processing components. A user interface 1912 may be integrated into proximal housing or removably supported by the housing.

First addressing the power components of base station 1904 and housing 1910, electrical wall power is used to energize an electrical inductive charge coil of the base station, which energizes an inductive coil of the housing 1910, the coils forming an inductive coil pair 1920 when the housing is placed in a receptacle of the base station. Power from inductive coil pair 1920 charges a battery, which is used to power the electrical circuitry supported by the proximal housing when the housing is removed from the receptacle. Note that another inductive coil pair may charge a battery of the user interface 1912 if it is to be used when separated from the housing, and that electrical contacts along the housing and receptacle (and between the user interface and housing) may be used in place of inductive charging components in some embodiments. Inductive charging may, however, have advantages, including facilitating the use of a simple sterile drape 1924 or sterilizable housing material so as to inhibit cross-contamination between patients.

Still referring to FIG. 29A, telemetry between the components in housing 1910, base 1904, and a network system 1930 are also illustrated. Wireless communication modules 1932 will often provide wireless communication between the base station and a processor of the proximal housing, though electrical contacts, wires, or even optical cables might be used. Regardless, the processor of housing 1910 may transmit a wide range of data to a processor 1934, typically including catheter ID data associated with ID tag 1908 (as obtained via an RFID reader or the like). Additional data may include data identifying the proximal housing unit type, specific ID, and the like; user data; patient data (with appropriate HIPAA compliance verification), and the like. Still further data that may be transmitted to the base station, including manifold diagnostic data, fluid use data, articulation and command/articulation response data, and the like. Some of this data and/or other data may be entered into a user interface of the base station or obtained by the base station from other networked devices of the clinical setting, and/or from an electronic medical record data repository 1940 for the patient. Any of this data may be communication between processor 1934 of the base station and a server 1936 of network system 1930, either via wireless module 1932 of the base station, a different wireless communication device of the base station, or a wired network connection between the base station and server 1936 and processor 1932. Any of a variety of wireless or wired router systems may be used to handle these communications.

Server 1936 may be included in a local network configured to handle clinical data, including one or more clinical workstations 1942 or other devices (such as clinician desktop computers for entering patient data, mobile physician touchscreen devices, or the like), clinical data acquisition systems 1944 (such as image data systems, EKG sensors, and the like). Suitable data from the catheter system and other network devices may be directed to the electronic medical record 1940 for a particular patient.

Communication between the clinical network 1930 and other network components may be transmitted via a network such as the internet 1950, with data storage and transmission often employing any of a wide variety of cloud-based computing technologies, optionally as configured so as to maintain security appropriate for healthcare data of patients. Servers of other clinical sites 1952, 1954, . . . , may similarly transmit data via the internet. While communication between clinical sites may proceed directly on a peer-to-peer basis for specific patients, aggregate catheter system data (and associated aggregate patient data) transmitted from some, most, or all of the clinical servers having networks that include a networked robotic catheter system may be handled by a data processing system 1960 maintained by an entity having catheter data oversight responsibilities, such as a catheter manufacturer or seller. An advantageous feature of data processing system 1960 is that a database of safely usable catheter ID data can be accessed by a use processor, allowing the processor to verify that housing 1910 is being coupled to safe catheters (and can transmit permission for that or future procedures), and can remove single-use catheter ID's from the database after they are used. A clinical database 1964 can gather some, most, or all HIPAA compliant catheter-system data, and optionally any additional electronic medical record data or data from other networked devices used during the catheter procedure, as that data is available and approved for transmission from each of the clinical networks.

Referring now to FIGS. 30A-30D, an alternative interface 830 disposed at the proximal end of the catheter can be understood, along with mating of that proximal interface of the catheter to an alternative receptacle 832 of an alternative modular manifold 834. Proximal interface 830 may be permanently or removably affixed to the proximal end of the catheter and provides a quick-disconnect sealed communication between axially separated ports of up to three multilumen shafts 836 of the catheter to associated valves and fluid channels of the manifold. The ports of the multi-lumen shafts can be sealed to proximal interface 830 by axially compressing O-rings 838 or other deformable sealing bodies interleaved between more rigid interface members 840. Threaded compression members 842 maintain axial sealing compression between a proximal-most interface member and a distal-most interface member. Posts 844 of interface members 840 extend laterally and parallel to each other. Each interface member 840 includes a post 844 for each multi-lumen shaft, and the number of interface members included in proximal interface 830 is the same as the number of independently used lumens in each multi-lumen shaft, so that the posts form an array with the total number of posts being equal to the total number of independent multi-lumen channels in the articulated structure. Lumens extend radially from the ports of the multi-lumen shaft, through the posts 844, and to an interface port surrounded by a cap of deformable seal material.

Figure 30A:
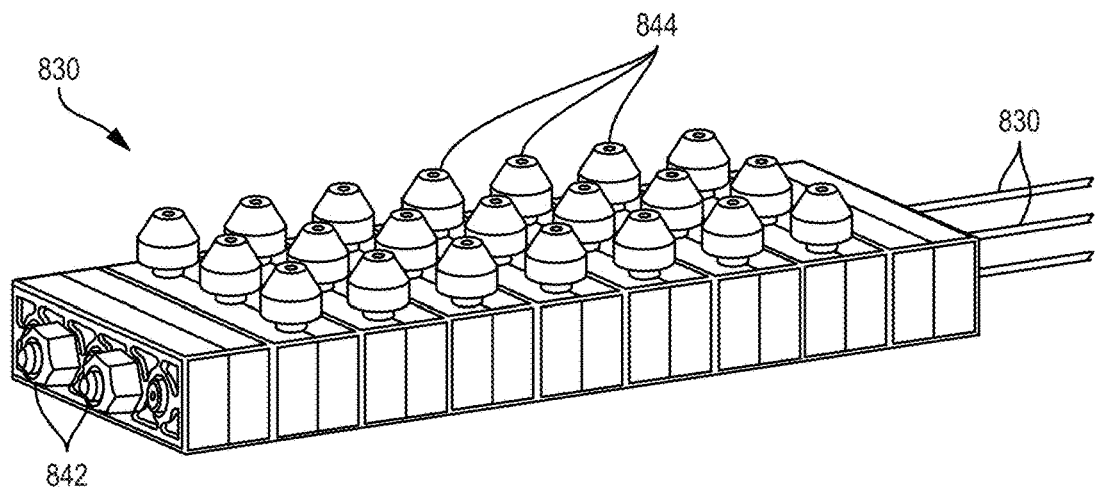
FIGS. 30A-30D illustrate an alternative interface for coupling a modular fluid manifold to a plurality of multi-lumen shafts so as to provide control over articulation of a catheter along a plurality of segments, each having a plurality of degrees of freedom, along with portions of some of the plate modules of the manifold, with the plate modules here having a receptacle member that helps couple the layers of the plates to posts of the interface.
Figure 30B:
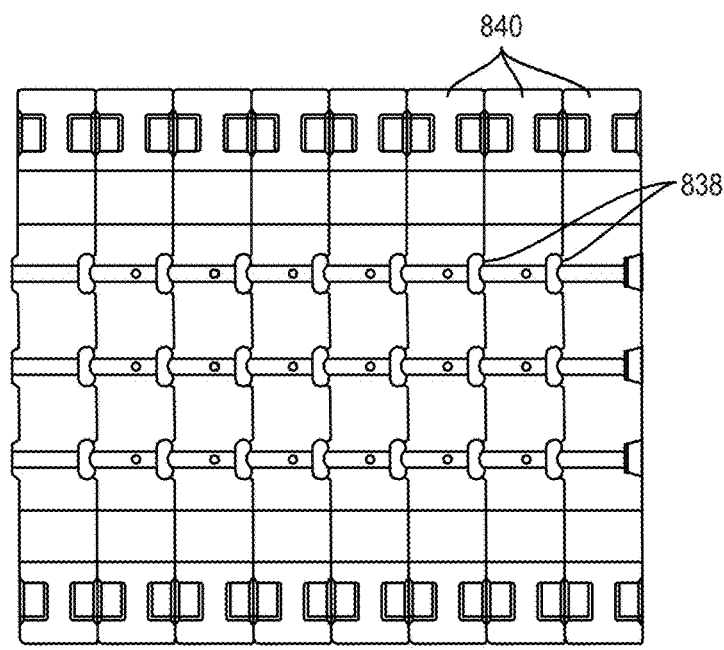
Figure 30C:
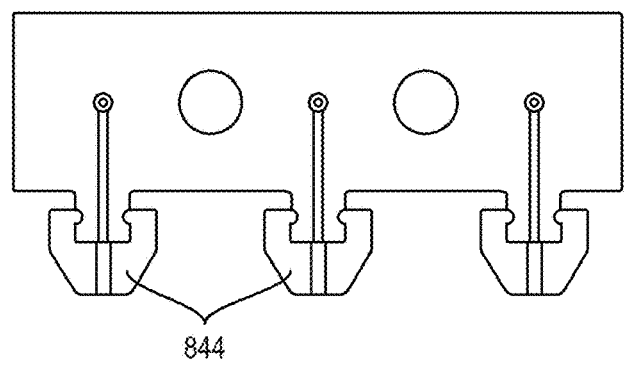
Figure 30D:
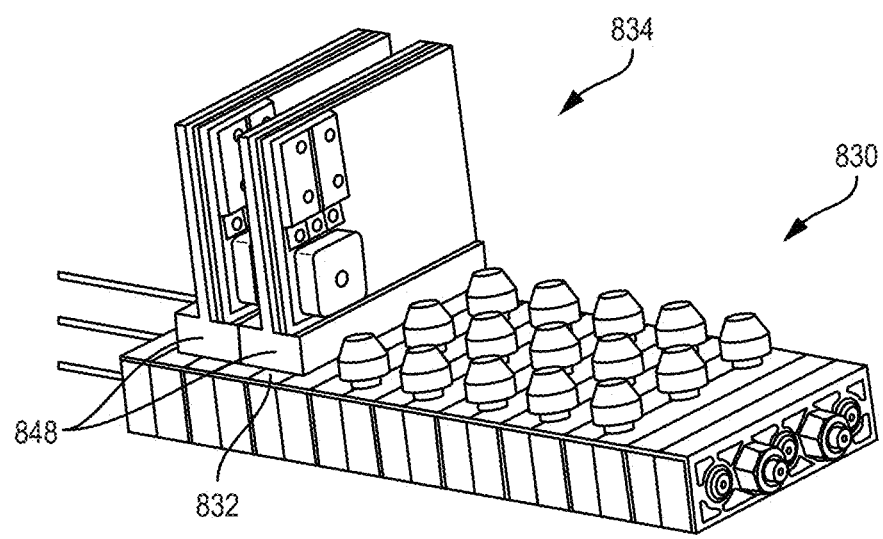

Referring to FIG. 30D, receptacle 832 of manifold assembly 834 has a series of indentations that correspond with posts 844 of proximal interface 830. The indentations have surfaces that correspond to the posts and seal to the deformable caps with the interface ports each in sealed fluid communication with an associated channel of an associated plate module. In this embodiment, the receptacle surfaces of each plate modules are on a receptacle member 848. The receptacle members support plate layers with channels formed between the layers, with MEMS valves and pressure sensors mounted to the plates as described above. Here, however, the plates of adjacent plate modules may not be in direct plate-plate contact, so that the supply and exhaust flows may extend axially through the receptacle members, through the proximal interface, or through another structure of the manifold assembly. As noted above, alternative embodiments may have plates that are in direct contact, with any housings for valves, pressure sensors, and the like formed as voids between layers, and with inflation and/or deflation fluid transmitted directly between plate modules through seals (such as O-rings, formed-in-place seals, gasket material affixed to flex circuit structures, or the like).

Figure 31B:
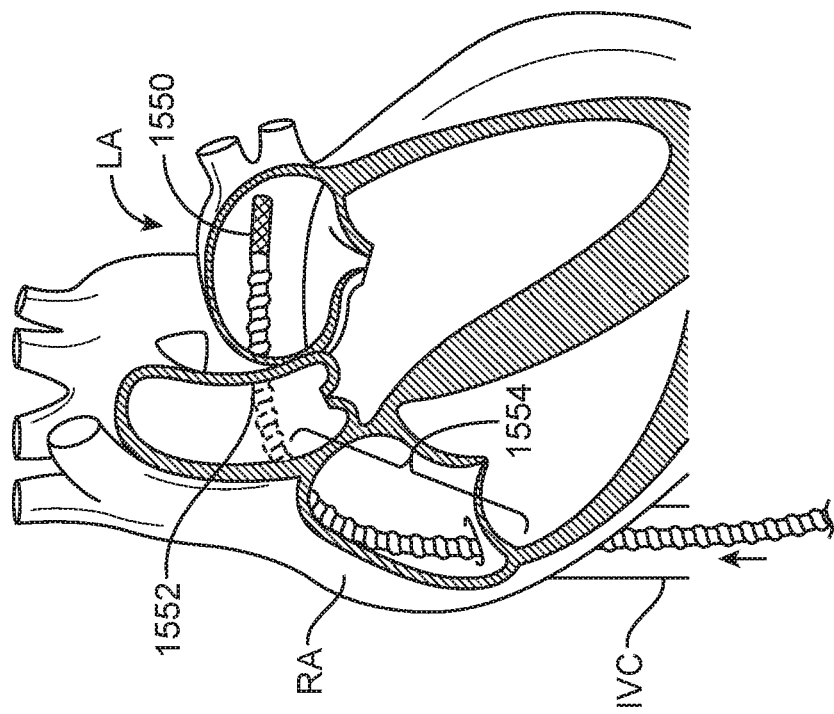
FIGS. 31A-31C schematically illustrate positioning and anchoring of a mitral valve delivery catheter system for deployment of a mitral valve prosthesis in heart of a patient FIGS. 32A-32C schematically illustrate positioning of a mitral valve prosthesis in five degrees of freedom by independent articulation of three axial segments of an articulated catheter.
Figure 31A:
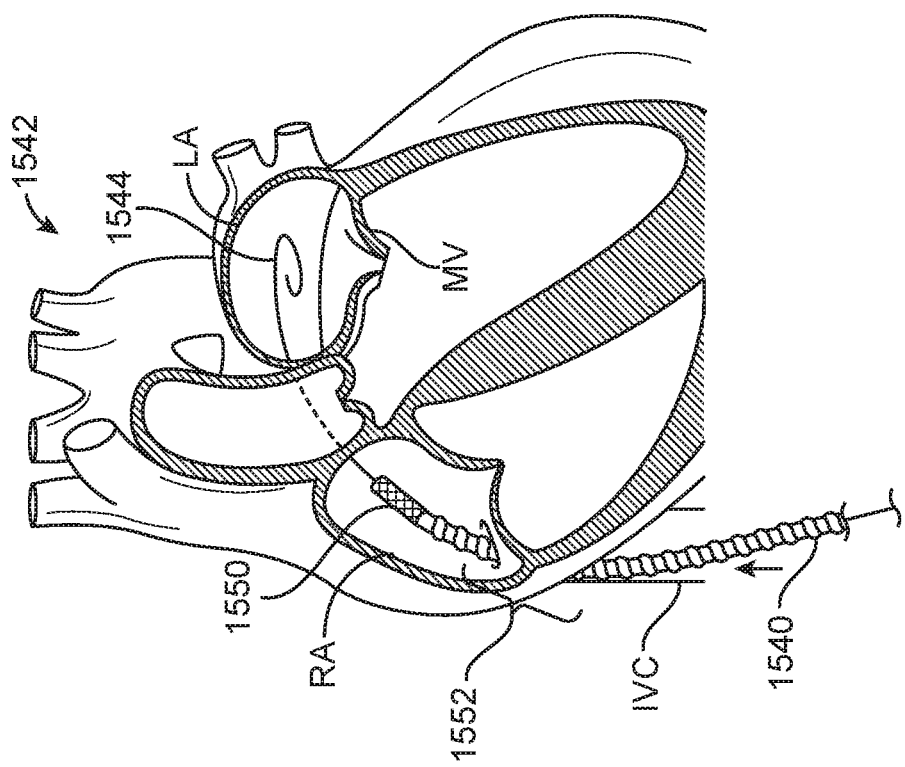
Figure 31C:
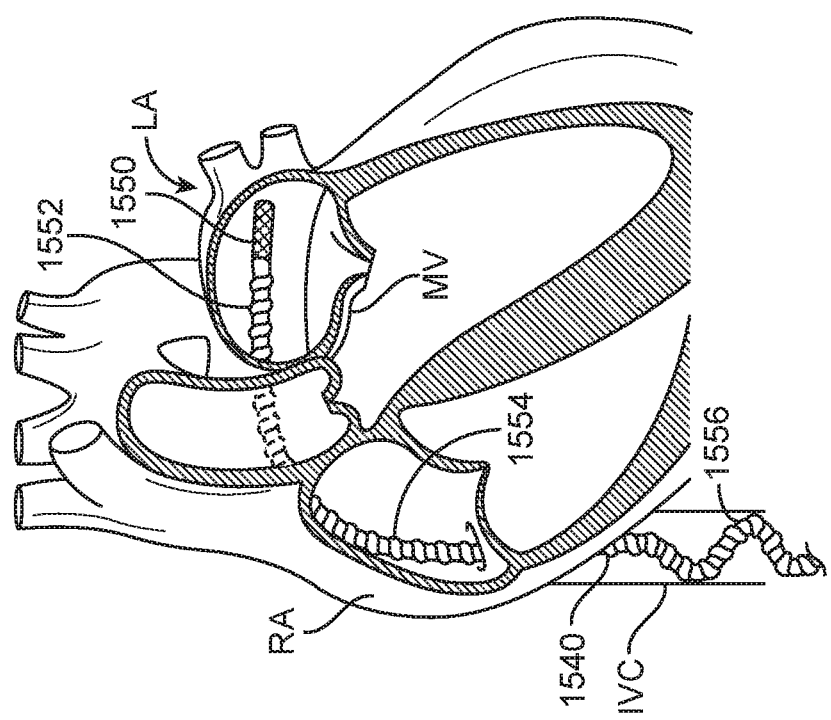

Referring now to FIGS. 31A-31C, advancement of a simplified valve deployment system 1540 in a heart 1542 of a patient body is schematically shown. In this schematic illustration of deployment system 1540, a prosthetic valve is supported at the distal end of an articulated catheter. While not shown for simplicity, a tapered dilation tip and/or a retractable sheath may be provided to facilitate advancement. A guidewire 1544 may be advanced to the heart via the inferior vena cava IVC using known techniques, and access to the mitral valve MV may be provided by crossing the right atrium RA and traversing the septum separating the right atrium from the left atrium LA using standard transsceptal access components. Optionally, steering capabilities of the deployment catheter may be used to help direct a transsceptal needle through the septum at or adjacent the fossa ovalis under fluoroscopic guidance. While more than one guidewire may be used to gain access, transceptal guidewire 1544 can eventually be positioned in the left atrium, and the deployment catheter 1540 can be advanced over the wire into the right atrium RA as shown in FIG. 31A. As can also be understood with reference to that figure, advancing of the valve from the IVC toward the septum may be facilitated by articulating one or more segments of the deployment catheter using the balloon array articulation systems described above.

For many patients, the fossa ovalis may be between 5 and 14.5 mm above (caudally of) the ostium of the IVC. Craniocaudal and antero-posterior fossa ovalis diameters may be 12.1±3.6 and 14.1±3.6 mm, respectively; the ostium of the IVC may have a diameter between about 18 mm and 30.2 mm, as detailed in an article entitled "Anatomy of the true interatrial septum for transseptal access to the left atrium" by Wieslawa Klimek-Piotrowska (Annals of Anatomy 205 (2016) 60-64), which may be accessed at: http://www-.heart.cm.uj.edu.pl/documents/104468614/110577839/ Anatomy%20of%/ 20the%20true%20interatrial%20septum%20for%20trans septal%20access%20to%20the.pdf the full disclosure of which is incorporated herein by reference. Within the separation space between the ostium of the IVC and the fossa ovalis (or other septal penetration site), the segments of catheter 1540 that are resident while gaining access and/or during a valve positioning or deployment may provide a controlled lateral bend angle in a range between about 60 to about 120 degrees, more typically between 70 and 110 degrees, and often of between about 80 and 100 degrees. Pediatric patients may benefit from deployment catheters capably of tighter bend radii, while larger patients and patients with enlarged hearts may use larger diameter catheters having larger bend radii.

Referring now to FIGS. 31A and 31B, while prosthetic valve 1550 is being advanced from the IVC and thru the right atrium, lateral bending of a distal segment 1552 of deployment catheter 1540 may help orient the valve to follow guidewire 1544 toward the left atrium LA. In some embodiments, while the dilation tip adjacent the valve engages the septum the catheter proximal of most or all of the distal segment may be braced against the opposed wall of the right atrium. Optionally, a more proximal segment may anchor the catheter in the IVC. Regardless, axial elongation of distal segment 1552 may help advance the valve into and/or through the septum, with or without distal advancement of a proximal, unarticulated portion of the catheter. In other embodiments, manual or automated advancement of the proximal portion of the catheter into the patient through an introducer valve may be used to move the valve from the right atrium RA to the left atrium LA. As the valve advances within the left atrium, distal segment 1552 may be driven to straighter configuration, and a more proximal segment (such as intermediate segment 1554) may be driven to bend about 80-100 degrees to span from the IVC to the septal crossing site.

Referring now to FIGS. 31B and 31C, when valve 1550 and some, most, or all of distal segment 1552 are within the left atrium LA, a proximal segment 1556 may be driven toward a helical or serpentine anchor configuration within the IVC, with the opposed bends of the segment having a nominal diameter that is larger than that of the surrounding IVC. In other embodiments, an alternative anchor may be employed, such as an elastic balloon that expands from one side of catheter 1540 proximal of the articulated segments, extending a loop of wire laterally from the catheter, or the like. The anchoring engagement between the IVC and catheter 1540 may provide a stable base for articulation of articulation segments that are distal of the anchor. In some embodiments, intermediate segment 1554 or another part of the catheter distal of the anchor may engage a surface of the right atrium opposite the septum. The catheter distal of the anchor will also engage heart tissue of the septum (optionally along the distal or intermediate segment), and these heart tissues may, to some extent, help stabilize the valve. The native mitral valve will move during beating of the heart, and the heart tissues engaging the catheter proximally of the valve may also move with physiological movement that differs from that of the mitral valve.

Figure 32A:
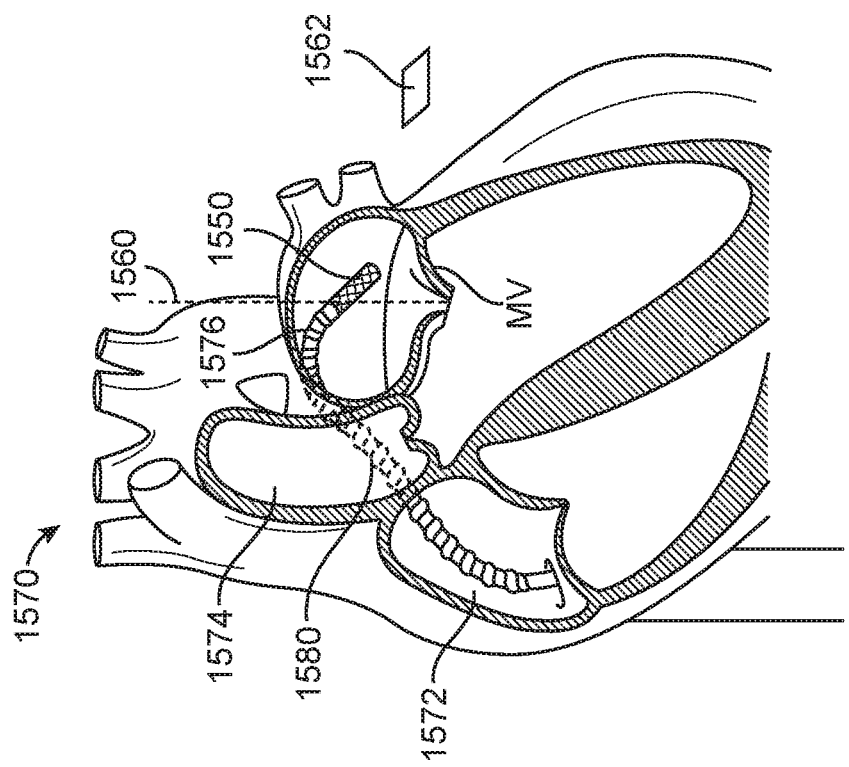
Figure 32C:
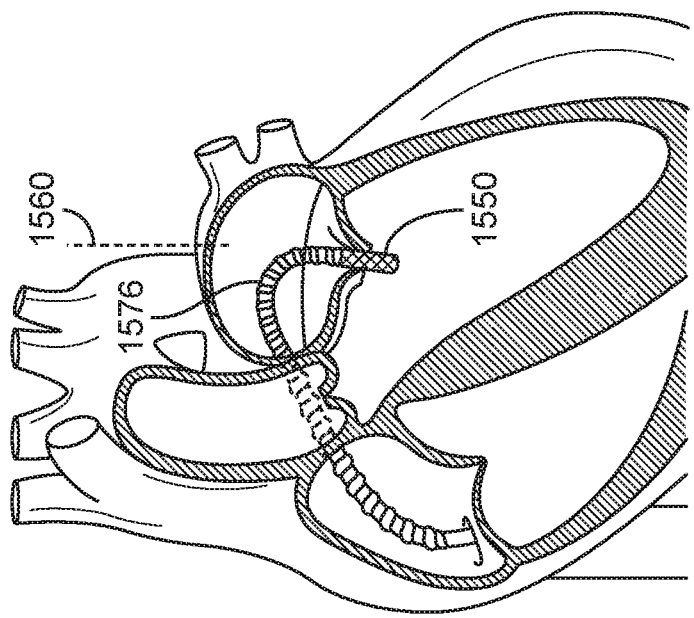
Figure 32B:
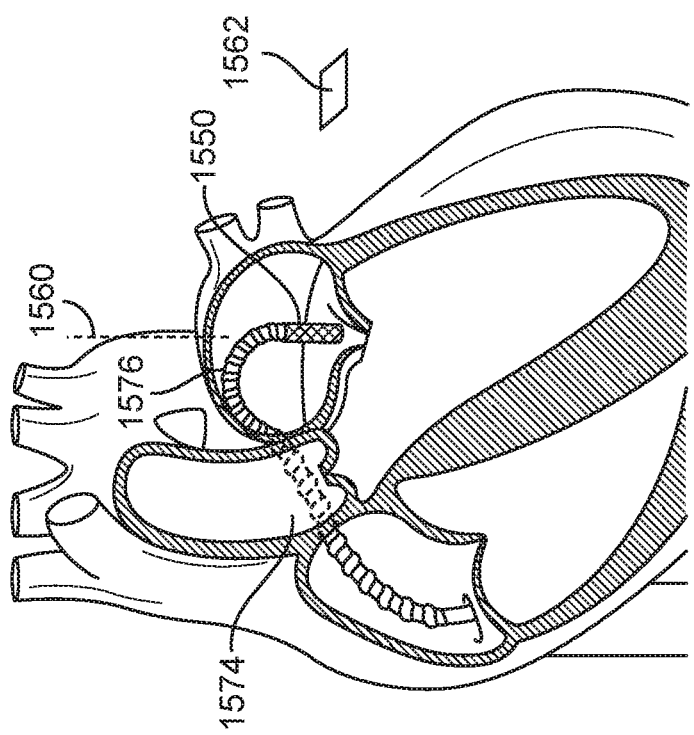

Referring now to FIGS. 32A-32C, exemplary movements of a three segment articulated catheter system for positioning of a prosthetic valve 1550 within a mitral valve MV can be understood. Mitral valve MV has an axis 1560, and a valve plane 1562 can be defined by the valve annulus, with the valve plane optionally being perpendicular to the axis. In some embodiments, prosthetic valve 1550 may be axisymmetric, so that desired positioning of the prosthetic valve can be defined by five degrees of freedom relative to the native valve. In other embodiments, the valve structure may be adapted to allow a relatively wide range of axial positioning, so that 4 accurate degrees of freedom are sufficient. In other embodiments, including those having a non-circular prosthetic valve cross-section or a non-planar prosthetic valve seat, six accurate degrees of freedom may be desired. Regardless, deployment system 1570 is shown here with a distal articulated portion having three independently articulatable axial segments 1572, 1574, and 1576 that may each be articulated in two or three degrees of freedom (DOFs) to position prosthetic valve 1550 as desired relative to the native tissues of mitral valve MV. In alternative embodiments, a proximal anchor segment may be used with an intermediate and a distal segment that can each be articulated with 3 DOFs. In still further alternatives, a single 3 DOF segment system may extend through a conventional steerable transceptal catheter.

As can be understood with reference to FIGS. 31C and 32A, it may be desirable to initially advance the distal end of prosthetic valve 1550 beyond the target deployment position, and then to lift the proximal end of the valve caudally within the right atrium. Toward that end, intermediate segment 1574 may curve upward, and distal segment may retract axially and bend downward as shown. As can be understood with reference to FIGS. 32A and 32B, as the axis of prosthetic valve 1550 comes into alignment with axis 1560, the prosthetic valve may remain above the plane 1562 of the native valve tissues. The proximal, intermediate, and distal segments 1572, 1574, 1576 may curve laterally as desired into and/or out of the plane of the images shown so as to bring the prosthetic valve into alignment, with the catheter pivoting about the transceptal axis site 1580, sliding axially through the site 1580, and/or gently laterally displacing cite 1580. As can be understood with reference to FIGS. 32B and 32C, once the distal end of prosthetic valve 1550 has been aligned with the opening of the valve the intermediate segment 1574 can be driven to straighten and then curve downward. Distal segment 1576 may straighten somewhat, and segment(s) 1572, 1574, and/or 1576 may axialy elongate to finalize axial alignment and also to axially advance the prosthetic valve to the desired position relative to the plane of the native mitral valve tissues. The valve can then be deployed, often by balloon expansion, proximal retraction of a surrounding sheath, or the like.

Regarding the articulation capabilities of the distal segments, the segments may have similar structures, bend radii, elongation capabilities, and the like. Bending angles and space constrains for the segment(s) spanning the right atrium are described above. For the segment(s) moving within the left atrium, the size of the left atrium may increase with diseases associated with valve disease. As explained in, for example: in a four chamber sonography view the left atrium may have a diameter of between about 28 and 40 mm and a major axis of from about 41 to 61 mm; these dimensions may increase by as much as 100% or more in a severely dilated heart. The articulated catheter segment(s) within the left atrium (usually including most or all of the distal segment, and optionally including a portion of the proximally adjacent segment) will accommodate bends of from 80 to 120 degrees when extending from the transceptal access site, and then bending to extend along the axis of the mitral valve (which may be found at a separation distand of less than one half the LA diameter from the septal wall). Elongation capabilities of each elongatable segment will preferably be at least 5% of the length of that segment in its shortest configuration, often being at least 10% and ideally being 12.5% or more. Articulated portion lengths (in the short configuration, where elongatable, and including all segments and connections therebetween) for valve delivery and/or other valve therapies may be from 2.5 in. to about 11 in., often being between about 4.5 and 8.5 inches.

Figure 33B:
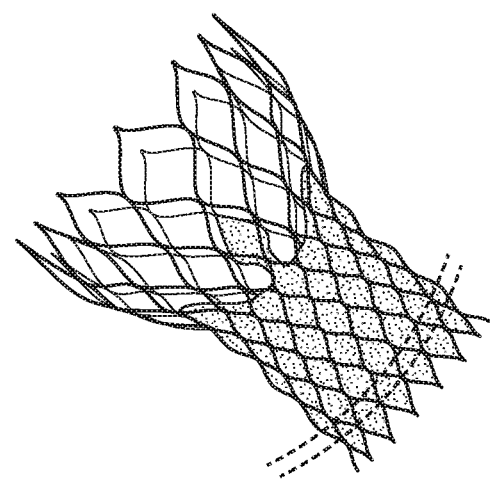
FIGS. 33A and 33B illustrate alternative prosthetic valve structures which may be delivered using the deployment systems described herein.
Figure 33A:
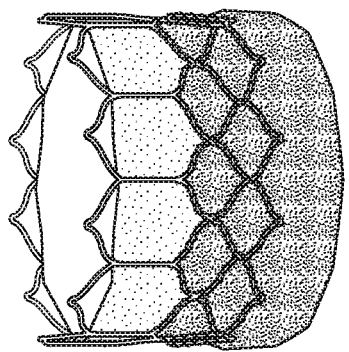

Referring now to FIGS. 33A and 33B, representative prosthetic valve structures which might be deployed using the valve therapy devices described herein are shown. These and other suitable prosthetic replacement valve structures may be commercially available from Abbott Laboratories, Tendyne Holdings, Edwards Lifesciences, Medtronic, Twelve, Boston Scientific, St. Jude, CardiAQ, Micro Interventional Devices, Neovasc, and others, and additional information regarding specific valve structures may be found from the publications of these entities. Some embodiments of these prosthetic devices may be balloon expanded (so that once they are positioned, the frame of the valve is plastically expanded by inflating a deployment balloon). While the deployment balloon inflation system might optionally be integrated with the articulation balloon inflation system, in many embodiments a separate standard balloon inflation system and lumen may be provided, with that lumen extending distally along a shaft disposed within the inner sheath of one of the articulation devices described herein. In other embodiments, the frame is biased to expand, and is expanded at the target site by releasing the frame such as by withdrawing a surrounding sheath proximally while one of the articulated catheter structures provided herein holds the prosthesis at the target site within the sheath. Known variations for deployment of balloon expanded and resilient expansion of existing valves and stents may also be used, including tethers and other systems for retrieving partially deployed valves and stents.

Figure 34:
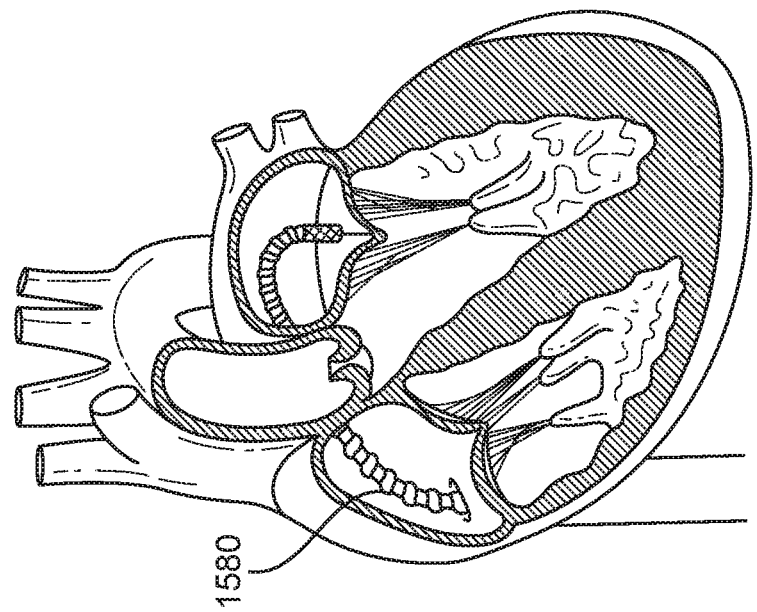
FIG. 34 shows a valve leaflet application clip and associated deployment system.
Figure 35H:
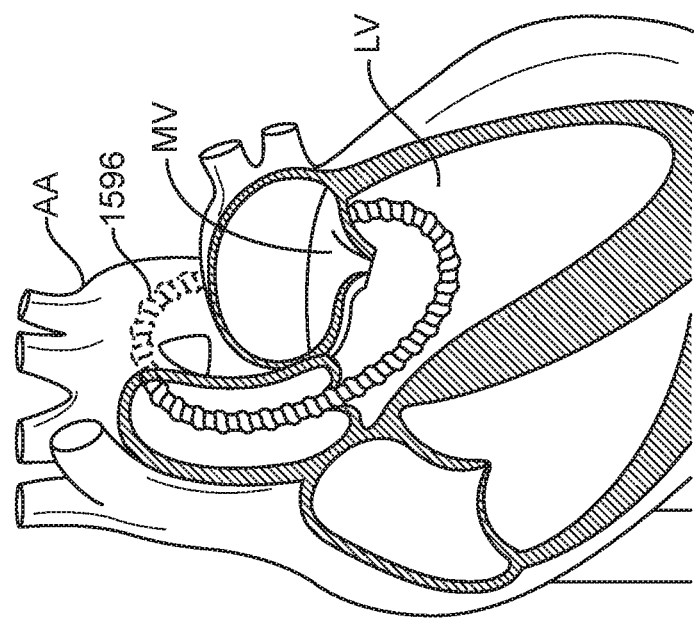
FIGS. 35G and 35H illustrate trans-aortic access to the left ventricle and retrograde treatment of the mitral annulus.

Referring now to FIGS. 34-35H, the devices and systems described herein may be used in a number of additional valve therapies. For example, in FIG. 34 a multi-segment balloon articulated catheter 1580 is used to deploy a mitral valve leaflet plication clip that can affix a central portion of the mitral valve leaflets together so as to inhibit mitral regurgitation. The clip may replicate the Alfieri stitch used in some open procedures, and additional information on the clip device and its deployment using nested pull-wire steerable catheters can be found from publications by Abbott regarding the Mitraclip™ system. When delivered using balloon articulated catheter 1580, a prosthetic valve leaflet plication tip may be carried on a shaft passing through the catheter to facilitate rotation about the catheter axis. Alternatively, a range of rotation may be provided by coordination between the articulated segments, and/or by including a balloon articulation segment as described below.

Referring now to FIGS. 35A-35C, an alternative valve repair device that can be carried on a balloon articulated catheter 1590 (optionally having two, three, or more independently articulated segments as described above) can be used to deploy an annuloplasty ring 1592. As can be understood in more detail with reference to the standard deployment systems described in publications by Valtech (and/or in http://citoday.com/pdfs/cit0515_Valve%20Update_Tobis.pdf), systems being developed by Valtech and others can deploy annuloplasty rings around the annulus of the mitral valve by advancing a series of anchors from a catheter system into the support tissue surrounding the native valve leaflets so as to re-shape the valve such that mitral regurgitation can be inhibited. Replacing a standard catheter system with any of the balloon array articulation structures described herein may significantly facilitate anchor placement, provide greater accuracy, and decrease deployment time. Optionally, combination catheter-deployed therapies may also be employed, for example, with catheter-based deployment of an annuloplasty ring being combined with deployment of a prosthetic valve within that ring (and the native valve tissue) if the ring alone does not provide the desired result (or even as a pre-planned therapy).

Figure 35G:
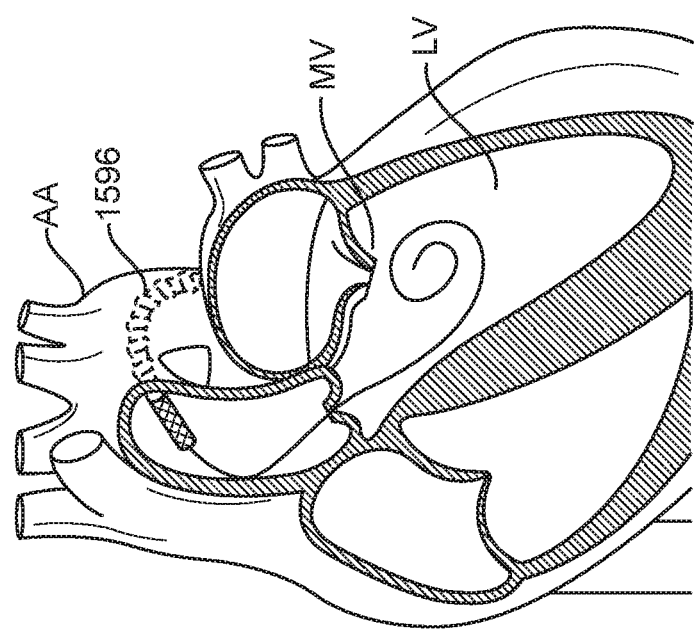

Referring now to FIGS. 35D-35F, mitral annulus plication is a still further alternative mitral valve therapy which may benefit by modifying existing deployment technology so as to take advantage of the balloon articulated systems described herein. As shown here (and as can be further understood by reference to the publication of Mitralign and others), pledgets 1590 may be affixed to the mitral annulus at locations separated by a desired distance using either two separate balloon articulated catheters 1592a, 1592b (or sequentially using a single balloon articulated catheter). A suture between the deployed pledgets can be tensioned to approximate an associated segment of the valve annulus, and a clip can hold the suture in place after the catheter system is withdrawn. For this and some other valve therapies, it may be advantageous to access the lower surface of the valve annulus from within the left ventricle. Access can be obtained by advancing a distal end of a transceptal catheter down through the mitral valve and then articulating one or two distal segments of the catheter within the ventricle using a retrograde approach. An alternative retrograde approach is illustrated in FIGS. 35G and 35H, in which a multi-segment balloon articulated catheter 1596 is articulated to facilitate across the aortic valve and into the left ventricle LV over a guidewire. One or two distal segments are then driven angles in a range from 120 to 270 degrees to provide retrograde access to the lower annulus tissues of the mitral valve MV.

Additional benefits may be available using the devices and systems described herein. For example, partial inflation of articulation balloons may locally decrease a lateral stiffness of the catheter so as to tailor a pushability and/or trackability of the catheter for a particular body lumen. Trackability, pushability, torqueability, and crossability of are known characteristics of catheters which may be quantitatively determined subjectively (by asking a number of users to rate the catheters for one or more of these characteristics), empirically (by measuring movement inputs and outputs in a controlled test), and/or analytically (by modelling interaction of the catheter and resulting catheter performance based on characteristics or properties of the catheter structure). Pushability generally reflects the ability of a distal end of the catheter to advance distally within a bending lumen in response to an axial insertion performed from proximally of the lumen, while trackability generally reflects the ability of the distal end of the catheter to follow a path through a bending lumen (optionally as defined by a guidewire or the luminal wall) in response to axial insertion. Both pushability and trackability can vary with a number of different characteristics of the catheter structure (both often improving with increased outer lubricity, for example), but in at least some circumstances they may contradict each other. For example, pushability may be enhanced by increasing an axial stiffness of at least an axial segment of a catheter, while trackability may be enhanced by decreasing that axial stiffness. The fluid articulated catheters described herein may help overcome this challenge for a particular body lumen, because the axial stiffness of the catheter segments can be independently varied by varying balloon pressure, optionally without applying pressure so as to impose lateral bends in any particular direction (absent environmental forces against the catheter).

In one example, good overall pushability and trackability of the catheter may benefit from a catheter structure with high lateral flexibility (low stiffness) along a distal catheter segment, and a relatively high stiffness (low flexibility) along an intermediate and proximal catheter segments. As the catheter advances distally, trackability may benefit from increasing the flexibility of the distal segment, while pushability and trackability may overall benefit by decreasing the stiffness of proximal segment (as it approaches or reaches a bend), and increasing the stiffness of the intermediate segment (as it leaves the bend and/or extends along a straight section. Catheter segments approaching or along greater curvature may be made less stiff (often by partial balloon inflation, or by partial deflation of opposed balloons), and so that catheter segments approaching or along straighter path portions are more stiff (such as by compete deflation or inflation of the balloons of those segments, or by increasing inflation pressure of opposed balloons).

Figure 36B:
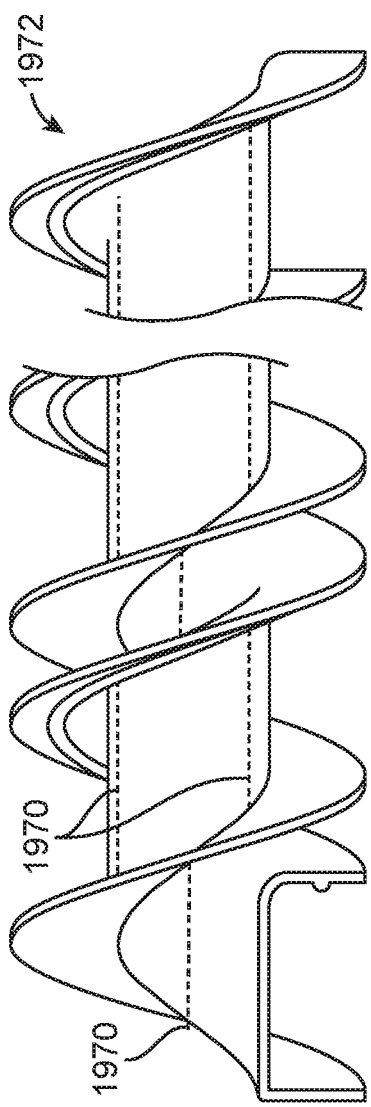
FIGS. 36A-37D schematically illustrate alternative helical frame structures having cuts and channels to enhance flexibility and/or provide access to balloon end surfaces to promote rotational alignment of subsets of balloons.
Figure 36A:
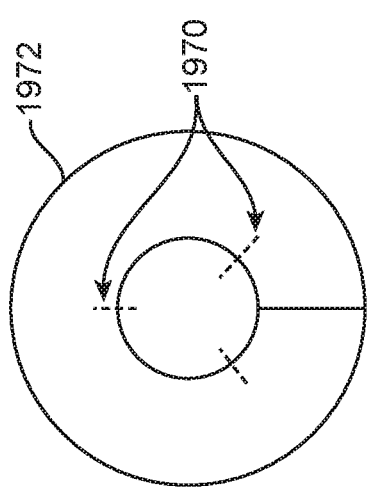
Figure 37D:
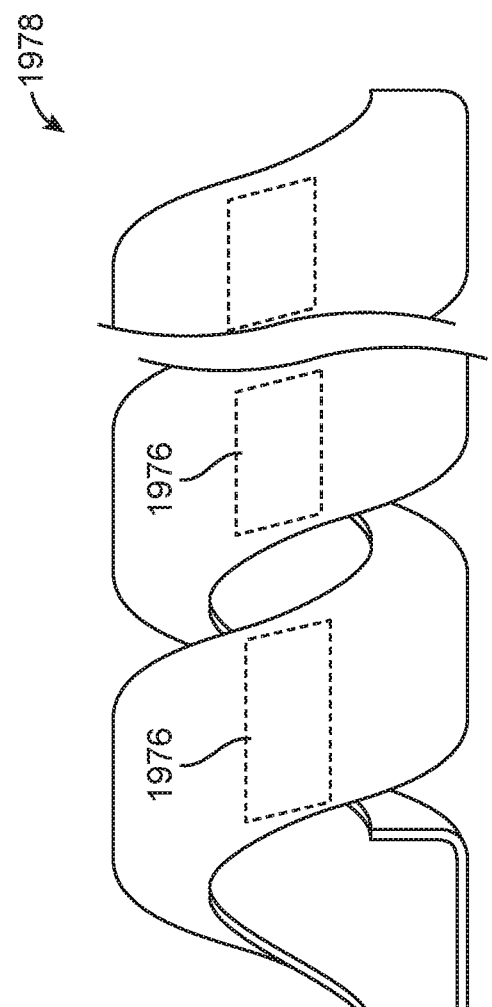
Figure 37C:
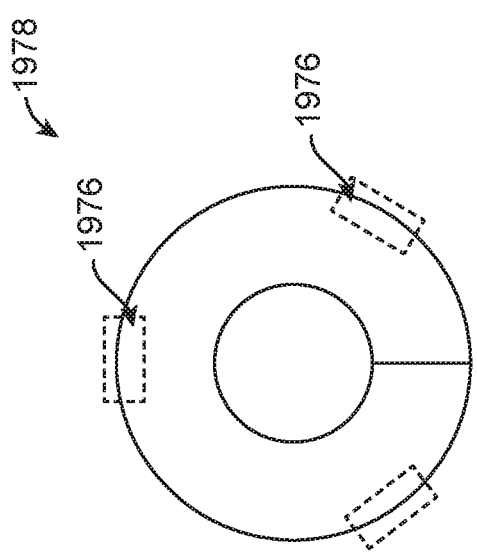
FIGS. 37E, 37F, and 37G illustrate components that may be used to help promote rotational alignment of balloons within helical frame structures.
Figure 37G:
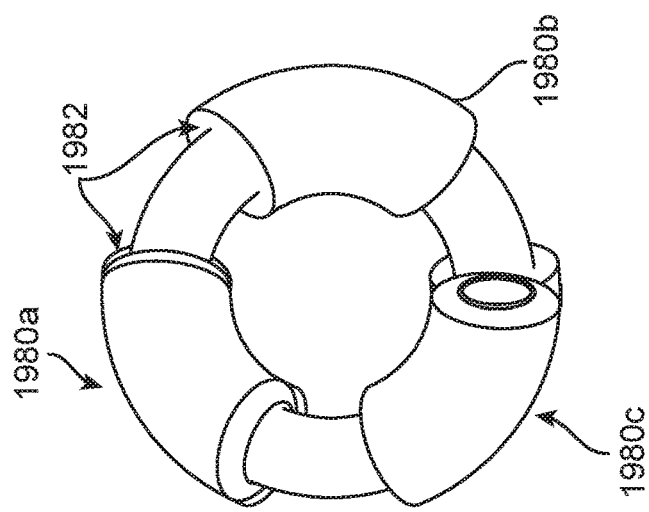
Figure 37F:
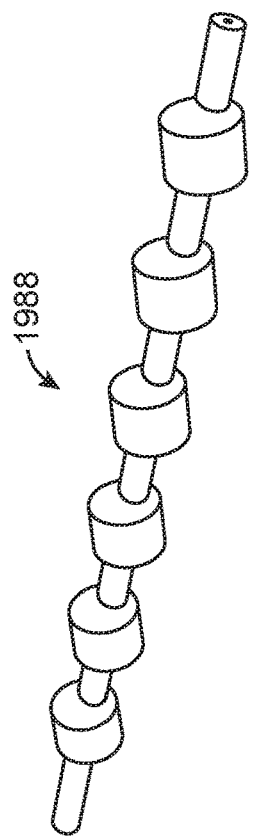
Figure 37E:
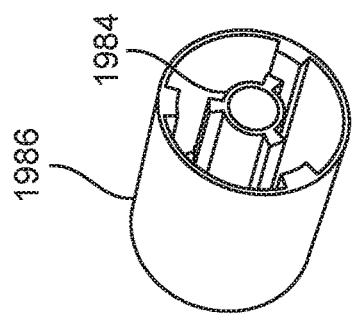

Referring now to FIGS. 36A-38B, a number of modifications are shown to the inner and outer helical frame structures described above, along with some associated components that may help maintain component alignment within the catheter assemblies. As shown in FIGS. 36A and 36B, radial cuts 1970 or slots may be made in the web of an inner helical frame 1972, with the cuts optionally extending axially and being formed at three locations separated by about 120 degrees about the frame axis, so that the cuts can be positioned between balloons of the assembly. The cuts may extend through the web between flanges, and optionally along an adjacent inner radial portion of the flanges. Sliding adjacent the opposed cut surfaces may facilitate local axial translation of arc-segments of the inner frame between cuts in response to balloon actuation, and thereby enhance axial bending and/or elongation of the overall catheter frame.

Referring now to FIGS. 37A-37G, alternative inner and outer helical frame structures 1974, 1978, respectively, both have open regions 1976 that can be formed, for example, by cutting and removing material from the webs and adjacent flanges of each loop in 3 places, spaced about 120 degrees apart, with the openings ideally being axially aligned with openings on adjacent loops. The openings may have a circumferential width in a range from about 0.005" to about 0.030", and may extend radially along the adjacent flanges for a distance in a range from about 0.010" to about 0.030." Flexing of the flanges adjacent the openings may facilitate local axial translation of the helical frame segments between openings, and hence axial bending and/or elongation of the overall frame. The radial openings in the frames may also be used to help promote axial alignment of balloon subsets. More generally, it may be advantageous to have structures or features disposed along the helical frames described herein to help promote axial alignment of subsets of balloons, such as sets 1980a, 1980b, 1980c. Discrete features may be affixed to some or all of the loops (such as by additive manufacturing or 3-D printing onto the extruded frame structures) with the features having surfaces that are disposed between and will engage against the ends of some or all of the balloons. Alternatively, an inner and/or outer sheath 1984, 1986 may have a radially protruding surface that can extend radially through the openings 1976 in the inner frame 1974, outer frame 1978, or both. The extending of openings 1976 along the web and a radial portion of the flange may allow the protruding surfaces of the sheath(s) to extend continuously between frame arc segments, keeping the frame segments in axial alignment. Similarly, the protruding surfaces may engage any balloon ends if they begin to move out of alignment with their subset. Note that one or more protruding feature in one of the sheaths may be sufficient, and that the balloons may be angled on the balloon assemblies so as to promote axial movement of the frame segments and/or provide axially oriented ends that more evenly engage the protruding radial alignment surfaces of the sheath(s). Optionally, the pitch angles of the flanges may vary circumferentially, for example, with the flanges along the cut sections having a greater pitch angle (measured from a lateral plane) than the flanges between cuts. The balloons being disposed at an angle along the multi-lumen shaft may help limit circumferential loads to the frames while enhancing axial loads against the flanges.

Referring now to FIGS. 38A and 38B, a still further alternative helical inner frame structure 1990 may have edge channels or cuts 1992. By, for example, cutting and removing material from the flanges and adjacent webs in 3 places on each loop (120 degrees apart), flexibility of the frame may be greatly enhanced. The removed material may have a circumferential width at the flange/web junction of 0.005-0.030", and may extend radially along the full radial length of the flanges. Flexing of the web by balloons disposed between removed flange regions may facilitate local axial translation of frame segmetns between flanges and axial bending of overall frame. Shape of material removed from web may be "V" (with straight cuts, as shown), "C" (with curved cuts, optionally being drilled), "U" (with straight and curved cuts), or the like.

Figure 39A:
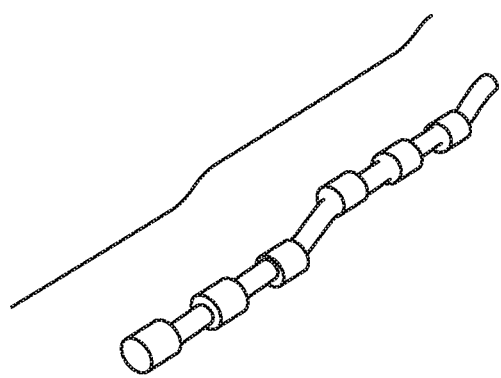
FIGS. 39A-39D illustrate alternative ring frame assembly components.
Figure 39B:
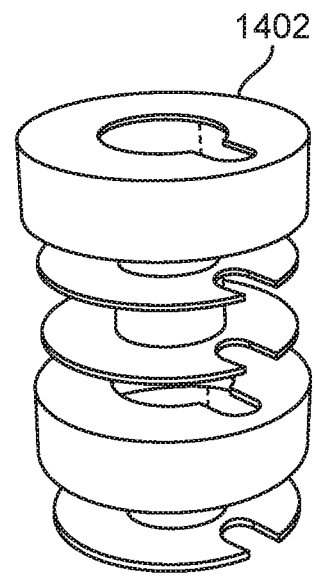
Figure 39C:
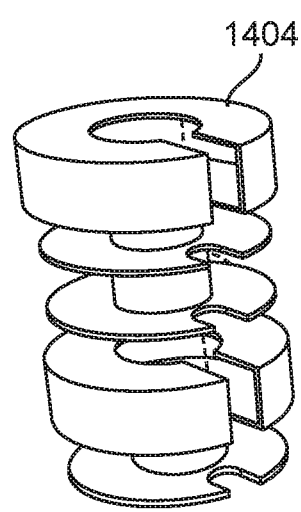
Figure 39D:
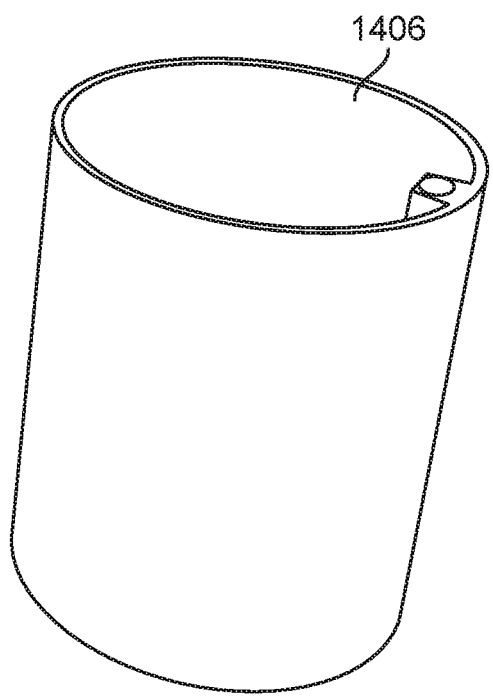

Referring now to FIGS. 39A-39D, alternative ring frame structures 1402, 1404 include axial openings in the flanges of the inner and outer frame rings (in FIG. 39B), and optional slots traversing the web of the inner or outer frame between openings (see FIG. 39C). A helical balloon coil has a series of balloons formed using a continuous balloon tube sealed over a multi-lumen shaft as described above, with the assembly here having helical coils formed from perpendicular (or near perpendicular) loops connected together by axially angled sections between loops. The balloons along each loop may be mounted so that the group is at an angle relative to the multi-lumen shaft so that the balloons may remain circumferentially aligned between a pair of flanges while the shaft angles slightly axially. Regardless, the balloon assembly can be wrapped around the frames and the frames assembled together using the axial apertures. Hence, the helical balloon assemblies described herein can be assembled with the ring frame structures as well as the helical frames. Optionally, an inner or outer sheath 1406 may have a radial protrusion that can extend into the slot in the ring frames to maintain axial alignment of the ring frames and balloons. A channel in the radial protrusion may also accommodate a multi-lumen shaft that can be used to articulate a more distal segment, as shown in FIG. 39D.

Figure 40B:
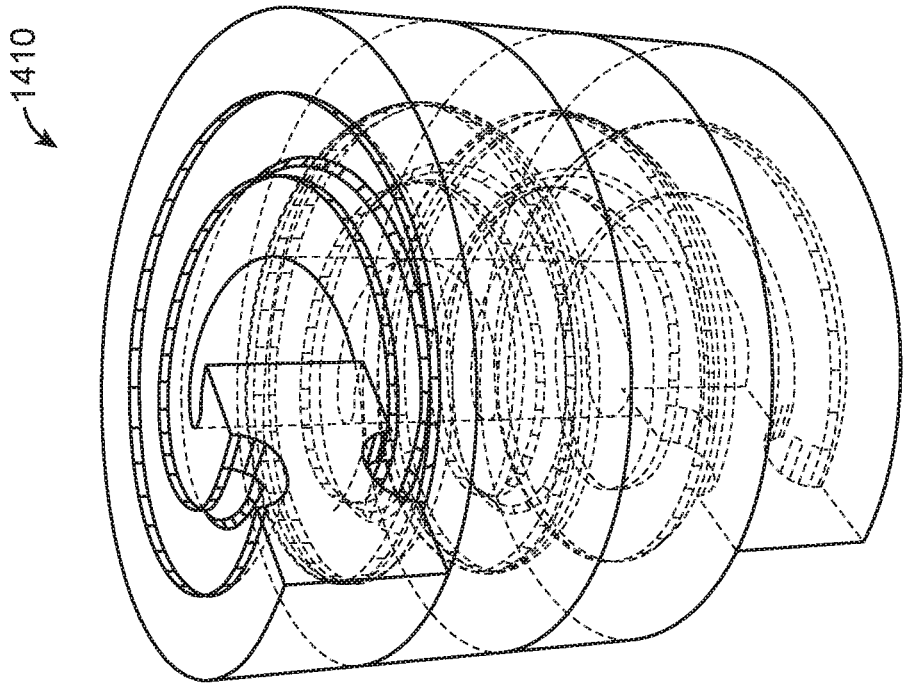
FIGS. 40A-40D illustrate an alternative coiled frame assembly that can accommodate a helical balloons assembly, and in which opposed balloons of the array bend the frame perpendicular to an axis of the frame.
Figure 40A:
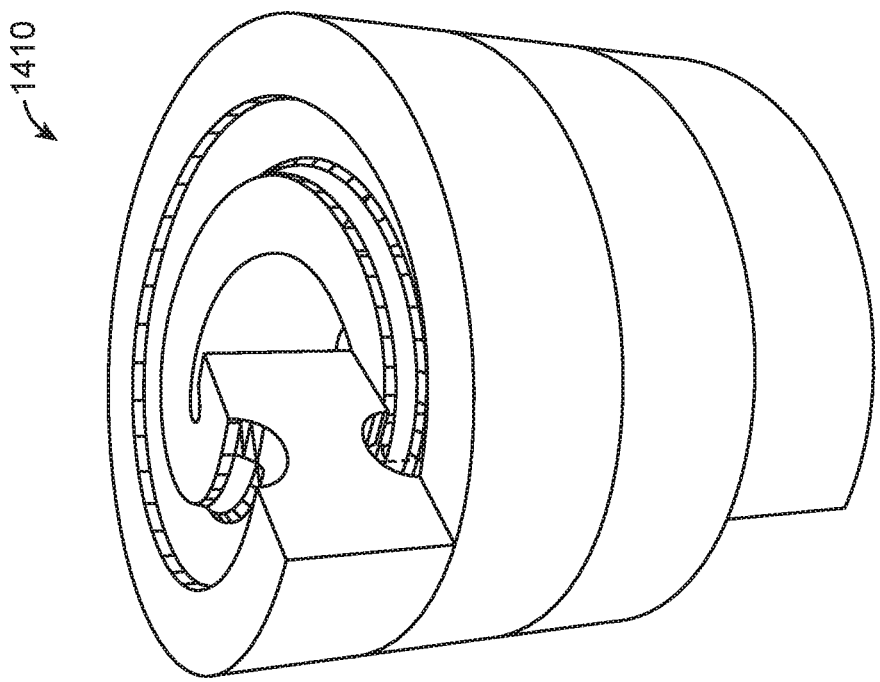
Figure 40D:
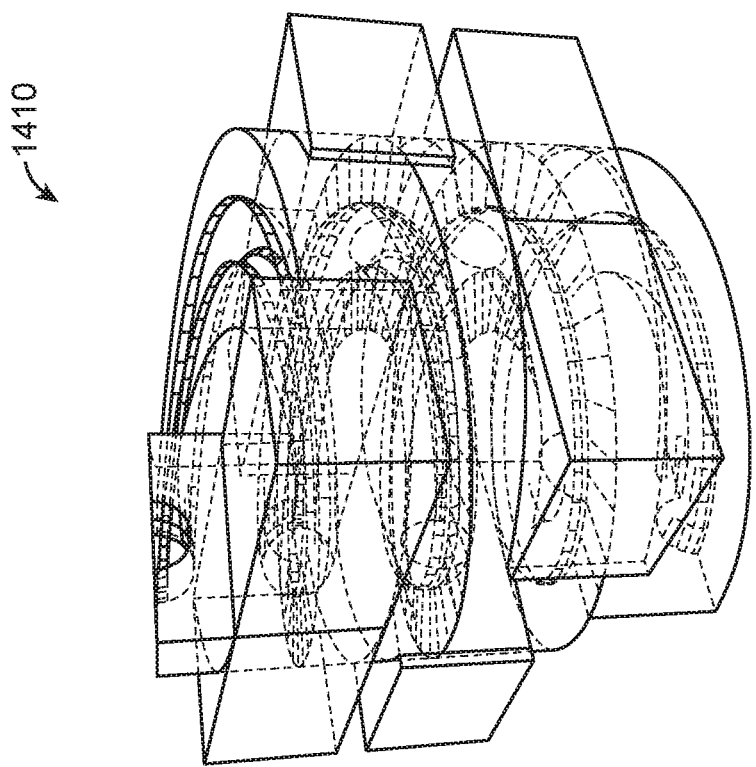
Figure 40C:
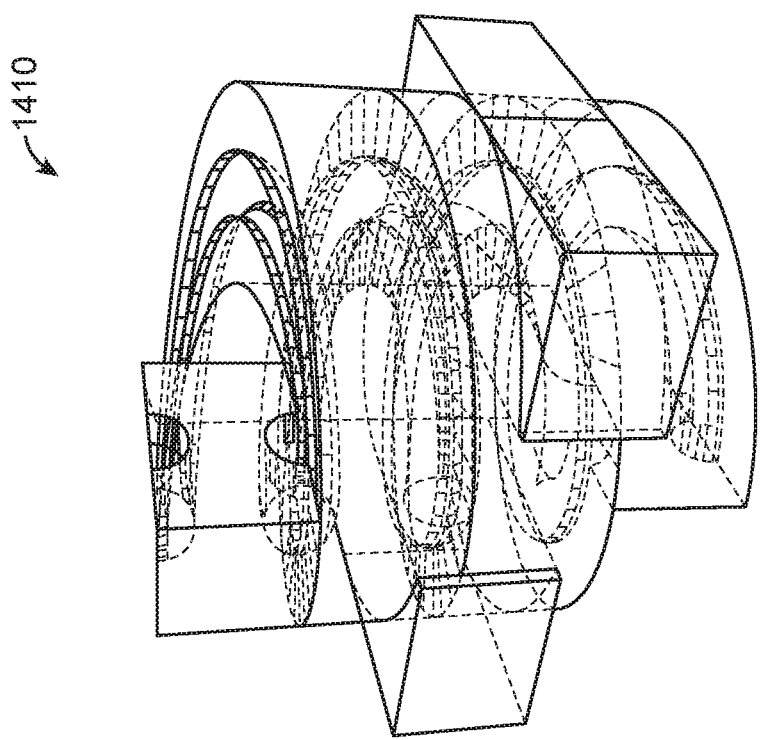

Referring now to FIGS. 40A-40D, a still further alternative frame structure 1410 makes use of a helical frame that can accommodate the helical balloon assemblies described herein, in which the loops of the frame may be bonded to each other (or otherwise held together) during articulation. As can be understood with reference to FIG. 40A, a surfaced model of a soft polymer helical base is shown. The base may be extruded or molded in sections and bonded or otherwise affixed together. A clear model of the helical base in FIG. 40B shows a helical channel formed between adjacent loops that can receive multi-lumen shaft/balloon assembly. As can be understood with reference to FIG. 40C, two opposed lateral cuts can be made in the coil (the cuts shown here as boxes containing material to remove). Each cut can receives a balloon of the balloon assembly, and each balloon pushes the axial surfaces of the coiled frame adjacent the cut apart when the balloon is inflated. The balloons of the opposed cuts act in opposition about the helical axis to provide +X/−X bending. As can be understood with reference to FIG. 40D, additional +Y/−Y lateral cuts may similarly each receive a balloon, allowing transverse bending. The frame loops, cuts and balloons can be repeated along the helical axis, with the +X balloons being on one common lumen of the multi-lumen shaft, the −X balloons on another, etc. When adjacent loops of the helical frame are affixed together, this assembly may be well-suited to provide X/Y lateral articulation.

Referring now to FIGS. 41A-41F, the helical articulated structures may take advantage of a coupling between axial elongation and twist so as to provide control over the orientation of the distal end of catheters and other elongate flexible bodies, optionally by including helical structures with opposed wind orientations. First addressing the elongation/axial twist coupling, a helical structure is shown schematically as a simple coil 1420 in FIGS. 41A and 41B, but may represent any of the inner and/or outer helical frames shown herein, the helical multi-lumen shafts and/or balloons assemblies, or the like. Coil 1420 has a proximal end 1422 and a distal end 1446 with an axis therebetween. The distal end has a rotation orientation about the axis, and an initial number of loops of the helical structure are disposed along the coil between the ends. As coil 1420 elongates (either by balloons or other actuators pushing the loops apart, or by environmental forces acting on the coil), distal end 1444 will tend to unwind or twist relative to proximal end 1442 in a direction so as to decrease the number of loops along the helical coil (at least fractionally). Shortening of the coil reverses the unwinding. Additionally, as can be understood with reference to FIGS. 41C and 41D, another helical coil 1430 that is wound with the reverse orientation as the first coil 1420 will unwind similarly, but in the opposition twist direction. Hence, if the two coils 1420, 1430 are affixed together axially with the distal end of the first coil 1444 attached to the proximal end 1444' of the reverse-wound second coil, when the two coils axially elongate in unison by the same amount, the twists cancel each other out, and the distal end of the second coil 1444" remains at the same rotational orientation about the axis throughout any elongation and/or contraction. The structures described herein can take advantage of this by separating the helical structures of an articulated segment into first and second regions, with the two regions having opposed wind orientations. This can be used to help inhibit twisting during elongation of a segment that will be articulated as a unit, i.e., where the balloons or other actuators along the segment (for at least one articulation orientation) are functionally coupled together to be inflated as a subset (such as being in fluid communication with a common lumen of a multi-lumen shaft).

Figures 41A, 41B, 41C, 41D, 41E, 41F:
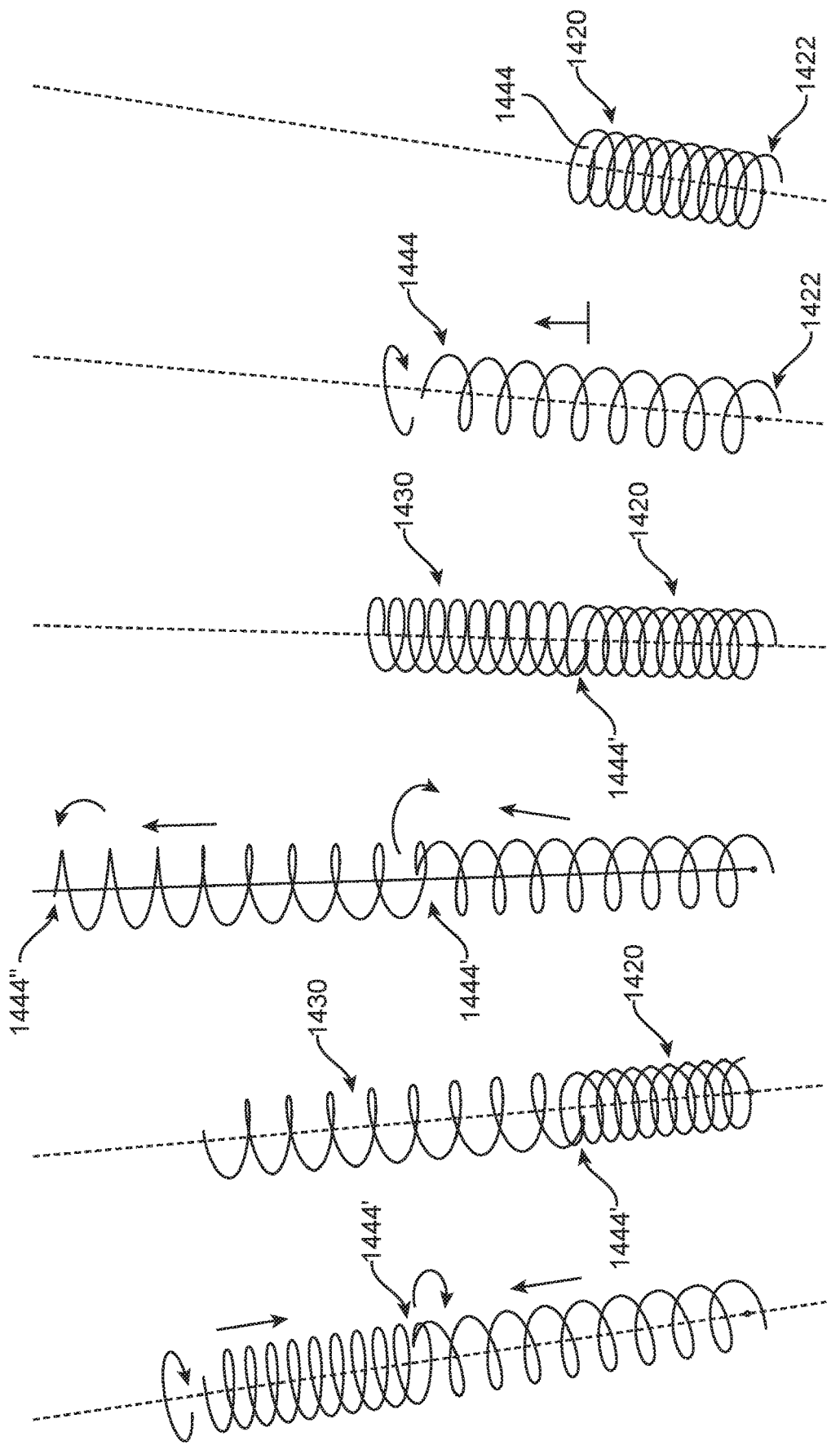
FIGS. 41A-41F schematically illustrate helical frame structures in which a wind orientation of one region of the frame is reversed from that of another region of the frame, and also shows how coupling between axial twisting and elongation of the frame can be used to control overall length of the frame, overall twist of the frame, or both.
Figure 42A:
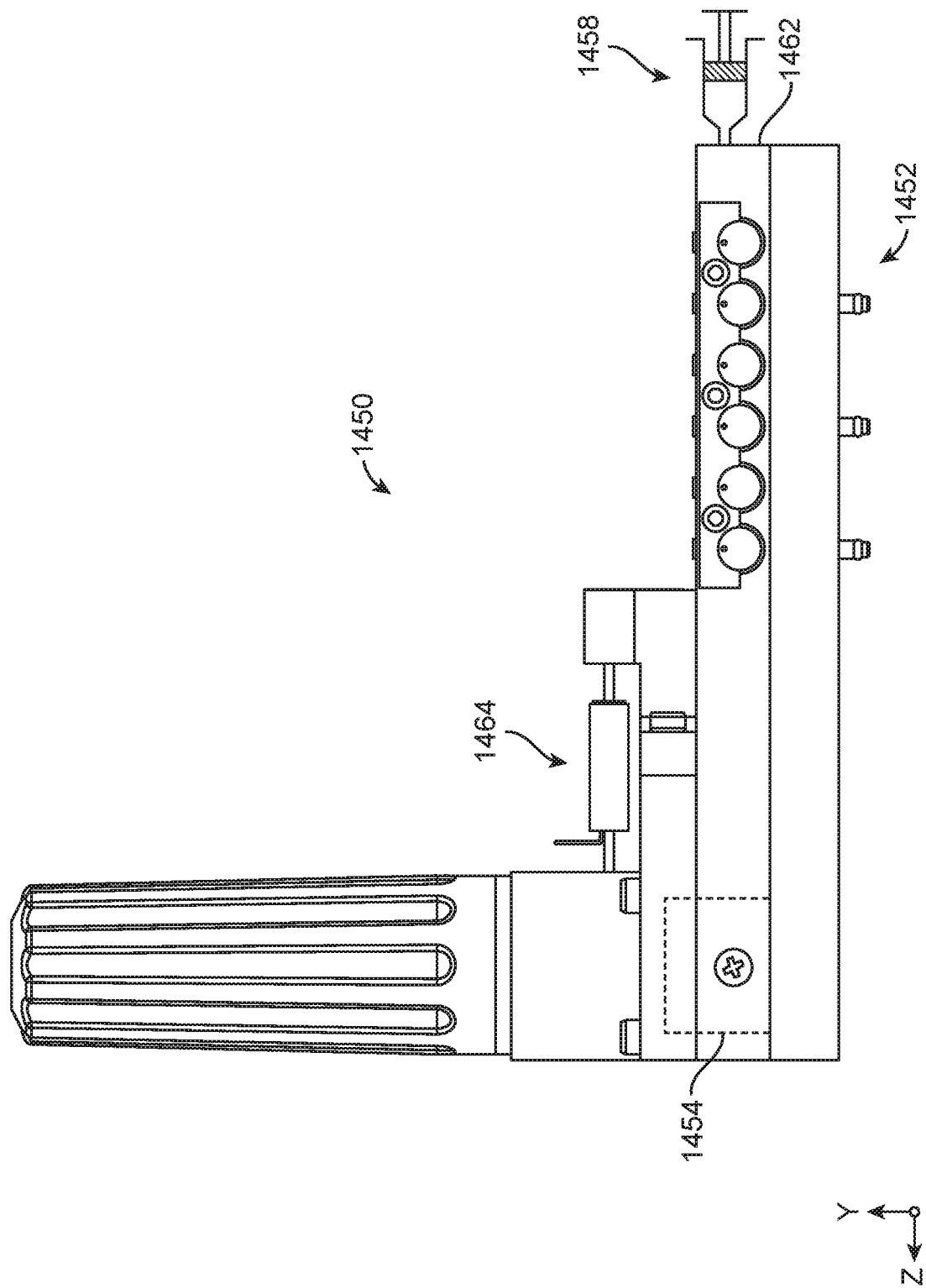
FIGS. 42A-42D illustrate an alternative manifold assembly and manifold components.
Figure 42B:
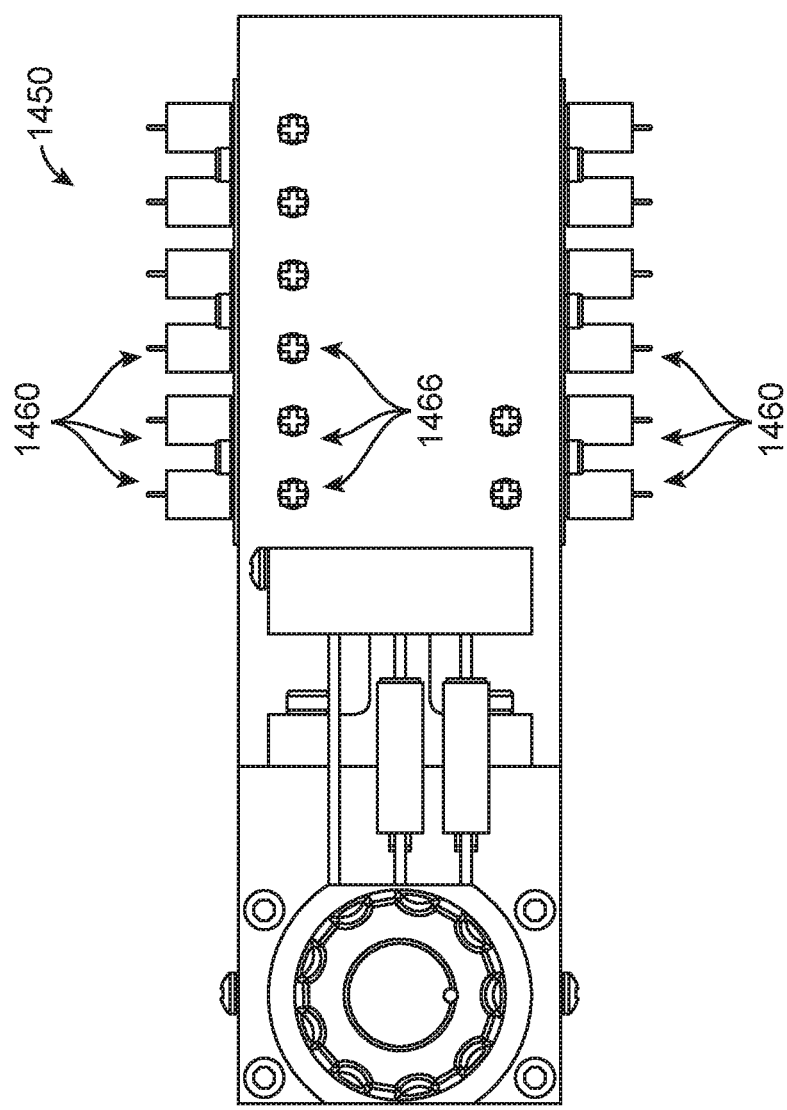
Figure 42D:
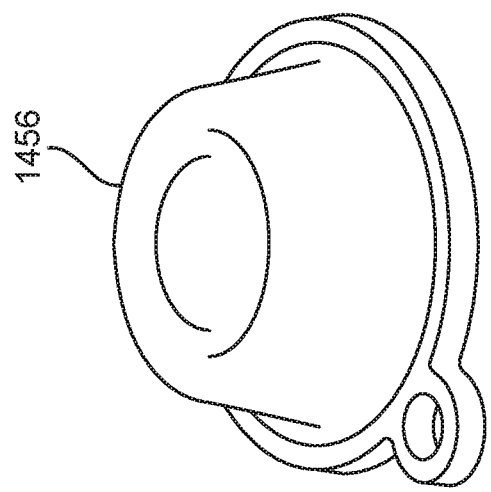
Figure 42C:
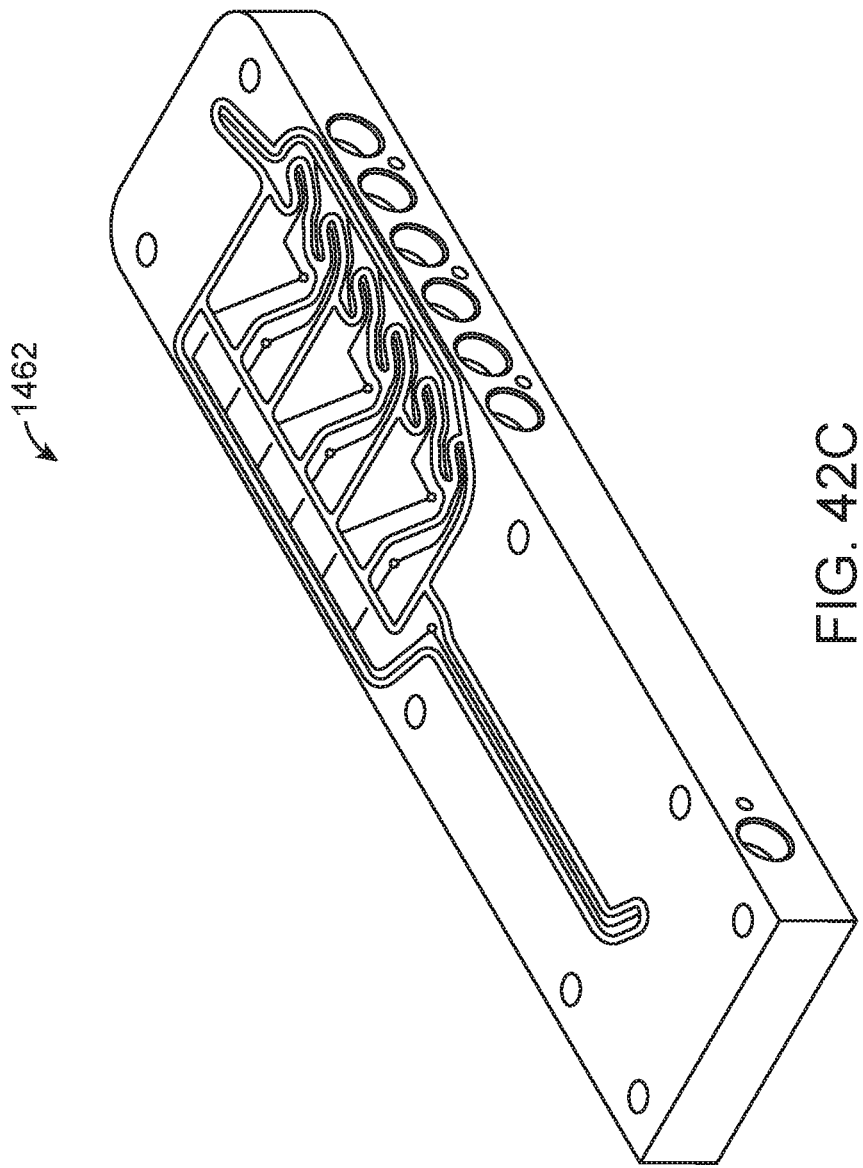

Referring now to FIGS. 41E and 41F, by differentially articulating (and specifically, differentially elongating) the reverse-wound coil regions it is possible to make use of the elongation/twist coupling of helical structures to provide additional control over the rotational orientation of the distal end of an assembly about the axis relative to the proximal end. In the relatively simple embodiment shown the combined length of the two coils may be kept constant (for example, by logic of the controller in response to a twist command, or by affixing an axial structure of the assembly that to both ends, and/or by coupling elongation balloons of one region to shortening balloons of the other, or the like). If the proximal coil portion starts in a relatively short configuration and elongates, the distal end of that coil will tend to unwind or twist in the first direction. As the distal coil has a reverse wind orientation and starts long, it will simultaneously tend to wind, twisting in the same first direction. The two coil regions 1420, 1430 are coupled together, so that the distal end of the second coil rotates with the combined twisting of both regions. As can be further understood with reference to FIGS. 41A-41F, by independently articulating the two regions, the combined length and rotational orientation of the distal end of the distal segment can be independently controlled (within a range of motion), so that the twist can be used as a degree of freedom of the system for aligning tools (such as asymmetric prosthetic heart valves) with target tissues or other structures. Advantageously, this independent twist and elongation may optionally be further combined with lateral bending DOFS of one or both segments, allowing two 3-DOF reverse-wound segments to have additional dexterity.

Referring now to FIGS. 42A-42D, exemplary manifold components and assemblies can be seen. As described above, when using manifold 1450, an N2O canister provides pressurized fluid to articulate a catheter coupled to a receptacle 1452 of the manifold. As was also described above, the canister here pressurizes a plenum 1454 to a controlled pressure. A diaphragm 1456 within the manifold separates the N2O (primarily a gas in the plenum) from a liquid such as saline, pressurizing the saline so that it can inflate the balloons. A latchable syringe 1458 can be coupled to a port of the exhaust header, providing a simple vacuum source or exhaust plenum that can be used to draw fluid from the channels of the manifold and catheter, and from the balloons, including for removing gas from the balloons and multi-lumen channels in preparation for use of the system. As described above, and inflation header channel directs inflation fluid (often liquid) from the plenum toward the inflation valves, which help control fluid flow to the balloons. Optionally, a gas valve may couple the N2O side of the diaphragm within the plenum to the inflation header, facilitating removal of fluid after use and/or allowing gas (or controlled mixtures of gas and liquid) to be introduced. Hence, the system may control flows of gas (from a first source or plenum region), liquid (from a second source or plenum region), and/or deflation fluid (to the atmosphere or a vacuum source). The fluid network channels to/from the balloon inflation and deflation valves 1460 are largely formed along a surface of a valve plate 1462, Flows between the canister and the plenum are controlled by high-pressure valves 1464. The surface of the valve plate 1462 opposite the receptacle 1452 may be recessed below the valve engaging edges so as to limit a volume of pressure sensing channels extending between the balloon inflation channels and a pressure sensing array 1466.

While the exemplary embodiment have been described in some detail for clarity of understanding and by way of example, a variety of modifications, changes, and adaptations of the structures and methods described herein will be obvious to those of skill in the art. Hence, the scope of the present invention is limited solely by the claims attached hereto.

What is claimed is:

1. A catheter system comprising:
    an elongate catheter body having a proximal end and a distal end and defining an axis therebetween, the catheter body having an articulated portion adjacent the distal end;
    a proximal housing coupleable with the proximal end of the catheter body, the proximal housing sized for movement by a hand of a user and supporting:
        an articulation drive system configured to effect articulation of the articulated portion;
        a processor coupled to the drive system so as to transmit drive signals thereto in response to commands input by the user; and
        a battery coupled to the processor and to a charge receiving coupler; and
    a base station having a receptacle configured to receive the housing, the base station having a charge providing coupler positioned so as to couple with the charge receiving coupler when the housing is in the receptacle;
    wherein the drive system comprises a plurality of fluid expandable bodies and further comprising a plurality of pressure sensors in communication with the fluid expandable bodies, a source of pressurized fluid, and a plurality of valves between the fluid source and the expandable bodies, wherein the processor is coupled with the valves and configured to induce movement of the catheter body toward a new position in response to the commands input by a system user, and wherein the processor comprises a closed loop valve controller configured to actuate the valves and provide desired pressures in the expandable bodies; and
    wherein the processor comprises a module configured to determine a desired state of the body, an inverse kinematics module configured to determine a desired joint state, a module configured to determine a difference between an actual joint state and the desired joint state so as to define a joint error, and a joint trajectory planner, wherein the trajectory planner defines a joint error trajectory in response to the desired joint state and the joint error, and wherein the joint trajectory is transmitted to an inverse fluidic calculator to determine command signals for the valves.

2. The catheter system of claim 1, wherein the charge receiving coupler comprises an inductive charge receiving coupler, and wherein the charge providing coupler comprises an inductive charge providing coupler, and further comprising a sterile barrier configured for maintaining sterile separation between the base station and the proximal housing when the housing is in the receptacle; and wherein the base station further comprises a server including a first wireless communication module, and wherein the proximal housing contains a second wireless communication module configured to communicate with the first wireless communication module so as to transmit data.

3. The catheter system of claim 1, wherein the base station further comprises a server coupleable with a network, the processor of the proximal housing coupleable with the server so as to transmit data between the network and the processor, wherein the catheter has an ID tag embodying machine-readable catheter identity data, wherein the processor of the housing transmits ID data, in response to the catheter identity data of the tag, to the server when the server is coupled with a processor of the base station, wherein the server obtains approval data from the network, and wherein the processor inhibits use of the catheter absent the approval data.

4. The catheter system of claim 1, wherein the articulated portion comprises an array of articulation balloons.

5. The catheter system of claim 1, wherein the fluid expandable bodies comprise piston assemblies.

6. An articulatable structure comprising:
    an elongate flexible body having a proximal end and a distal end with an axis therebetween; and
    an array of actuators mounted along the body so as to articulate the body;
    wherein the actuators comprise fluid expandable bodies and further comprising a plurality of pressure sensors in communication with the fluid expandable bodies, a source of pressurized fluid, and a plurality of valves between the fluid source and the expandable bodies, wherein a processor is coupled with the valves and configured to induce movement of the body toward a new position in response to a command input by a system user, and wherein the processor comprises a closed loop valve controller configured to actuate the valves and provide desired pressures in the expandable bodies; and
    wherein the processor comprises a module configured to determine a desired state of the body, an inverse kinematics module configured to determine a desired joint state, a module configured to determine a difference between an actual joint state and the desired joint state so as to define a joint error, and a joint trajectory planner, wherein the trajectory planner defines a joint error trajectory in response to the desired joint state and the joint error, and wherein the joint trajectory is transmitted to an inverse fluidic calculator to determine command signals for the valves.

7. The structure of claim 6, wherein the body comprises a helical frame having a proximal flange and a distal flange with an axial wall extending therebetween, wherein the actuators urge the flanges axially so as to locally deflect the axis, and wherein the frame has openings in the axial wall circumferentially between the actuators so as to enhance lateral flexibility of the frame.

8. The structure of claim 6, wherein the body has an ID tag embodying machine-readable data, and further comprising a processor coupled with the actuators so as to transmit drive signals thereto, the processor configured for coupling with a server in communication with a network so as to transmit ID data.

9. The structure of claim 6, further comprising a feedback system configured to sense an actual position or state of the body using a sensor, the sensor comprising an electromagnetic navigation system, an ultrasound navigation system, an image processor coupled to a 3D image acquisition system, an optical fiber shape sensor, or an electrical shape sensor.

10. An articulatable structure comprising:
an elongate flexible body having a proximal end and a distal end with an axis therebetween;
an array of actuators mounted along the body so as to articulate the body;
a manifold for articulating the elongate body, the array of actuators comprising an array of articulation balloons, the manifold comprising:
a liquid inflation fluid source;
a gas inflation fluid source; and
a processor coupled with the fluid sources, wherein in use, at least one fluid channel of the structure contains gas inflation fluid and liquid inflation fluid, and wherein the processor is configured to alter relative amounts of the gas inflation fluid and liquid inflation fluid in the channel in response to a command to change a compliance of a subset of the balloons in communication with the channel.

11. An articulatable structure comprising:
an elongate flexible body having a proximal end and a distal end with an axis therebetween;
an array of actuators mounted along the body so as to articulate the body;
a manifold for articulating the elongate body, the body having an array of articulation balloons, the manifold comprising:
a receptacle configured to receive a canister having a first inflation fluid;
a deformable diaphragm having a first side and a second side, wherein in use, the first side is in fluid communication with the first inflation fluid and the second side is in fluid communication with a second inflation fluid; and a valve coupling the canister to the first side of the diaphragm so as to control a pressure of the first and second inflation fluids;
wherein the second side of the diaphragm is in fluid communication with the balloons to selectively inflate the balloons with the second inflation fluid.

12. The structure of claim 11, wherein the body comprises a catheter body, and wherein the first inflation fluid comprises a gas and the second inflation fluid comprises a liquid.

13. A heart valve therapy system for structurally altering a valve of a heart in a patient body, the therapy system comprising:
an elongate flexible cardiac catheter body having a proximal end and a distal end with an axis therebetween;
a therapeutic valve tool mounted near the distal end of the catheter body;
the catheter body having an articulated portion adjacent the distal end; and
an articulation drive system configured to effect articulation of the articulated portion;
wherein the drive system comprises a plurality of fluid expandable bodies and further comprising a source of pressurized fluid and a plurality of valves between the fluid source and the expandable bodies, wherein the processor is coupled with the valves and configured to induce movement of the catheter body toward a new position in response to the commands input by a system user; and
wherein the processor comprises a module configured to determine a desired state of the body, an inverse kinematics module configured to determine a desired joint state, and a module configured to determine a difference between an actual joint state and the desired joint state so as to define a joint error, and wherein the processor is configured to transmit command signals to the valves in response to the joint error.

14. The therapy system of claim 13, wherein the tool comprises a valve leaflet plication clip.

15. The therapy system of claim 13, wherein the tool comprises an annuloplasty ring.

16. The therapy system of claim 13, wherein the tool comprises an annular plication tool.

17. The therapy system of claim 13, further comprising a plurality of pressure sensors in communication with the fluid expandable bodies, wherein the processor comprises a closed loop valve controller configured to actuate the valves and provide desired pressures in the expandable bodies.

18. The therapy system of claim 17, wherein the processor comprises a joint trajectory planner, wherein the trajectory planner defines a joint error trajectory in response to the desired joint state and the joint error, and wherein the joint trajectory is transmitted to an inverse fluidic calculator to determine the command signals for the valves.

19. The therapy system of claim 13, wherein the pressure source comprises a canister of liquid, the liquid configured to vaporize to a gas so as to pressurize the manifold.

20. The therapy system of claim 13, wherein the fluid expandable bodies comprise piston assemblies.

* * * * *